US011060114B2

(12) United States Patent
Qimron et al.

(10) Patent No.: US 11,060,114 B2
(45) Date of Patent: Jul. 13, 2021

(54) TARGETED ELIMINATION OF BACTERIAL GENES

(71) Applicant: TECHNOLOGY INNOVATION MOMENTUM FUND (ISRAEL) LIMITED PARTNERSHIP, Tel Aviv (IL)

(72) Inventors: Ehud Qimron, Tel Aviv (IL); Ido Yosef, Moshav Netiv Ha'Asara (IL); Miriam Manor, Jerusalem (IL)

(73) Assignee: TECHNOLOGY INNOVATION MOMENTUM FUND (ISRAEL) LIMITED PARTNERSHIP, Tel Aviv (IL)

( * ) Notice: Subject to any disclaimer, the term of this patent is extended or adjusted under 35 U.S.C. 154(b) by 617 days.

(21) Appl. No.: 15/605,098

(22) Filed: May 25, 2017

(65) Prior Publication Data

US 2017/0260546 A1    Sep. 14, 2017

Related U.S. Application Data

(63) Continuation-in-part of application No. PCT/IL2015/051154, filed on Nov. 26, 2015.

(60) Provisional application No. 62/084,703, filed on Nov. 26, 2014.

(51) Int. Cl.
| | | |
|---|---|---|
| C12N 15/90 | (2006.01) | |
| C12N 15/74 | (2006.01) | |
| A61K 35/76 | (2015.01) | |
| C12N 15/63 | (2006.01) | |
| C12N 15/11 | (2006.01) | |

(52) U.S. Cl.
CPC ............ *C12N 15/902* (2013.01); *A61K 35/76* (2013.01); *C12N 15/111* (2013.01); *C12N 15/63* (2013.01); *C12N 15/74* (2013.01); *C12N 2310/20* (2017.05); *C12N 2320/30* (2013.01)

(58) Field of Classification Search
None
See application file for complete search history.

(56) References Cited

U.S. PATENT DOCUMENTS

| | | | |
|---|---|---|---|
| 8,865,158 B2 | 10/2014 | Qimron et al. | |
| 2008/0124725 A1 | 5/2008 | Barrangou et al. | |
| 2013/0315869 A1 | 11/2013 | Qimron et al. | |
| 2014/0068797 A1* | 3/2014 | Doudna | A01H 6/4684 800/18 |
| 2014/0113376 A1 | 4/2014 | Sorek et al. | |
| 2015/0064138 A1 | 3/2015 | Lu et al. | |

FOREIGN PATENT DOCUMENTS

| | | |
|---|---|---|
| NZ | 597299 B | 3/2013 |
| WO | 2008/108989 A2 | 9/2008 |
| WO | 2010075424 A2 | 7/2010 |
| WO | 2014124226 A1 | 8/2014 |

OTHER PUBLICATIONS

Abuladze et al. (2008). "Bacteriophages Reduce Experimental Contamination of Hard Surfaces, Tomato, Spinach, Broccoli, and Ground Beef by *Escherichia coli* 0157:117" Appl Environ Microbiol 74(20):6230-6238.
Baba et al. (2006) "Construction of *Escherichia coli* K-12 in-frame, single-gene knockout mutants: the Keio collection" Mol Syst Biol 2:1-11.
Barrangou et al. (2007) "CRISPR Provides Acquired Resistance Against Viruses in Prokaryotes" Science 315(5819):1709-1712).
Bikard et al. (2014) "Development of sequence-specific antimicrobials based on programmable CRISPR-Cas nucleases" Nat Biotechnol. vol. 32 No. 11, p. 1146-1150.
Bolotin et al. (2005) "Clustered regularly interspaced short palindrome repeats (CRISPRs) have spacers of extrachromosomal origin" Microbiology 151(Pt 8): 2551-61.
Boucher et al. (2009) "Bad Bugs, No Drugs: No ESKAPEI An Update from the Infectious Diseases Society of America" Clin Infect Dis 48(1):1-12.
Brouns et al. (2008) "Small CRISPR RNAs Guide Antiviral Defense in Prokaryotes" Science 321(5891):960-964.
Bush et al. (2011) "Epidemiological Expansion, Structural Studies, and Clinical Challenges of New β-Lactamases from Gram-Negative Bacteria" Annu Rev Microbiol 65:455-478.
Citorik et al. (2014) "Sequence-specific antimicrobials using efficiently delivered RNA-guided nucleases" Nat. Biotechnol. vol. 32, No. 11, p. 1141-1145.
Datsenko et al. (2000) "One-step inactivation of chromosomal genes in *Escherichia coli* K-12 using PCR products" Proc Natl Acad Sci U S A 97(12):6640-6645.
Edgar et al. (2010) "The *Escherichia coli* CRISPR System Protects from λ Lysogenization, Lysogens, and Prophage Induction" J Bacteriol 192(23):6291-6294.
Garneau et al. (2010) "The CRISPR/Cas bacterial immune system cleaves bacteriophage and plasmid DNA" Nature 468(7320):67-71.

(Continued)

*Primary Examiner* — James D Schultz
(74) *Attorney, Agent, or Firm* — Vorys, Sater, Seymour and Pease LLP; Anthony P. Venturino

(57) ABSTRACT

Provided is a kit or a system including two elements or components. The first component (i) is a selective component including a nucleic acid sequence and at least one proto-spacer. The second component (ii) includes at least one sensitizing component including at least one cas gene and at least one CRISPR array. At least one spacer of the CRISPR targets a proto-spacer included within a pathogenic gene of a bacterium so as to specifically inactivate said pathogenic gene in said bacterium and wherein at least one spacer of said CRISPR targets a proto-spacer included within said selective component of (i) so as to specifically inactivate said selective component. Further provided is a method using the components or kits of the invention for interference with a horizontal transfer of a pathogenic gene between bacteria and for preventing a pathologic condition in a mammalian subject caused by a bacterial infection.

27 Claims, 7 Drawing Sheets

Specification includes a Sequence Listing.

(56) References Cited

OTHER PUBLICATIONS

Genebank accession No. AB089608 (2003).
Genebank accession No. AF015628 (2016).
Genebank accession No. AF117258 (2016).
Genebank accession No. AF117259 (2016).
Genebank accession No. AF368302 (2016).
Genebank accession No. AJ867812 (2016).
Genebank accession No. DQ176450 (2005).
Genebank accession No. DQ241380 (2005).
Genebank accession No. DQ388126 (2007).
Genebank accession No. DQ489717 (2006).
Genebank accession No. FJ411076 (2016).
Genebank accession No. J05162 (1990).
Genebank accession No. M34933 (2002).
Genebank accession No. NC_000913 (2016).
Genebank accession No. NC_000962 (2016).
Genebank accession No. NC_002525 (2014).
Genebank accession No. NC_003210.1 (2009).
Genebank accession No. NC_004566 (2014).
Genebank accession No. NC_005327 (2014).
Genebank accession No. NC_005773 (2017).
Genebank accession No. NC_007682 (2005).
Genebank accession No. NC_009140 (2017).
Genebank accession No. NC_009648 (2001).
Genebank accession No. NC_009980 (2007).
Genebank accession No. NC_010119 (2015).
Genebank accession No. NC_010170 (2008).
Genebank accession No. NC_010410 (2017).
Genebank accession No. NC_010488 (2017).
Genebank accession No. NC_010558 (2015).
Genebank accession No. NC_010870 (2007).
Genebank accession No. NC_010886 (2006).
Genebank accession No. NC_011742 (2017).
Genebank accession No. NW_139440 (2004).
Genebank accession No. X07848 (2016).
Genebank accession No. X75562 (1995).
Genebank accession No. Z83311 (2016).
Gomaa et al. (2014) "Programmable Removal of Bacterial Strains by Use of Genome-Targeting CRISPR-Cas Systems" MBio 5(1):e00928-00913.
Hagens et al. (2003) "Gentically modified filamentous phage as bactericidal agents: a pilot study" Lett Appl Microbiol.;37(4):318-323.
Hale et al. (2009) "RNA-Guided RNA Cleavage by a CRISPR RNA-Cas Protein Complex" Cell 139(5):945-956.
Kiro et al. (2013) "Gene product 0.4 increases bacteriophage T7 competitiveness by inhibiting host cell division" Proc Natl Acad Sci U S A 110(48):19549-19554.
Lang (2006) "FDA Approves Use of Bacteriophages to be Added to Meat and Poultry Products" Gastroenterology 131(5):1370.
Levin (2013) "The Population and Evolutionary Dynamics of Phage and Bacteria with CRISPR-Mediated Immunity", PLOS Genetics, vol. 9, No. 3, e1003312, https://doi.org/10.1371/journal.pgen.1003312.
Lu et al. (2009) "Engineered bacteriophage targeting gene networks as adjuvants for antibiotic therapy", Proc Natl Acad Sci U S A 106(12):4629-4634.
Marraffini et al. (2008) "CRISPR Interference Limits Horizontal Gene Transfer in Staphylococci by Targeting DNA" Science 322:1843-1845.
Marraffini et al. (2010) "CRISPR interference: RNA-directed adaptive immunity in bacteria and archaea", Nat Rev Genet 11(3):181-190.
Merril et al. (2003) "The prospect for bacteriophage therapy in Western medicine" Nat Rev Drug Discov 2(6):489-497.
Parmley (2014) "Programmable sensitivity" SciBX: Science-Business eXchange; 3 pages.
Pendleton et al., (2013) "Clinical relevance of the ESKAPE pathogens", Expert Rev. Anti Infect. Ther., 11(3), 297-308.
Qimron et al. (2006) "Genomewide screens for *Escherichia coli* genes affecting growth of T7 bacteriophage" Proc Natl Acad Sci USA 103(50):19039-19044.4.
Sharan et al. (2009) "Recombineering: A Homologous Recombination-Based Method of Genetic Engineering" Nat Protoc 4(2):206-223.
Yosef et al. (2011) "High-temperature protein G is essential for activity of the *Escherichia coli* clustered regularly interspaced short palindromic repeats (CRISPR)/Cas system" Proc Natl Acad Sci U S A 108(50):20136-20141.
Yosef et al. (2012) "Proteins and DNA elements essential for the CRISPR adaptation process in *Escherichia coli*" Nucleic Acids Res 40(12):5569-5576.
Yosef et al. (2014) "Different approaches for using bacteriophages against antibiotic-resistant bacteria" Bacteriophage 4(1):e28491.
Yosef et al. "Temperate and lytic bacteriophages programmed to sensitize and kill antibiotic-resistant bacteria" vol. 112, No. 23, p. 7267-7272. Jun. 9, 2015.
Yu et al. (2000) "An efficient recombination system for chromosome engineering in *Escherichia coli*" Proc Natl Acad Sci U S A 97(11):5978-5983.
Chylinski et al., "The tracrRNA and Cas9 families of type II CRISPR-Cas immunity systems", RNA Biology, 10:5, 726-737, (2013).
Dupuis et al., "CRISPR-Cas and restriction-modification systems are compatible and increase phage resistance", Nat. Commun., 4:2087, 7 pages, (2013).
Seed et al., "A bacteriophage encodes its own CRISPR/Cas adaptive response to evade host innate immunity", Nature, vol. 494, No. 7438, pp. 489-491, (2013).

* cited by examiner

TARGETED ELIMINATION OF BACTERIAL GENES

The work leading to this invention has received funding from the European Research Council under the European Union's Seventh Framework Programme (EP7/2007-2013)/ERC grant agreement No. 336079.

SEQUENCE LISTING

The Sequence Listing submitted in text format (.txt) filed on May 25, 2017, named "SequenceListing.txt", created on Mar. 13, 2017, 199 KB), is incorporated herein by reference."

FIELD OF THE INVENTION

The invention relates to methods for a specific targeted elimination of bacterial genes. More specifically, the invention provides kits, systems, compositions and methods using engineered RNA guided nucleases (RGNs) systems for targeting and eliminating bacterial pathogenic genes.

BACKGROUND REFERENCES

1. Lu T K & Collins J J (2009) *Proc Natl Acad Sci USA* 106(12):4629-4634.
2. Merril C R, et al. (2003) *Nat Rev Drug Discov* 2(6):489-497.
3. Qimron U, et al. (2006) *Proc Natl Acad Sci USA* 103(50):19039-19044.4
4. Lang L H (2006) *Gastroenterology* 131(5):1370.
5. Abuladze T, et al. (2008). *Appl Environ Microbiol* 74(20): 6230-6238.
6. Hagens and Blassi (2003) *Lett Appl Microbiol.*; 37(4): 318-23.
7. Qimron U, et al. (2014) U.S. Pat. No. 8,865,158.
8. Gomaa A A et al. (2014) *MBio* 5(1):e00928-00913.
9. Gameau J E et al. (2010) *Nature* 468(7320):67-71.
10. Citorik R J et al. (2014) *Nat. Biotechnol.*
11. Bikard D et al. (2014) *Nat Biotechnol.*
12. Barrangou et al. (2007) *Science* 315(5819): 1709-12.
13. Bolotin et al. (2005) *Microbiology* 151(Pt 8): 2551-61.
14. Marraffini et al. (2008) *Science* 322: 1843-1845.
15. Yosef I et al. (2014) *Bacteriophage* 4(1):e28491.
16. Barrangou R, et al. (2007) *Science* 315(5819):1709-1712).
17. Hale C R, et al. (2009) *Cell* 139(5):945-956.
18. Pendleton J N, et al. (2013) *Expert Rev Anti Infect Ther* 11(3):297-308.
19. Boucher H W, et al. (2009) *Clin Infect Dis* 48(1):1-12.
20. Marraffini L A et al. (2010) *Nat Rev Genet* 11(3):181-190.
21. Hale C R et al. (2009) *Cell* 139(5):945-956.
22. Datsenko K A et al. (2000) *Proc Natl Acad Sci USA* 97(12):6640-6645.
23. Yosef I et al. (2012) *Nucleic Acids Res* 40(12):5569-5576.
24. Sharan S K et al. (2009) *Nat Protoc* 4(2):206-223.
25. Yu D et al. (2000) *Proc Natl Acad Sci USA* 97(11):5978-5983.
26. Yosef I et al. (2011) *Proc Natl Acad Sci USA* 108(50): 20136-20141.
27. Kiro R et al. (2013) *Proc Natl Acad Sci USA* 110(48): 19549-19554.
28. Bush K et al. (2011) *Annu Rev Microbiol* 65:455-478.
29. Brouns S J et al. (2008) *Science* 321(5891):960-964.
30. Baba T et al. (2006) *Mol Syst Biol* 2:1-11.
31. Edgar R and Qimron U (2010) *J Bacteriol* 192(23): 6291-6294.

Acknowledgement of the above references herein is not to be inferred as meaning that these are in any way relevant to the patentability of the presently disclosed subject matter.

BACKGROUND OF THE INVENTION

Bacteria have evolved to overcome a wide range of antibiotics, and resistance mechanisms against most of the conventional antibiotics have been identified in some bacteria. Accelerated development of newer antibiotics is being overrun by the pace of bacterial resistance. In the USA, for example, over 70% of hospital-acquired infections involve bacteria resistant to at least one antibiotic, and in Japan over 50% of the clinical isolates of *Staphylococcus aureus* are multidrug-resistant.

Antibiotic resistance of pathogen is a growing concern to human health, leading to renewed interest in phage therapy. This therapy uses phages, the natural bacterial enemies, to kill pathogens. However, the therapy is currently not feasible mainly due to delivery barriers into the tissues as well as bacterial resistance to the phages. Major concerns over the use of phage therapy include neutralization of phages by the spleen/liver and by the immune system, their narrow host range, bacterial resistance to the phage, and lack of sufficient pharmacokinetic and efficacy studies in humans and animals.

Several studies used phages as a genetic tool to increase bacterial susceptibility to antibiotics. One study used phage M13, of the Gram-negative *Escherichia coli*, to genetically target several gene networks, thus rendering the bacteria more sensitive to antibiotics (1). It demonstrated that disrupting the SOS response by M13-mediated gene-targeting renders the bacteria several-fold more sensitive to a variety of antibiotics. It also demonstrated that phage-mediated gene transfer combined with antibiotics increases the survival of mice infected with pathogenic *E. coli*. Overall, the study showed that transferring genes by phage M13 weakens the bacteria, and render them more susceptible to killing by antibiotics. The end result is very similar to conventional phage-therapy practices, in which phages are used to directly kill the pathogen.

Different approaches make use of phages as "disinfectants" of pathogens present on edible foods, plants, and farm animals. In addition to increasing the shelf life of these products, the treatment is intended to prevent occasional outbreaks of disease.

However, implementation of this strategy must overcome several barriers. One characteristic of most phage infections is their narrow host range. Most phages infect only one species of bacteria and some are limited to certain strains within a species (2). This feature can be advantageous, on the one hand, as it allows targeting specific pathogens without disrupting other bacterial populations (2). On the other hand, this narrow host range may constitute a significant shortcoming, as uninfected pathogens would remain untreated. One way to expand the host range of phages is to select for phage mutants that infect new hosts. In many cases, the selected mutants that adapted to new hosts also maintain their infectivity to the original host, and thus the range is extended (3). An additional way to partially overcome this issue is to use a mixture of phages to target an extended range of the same bacterial species. Successful examples of such approach is the use of mixtures of phages against *Listeria monocytogenes, E. coli*, and *Salmonella*

*enterica* in the respective products ListShield, EcoShield, and SalmoFresh, all approved by the US Food and Drug Administration (FDA) (4). These phage mixtures were shown to effectively eradicate targeted pathogens on food and surfaces (5). Moreover, all of these products were given the "ready-to-eat" approval from the US FDA, demonstrating the safety of spreading phages on consumed products and on surfaces (4).

Other phage cocktails have been approved as food additives in Europe, and many are currently being developed by phage biotech companies. These applications demonstrate that phages can be dispersed in the environment and efficiently target pathogens in their surroundings.

Pathogen resistance to antibiotics is a rapidly growing problem, leading to an urgent need for novel antimicrobial agents. Unfortunately, development of new antibiotics faces numerous obstacles, and a method that will re-sensitize pathogens to approved antibiotics therefore holds key advantages.

Lu and Collins (1) teach genetically modified bacteriophage which serve to weaken bacteria such that they are more susceptible to antibiotics. Hagens and Blassi (6) teach genetically modified filamentous phage as bactericidal agents. The inventors have previously described (7) a genetically modified bacteriophage encoding a dominant sensitive resistance gene, for example, 30S ribosomal subunit protein S12, gyrase, RNA Polymerase B Subunit and thymidylate synthase and additionally, a tellurite resistance gene, and uses thereof in reducing bacterial antibiotic resistance.

The clustered regularly interspaced short palindromic repeats (CRISPR) and their associated Cas proteins (CRISPR-Cas) have revolutionized molecular biology by providing an efficient tool to precisely delete and edit the genome of human, primate, rodent, fish, fly, worm, plant, yeast, bacterial cells, and bacteriophages. The CRISPR-Cas system has also recently been used to phenotypically correct a genetic disease in live animals and its utility is being explored for various therapeutic approaches in mammals. Nevertheless, only limited studies have shown the use of the CRISPR-Cas system to target antibiotic-resistance genes or specific population of virulent bacterial strains (8, 10, 11).

CRISPR is a genetic system comprised of a cluster of short repeats interspersed by similarly sized non repetitive sequences (called spacers). Additional components of the system include CRISPR-associated (cas) genes and a leader sequence.

Transcribed spacers guide Cas proteins to homologous sequences within the foreign nucleic acid, called protospacers, which are subsequently cleaved. This system is abundant among prokaryotes, and computational analyses show that CRISPRs are found in ~40% of bacterial and ~90% of archaeal genomes sequenced to date.

CRISPR arrays and cas genes vary greatly among microbial species. The direct repeat sequences frequently diverge between species, and extreme sequence divergence is also observed in the cas genes. The size of the repeat can vary between 24 and 47 bp, with spacer sizes of 26-72 bp. The number of repeats per array can vary from 2 to the current record holder, *Verminephrobacter eiseniae*, which has 249 repeats per array and, although many genomes contain a single CRISPR locus, *M. jannaschii* has 18 loci. Finally, although in some CRISPR systems only 6, or fewer, cas genes have been identified, others involve more than 20. Despite this diversity, most CRISPR systems have some conserved characteristics.

It has been previously demonstrated that in response to phage infection bacteria integrate new spacers that are derived from phage genomic sequences, resulting in CRISPR-mediated phage resistance. The new repeat-spacer units were added at the leader-proximal end of the array, and had to match the phage sequence exactly (100% identity), to provide complete resistance. When such phage-derived spacers were artificially introduced into the CRISPR array of a phage-sensitive *S. thermophilus* strain, it became phage-resistant (12). Indeed, spacers found in naturally occurring CRISPR arrays are frequently derived from phages and other extrachromosomal elements (13).

Marraffini et al. 2008 (14) teach manipulation of CRISPR arrays for impeding the spread of antibiotic resistance genes and virulence factors in bacterial pathogens. Gameau et al., (9) teach that CRISPR arrays cleave plasmid DNA encoding antibiotic resistance genes.

Two recent elegant studies demonstrated that phage-transferable CRISPR-Cas systems are capable of specifically killing pathogens or re-sensitizing them to antibiotics (10, 11). These, and another study (8), also showed that the transferred CRISPR-Cas system is capable of enriching specific bacterial populations.

Furthermore, they demonstrated that the system might be used against pathogens to effectively treat infected animals. Consequently, it was suggested that the system could be used as a potent antimicrobial agent. Nevertheless, while the results of these studies highlight the potential of a transferable CRISPR-Cas system, the concept of using the system as a direct antimicrobial is similar to conventional phage therapy, which suffers from various difficulties (15). One may argue that it would be more efficient to directly kill a pathogen by a lytic phage if it were possible to deliver a specific DNA into this pathogen by a phage. Moreover, using the proposed system in an infected patient to resensitize the pathogens to antibiotics while antibiotics counter-select for these sensitized pathogens would most likely fail due to escape mutants that are selected by the antibiotics.

Thus, there is a pressing need to develop efficient antimicrobial approach to specifically target bacterial resistant genes and moreover, to eliminate horizontal transfer of antibiotic resistance.

SUMMARY OF THE INVENTION

A first aspect of the invention relates to a kit or a system comprising two elements or components. The first component (i) is a selective component comprising a nucleic acid sequence comprising at least one proto-spacer. The second component (ii) comprises at least one sensitizing component comprising at least one cas gene and at least one clustered, regularly interspaced short palindromic repeat (CRISPR) array, wherein at least one spacer of said CRISPR targets a proto-spacer comprised within a pathogenic gene of a bacterium so as to specifically inactivate said pathogenic gene in said bacterium and wherein at least one spacer of said CRISPR targets a proto-spacer comprised within said selective component of (i) so as to specifically inactivate said selective component. It should be noted that such inactivation renders a bacterium infected by said temperate phage insensitive and resistant to the selective component.

A second aspect of the invention relates to a method of interference with a horizontal transfer of a pathogenic gene between bacteria. More specifically, the method involves the step of contacting a solid surface containing bacteria harboring such pathogenic gene, with at least one of the selective and the sensitizing components of the invention or any kits comprising the same, specifically, any of the kits or systems of the invention, thereby inactivating the pathogenic gene and interfering with horizontal transfer thereof.

The invention further provides a method of preventing a pathologic condition in a mammalian subject caused by a bacterial infection of bacteria containing a pathogenic gene, using at least one of the selective and the sensitizing components of the invention or any kits comprising the same, specifically, any of the kits or systems provided herein.

Another aspect of the invention relates to a genetically modified, temperate bacteriophage comprising an engineered CRISPR. Still further, the invention encompasses any genetically modified lytic bacteriophage comprising the protospacers of the invention, specifically, any of the lytic phages described by the invention.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

The CRISPR associated genes of type I-E: cas3, cse1, cse2, cas7, cas5, and cas6e (dark bars) were inserted in place of nucleotides at position 19014-27480 of the λ chromosome (NCBI Reference Sequence: NC_001416.1, SEQ ID NO. 36) yielding the control lysogenizing phage $\lambda_{cas}$ (bottom). The $\lambda_{cas\text{-}CRISPR}$ phage (top) encodes in addition to the cas genes, a CRISPR array with spacers targeting the genes ndm-1 ($N_1$, $N_2$, $N_3$, as denoted by SEQ ID NO. 37, 38, 39 respectively) and ctx-M-15 ($C_1$, $C_2$, $C_3$, as denoted by SEQ ID NO. 40, 41, 42, respectively). $P_{T7}$, T7 promoter.

Figure 2A:
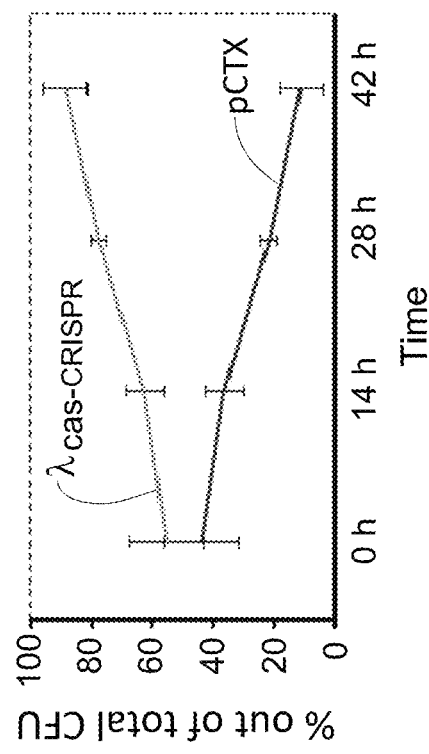

FIG. 2A-2D. Competitive Fitness of a lysogen compared to bacteria harboring resistance plasmid/s FIG. 2A shows cultures of bacteria encoding the λcas-CRISPR prophage and pVec plasmids, mixed at a 1:1 ratio.

Figure 2B:
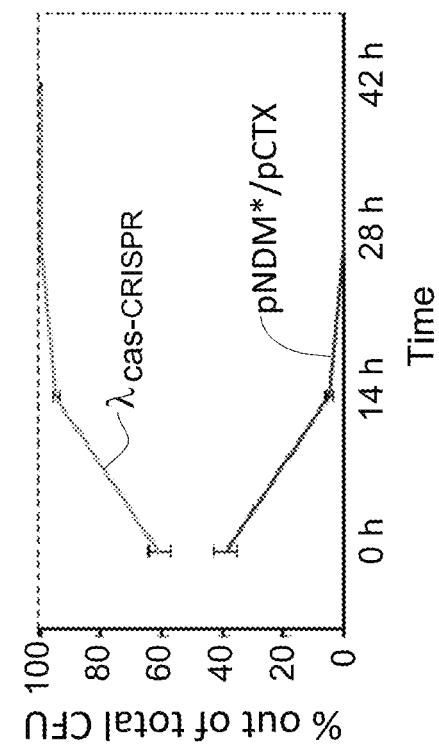

FIG. 2B shows cultures of bacteria encoding the λcas-CRISPR prophage and pCTX plasmids, mixed at a 1:1 ratio.

Figure 2C:
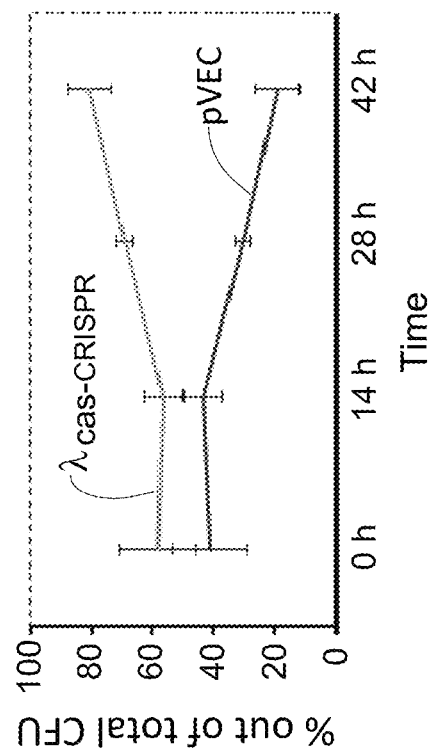

FIG. 2C shows cultures of bacteria encoding the λcas-CRISPR prophage and pNDM plasmids, mixed at a 1:1 ratio.

Figure 2D:
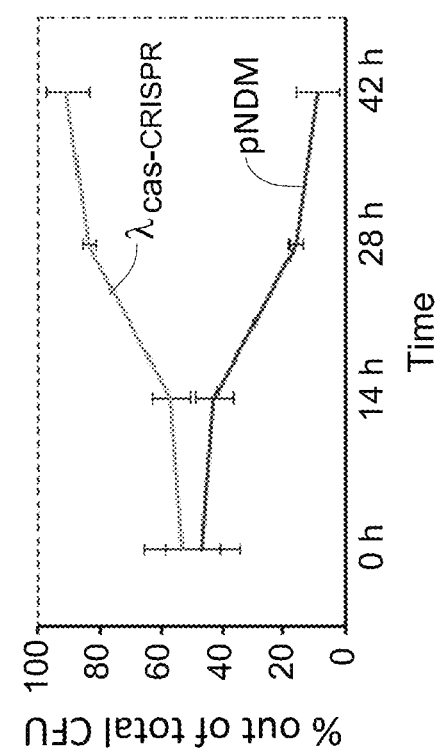

FIG. 2D shows cultures of bacteria encoding the cas-CRISPR prophage and pNDM*+pCTX plasmids, mixed at a 1:1 ratio.

Bacteria from the panels A, B, C, and D, were cultured together in LB at 32° C. for 14 h. The cells were then diluted 1/800 in LB and grown for an additional 14 h at 32° C. Samples from the mixed cultures were taken at the indicated time points and plated on either kanamycin or streptomycin or streptomycin+gentamicin agar plates to differentiate between lysogens (kanamycin$^r$) and plasmid-harboring bacteria (streptomycin$^r$ for panels A, B, C or streptomycin$^r$+gentamicin$^r$ for panel D). The CFU ratio of each strain was then determined by calculating the number of each type of resistant CFU out of the total resistant CFU.

Figure 3:
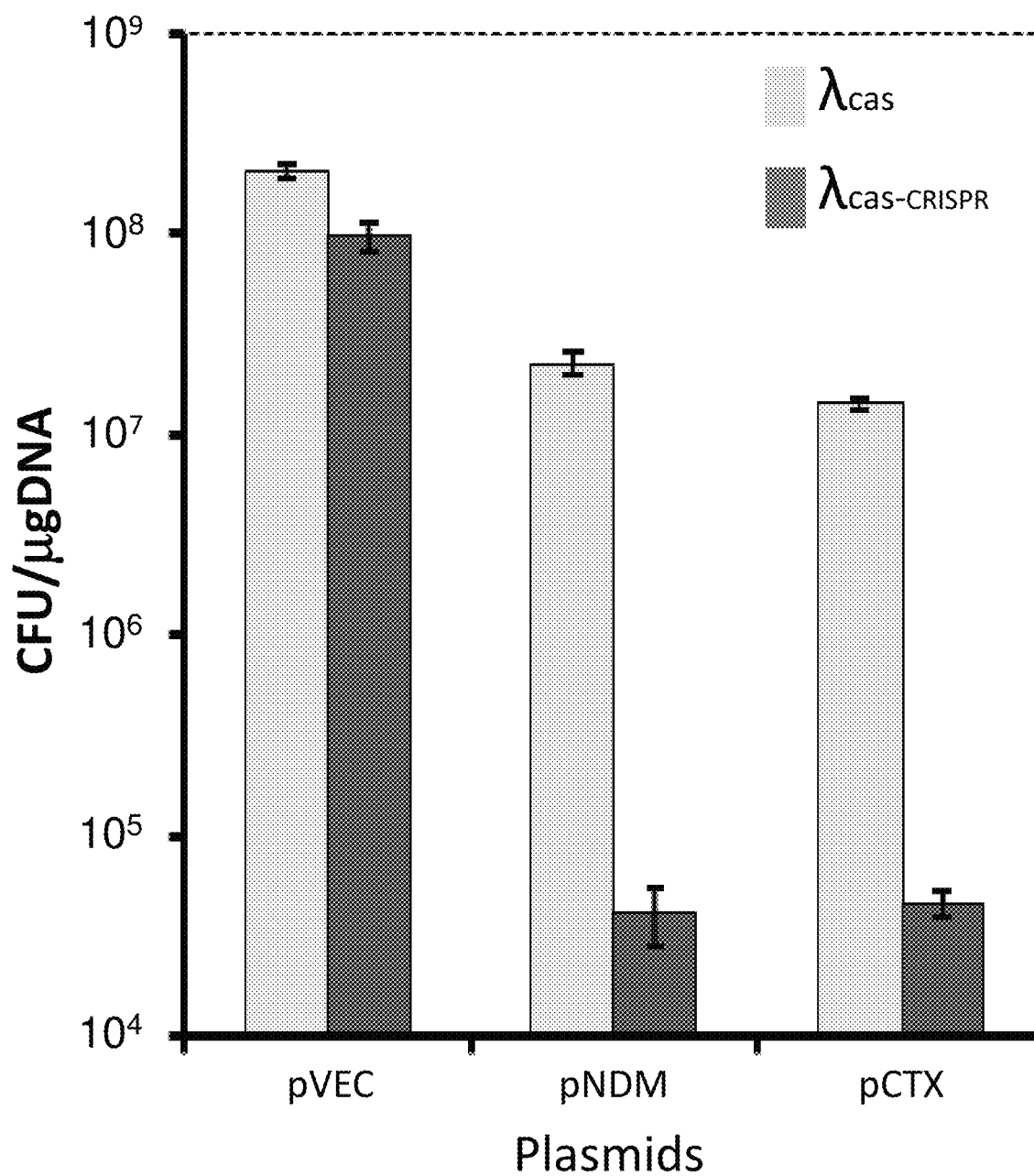

FIG. 3. Lysogenization effect on transformation of antibiotic resistance plasmids E. coli K-12 were lysogenized with $\lambda_{cas}$ (light grey bars) or $\lambda_{cas\text{-}CRISPR}$ (dark grey bars). These lysogens were transformed with a control (pVEC), ndm-1 (pNDM), or ctx-M-15 (pCTX) encoding plasmids and plated on agar plates supplemented with streptomycin. Bars represent average and standard deviation of the number of colony forming units (CFU) per ml counted after plating serial dilutions of the cultures in three independent experiments.

Figure 4:
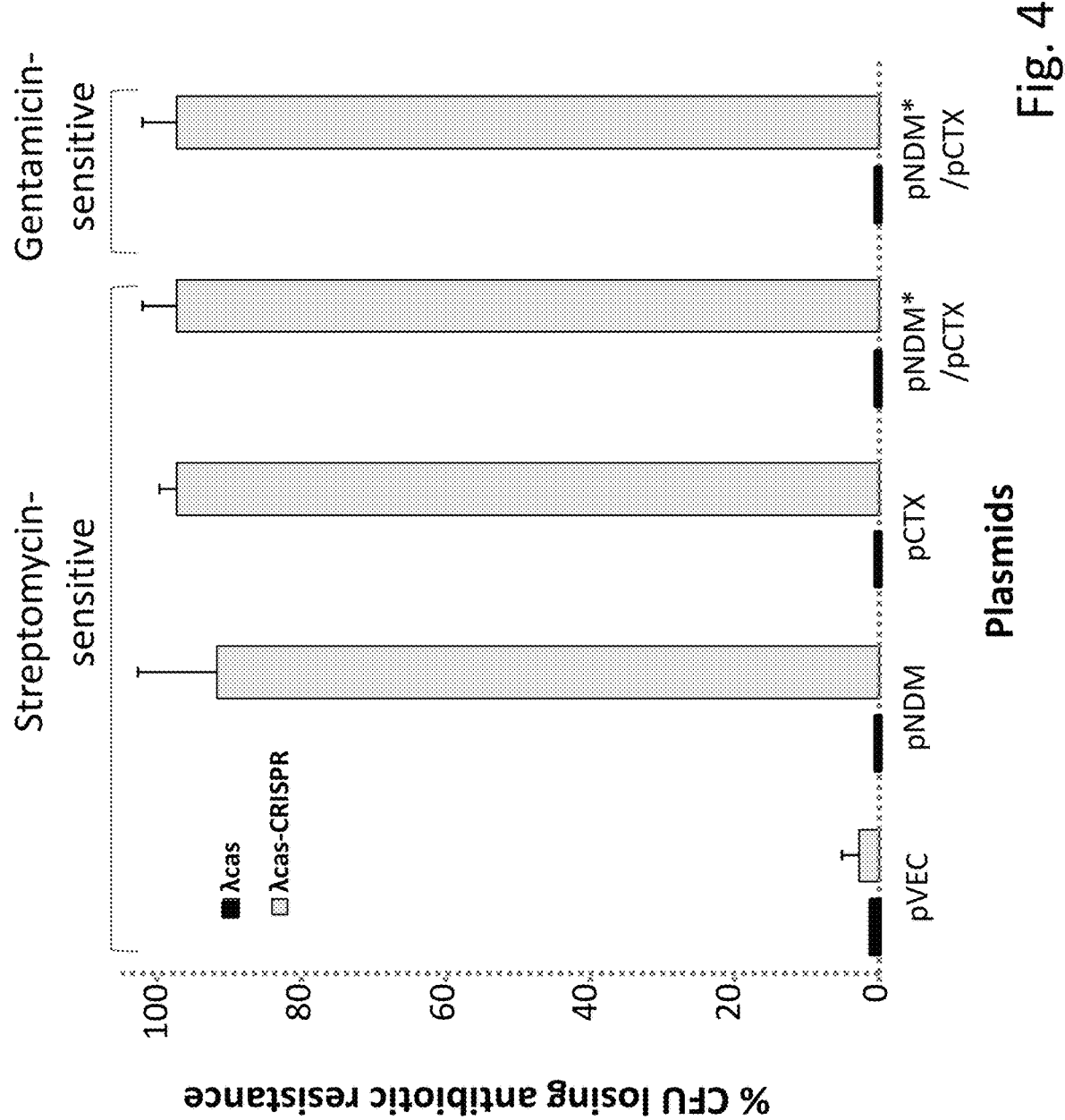

FIG. 4. Sensitization of antibiotic resistant bacteria by lysogenization

E. coli K-12 harboring a control (pVEC), ndm-1 (pNDM), ctx-M-15 (pCTX), or ndm-1+ctx-M-15 (pNDM*/pCTX) encoding plasmids were treated with $\lambda_{cas}$ (light grey bars) or $\lambda_{cas\text{-}CRISPR}$ (dark grey bars) and plated on LB plates supplemented with 5 µg/ml tetracycline and 0.2% arabinose. Colonies (24 of each strain) were then inoculated on plates supplemented with 5 µg/ml tetracycline and 0.2% arabinose and having or lacking streptomycin or gentamicin. Bars represent percentage and standard deviation from three independent experiments of streptomycin- or gentamicin-sensitive bacteria scored as CFU unable to grow on plates with streptomycin or gentamicin out of the total number of CFU able to grow on plates lacking these antibiotics.

Figure 5:
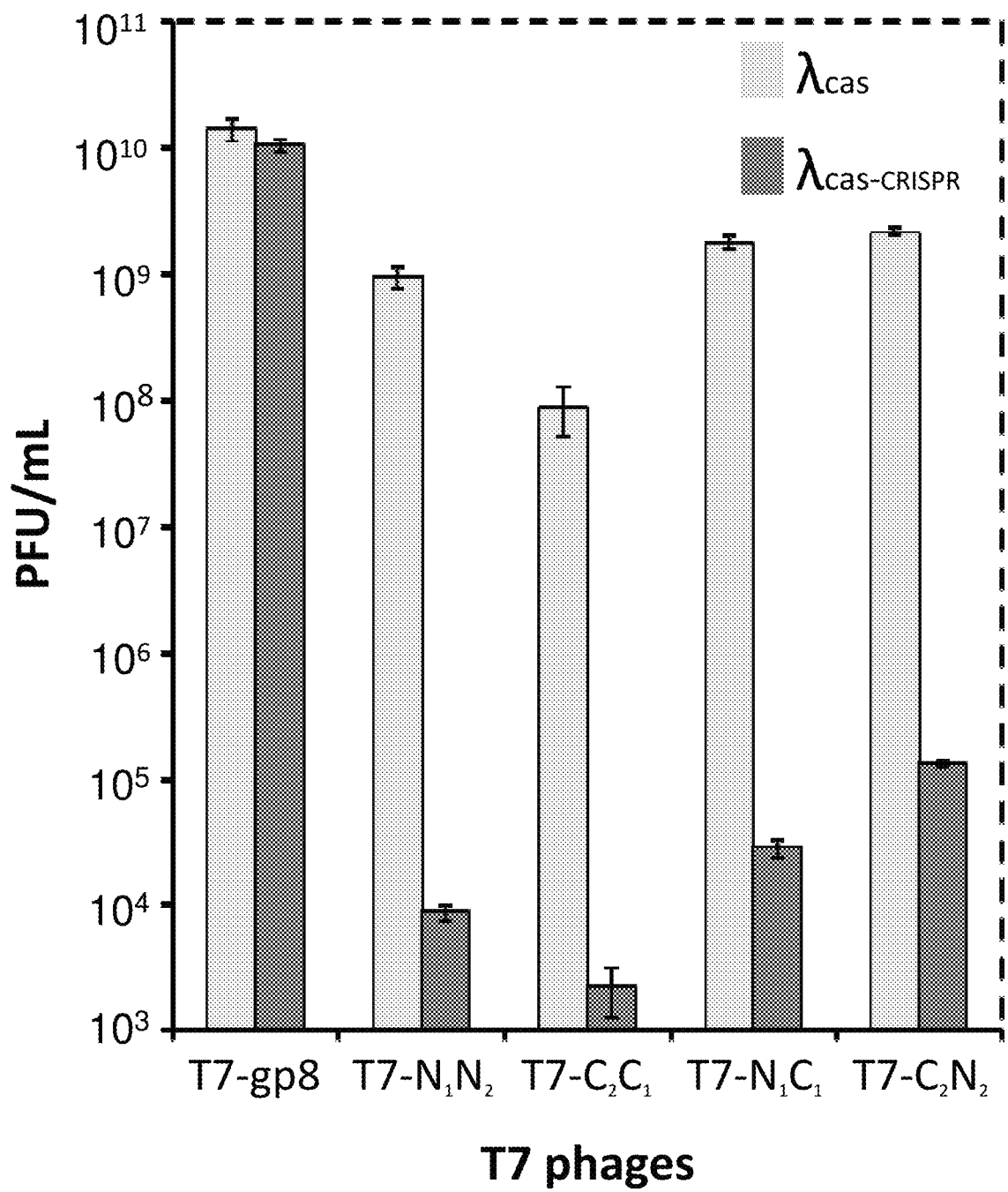

FIG. 5. Lysogenization effect on protection against lytic phages

E. coli K-12 were lysogenized with $\lambda_{cas}$ (light grey bars) or $\lambda_{cas\text{-}CRISPR}$ (dark grey bars). These lysogens were infected with a control T7-gp8 lacking targeted protospacers, or with T7 phages encoding two protospacers of ndm-1 (T7-$N_1N_2$, as denoted by SEQ ID NO. 55) or two protospacers of ctx-M-15 (T7-$C_2C_1$, as denoted by SEQ ID NO. 56) or one spacer of each (T7-$N_1C_1$, as denoted by SEQ ID NO. 57 and T7-$C_2N_2$, as denoted by SEQ ID NO. 58). Bars represent average and standard deviation of the number of plaque forming units (PFU) per ml counted after plating serial dilutions of the phages in three independent experiments.

Figure 6A:
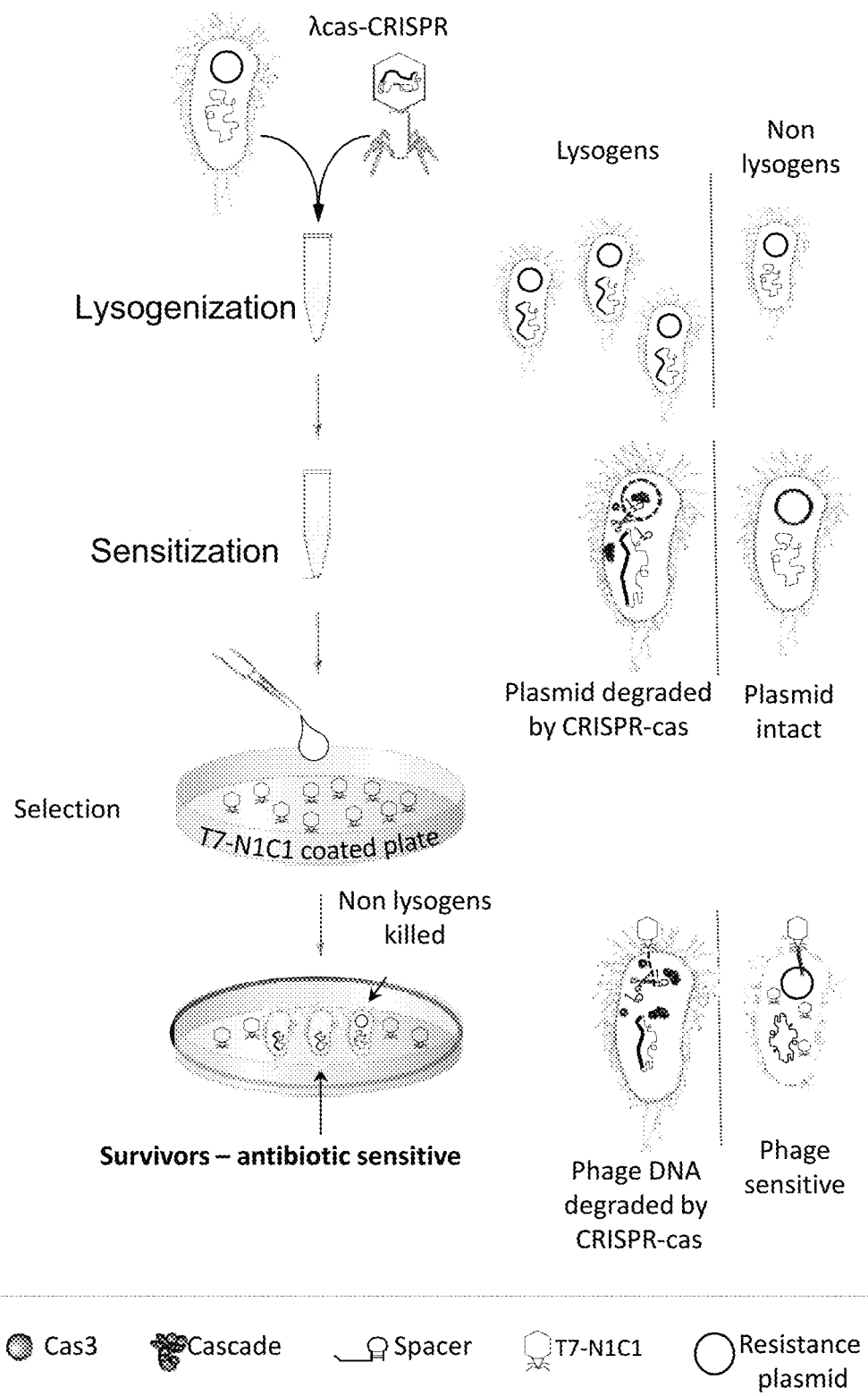
Figure 6B:
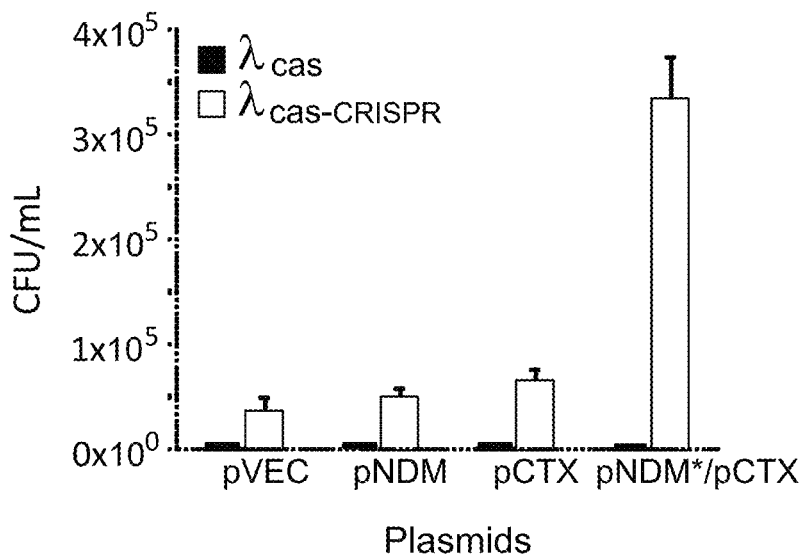
Figure 6C:
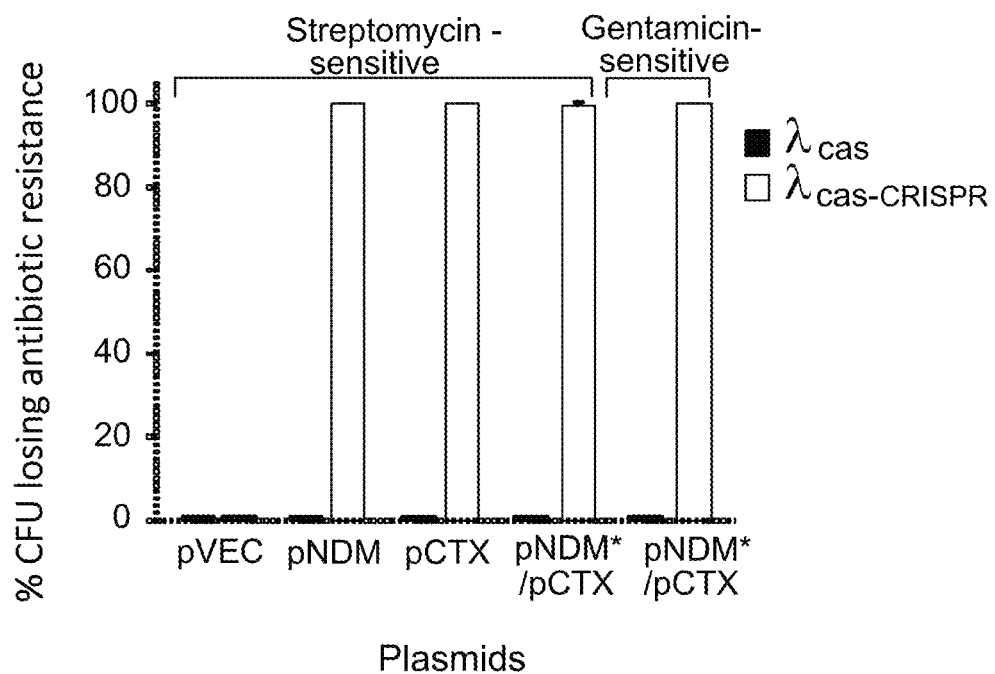

FIG. 6A-6C. Enrichment of antibiotic-sensitized bacteria by lytic phages

FIG. 6A. shows schematic presentation of the procedure to enrich for antibiotic-sensitive bacteria. A bacterial culture is mixed with lysogenizing phages, resulting in both lysogens and non-lysogens in the culture. Lysogens are both antibiotic-sensitized and phage resistant, as the CRISPR-Cas system degrades the antibiotic-resistance-conferring plasmid and the lytic-phage chromosome. The treated culture is inoculated on agar containing lytic phages that selectively kill the non-lysogens and enrich for antibiotic-sensitive bacteria.

FIG. 6B. Enrichment of phage-resistant E. coli. E. coli K-12 harboring a control (pVEC), ndm-1 (pNDM), ctx-M-15 (pCTX) or ndm-1+ctx-M-15 (pNDM*/pCTX) encoding plasmids were treated with $\lambda_{cas}$ (light grey bars) or $\lambda_{cas\text{-}CRISPR}$ (dark grey bars) and plated on T7-N1C1 (as denoted by SEQ ID NO. 57)-coated plates as shown in the scheme presented in panel A. Bars represent average and standard deviation of the number of surviving CFU per ml counted in three independent experiments.

FIG. 6C. Enrichment of antibiotic-sensitive E. coli. Surviving colonies (20-48 CFU) from each culture described in panel B were inoculated on plates having or lacking streptomycin or gentamycin. Bars represent percentage and standard deviation of from three independent experiments of streptomycin- or gentamycin-sensitive bacteria scored as CFU unable to grow on plates with streptomycin or gentamycin out of the total number of CFU unable to grow on plates lacking these antibiotics.

DETAILED DESCRIPTION OF THE INVENTION

The present inventors use the CRISPR/Cas system both to confer selective advantage and as a genetic tool to destroy specific DNAs which confer antibiotic resistance or any pathogenicity to bacteria. The CRISPR/Cas system has been recently shown to function as an adaptive immune system in bacteria (16). The system's physiological role is to protect from phage attack and from undesired plasmid replication by targeting foreign DNA or RNA (16-17). CRISPR/Cas can be rationally designed to specifically target any DNA molecule, based on short homologous DNA sequences in a unique DNA array called CRISPR (see below, and FIG. 1). Rational design of the CRISPR array enables targeting any DNA molecule that encodes resistance determinants. In addition, the system, originally evolved as a defense mechanism against phages, can be designed to protect against lytic phages of choice. This allows the present inventors to genetically link a trait that is beneficial to the bacteria (i.e., genes conferring phage resistance) with DNA that reverses drug resistance and eliminates resistance determinants. This genetic linkage enables selecting for the sensitized bacterial population by using lytic phages as selection agents. In some embodiments, the lytic phages are engineered to contain sequences displaying an identity to at least one spacer in the engineered CRISPR array system of the invention. Such artificial phages that are used for selection, ultimately linking antibiotic sensitivity and phage resistance. Bacteria harboring defense against the lytic phages along with the sensitizing construct will survive, whereas other bacteria will be killed by the lytic phages, specifically, the engendered lytic phages of the invention. The integrated construct is designed to actively eradicate existing resistance genes and also eliminate horizontal transfer of these genes between pathogens. The CRISPR/Cas system proposed herein combining two elements, the sensitizing component being the CRISPR array and the selective element, being the lytic phage, has all of the components of a genetic tool to reverse drug resistance.

More specifically, the present invention provides a specific and effective technology to counteract the emerging threat of antibiotic resistant bacteria, which overcomes the above shortcomings. Instead of directly targeting the pathogens, a sophisticated approach is provided herein, an approach that sensitizes the pathogens on surfaces or in the human natural flora, enriches for specific sensitive populations, and thus enables the consequent use of traditional antibiotics in infected patients. In this technology, the CRISPR-Cas system is used to destroy specific DNAs that confer antibiotic resistance and to concomitantly confer a selective advantage to antibiotic-sensitive bacteria. The selective advantage enables efficient replacement of populations of antibiotic sensitive bacteria by selecting against untreated bacteria. The approach differs from conventional phage therapy in that it does not aim to directly kill treated bacteria, but rather to sensitize them to antibiotics and to kill the untreated bacteria. Therefore, there is no counter selection against the treatment. By using a selective advantage, the efficiency of delivery is maximized, as bacteria escaping the treatment are killed by the selection agent. By this strategy the inventors propose to sensitize the pathogens on surfaces or in the human skin flora while concomitantly enriching for these sensitized populations. Patients infected by these antibiotic-sensitive bacteria would thus be treatable by traditional antibiotics.

Thus, a first aspect of the invention relates to a kit or a system comprising at least two elements or components. The first component (i) is a selective component comprising a nucleic acid sequence comprising at least one proto-spacer. The second component (ii) comprises at least one sensitizing component comprising at least one cas gene and at least one clustered, regularly interspaced short palindromic repeat (CRISPR) array. It should be noted that at least one spacer of the CRISPR targets a proto-spacer comprised within a pathogenic gene of a bacterium (a bacterial pathogenic gene) so as to specifically inactivate the pathogenic gene in the bacterium. Moreover, in further embodiments, at least one spacer of the CRISPR of the invention targets a proto-spacer comprised within the selective component of (i) so as to specifically inactivate the selective component. In more specific embodiments, at least one spacer of the CRISPR array of the invention may be sufficiently complementary to a nucleic acid sequence comprised within at least one pathogenic gene (or a portion of said gene) of a bacterium, also referred to herein as a "proto-spacer" so as to target and inactivate at least one pathogenic gene in said bacterium.

"Selective component" as used herein, refers to an element or component of the kit of the invention that enables, facilitates, leads to and acts on selecting, choosing, electing or enriching a specific population of bacterial cells, specifically, a population of cells that carry the cas-CRISPR system of the invention, more specifically, a population of bacterial cells that carry the sensitizing component of the invention. The selective component provides selective advantage to the desired population, for example by imposing conditions that enable and allow only the survival of the selected desired population (in specific embodiments, any population or cells that carry the sensitizing component of the invention).

"Sensitizing component" as used herein refers to an element of the kit of the invention that enables an increased sensitivity or susceptibility and/or a reduced resistance of an organism that carry said element or component, to a certain substance, for example, to an antibiotic substance. In more specific embodiments, the sensitizing component of the invention, by specifically targeting, inactivating and/or destroying pathogenic bacterial-genes, for example, genes encoding antibiotic resistance or genes encoding a toxic compound, enables sensitization of the cells and reversion thereof to less resistant and more susceptible cells. In certain embodiments, "targeting" should be understood as to make an element or object or group of elements or objects a target, to elect or choose it or them to be acted upon, where the elected or chosen object/s or element/s is/are to be attacked, taken, degraded, inactivated or destroyed.

Moreover, at least one spacer of the CRISPR array of the invention may be sufficiently complementary to a nucleic acid sequence (or a proto-spacer) comprised within the selective component of the kit of the invention, so as to target and inactivate the selective component, where "inactivate" means delay, decrease, inhibit, eliminate, attenuate or stop the activity of the selective component. It should be noted that such inactivation renders a bacterium comprising said sensitizing element insensitive and resistant to the selective component of the kit of the invention. It should be appreciated that sufficient complementarity as used herein reflects any complementarty of between about 10% to 100%, more specifically, complementarity of about 10%, 15%, 20%, 25%, 30%, 35%, 40%, 45%, 50%, 65%, 70%, 75%, 80%, 85%, 90%, 95%, 96%, 97%, 98%, 99% and 100%.

In certain embodiments, "Complementarity" refers to a relationship between two structures each following the lock-and-key principle. In nature complementarity is the base principle of DNA replication and transcription as it is a property shared between two DNA or RNA sequences, such that when they are aligned antiparallel to each other, the nucleotide bases at each position in the sequences will be complementary (e.g., A and T or U, C and G).

The present invention, in some embodiments thereof, relates to KITS and methods of down regulating (e.g. eliminating) bacterial genes using CRISPR constructs. More specifically, the invention provides kits and methods for enriching bacterial populations with antibiotic sensitive bacteria that carry the sensitizing component of the kit of the invention.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The term "bacteria" (in singular a "bacterium") in this context refers to any type of a single celled microbe. Herein the terms "bacterium" and "microbe" are interchangeable. This term encompasses herein bacteria belonging to general classes according to their basic shapes, namely spherical (cocci), rod (bacilli), spiral (spirilla), comma (vibrios) or corkscrew (spirochaetes), as well as bacteria that exist as single cells, in pairs, chains or clusters.

It should be noted that the term "bacteria" as used herein refers to any of the prokaryotic microorganisms that exist as a single cell or in a cluster or aggregate of single cells. In more specific embodiments, the term "bacteria" specifically refers to Gram positive, Gram negative or Acid fast organisms. The Gram-positive bacteria can be recognized as retaining the crystal violet stain used in the Gram staining method of bacterial differentiation, and therefore appear to be purple-colored under a microscope. The Gram-negative bacteria do not retain the crystal violet, making positive identification possible. In other words, the term 'bacteria' applies herein to bacteria with a thicker peptidoglycan layer in the cell wall outside the cell membrane (Gram-positive), and to bacteria with a thin peptidoglycan layer of their cell wall that is sandwiched between an inner cytoplasmic cell membrane and a bacterial outer membrane (Gram-negative). This term further applies to some bacteria, such as Deinococcus, which stain Gram-positive due to the presence of a thick peptidoglycan layer, but also possess an outer cell membrane, and thus suggested as intermediates in the transition between monoderm (Gram-positive) and diderm (Gram-negative) bacteria. Acid fast organisms like *Mycobacterium* contain large amounts of lipid substances within their cell walls called mycolic acids that resist staining by conventional methods such as a Gram stain.

As indicated above, the kit of the invention may comprise at least two components, a selective component that enables the enrichment and selection of a bacterial population that carry the sensitizing component that is therefore a population that is sensitive to antibiotics, or a population having reduced or eliminated resistance.

It should be appreciated that the selective component of the invention may be any genetic element or vector that carry or comprise at least one protospaces displaying at least minimal identity (specifically, of about 70% or more) to at least one protospacer comprised within a pathogenic bacterial gene and/or is recognized by at least one spacer comprised within the sensitizing component of the invention. Such selective component may be for example a plasmid that further encodes a toxic element or protein that may harm, kill or eliminate bacterial cells. More specifically, it can also be a DNA-injected entity encoding genes that kill bacteria by inactivating its essential elements or otherwise disrupting essential components for growth of the bacterium. E.g. a DNA encoding such genes, and injected by specialized protein machineries derived of phage products.

In yet some specific embodiments, the selective component used by the kit of the invention may comprise at least one lytic bacteriophage. In more specific embodiments, such bacteriophage may comprise a nucleic acid sequence comprising at least one proto-spacer that serves as a target for the spacers of the sensitizing component.

Under the term bacteriophage is meant a virus that infects and replicates within prokaryotes, such as bacteria. It should be note that the term "bacteriophage" is synonymous with the term "phage". Phages are composed of proteins that encapsulate a DNA or RNA genome, which may encode only a few or hundreds of genes thereby producing virions with relatively simple or elaborate structures. Thus, bacteriophages are among the most common and diverse entities in the biosphere. Phages are classified according to the International Committee on Taxonomy of Viruses (ICTV) considering morphology and the type of nucleic acid (DNA or RNA, single- or double-stranded, linear or circular). About 19 phage families have been recognized so far that infect bacteria and/or archaea (a prokaryotic domain previously classified as archaebacteria). Many bacteriophages are specific to a particular genus or species or strain of cell.

As noted above, in certain specific and non-limiting embodiments, the bacteriophage used as the selective component of the kit of the invention may be a lytic bacteriophage. A lytic bacteriophage is one that follows the lytic pathway through completion of the lytic cycle, rather than entering the lysogenic pathway. A lytic bacteriophage undergoes viral replication leading to lysis of the cell membrane, destruction of the cell, and release of progeny bacteriophage particles capable of infecting other cells.

In certain embodiments, the lytic bacteriophage of the selective component of the kit of the invention may be genetically modified bacteriophage comprising at least one proto-spacer having an identity of at least 70% to at least one nucleic acid sequence comprised within the bacterial pathogenic gene. In more specific embodiments, such bacteriophage may comprise at least one proto-spacer having an identity of about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% to at least one nucleic acid sequence comprised within the bacterial pathogenic gene.

In further embodiments, the sensitizing component may comprise at least one recombinant vector comprising a recombinant nucleic acid sequence encoding at least one cas protein. It should be noted that the vector may further comprise nucleic acid sequence of at least one of said CRISPR array/s. Such vector may be in certain embodiments, any plasmid, construct, phagemid or an engendered bacteriophage comprising the CRISPR system described herein.

As used herein, the term "recombinant DNA", "recombinant nucleic acid sequence" or "recombinant gene" refers to a nucleic acid comprising an open reading frame encoding one of the CRISPR system of the invention.

Thus, in some embodiments, the sensitizing element of the invention may be any vector that comprises the cas proteins and at least one of said CRISPR array/s of the invention. "Vectors" or "Vehicles", as used herein, encompass vectors such as plasmids, phagemides, viruses, bacteriophage, integratable DNA fragments, and other vehicles, which enable the integration of DNA fragments into the genome of the host, or enable expression of genetic elements that are not integrated. Vectors are typically self-replicating DNA or RNA constructs containing the desired nucleic acid sequences, and operably linked genetic control elements that are recognized in a suitable host cell and effect the translation of the desired spacers. Generally, the genetic control elements can include a prokaryotic promoter system or a eukaryotic promoter expression control system. Such system typically includes a transcriptional promoter, transcription enhancers to elevate the level of RNA expression. Vectors usually contain an origin of replication that allows the vector to replicate independently of the host cell. In yet some alternative embodiments, the expression vectors used by the invention may comprise elements necessary for integration of the desired CRISPR system of the invention into the bacterial chromosome.

Accordingly, the term control and regulatory elements includes promoters, terminators and other expression control elements. Such regulatory elements are described in Goeddel; [Goeddel., et al., Gene Expression Technology: Methods in Enzymology 185, Academic Press, San Diego, Calif. (1990)]. For instance, any of a wide variety of expression control sequences that control the expression of a DNA sequence when operatively linked to it may be used in these vectors to express DNA sequences encoding any desired protein using the method of this invention.

A vector may additionally include appropriate restriction sites, antibiotic resistance or other markers for selection of vector-containing cells. Plasmids are the most commonly used form of vector but other forms of vectors which serve an equivalent function and which are, or become, known in the art are suitable for use herein. See, e.g., Pouwels et al., Cloning Vectors: a Laboratory Manual (1985 and supplements), Elsevier, N.Y.; and Rodriquez, et al. (eds.) Vectors: a Survey of Molecular Cloning Vectors and their Uses, Buttersworth, Boston, Mass. (1988), which are incorporated herein by reference.

In yet some other embodiments, the sensitizing element of the invention may be a phagemid comprising the CRISPR system of the invention. "Phagemids" as used herein are plasmids modified to carry a phage packaging site and may also encode phage proteins. Phagemids may comprise, in general at least a phage packaging site and an origin of replication (ori). In some embodiments, phagemids of the present disclosure may further encode phage packaging sites and/or proteins involved in phage packaging.

Still further, in certain embodiments, the sensitizing element of the invention may be a genetically modified bacteriophage. More specifically, such genetically modified bacteriophage may comprise at least one CRISPR spacer that targets at least one nucleic acid sequence comprised within said lytic bacteriophage and at least one CRISPR spacer that targets a nucleic acid sequence comprised within said at least one pathogenic gene. In such way the sensitizing component of the invention may target and/or inactivate both, the lytic phage/s that serve as the selective component and the pathogenic gene of interest.

More specifically, the present inventors contemplate use of lytic (as the selective component) or temperate (as the sensitizing component), specifically, temperature-sensitive temperate bacteriophage. A "temperate phage", as used herein, relates to specific embodiments where at a particular temperature (e.g. at 36° C. or below, for example, 20, 21, 22, 23, 24, 25, 26, 27, 28, 29, 30, 31, 32, 33, 34 or 35° C.) the phage favors lysogeny, whereas higher temperatures induce lytic production of the phage. As noted herein above, lytic phage is a phage that uses the lytic cycle. The lytic cycle results in the destruction of the infected cell and its membrane. A key difference between the lytic and lysogenic phage cycles is that in the lytic phage, the viral DNA exists as a separate molecule within the bacterial cell, and replicates separately from the host bacterial DNA. The location of viral DNA in the lysogenic phage cycle is within the host cell, therefore in both cases the virus/phage replicates using the host DNA machinery, but in the lytic phage cycle, the phage is a free floating separate molecule to the host cell.

In some embodiments, the phages used in the kits of the invention, either as the selective or the sensitizing components, may be bacteriophages of a type that selectively infect a pathogenic type of bacteria, or a type of bacteria that can have pathogenic and nonpathogenic members in a mixed bacteria population, or can infect different types of bacteria in a mixed bacterial population. Such mixed bacterial populations are found in Hospital surfaces. Importantly, a few resistant pathogens such as *Enterococcus faecium, Staphylococcus aureus, Klebsiella pneumonia, Acinetobacter baumanni, Pseudomonas aeruginosa*, and *Enterobacter* species (also referred to herein as ESKAPE organisms or bacteria) are responsible for the lion's share of nosocomial infections in both the developed and developing countries. Those pathogens cause the majority of nosocomial infections and effectively escape the effects of antibiotics (18, 19). Thus, an efficient and effective treatment against these species, or even only a few of them, could significantly reduce fatalities and financial burden caused by resistant pathogen infections.

Thus, in some embodiments, the phages used by the kit of the invention may be bacteriophage/s specific for a particular bacterial genus, species or strains. In certain embodiments, the phage may be specific for a bacterial strain that may be a member of at least one of: *Escherichia coli, Streptococcus* spp., *Staphylococcus* spp., *Clostridium* spp., *Bacillus* spp., *Salmonella* spp., *Helicobacter* spp., *Neisseria* spp. (specifically, *N. gonorrhoeae* and *N. meningitidis*), or *Pseudomonas aeruginosa*.

A non-limiting example of this type of phage may be the λgt11 phage. Other λ phages having their cI gene changed to the cI857 allele are also contemplated since they will exhibit similar growth pattern. Preferably, the phage is selected such that it allows stable insertion of at least 1 kb of foreign DNA and more preferably at least 5 kb of foreign DNA. According to another embodiment, the phage comprises deletion mutants with minimal genes and is capable of efficient lysogenization.

Identification of phages capable of infecting additional bacteria is within the scope of one skilled in the art. The phages used for infecting the bacteria may be capable of integrating into a Gram-positive, Gram-negative bacteria or Acid fast organism and the like.

As noted above, in some embodiments, the lytic phage that serves as the selective element in the systems or kits of the invention may be a genetically modified phage. Such phage may be genetically engineered to comprise at least one nucleic acid sequence that is a proto-spacer. In more specific embodiments, such proto spacer may display an identity of at least 70% to at least one proto-spacer, or in other words, nucleic acid sequence comprised within the pathogenic gene of a bacterium, or any fragment, part or portion thereof.

In more specific embodiments, the vector comprised within the sensitizing component of the invention may be a genetically modified, temperate bacteriophage comprising at least one CRISPR spacer that targets a nucleic acid sequence comprised within the lytic bacteriophage (that serve as the selective component) and at least one CRISPR spacer that targets a nucleic acid sequence comprised within said bacterial pathogenic gene.

In further specific embodiments, at least one spacer of the CRISPR array of the invention should be sufficiently complementary to the nucleic acid sequence that is a proto-spacer comprised within the lytic genetically modified bacteriophage of the invention (the selective component) and also within the target pathogenic gene of a bacterium. In such a way, the CRISPR array of the sensitizing component of the invention targets and inactivates both, the lytic phage and the target pathogenic gene.

In yet other specific embodiments, the target pathogenic gene of a bacterium or any RNA transcribed therefrom targeted by the CRISPR system of the invention, may be a bacterial endogenous gene. It should be noted that "endogenous gene" as used herein, refers to DNA originated from the specific organism, in the current case, bacteria, and therefore may be a part of its chromosomal DNA.

According to other embodiments, the target pathogenic gene of a bacterium may be epichromosomal. In some particular and non-limiting embodiments such non-endogenous gene may be acquired by horizontal transfer. An "epichromosomal gene" as used herein, relates to a unit of genetic material, specifically, DNA in bacteria, for example a plasmid, that can either replicate independently as an extrachromosomal DNA, or in certain embodiments, may be integrated into the host chromosome.

In some specific embodiments, at least one target pathogenic gene of a bacterium may be a gene encoding a virulence factor or toxin, thereby rendering said bacteria virulent. The term "virulent" as used herein means bacteria that can cause a bacterial disease or infection. In some embodiments, virulent bacteria are those that cause a bacterial disease or infection in a human subject, or any other organism including but not limited to mammal, rodent, bird, fish, reptile, insect or a plant, who does not have a compromised immune system. Typically, virulent bacteria will produce certain proteins which are referred to as "virulence factors." Virulent bacteria are distinguishable from those bacteria that normally colonize one or more of a healthy host's tissue and for which they are thus undesirable to kill under ordinary therapeutic circumstances because the latter generally do not express virulence factors, or express lower amounts of virulence factors relative to virulent bacteria. As discussed above, the present disclosure includes in some embodiments CRISPR systems which comprise sequences encoding targeting RNA directed to bacterial DNA sequences which encode virulence factors. Such virulence factors include but are not necessarily limited to bacteria proteins that are involved in pathogenic adhesion, colonization, invasion, biofilm formation or immune response inhibitors, or toxins. Examples of virulence genes include, but are not limited to genes encoding toxins (e.g. Shiga toxin and cholera toxin), hemolysins, fimbrial and afimbrial adhesins, proteases, lipases, endonucleases, endotoxins and exotoxins cytotoxic factors, microcins and colicins and also those identified in the art. The sequences of bacterial genes from a wide array of bacteria types that encode these and other virulence factors are known in the art. Virulence factors can be encoded on the bacterial chromosome, or on a plasmid in the bacteria, or both. In some embodiments, the virulence factor may be encoded by a bacterial superantigen gene, such as a superantigen enterotoxin gene, one non-limiting example of which is the S. aureus Sek gene. Additional virulence factors for S. areus include but are not limited to cytolitic toxins, such as a-hemolysin, β-hemolysin, γ-hemolysin, leukocidin, Panton-Valentine leukocidin (PVL); exotoxins, such as toxic shock syndrome toxin-1 (TSST-1); enterotoxins, such as SEA, SEB, SECn, SED, SEE, SEG, SEH, and SEI, and exfoliative toxins, such as ETA and ETB. Homologues of all of these toxins expressed by other types of bacteria are contemplated herein as virulence gene targets as well.

More specifically, the term "toxin" as used herein means a substance generated by bacteria, which can be classified as either exotoxin or endotoxin. Exotoxins are generated and actively secreted; endotoxins remain part of the bacteria. Usually, an endotoxin is part of the bacterial outer membrane, and it is not released until the bacterium is killed by the immune system.

According to some specific and non-limiting embodiments of the invention, the bacterial virulence gene may be selected from the group consisting of actA (example is given in genebank accession no: NC_003210.1), Tem (example is given in genebank accession no: NC_009980), Shy (example is given in genebank accession no: NC_009648), oxa-1 (example is given in genebank accession no: NW_139440), oxa-7 (example is given in genebank accession no: X75562), pse-4 (example is given in genebank accession no: J05162), ctx-m (example is given in genebank accession no: NC_010870), ant(3")-Ia (aadA1) (example is given in genebank accession no: DQ489717), ant(2")-Ia (aadB)b (example is given in genebank accession no: DQ176450), aac(3)-IIa (aacC2) (example is given in genebank accession no: NC_010886), aac(3)-IV (example is given in genebank accession no: DQ241380), aph(3')-Ia (aphA1) (example is given in genebank accession no: NC_007682), aph(3')-IIa (aphA2) (example is given in genebank accession no: NC_010170), tet(A) (example is given in genebank accession no: NC_005327), tet(B) (example is given in genebank accession no: FJ411076), tet(C) (example is given in genebank accession no: NC_010558), tet(D) (example is given in genebank accession no: NC_010558), tet(E) (example is given in genebank accession no: M34933), tet(Y) (example is given in genebank accession no: AB089608), catI (example is given in genebank accession no: NC_005773), catII NC_010119, catIII (example is given in genebank accession no: X07848), floR (example is given in genebank accession no: NC_009140), dhfrI (example is given in genebank accession no: NC_002525), dhfrV (example is given in genebank accession no: NC_010488), dhfrVII (example is given in genebank accession no: DQ388126), dhfrIX (example is given in genebank accession no: NC_010410), dhfrXIII (example is given in genebank accession no: NC_000962), dhfrXV (example is given in genebank accession no: Z83311), suII (example is given in genebank accession no: NC_000913), suIII (example is given in genebank accession no: NC_000913), integron class 1 3'-CS (example is given in genebank accession no: AJ867812), vat (example is given in genebank accession no: NC_011742), vatC (example is given in genebank accession no: AF015628), vatD (example is given in genebank accession no: AF368302), vatE (example is given in genebank accession no: NC_004566), vga (example is given in genebank accession no: AF117259), vgb (example is given in genebank accession no: AF117258), and vgbB (example is given in genebank accession no: AF015628).

As noted above, the kit of the invention may specifically target any pathogenic bacterial gene, for example, any gene/s that provides resistance or in other words, inhibits, reduces, suppress or attenuates the susceptibility of the bacteria to any antimicrobial agent. The term "antimicrobial agent" as used herein refers to any entity with antimicrobial activity (either bactericidal or bacteriostatic), i.e. the ability to inhibit the growth and/or kill bacterium, for example Gram positive- and Gram negative bacteria. An antimicrobial agent may be any agent which results in inhibition of growth or reduction of viability of a bacteria by at least about 10%, 20%, 30% or at least about 40%, or at least about 50% or at least about 60% or at least about 70% or more than 70%, for example, 75%, 80%, 85%, 90%, 95%, 100% or any integer between 30% and 70% or more, as compared to in the absence of the antimicrobial agent. Stated another way, an antimicrobial agent is any agent which reduces a population of microbial cells, such as bacteria by at least about 30% or at least about 40%, or at least about 50% or at least about 60% or at least about 70% or more than 70%, or any integer between 30% and 70% as compared to in the absence of the antimicrobial agent. In one embodiment, an antimicrobial agent is an agent which specifically targets a bacteria cell. In another embodiment, an antimicrobial agent modifies (i.e. inhibits or activates or increases) a pathway which is specifically expressed in bacterial cells. An antimicrobial agent can include any chemical, peptide (i.e. an antimicrobial peptide), peptidomimetic, entity or moiety, or analogues of hybrids thereof, including without limitation synthetic and naturally occurring non-proteinaceous entities. In some embodiments, an antimicrobial agent is a small molecule having a chemical moiety. For example, chemical moieties include unsubstituted or substituted alkyl, aromatic or heterocyclyl moieties including macrolides, leptomycins and related natural products or analogues thereof. Antimicrobial agents can be any entity known to have a desired activity and/or property, or can be selected from a library of diverse compounds.

As noted above, the sensitizing element of the kits, systems and methods of the invention may target any gene that provides antibiotic resistance. As used herein, the term "resistance" is not meant to imply that the bacterial cell population is 100% resistant to a specific antibiotic compound, but includes bacteria that are tolerant of the antibiotics or any derivative thereof. More specifically, the term "bacterial resistance gene/s" refers to gene/s conferring about 100%, 90%, 80%, 70%, 60%, 50%, 40%, 30%, 20%, or 10% protection from an antibiotic compound, thereby reversing susceptibility and sensitivity thereof to said antibiotic compound.

Thus, in some embodiments, the bacterial pathogenic gene may be any gene that provides resistance to any of the anti-bacterial compounds described herein above.

Still further, in other embodiments, the at least one target pathogenic gene of a bacterium, may be a gene encoding an antibiotic resistance factor.

The phrase "antibiotic resistance genes" as used herein refers to genes that confer resistance to antibiotics, for example by coding for enzymes which destroy said antibiotic compound, by coding for surface proteins which prevent the entrance of an antibiotic compound to the microorganism, actively exports it, or by being a mutated form of the antibiotic's target thereby preventing its antibiotic function.

Antibiotic resistance genes carried by a variety of bacteria are known in the art and the sequences of antibiotic resistance genes in any particular bacteria can be determined if desired. In certain non-limiting embodiments, the present disclosure includes CRISPR systems which comprise spacers encoding targeting RNA that is directed to bacterial DNA sequences which comprise antibiotic resistance genes. In some embodiments, the resistance gene confers resistance to a narrow-spectrum beta-lactam antibiotic of the penicillin class of antibiotics. In other embodiments, the resistance gene confers resistance to methicillin (e.g., methicillin or oxacillin), or flucloxacillin, or dicloxacillin, or some or all of these antibiotics. Thus, in some embodiments, the CRISPR system is suitable for selectively targeting antibiotic resistant genes in what has colloquially become known as methicillin-resistant *S. aureus* (MRSA) which in practice refers to strains of *S. aureus* that are insensitive or have reduced sensitivity to most or all penicillins. In other embodiments, the CRISPR system is suitable for targeting vancomycin resistance in vancomycin resistant *S. aureus* (VRSA). In certain embodiments, vancomycin resistant *S. aureus* may also be resistant to at least one of linezolid (ZYVOX™), daptomycin (CUBICIN™), and quinupristin/dalfopristin (SYERCID™).

Additional antibiotic resistant genes include but are not limited to fosfomycin resistance gene fosB, tetracycline resistance gene tetM, kanamycin nucleotidyltransferase aadD, bifunctional aminoglycoside modifying enzyme genes aacA-aphD, chloramphenicol acetyltransferase cat, mupirocin-resistance gene ileS2, vancomycin resistance genes vanX, vanR, vanH, vraE, vraD, methicillin resistance factor femA, fmtA, mecl, streptomycin adenylyltransferase spc1, spc2, antl, ant2, pectinomycin adenyltransferase spd, ant9, aadA2, and any other resistance gene.

In some specific embodiments, the pathogenic gene may be a gene encoding any gene conferring resistance to any β-lactam antibiotic compound. In more specific embodiments, such gene may encode at least one β-lactamase. As used herein, the term "β-lactamase" denotes a protein capable of catalyzing cleavage of a β-lactamase substrate such as a β-lactam containing molecule (such as a β-lactam antibiotic) or derivative thereof.

β-lactamases are organized into four molecular classes (A, B, C and D) based on their amino acid sequences. Class A enzymes have a molecular weight of about 29 kDa and preferentially hydrolyze penicillins. Examples of class A enzymes include RTEM and the β-lactamase of *Staphylococcus aureus*. Class B enzymes include metalloenzymes that have a broader substrate profile than the other classes of β-lactamases. Class C enzymes have molecular weights of approximately 39 kDa and include the chromosomal cephalosporinases of gram-negative bacteria, which are responsible for the resistance of gram-negative bacteria to a variety of both traditional and newly designed antibiotics. In addition, class C enzymes also include the lactamase of P99 *Enterobacter cloacae*, which is responsible for making this *Enterobacter* species one of the most widely spread bacterial agents in United States hospitals. The class D enzymes are serine hydrolases, which exhibit a unique substrate profile.

As noted above, in more specific embodiments, the kits and systems of the invention may be directed against any gene that may confer resistance to any β lactam antibiotics.

The term "β-lactam" or "β lactam antibiotics" as used herein refers to any antibiotic agent which contains a β-lactam ring in its molecular structure.

β-lactam antibiotics are a broad group of antibiotics that include different classes such as natural and semi-synthetic penicillins, clavulanic acid, carbapenems, penicillin derivatives (penams), cephalosporins (cephems), cephamycins and monobactams, that is, any antibiotic agent that contains a β-lactam ring in its molecular structure. They are the most widely-used group of antibiotics. While not true antibiotics, the β-lactamase inhibitors are often included in this group.

β-lactam antibiotics are analogues of D-alanyl-D-alanine the terminal amino acid residues on the precursor NAM/NAG-peptide subunits of the nascent peptidoglycan layer. The structural similarity between β-lactam antibiotics and D-alanyl-D-alanine prevents the final crosslinking (transpeptidation) of the nascent peptidoglycan layer, disrupting cell wall synthesis.

Under normal circumstances peptidoglycan precursors signal a reorganisation of the bacterial cell wall and, as a consequence, trigger the activation of autolytic cell wall hydrolases. Inhibition of cross-linkage by β-lactams causes a build-up of peptidoglycan precursors, which triggers the digestion of existing peptidoglycan by autolytic hydrolases without the production of new peptidoglycan. As a result, the bactericidal action of β-lactam antibiotics is further enhanced.

Generally, β-lactams are classified and grouped according to their core ring structures, where each group may be divided to different categories. The term "penam" is used to describe the core skeleton of a member of a penicillin antibiotic. i.e. a β-lactam containing a thiazolidine rings. Penicillins contain a β-lactam ring fused to a 5-membered ring, where one of the atoms in the ring is sulfur and the ring is fully saturated. Penicillins may include narrow spectrum penicillins, such as benzathine penicillin, benzylpenicillin (penicillin G), phenoxymethylpenicillin (penicillin V), procaine penicillin and oxacillin. Narrow spectrum penicillinase-resistant penicillins include methicillin, dicloxacillin and flucloxacillin. The narrow spectrum β-lactamase-resistant penicillins may include temocillin. The moderate spectrum penicillins include for example, amoxicillin and ampicillin. The broad spectrum penicillins include the co-amoxiclav (amoxicillin+clavulanic acid). Finally, the penicillin group also includes the extended spectrum penicillins, for example, azlocillin, carbenicillin, ticarcillin, mezlocillin and piperacillin.

Other members of this class include pivampicillin, hetacillin, bacampicillin, metampicillin, talampicillin, epicillin, carbenicillin, carindacillin, ticarcillin, azlocillin, piperacillin, mezlocillin, mecillinam, pivmecillinam, sulbenicillin, clometocillin, procaine benzylpenicillin, azidocillin, penamecillin, propicillin, pheneticillin, cloxacillin and nafcillin.

β-lactams containing pyrrolidine rings are named carbapenams. A carbapenam is a β-lactam compound that is a saturated carbapenem. They exist primarily as biosynthetic intermediates on the way to the carbapenem antibiotics.

Carbapenems have a structure that renders them highly resistant to β-lactamases and therefore are considered as the broadest spectrum of β-lactam antibiotics. The carbapenems are structurally very similar to the penicillins, but the sulfur atom in position 1 of the structure has been replaced with a carbon atom, and hence the name of the group, the carbapenems. Carbapenem antibiotics were originally developed from thienamycin, a naturally-derived product of *Streptomyces cattleya*. The carbapenems group includes: biapenem, doripenem, ertapenem, imipenem, meropenem, panipenem and PZ-601.

β-lactams containing 2, 3-dihydrothiazole rings are named penems. Penems are similar in structure to carbapenems. However, where penems have a sulfur, carbapenems have another carbon. There are no naturally occurring penems; all of them are synthetically made. An example for penems is faropenem.

β-lactams containing 3, 6-dihydro-2H-1, 3-thiazine rings are named cephems. Cephems are a sub-group of β-lactam antibiotics and include cephalosporins and cephamycins. The cephalosporins are broad-spectrum, semisynthetic antibiotics, which share a nucleus of 7-aminocephalosporanic acid. First generation cephalosporins, also considered as the moderate spectrum includes cephalexin, cephalothin and cefazolin. Second generation cephalosporins that are considered as having moderate spectrum with anti-*Haemophilus* activity may include cefaclor, cefuroxime and cefamandole. Second generation cephamycins that exhibit moderate spectrum with anti-anaerobic activity include cefotetan and cefoxitin. Third generation cephalosporins considered as having broad spectrum of activity includes cefotaxime and cefpodoxime.

Finally, the fourth generation cephalosporins considered as broad spectrum with enhanced activity against Gram positive bacteria and β-lactamase stability include the cefepime and cefpirome. The cephalosporin class may further include: cefadroxil, cefixime, cefprozil, cephalexin, cephalothin, cefuroxime, cefamandole, cefepime and cefpirome.

Cephamycins are very similar to cephalosporins and are sometimes classified as cephalosporins. Like cephalosporins, cephamycins are based upon the cephem nucleus. Cephamycins were originally produced by *Streptomyces*, but synthetic ones have been produced as well. Cephamycins possess a methoxy group at the 7-alpha position and include: cefoxitin, cefotetan, cefmetazole and flomoxef.

β-lactams containing 1, 2, 3, 4-tetrahydropyridine rings are named carbacephems. Carbacephems are synthetically made antibiotics, based on the structure of cephalosporin, a cephem. Carbacephems are similar to cephems but with a carbon substituted for the sulfur. An example of carbacephems is loracarbef.

Monobactams are b-lactam compounds wherein the β-lactam ring is alone and not fused to another ring (in contrast to most other β-lactams, which have two rings). They work only against Gram-negative bacteria. Other examples of monobactams are tigemonam, nocardicin A and tabtoxin.

β-lactams containing 3, 6-dihydro-2H-1, 3-oxazine rings are named oxacephems or clavams. Oxacephems are molecules similar to cephems, but with oxygen substituting for the sulfur. Thus, they are also known as oxapenams. An example for oxapenams is clavulanic acid. They are synthetically made compounds and have not been discovered in nature. Other examples of oxacephems include moxalactam and flomoxef.

Another group of β-lactam antibiotics is the β-lactamase inhibitors, for example, clavulanic acid. Although they exhibit negligible antimicrobial activity, they contain the β-lactam ring. Their sole purpose is to prevent the inactivation of β-lactam antibiotics by binding the β-lactamases, and, as such, they are co-administered with β-lactam antibiotics. β-lactamase inhibitors in clinical use include clavulanic acid and its potassium salt (usually combined with amoxicillin or ticarcillin), sulbactam and tazobactam.

It should be therefore understood that the kit of the invention, by targeting and destroying antibiotic resistance genes, lead to sensitization of bacterial populations to any of the antibiotic compounds indicated herein above. It should be thus appreciated that such sensitization increase the sensitivity of the bacteria to said compound thereby enhancing its effectivity that may lead to reduction in the amounts required. A combined treatment with the kit of the invention and any of the antibiotic compounds disclosed herein is also contemplated by the invention. In yet some further embodiments, the kits of the invention may further comprise at least one antibiotic compound. In more specific embodiments, such compound may be any of the antibiotic compounds disclosed by the invention.

In more specific embodiments, the antibiotic resistance factor or gene, that is the target pathogenic gene for the kit of the invention may be any one of an extended-spectrum beta-lactamase resistance factor (ESBL factor), CTX-M-15, beta lactamase, New Delhi metallo-β-lactamase (NDM)-1, 2,5,6 and tetracycline A (tetA).

New Delhi metallo-β-lactamase (NDM-1) is an enzyme that renders bacteria resistant to all currently used β-lactam antibiotics. The NDM-1 resistance spectrum includes the antibiotics of the carbapenem family, which are a mainstay for the treatment of antibiotic-resistant bacterial infections. The gene for NDM-1 is one member of a large gene family that encodes β-lactamase enzymes called carbapenemases. Bacteria that produce carbapenemases are notoriously difficult to treat. Importantly, the gene for NDM-1 can spread from one strain of bacteria to another by horizontal gene transfer, and can therefore spread easily. In certain specific and non-limiting embodiments, the NDM-1 protein may be the *Klebsiella pneumoniae* metallo-beta-lactamase gene blaNDM-1, of protein_id CAZ39946.1. In some specific embodiments said NDM-1 protein may comprise the amino acid sequence encoded by the nucleic acid sequence as denoted by SEQ ID NO. 75. In yet some further specific embodiments, the NDM-1 protein of the invention may comprise the amino acid sequence as denoted by SEQ ID NO. 74.

Still further, CTX-M-15, as used herein is a member of the CTX-M family (Cefotaximases (CTX-M-ases)) of extended-spectrum β-lactamases (ESBLs) that were initially described in *E. coli, Klebsiella pneumoniae*, and *Salmonella* spp. but rapidly emerged in other Enterobacteriaceae, as well as in non Enterobacteriaceae species including *Pseudomonas aeruginosa*. This family includes the CTX-M-3, CTX-M-9, CTX-M-14, and CTX-M-15 enzymes. In some specific embodiments, the CTX-M-15 used as a target for the kits of the invention may be the *Escherichia coli* beta-lactamase CTX-M-15, of protein_id AAL02127.1. In some specific embodiments said CTX-M-15protein may comprise the amino acid sequence encoded by the nucleic acid sequence as denoted by SEQ ID NO. 77. In yet some further specific embodiments, the CTX-M-15protein of the invention may comprise the amino acid sequence as denoted by SEQ ID NO. 76.

According to some embodiments, at least one spacer of the CRISPR array in the sensitizing element of the kit or system of the invention may comprise a nucleic acid sequence that targets at least one of: at least one proto-spacer of CTX-M-15, at least one proto-spacer of NDM-1 and at least one nucleic acid sequence comprised within a lytic phage genome.

It must be appreciated that any sequence, sub-sequence or fragment comprising about 10 to about 50 nucleotides, specifically, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 56, 47, 48, 49 or 50 nucleotides, or more specifically, about 35 nucleotides of any of the resistance conferring genes described herein before, may be use as a protospacer, and therefore as a target to the sensitizing component of the invention and specifically to the particular spacers comprised within. In some specific embodiments, any sequence, sub-sequence or fragment comprising about 10 to about 50 nucleotides of at least one of the NDM-1 and the CTX-M-15 genes, and specifically of those having or comprising the nucleic acid sequences as denoted by any one of SEQ ID NO. 74 and 77, respectively, may be used as an appropriate and effective protospacer. In some specific embodiments, such protospacers may comprise at least one protospacer adjacent motif (PAM) sequence. In further specific embodiments, such PAM sequences may be any one of AAA, AAC, AAG, AAT, CAG, GAA, GAC, GAG, TAA, TAC, TAG, AGA, AGC, AGG, GGG, TGG, ATA, ATC, ATG, ATT, CTG, GTG, TTG. In yet some other embodiments, such PAM may be AWG, wherein "W" may represent any one of "A" or "T". Still further, in certain embodiments, the protospacers of the invention may comprise at last one of said PAM sequences at the 5' end of the protospacer sequence.

In yet some other particular and non-limiting embodiments, the CRISPR system of the invention, specifically, the sensitizing component thereof, may comprise at least one of: at least spacer that targets at least one proto-spacer of CTX-M-15. In more specific embodiments, such protospacer/s may comprise a nucleic acid sequence as denoted by any one of SEQ ID NO. 49, 50 and 51 (also referred to herein as C1, C2 and C3, respectively), at least one spacer that targets at least one proto-spacer of NDM-1, specifically, such protospacer may comprise a nucleic acid sequence as denoted by any one of SEQ ID NO. 46, 47 and 48 (also referred to herein as N1, N2 and N3, respectively).

Still further, the genetically modified lytic phage that is the selective component of the kit of the invention may comprise at least one proto-spacer of at least one of: (a) at least one proto-spacer of CTX-M-15. In some specific embodiments such protospacer may comprise a nucleic acid sequence as denoted by any one of SEQ ID NO. 49, 50 and 51 (also referred to herein as C1, C2 and C3, respectively). In yet some other embodiments, the genetically modified lytic phage may comprise in addition or instead, (b) at least one proto-spacer of NDM-1. In more specific embodiments, such protospacer may comprise a nucleic acid sequence as denoted by any one of SEQ ID NO. 46, 47 and 48 (also referred to herein as N1, N2 and N3, respectively). It should be noted that in certain embodiments, the protospacers of NDM-1 comprising a nucleic acid sequence as denoted by any one of SEQ ID NO. 46, 47 and 48 may be targeted by spacers as denoted by SEQ ID NO. 37, 38 and 39, respectively. Still further, the proto-spacer of CTX-M-15, comprising a nucleic acid sequence as denoted by any one of SEQ ID NO. 49, 50 and 51 may be targeted by spacers as denoted by SEQ ID NO. 40, 41 and 42, respectively.

In certain embodiments, the selective component of the invention may comprise at least one lytic phage. In some embodiments, such lytic phage of the invention may be at least one of T7-likevirus and T4-like virus. In further specific embodiments, the lytic phage used by the kit of the invention may be a T7-like-virus, specifically, at least one Enterobacteria phage T7. Bacteriophage T7 are DNA viruses having a lytic life cycle. These phages belong to the order Caudovirales, familyPodoviridae and the genus T7-like viruses.

It should be appreciated that any suitable lytic phage may be used by the kits, systems and methods of the invention. One non-limiting example may be the phages that are members of the Myoviridae family. Members of Myoviridae are non-enveloped phages having a characteristic structure of head-and-tail separated by a neck. Myoviridae genome is a linear dsDNA of about 33.6-170 Kb in length, which encodes up to 200-300 proteins that are transcribed in operons. Most of the Myoviridae are lytic phages, lacking the genes required to become lysogenic (become integrated into the host bacterium's genome or forming a circular replicon in the bacterium's cytoplasm) but a number of lysogenic species are known. Myoviridae have been divided into four subfamilies, of which the most relevant to the present context is the Tevenvirinae subfamily (also Teequatrovirinae, Taxonomy ID: 1198136) to which, among others, belong the T4likevirus phages.

Therefore, in more specific embodiments, lytic phage may be at least one host-DNA degrading bacteriophage, for example any member of the Tevenvirinae phages.

Members of Tevenvirinae have similar morphology characterized by moderately elongated heads of about 110 nm in length, 114 nm long tails with a collar, base plates with short spikes and six long kinked tail fibers. This subfamily is divided into two genera on the basis of head morphology (i.e. T4likevirus and Schizot4likevirus) and within the genera—on the basis of protein homology the species have been divided into a number of groups. The complete Tevenvirinae lineage includes phages from the genus T4likevirus and Schizot4likevirus.

Specifically, the present invention pertains to the T4likevirus bacteriophages including *Acinetobacter* phage 133, *Aeromonas* phage 25, *Aeromonas* phage 31, *Aeromonas* phage 44RR2.8t, *Aeromonas* phage 65, *Aeromonas* phage Aeh1, Enterobacteria phage SV14, Enterobacteria phage T4 sensu lato, *Vibrio* phage nt-1 sensu lato, Unclassified T4-like viruses species (according to ICTV). More specifically, the present invention pertains to bacteriophages from the Enterobacteria phage T4 sensu lato species, including Enterobacteria phage C16, Enterobacteria phage FSalpha, Enterobacteria phage MV 72, Enterobacteria phage MV SS, Enterobacteria phage MV12, Enterobacteria phage MV13, Enterobacteria phage MV14, Enterobacteria phage MV9, Enterobacteria phage PST, Enterobacteria phage T2, Enterobacteria phage T4, Enterobacteria phage T6 subspecies; and further to bacteriophages from the Unclassified T4-like viruses species, including *Acinetobacter* phage Ac42, *Acinetobacter* phage Acj61, *Acinetobacter* phage Acj9, *Acinetobacter* phage ZZ1, *Aeromonas* phage Aes002, *Aeromonas* phage Aes007, *Aeromonas* phage AesO12, *Aeromonas* phage Aesl20, *Aeromonas* phage Aes123, *Aeromonas* phage Aes144, *Aeromonas* phage Aesl51, *Aeromonas* phage Aes508, *Aeromonas* phage Aes509, *Aeromonas* phage Aes512, *Aeromonas* phage Aes516, *Aeromonas* phage Aes517, *Aeromonas* phage CC2, *Aeromonas* phage phiAS4, *Aeromonas* phage phiAS5, *Aeromonas* phage PX29, *Burkholderia* phage 42, *Citrobacter* phage Miller, Cronobacter phage vB_CsaM_GAP161, Cyanophage 2B096, Cyanophage 2Bnp, Cyanophage 2Gdp, Cyanophage 4B092, Cyanophage 4B09p, Cyanophage 5Bd2, Cyanophage 5Bnp, Cyanophage 6Bnp, Cyanophage 7E02p, Cyanophage 7G09p, Cyanophage 7Gmp, Cyanophage 8B026, Cyanophage 8B092, Cyanophage 8G092, Cyanophage P-TIM3, Cyanophage S-TIM4, Enterobacteria phage 1, Enterobacteria phage Ac3, Enterobacteria phage AR1, Enterobacteria phage Baker, Enterobacteria phage Bp7, Enterobacteria phage CC31, Enterobacteria phage CEV1, Enterobacteria phage DD VI, Enterobacteria phage ELY-1, Enterobacteria phage GEC-3S, Enterobacteria phage HX01, Enterobacteria phage IME08, Enterobacteria phage ime09, Enterobacteria phage JS, Enterobacteria phage JS10, Enterobacteria phage JS98-C3, Enterobacteria phage JSE, Enterobacteria phage K3, Enterobacteria phage KC69, Enterobacteria phage LZ1, Enterobacteria phage LZ10, Enterobacteria phage LZ2, Enterobacteria phage LZ3, Enterobacteria phage LZ4, Enterobacteria phage LZ5, Enterobacteria phage LZ6, Enterobacteria phage LZ7, Enterobacteria phage LZ8, Enterobacteria phage LZ9, Enterobacteria phage M1, Enterobacteria phage Mi, Enterobacteria phage MV BS, Enterobacteria phage nvv1, Enterobacteria phage Ox2, Enterobacteria phage Phi1, Enterobacteria phage Pol, Enterobacteria phage RB1, Enterobacteria phage RB10, Enterobacteria phage RB14, Enterobacteria phage RB15, Enterobacteria phage RB16, Enterobacteria phage RB18, Enterobacteria phage RB2, Enterobacteria phage RB21, Enterobacteria phage RB23, Enterobacteria phage RB25, Enterobacteria phage RB26, Enterobacteria phage RB27, Enterobacteria phage RB3, Enterobacteria phage RB30, Enterobacteria phage RB32, Enterobacteria phage RB33, Enterobacteria phage RB42, Enterobacteria phage RB43, Enterobacteria phage RB49, Enterobacteria phage RB5, Enterobacteria phage RB51, Enterobacteria phage RB6, Enterobacteria phage RB61, Enterobacteria phage RB62, Enterobacteria phage RB68, Enterobacteria phage RB69, Enterobacteria phage RB70, Enterobacteria phage RB8, Enterobacteria phage RB9, Enterobacteria phage SC1, Enterobacteria phage SCI, Enterobacteria phage SV76, Enterobacteria phage Tula, Enterobacteria phage Tulb, Enterobacteria phage U4, Enterobacteria phage U5, Enterobacteria phage vB_EcoM-VR7, Enterobacteria phage vB_EcoM ACG-C40, *Escherichia* phage ell/2, *Escherichia* phage IME08, *Escherichia* phage Lwl, *Escherichia* phage LZ, *Escherichia* phage LZ1, *Escherichia* phage LZ9, *Escherichia* phage vB_EcoM JS09, *Escherichia* phage vB_EcoM_PhAPEC2, *Escherichia* phage wV7, *Klebsiella* phage KP15, *Klebsiella* phage KP27, Phage LZ, Phage LZ11, Prochlorococcus phage P-SSM2, Prochlorococcus phage P-SSM4, *Salmonella* phage S16, *Serratia* phage PS2, *Shigella* phage Shfl2, *Shigella* phage SP18, *Sinorhizobium* phage phiM12, *Stenotrophomonas* phage IME13, *Stenotrophomonas* phage Smpl4, Synechococcus phage metaG-MbCM1, Synechococcus phage S-MbCM100, Synechococcus phage S-MbCM6, Synechococcus phage S-MbCM7, Synechococcus phage S-PM2, Synechococcus phage S-RSM4, Synechococcus phage syn9 and *Yersinia* phage PST subspecies (according to ICTV).

It should be appreciated that the selective component of the invention may comprise any lytic phage that infects *E. coli*. In yet some other embodiments, such lytic phages may be any phages that target any pathogenic bacteria.

As noted above, the selective element of the invention may be a DNA sequence encoding bacterial killers as described herein before and at least one protospacer. In yet some other specific and non-limiting embodiments, the selective component may comprise at least one lytic bacteriophage, specifically, a genetically modified lytic phage. In some specific embodiments, such lytic phage may be at least one T7 bacteriophage. In some particular and non-limiting embodiments, the lytic phage used as the selective component in the kit of the invention may be a T7 genetically modified phage comprising one proto-spacer of NDM-1, N1 as denoted by SEQ ID NO. 46, and a proto-spacer of CTX-M-15, C1, as denoted by SEQ ID NO. 49, said phage is referred to herein as T7-N1C1. In some embodiments, the recombinant or genetically modified lytic phage T7-N1C1 may comprise the nucleic acid sequence as denoted by SEQ ID NO. 57. In yet another embodiment, the selective element of the invention may be a genetically modified lytic phage, specifically, a T7 bacteriophage comprising two proto-spacers of NDM-1, N1 and N2, as denoted by SEQ ID NO. 46 and 47, respectively, said phage is referred to herein as T7-N1N2. In some embodiments, the recombinant or genetically modified lytic phage T7-N1N2 may comprise the nucleic acid sequence as denoted by SEQ ID NO. 55. Still further, the selective element of the invention may be a genetically modified lytic phage, specifically, a T7 bacteriophage comprising two proto-spacers of CTX-M-15, for example, C2 and C1, as denoted by SEQ ID NO. 50 and 49, respectively, said phage is referred to herein as T7 C2C1. In some embodiments, the recombinant or genetically modified lytic phage T7-C2C1 may comprise the nucleic acid sequence as denoted by SEQ ID NO. 56. In yet another embodiment, the selective element of the invention may be a genetically modified lytic phage, specifically, a T7 bacteriophage comprising one proto-spacer of CTX-M-15, C2, as denoted by SEQ ID NO. 50, and a proto-spacer of NDM-1, N2, as denoted by SEQ ID NO. 47, said phage is referred to herein as T7-C2N2. In some embodiments, the recombinant or genetically modified lytic phage T7-C2N2 may comprise the nucleic acid sequence as denoted by SEQ ID NO. 58.

In some alternative embodiments, the selective component of the kit or a system of the invention may be a non-engineered phage. Accordingly, the CRISPR array of the sensitizing component of the invention should be designed to target such phages. As such, at least one CRISPR spacer must be sufficiently complementary to a nucleic acid sequence comprised within an essential gene of said lytic phage.

Thus, in some embodiments, at least one CRISPR spacer targets a nucleic acid sequence comprised within an essential gene of said lytic phage. In some specific embodiments such lytic phage may be at least one of T7-like-virus and T4like virus. More specific embodiments relate to at least one of Enterobacteria phage T7 and Enterobacteria phage T4. In more specific embodiments, the lytic phage used as the selective component of the kit or a system of the invention may be at least one of T4 and T7. In such specific cases, the CRISPR array may comprise spacers that target and recognize nucleic acid sequences of these phages.

In some specific and non-limiting embodiments, such spacers may comprise spacers that target proto-spacers in T7 bacteriophage. More specific embodiments relate to spacers comprising any one of SEQ ID NO. 43, 44 and 45. In yet more specific embodiments, such spacers target proto-spacers that comprise the nucleic acid sequence of any one of SEQ ID NO. 52, 53 and 54, respectively. In more specific embodiments, these proto-spaces are comprised within the lytic phage of the invention.

It should be understood that the invention further encompasses as a further aspect thereof any one of the genetically modified or engineered lytic bacteriophages as described herein before.

According to some embodiments, the bacteriophage used for the sensitizing component of the kit or system of the invention may be a lambda phage. In more specific embodiments, such phage may be a lambda temperate phage.

In more specific embodiments, an example for a temperate phage may be a lambda phage having the nucleic amino acid sequence as denoted by SEQ ID NO. 36 (NCBI Reference Sequence: NC_001416.1).

By way of example, the bacteriophages used for the kits and systems of the invention include, but are not limited to, those bacteriophage, either lytic or temperate bacteriphages, capable of infecting any nosocomial bacteria.

By way of another example, the bacteriophage include, but are not limited to, those bacteriophage (lytic or temperate) capable of infecting a bacterium including but not limited to any one of the proteobacteria, Firmicutes and Bacterioidetes phyla.

By way of further example, the bacteriophage include but are not limited to, those bacteriophage capable of infecting bacteria belonging to the following genera: *Escherichia coli*, *Pseudomonas*, *Streptococcus*, *Staphylococcus*, *Clostidium*, *Enterococcus*, *Klebsiella Acinetobacter* and *Enterobacter*.

Other lytic phages infecting other organisms, and particularly the ESKAPE organisms listed above could also be used as a selective agent in a kit targeting these organisms. The selective agent can also be a DNA encoding a bacterial-killing agent that is injected through a phage capsid or another method. In yet some other embodiments, other temperate phages infecting other organisms, and particularly the ESKAPE organisms listed above could also be used as the sensitizing component in a kit targeting these organisms. More specifically, it should be appreciated that any bacteriophage, either a lytic phage or a temperate bacteriophage, may be applicable for the purpose of the invention, specifically, as the selective and the sensitizing components of the invention. Of particular interest are bacteriophages that specifically target any of the "ESKAPE" pathogens. As used herein, these pathogens include but are not limited to *Enterococcus faecium, Staphylococcus aureus, Klebsiella pneumoniae, Acinetobacter baumanii, Pseudomonas aeruginosa*, and *Enterobacter*. To name but few, these bacteriophages, either lytic or temperate, may include but are not limited to bacteriophages specific for *Staphylococcus aureus*, specifically, at least one of vB_Sau. My D1, vB_Sau My 1140, vB_SauM 142, Sb-1, vB_SauM 232, vB_SauS 175, vB_SauM 50, vB_Sau 51/18, vB_Sau.M. 1, vB_Sau.M. 2, vB_Sau.S. 3, vB_Sau.M. 4, vB_Sau.S. 5, vB_Sau.S. 6, vB_Sau.M.7, vB_Sau.S.8, vB_Sau.S.9, vB_Sau.M.10, vB_Sau.M.11. In yet some further embodiments, lytic or temperate bacteriophages specific for *Klebsiella pneumoniae*, may be also applicable for the present invention. In more specific embodiments, these phages may include vB_Klp 1, vB_Klp 2, vB_Klp. M.1, vB_Klp. M.2, vB_Klp. P.3, vB_Klp. M.4, vB_Klp. M.5, vB_Klp. M.6, vB_Klp. 7, vB_Klp. M.8, vB_Klp. M.9, vB_Klp. M.10, vB_Klp. P.11, vB_Klp. P.12, vB_Klp. 13, vB_Klp. P.14, vB_Klp. 15, vB_Klp. M.16. Still further, in certain embodiments, bacteriophages specific for *Pseudomonas aeruginosa*, may be applicable for the selective and/or sensitizing components of the invention or any kits or methods using these components. Non-limiting examples for such bacteriophages include but are not limited to vB_Psa.Shis 1, vB_PsaM PAT5, vB_PsaP PAT14, vB_PsaM PAT13, vB_PsaM ST-1, vB_Psa cT 27, vB_Psa cT 44 K, vB_Psa cT 44 M, vB_Psa 16, vB_Psa Ps-1, vB_Psa 8-40, vB_Psa 35 K, vB_Psa 44, vB_Psa 1, vB_Psa 9, vB_Psa 6-131 M, vB_Psa cT 37, vB_Psa cT 45 S, vB_Psa cT 45 M, vB_Psa cT 16 MU, vB_Psa cT 41, vB_Psa cT 44 MU, vB_Psa cT 43, vB_Psa cT 11 K, vB_Psa 1638, vB_Psa Ps-2, vB_Psa 35 CT, vB_Psa 35 M, vB_Psa S.Ch.L, vB_Psa R1, vB_Psa SAN, vB_Psa L24, vB_Psa F8, vB_Psa BT-4, vB_Psa BT-2(8), vB_Psa BT-1(10), vB_Psa BT-4-16, vB_Psa BT-5, vB_Psa F-2, vB_Psa B-CF, vB_Psa Ph7/32, vB_Psa Ph7/63, vB_Psa Ph5/32, vB_Psa Ph8/16, vB_Psa Ph11/1, vB_Psa, vB_Psa 3, vB_Psa 4, vB_Psa 5, vB_Psa 6, vB_Psa 7, vB_Psa.P. 15, vB_Psa.17, vB_Psa.M. 18, vB_Psa. 28, vB_Psa.M 0.2, vB_Psa.M 3, vB_Psa.23, vB_Psa.P. 8, vB_Psa.M. PST7, vB_Psa.M.C5, vB_Psa.M.D1038. In further embodiments, bacteriophages specific for *Acinetobacter baumanii*, may be applicable for the present invention. Such lytuic or temperate phages may include any one of vB_Aba B37, vB_Aba G865, vB_Aba G866, vB_Aba U7, vB_Aba U8, vB_Acb 1, vB_Acb 2. In yet some further embodiments, bacteriophages specific for *Enterobacter* may be used for the kits and methods of the invention, specifically, any one of vB_Eb 1, vB_Eb 2, vB_Eb 3, vB_Eb 4 bacteriophages. In yet some further embodiments, *Enterococcus faecalis* specific bacteriophages may be used. Several non-limiting examples include any one of, vB_Ec 1, vB_Ec 2, vB_Enf.S.4, vB_Enf.S.5 bacteriophages.

In yet some further embodiments, bacteriophages that specifically infect *Bacillus anthracis*, for example, vB_BaK1, vB_BaK2, vB_BaK6, vB_BaK7, vB_BaK9, vB_BaK10, vB_BaK11, vB_BaK12, vB_BaGa4, vB_BaGa5, vB_BaGa6, may be also applicable for the present invention. Still further, bacteriophages specific for *Brucella abortus* for example, Tb, vB_BraP IV, vB_BraP V, vB_BraP VI, vB_BraP VII, vB_BraP VIII, vB_BraP IX, vB_BraP X, vB_BraP XII, vB_BraP 12(b), vB_BraP BA, vB_BraP 544, vB_BraP 141A, vB_BraP 141m, vB_BraP 1931, vB_BraP 19m, vB_BraP 9, bacteriophages specific for *Brucella canis*, specifically, vB_BrcP 1066, bacteriophages specific for *Clostridium perfigenes* A.B.C.D.E, for example, vB_CpPI, vB_CpII, vB_CpIII, vB_CpIV, bacteriophages specific for *Desulfovibrio vulgaris*, specifically, vB_DvRCH1/M1, vB_DvH/P15, vB_DvH/M15, those specific for *Enterococcus faecalis*, specifically, vB_Ec 1, vB_Ec 2, vB_Enf.S.4, vB_Enf.S.5, bacteriophages specific for *Escherichia coli*, specifically, vB_Eschc.pod 9, vB_Eschc.Pod 4, vB_Eschc.Shis 7, vB_Eschc.Shis 14, vB_Eschc.Shis 5, vB_Eschc.My 2, PhI-1, PhI-2, PhI3, PhI4, PhI5, T2, T4, T5, DDII, DDVI, DDVII, vB_Eschc.Shis 7/20, vB_Eschc.Shis 1161, vB_Eschc.Shis 8963, vB_Eschc 4, vB_Eschc 11/24, vB_Eschc.Shis 18, vB_Shis 3/14, vB_Sau A, vB_Shis G, vB_Eschc.Shis W, vB_Shis GE25, vB_Eschc.Shis 8962, vB_Eschc 90/25, vB_Eschc 5/25, vB_Eschc 12/25, vB_Eschc H, T3, T6, T7, vB_Eschc 4, vB_Eschc 121, vB_Eschc BaK2, vB_Eschc L7-2, vB_Eschc L7-3, vB_Eschc L7-7, vB_Eschc L7-8, vB_Eschc L7-9, vB_Eschc L7-10, vB_Eschc 18, vB_Eschc.Shis 20, vB_Eschc.Shis 25, vB_Eschc.Shis 27, vB_Eschc.Shis MY, vB_Eschc 11, vB_Eschc 12, vB_Eschc 13, vB_Eschc 17, vB_Eschc 18, vB_Eschc 19, vB_Eschc 20, vB_Eschc 21, vB_Eschc 22, vB_Eschc 23, vB_Eschc 24, vB_Eschc 25, vB_Eschc 26, vB_Eschc 27, vB_Eschc 28, vB_Eschc 29, vB_Eschc 30, vB_Eschc 31, vB_Eschc 32, vB_Eschc 34, vB_Eschc 35, vB_Eschc 37, vB_Eschc 38, vB_Eschc 39, vB_Eschc 44, vB_Eschc 45, vB_Eschc 46, vB_*E. coli*.M. 1, vB_*E. coli*.M. 2, vB_*E. coli*. P.3, vB_*E. coli*. P.4, vB_*E. coli*. P.5, vB_*E. coli*. P.6, vB_*E. coli*. P.7, vB_*E. coli*. P.8, phages specific for *Salmonella paratyphi*, specifically, vB_SPB Diag 1, vB_SPB Diag 2, vB_SPB Diag 3, vB_SPB Diag 3b, vB_SPB Diag Jersey, vB_SPB Diag Beecles, vB_SPB Diag Taunton, vB_SPB DiagB.A.O.R, vB_SPB Diag Dundee, vB_SPBDiagWorksop, vB_SPB Diag E, vB_SPB Diag D, vB_SPB Diag F, vB_SPB Diag H, specific for *Salmonella typhi abdominalis* vB_Sta Diag A, vB_Sta Diag B1, vB_Sta Diag B2, vB_Sta Diag C1, vB_Sta Diag C2, vB_Sta Diag C3, vB_Sta Diag C4, vB_Sta Diag C5, vB_Sta Diag C6, vB_Sta Diag C7, vB_Sta Diag D1, vB_Sta Diag D2, vB_Sta Diag D4, vB_Sta Diag D5, vB_Sta Diag D6, vB_Sta Diag D7, vB_Sta Diag D8, vB_Sta Diag E1, vB_Sta Diag E2, vB_Sta Diag E5, vB_Sta Diag E10, vB_Sta Diag F1, vB_Sta Diag F2, vB_Sta Diag F5, vB_Sta Diag G, vB_Sta Diag H, vB_Sta Diag J1, vB_Sta Diag J2, vB_Sta Diag K, vB_Sta Diag L1, vB_Sta Diag L2, vB_Sta Diag M1, vB_Sta Diag M2, vB_Sta Diag N, vB_Sta Diag O, vB_Sta Diag T, vB_Sta Diag Vi1, vB_Sta Diag27, vB_Sta Diag 28, vB_Sta Diag 38, vB_Sta Diag 39, vB_Sta Diag 40, vB_Sta Diag 42, vB_Sta Diag 46, *Salmonella typhimurium*, specifically, vB_Stm.My 11, vB_Stm.My 28, vB_Stm.Shis 13, vB_Stm.My 760, vB_Stm.Shis 1, IRA, vB_Stm 16, vB_Stm 17, vB_Stm 18, vB_Stm 19, vB_Stm 20, vB_Stm 21, vB_Stm 29, vB_Stm 512, vB_Stm Diag I, vB_Stm Diag II, vB_Stm Diag III, vB_Stm Diag IV, vB_Stm Diag V, vB_Stm Diag VI, vB_Stm Diag VII, vB_Stm Diag VIII, vB_Stm Diag IX, vB_Stm Diag X, vB_Stm Diag XI, vB_Stm Diag XII, vB_Stm Diag XIII, vB_Stm Diag XIV, vB_Stm Diag XV, vB_Stm Diag XVI, vB_Stm Diag XVII, vB_Stm Diag XVIII, vB_Stm Diag XIX, vB_Stm Diag XX, vB_Stm Diag XXI, vB_Stm Diag 1, vB_Stm Diag 2, vB_Stm Diag 3, vB_Stm Diag 4, vB_Stm Diag 5, vB_Stm Diag 6, vB_Stm Diag 7, vB_Stm Diag 8, vB_Stm Diag 9, vB_Stm Diag 10, vB_Stm Diag 11, vB_Stm Diag 12, vB_Stm Diag 13, vB_Stm Diag 14, vB_Stm Diag 15, vB_Stm Diag 16, vB_Stm Diag 17, vB_Stm Diag 18, vB_Stm Diag 19, vB_Stm Diag 20, vB_Stm Diag 21, vB_Stm Diag 22, vB_Stm Diag 23, vB_Stm Diag 24, vB_Stm Diag 25, vB_Stm Diag 26, vB_Stm Diag 27, vB_Stm Diag 28, vB_Stm Diag 29, vB_Stm Diag 30, vB_Stm Diag 31, vB_Stm Diag 32, vB_Stm Diag 33, vB_Stm Diag 34, vB_Stm Diag 35, vB_Stm Diag 36, vB_Stm Diag 37, vB_Stm Diag 38, vB_Stm Diag 39, vB_Stm Diag 40, vB_Stm Diag 41, vB_Stm Diag 42, vB_Stm Diag 43, vB_Stm Diag 44, vB_Stm Diag 45, vB_Stm Diag 46, vB_Stm Diag 47, vB_Stm Diag 48, vB_Stm Diag 49, vB_Stm Diag 50, vB_Stm Diag 51, vB_Stm Diag 52, vB_Stm Diag 53, vB_Stm Diag 54, vB_Stm Diag 55, vB_Stm Diag 56, vB_Stm Diag 57, vB_Stm Diag 58, vB_Stm Diag 59, vB_Stm Diag 60, vB_Stm Diag 61, vB_Stm Diag 62, vB_Stm Diag 63, vB_Stm Diag 64, vB_Stm Diag 65, vB_Stm. P. 1, vB_Stm. P. 2, vB_Stm. P. 3, vB_Stm. P. 4, *Shigella sonnei*, specifically, vB_Shs.Pod 3, vB_Eschc.Shis 7/20, vB_Eschc.Shis 1161, vB_Eschc.Shis 8963, vB_Eschc.Shis 8962, vB_Shis GE25, vB_Eschc.Shis W, vB_Shis G, vB_Shis 3/14, vB_Eschc.Shis 18, vB_Shis 1188, vB_Shis 1188 F, vB_Shis 1188 Y, vB_Shis 1188 X, vB_Shis 5514, vB_Shis L7-2, vB_Shis L7-4, vB_Shis L7-5, vB_Shis L7-11, vB_Shis K3, vB_Shis Tul A, vB_Shis Ox2, vB_Shis SCL, vB_Shis Bak C2, vB_Shis 4/1188, vB_Shis 8962, vB_Shis 8963, vB_Shis XIV, vB_Shis 116, vB_Shis 106/8, vB_Shis 20, vB_Shis 90/25, vB_Shis 87/25, vB_Shis 16/25, vB_Shs 7, vB_Shs 38, vB_Shs 92, vB_Shs 1391, vB_Shs. P. 1, vB_Shs. P. 2, vB_Shs. P. 3. It should be further appreciated that any bacteriophage, either lytic or temperate, specific for any pathogenic bacteria, and specifically to any of the pathogenic bacteria disclosed herein, may be applicable for the kits and methods of the invention or to any component thereof, specifically, the selective and the sensitizing components.

The CRISPR-Cas system has evolved in prokaryotes to protect against phage attack and undesired plasmid replication by targeting foreign DNA or RNA (16, 20, 21). The *Escherichia coli* CRISPR-Cas system, targets DNA molecules molecules based on short homologous DNA sequences, called spacers that exist between repeats within the bacterial genome. These spacers guide CRISPR-associated (Cas) proteins to matching (and/or complementary) sequences within the foreign DNA, called protospacers, which are subsequently cleaved. The spacers can be rationally designed to target any DNA sequence, including those that encode resistance genes and lytic phages. This allows genetically linking a trait that is beneficial to the bacteria (i.e., elements conferring phage resistance) with a trait that reverses drug resistance (i.e. elements eliminating resistance genes). This genetic linkage enables selecting a sensitized bacterial population by using lytic phages as selection agents. Bacteria harboring both a defense against the lytic phages and a sensitizing construct survive on the treated surfaces, whereas those that lack these factors are killed by the lytic phages. The integrated construct/s of the invention are designed not only to actively eradicate existing resistance genes but also to eliminate horizontal transfer of genes between bacteria.

In some further embodiments, the temperate bacteriophage further comprises a nucleic acid sequence encoding a CRISPR leader sequence.

As indicated above, the sensitizing component of the kit of the invention may comprise at least one Cas gene and the CRISPR system. With respect to CRISPR systems, as will be recognized by those skilled in the art, the structure of a naturally occurring CRISPR locus includes a number of short repeating sequences generally referred to as "repeats". The repeats occur in clusters and up to 249 repeats have been identified in a single CRISPR locus and are usually regularly spaced by unique intervening sequences referred to as "spacers." Typically, CRISPR repeats vary from about 24 to 47 base pair (bp) in length and are partially palindromic. In some embodiments, the CRISPR repeats included in the sensitizing component of the kit of the invention may comprise repeats having about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more bp. The repeats are generally arranged in clusters (up to about 20 or more per genome) of repeated units. The spacers are located between two repeats and typically each spacer has unique sequences that are from about 20 or less to 72 or more bp in length. Thus, in certain embodiments the CRISPR spacers used in the sensitizing component of the invention may comprise between 20 to 72 nucleotides (nt.) each. More specifically, about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71 72 or more. Many spacers are identical to or have high homology with known phage sequences. In addition to repeats and spacers, a CRISPR locus also includes a leader sequence and often at least one associated Cas gene, specifically, a set of two to six or more associated Cas genes. The leader sequence typically is an AT-rich sequence of up to 550 bp directly adjoining the 5' end of the first repeat. New repeat-spacer units are believed to be almost always added to the CRISPR locus between the leader and the first repeat.

As indicated above, the engineered temperate phage used as the sensitizing element in the kit or a system of the invention comprises CRISPR (Clustered Regularly Interspaced Short Palindromic Repeats) arrays together with the cas genes form the CRISPR system. As used herein, CRISPR arrays also known as SPIDRs (Spacer Interspersed Direct Repeats) constitute a family of recently described DNA loci that are usually specific to a particular bacterial species. The CRISPR array is a distinct class of interspersed short sequence repeats (SSRs) that were first recognized in *E. coli*. In subsequent years, similar CRISPR arrays were found in *Mycobacterium tuberculosis, Haloferax mediterranei, Methanocaldococcus jannaschii, Thermotoga maritima* and other bacteria and archaea. It should be understood that the invention contemplates the use of any of the known CRISPR systems, particularly and of the CRISPR systems disclosed herein.

As used herein, the phrase "CRISPR array polynucleotide" refers to a DNA or RNA segment which comprises sufficient CRISPR repeats such that it is capable of down regulating (e.g. eliminating) a complementary gene.

According to one embodiment, the CRISPR array polynucleotide comprises at least 2 repeats with 1 spacer between them. In yet some further embodiments, the CRISPR array of the sensitizing component of the invention may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more, specifically, 110, 120, 130, 140, 150, 160, 170, 180, 190, 200 or more spacers. It should be further understood that the spacers of the sensitizing component of the invention may be either identical or different spacers. In more embodiments, these spacers may target either an identical or different target bacterial pathogenic gene. In yet some other embodiments, such spacer may target at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more pathogenic bacterial gene/s.

In an exemplary embodiment, the CRISPR array polynucleotide comprises all of the CRISPR repeats, starting with the first nucleotide of the first CRISPR repeat and ending with the last nucleotide of the last (terminal) repeat.

Various computer software and web resources are available for the analysis of and identification of CRISPR systems and therefore CRISPR arrays. These tools include software for CRISPR detection, such as PILERCR, CRISPR Recognition Tool and CRISPRFinder; online repositories of pre-analyzed CRISPRs, such as CRISPRdb; and tools for browsing CRISPRs in microbial genomes, such as Pygram.

It has been revealed that CRISPR systems are found in approximately 40% and 90% of sequenced bacterial and archaeal genomes, respectively, and the present inventor contemplates the use of CRISPR arrays from all such CRISPR systems.

According to one embodiment, the CRISPR array polynucleotide comprises a nucleic acid sequence which, apart from the spacer, (or spacers) which is replaced so as to down-regulate (e.g. eliminate) the gene of interest, is 100% homologous to the naturally occurring (wild-type) sequence.

According to another embodiment, the CRISPR array polynucleotide comprises a nucleic acid sequence which, apart from the spacer, (or spacers) which is replaced so as to down-regulate a gene of interest, is 99% homologous to the naturally occurring (wild-type) sequence. In yet some other embodiments, the CRISPR array polynucleotide comprises a nucleic acid sequence which, apart from the spacer, (or spacers) which is replaced so as to down-regulate or eliminate a gene of interest and specifically, RNA encoded thereby, is 98%, 97%, 96%, 95%, 90%, 85%, 80%, 75%, 70%, 65%, 60%, 55% or 50% homologous to the naturally occurring (wild-type) sequence.

As used herein, the term "spacer" refers to a non-repetitive spacer sequence that is found between multiple short direct repeats (i.e., CRISPR repeats) of CRISPR arrays. In some preferred embodiments, CRISPR spacers are located in between two identical CRISPR repeats. In some embodiments, CRISPR spacers are identified by sequence analysis at the DNA stretches located in between two CRISPR repeats.

In some preferred embodiments, CRISPR spacer is naturally present in between two identical, short direct repeats that are palindromic. It should be noted that the spacers of the invention may be located or present between two identical or not identical repeats.

The phrase "portion of a gene" or "a nucleic acid sequence comprise within a gene" relates to a portion from the coding or non-coding region of the gene.

The phrase "sufficiently complementary" as used herein, refers to the sequence of the spacer being adequately complementary such that it is capable of down regulating expression of the gene.

According to one embodiment of this aspect of the present invention, a sequence which is sufficiently complementary to a portion of the gene and specifically, RNA encoded by said gene is one which is at least about 70, about 75, about 80, about 85, or about 90% identical, or at least about 91, about 92, about 93, about 94, about 95, about 96, about 97, about 98, or about 99% identical to the gene. In some preferred embodiments, the sequence is 100% complementary to the gene.

The targeting RNA encoded by the CRISPR system may be a CRISPR RNA (crRNA). The sequence of the targeting RNA encoded by the CRISPR spacers is not particularly limited, other than by the requirement for it to be directed to (i.e., having a segment that is the same as or complementarity to) a target sequence in a pathogenic gene of a bacteria that is also referred to herein as a "proto-spacer". Such proto-spacers comprise nucleic acid sequence having sufficient complementarity to a targeting RNA encoded by the CRISPR spacers comprised within the sensitizing system of the invention.

In some embodiments, a crRNA comprises or consists of 20, 21, 22, 23, 24, 25, 26, 27, 28, 29, 30, 31, 32, 33, 34, 35, 36, 37, 38, 39 or 40 nt of the spacer (targeting) sequence followed by 19-36 nt of repeat sequence. In specific and non-limiting embodiments, the targeting spacer will comprise or consist of a segment that targets any one of the genes for which representative spacer sequences are indicated herein.

It should be noted that in some embodiments, the spacers of the CRISPR system of the invention may encode a targeting RNA. A "targeting RNA" is an RNA that, when transcribed from the portion of the CRISPR system encoding it, comprises at least a segment of RNA sequence that is identical to (with the exception of replacing T for U in the case of RNA) or complementary to (and thus "targets") a DNA sequence in the bacterial chromosome, or a sequence on a plasmid within the targeted bacteria. The CRISPR systems of the present disclosure can encode more than one targeting RNA, and the targeting RNAs can be directed to one or more sequences in the bacterial chromosome, or plasmid, or combinations thereof. The sequence of the targeting RNA thus dictates what is targeted by the CRISPR system carried by the sensitizing element of the invention, specifically, the genetically modified phage of the invention.

The modified CRISPR array of the present invention may also comprise a nucleic acid sequence encoding one or more Cas proteins (i.e. cas genes).

As used herein, the term "cas gene" refers to the genes that are generally coupled, associated or close to or in the vicinity of flanking CRISPR arrays that encode Cas proteins.

CRISPR arrays are typically found in the vicinity of four genes named cas1 to cas4. The most common arrangement of these genes is cas3-cas4-cas 1-cas2. The Cas3 protein appears to be a helicase, whereas Cas4 resembles the RecB family of exonucleases and contains a cysteine-rich motif, suggestive of DNA binding. The cas1 gene (NCBI COGs database code: COG1518) is especially noteworthy, as it serves as a universal marker of the CRISPR system (linked to all CRISPR systems except for that of *Pyrococcus abyssii*). cas2 remains to be characterized. cas1-4 are typically characterized by their close proximity to the CRISPR loci and their broad distribution across bacterial and archaeal species. Although not all cas1-4 genes associate with all CRISPR loci, they are all found in multiple subtypes.

In addition, there is another cluster of three genes associated with CRISPR structures in many bacterial species, referred to herein as cas IB, cas5 and cas6. In some embodiments, the cas gene is selected from cas1, cas2, cas3, cas4, cas IB, cas5 and/or cas6, fragments, variants, homologues and/or derivatives thereof. In some additional embodiments, a combination of two or more cas genes find use, including any suitable combinations.

In some embodiments, the cas genes comprise DNA, while in other embodiments, the cas comprise RNA. In some embodiments, the nucleic acid is of genomic origin, while in other embodiments, it is of synthetic or recombinant origin. In some embodiments, the cas genes are double-stranded or single-stranded whether representing the sense or antisense strand or combinations thereof.

In some embodiments it is preferred that the cas gene is the cas gene that is closest to the leader sequence or the first CRISPR repeat at the 5' end of the CRISPR locus-such as cas4 or cas6.

It will be appreciated that a given set of cas genes or proteins is typically associated with a given repeated sequence within a particular CRISPR array. Thus, cas genes appear to be specific for a given DNA repeat (i.e., cas genes and the repeated sequence form a functional pair).

Still further, three major types of CRISPR-Cas system are delineated: Type I, Type II and Type III.

Type I CRISPR-Cas systems contain the cas3 gene, which encodes a large protein with separate helicase and DNase activities, in addition to genes encoding proteins that probably form Cascade-like complexes with different compositions. These complexes contain numerous proteins that have been included in the repeat-associated mysterious proteins (RAMPs), which form a large superfamily of Cas proteins, and contain at least one RNA recognition motif (RRM; also known as a ferredoxin-fold domain) and a characteristic glycine-rich loop. RAMP superfamily encompasses the large Cas5 and Cas6 families on the basis of extensive sequence and structure comparisons. Furthermore, the Cas7 (COG1857) proteins represent another distinct, large family within the RAMP superfamily.

The type I CRISPR-Cas systems seem to target DNA where the target cleavage is catalysed by the HD nuclease domains of Cas3. As the RecB nuclease domain of Cas4 is fused to Cas1 in several type I CRISPR-Cas systems, Cas4 could potentially play a part in spacer acquisition instead. It should be noted that any type I CRISPR-Cas systems may be applicable in the present invention, specifically, any one of type I-A, B, C, D, E, and F.

The type II CRISPR-Cas systems include the 'HNH'-type system (*Streptococcus*-like; also known as the Nmeni subtype, for *Neisseria meningitidis* serogroup A str. Z2491, or CASS4), in which Cas9, a single, very large protein, seems to be sufficient for generating crRNA and cleaving the target DNA, in addition to the ubiquitous Cas1 and Cas2. Cas9 contains at least two nuclease domains, a RuvC-like nuclease domain near the amino terminus and the HNH (or McrA-like) nuclease domain in the middle of the protein, but the function of these domains remains to be elucidated. However, as the HNH nuclease domain is abundant in restriction enzymes and possesses endonuclease activity, it is likely to be responsible for target cleavage.

Type II systems cleave the pre-crRNA through an unusual mechanism that involves duplex formation between a tracrRNA and part of the repeat in the pre-crRNA; the first cleavage in the pre-crRNA processing pathway subsequently occurs in this repeat region. This cleavage is catalysed by the housekeeping, double-stranded RNA-specific RNase III in the presence of Cas9. Still further, it should be noted that type II system comprise at least one of cas9, cas1, cas2 csn2, and cas4 genes. It should be appreciated that any type II CRISPR-Cas systems may be applicable in the present invention, specifically, any one of type II-A or B.

The type III CRISPR-Cas systems contain polymerase and RAMP modules in which at least some of the RAMPs seem to be involved in the processing of the spacer-repeat transcripts, analogous to the Cascade complex. Type III systems can be further divided into sub-types III-A (also known as Mtube or CASS6) and III-B (also known as the polymerase-RAMP module). Subtype III-A systems can target plasmids, as has been demonstrated in vivo for *S. epidermidis*, and it seems plausible that the HD domain of the polymerase-like protein encoded in this subtype (COG1353) might be involved in the cleavage of target DNA. There is strong evidence that, at least in vitro, the type III-B CRISPR-Cas systems can target RNA, as shown for a subtype III-B system from *furiosus*. It should be appreciated that any cas gene that belongs to the type III CRISPR system may be used for the purpose of the invention, for example, any one of cas6, cas10, csm2, csm3, csm4, csm5, csm6, cmr1, cmr3, cmr4, cmr5, cmr6, cas1 and cas2. Still further, any one of typeII-A or typeIII-B systems may be used for the kits, components and method of the invention. Of particular interest, specifically in cases where endogenous pathogenic genes are targeted by the kits and methods of the invention, the typeIII-B system may be used. The three types of CRISPR systems show a distinctly non-uniform distribution among the maj or lineages of the Archaea and the Bacteria. In particular, the type II systems have been found exclusively in the Bacteria so far, whereas type III systems are more common in the Archaea.

Typically, a repeat cluster is preceded by a 'leader' sequence, an AT-rich region several hundred base pairs long with intraspecies but not interspecies conservation. CRISPR-associated ("cas") genes, a set of conserved protein-coding genes that are associated with these loci, are usually present on one side of the array. Analysis of spacer sequences in several CRISPR loci revealed that spacers match sequences from foreign, mobile genetic elements, such as bacteriophages and plasmids. Approximately 40% of sequenced bacterial genomes, and about 90% of those from archaea (prokaryotes), contain at least one CRISPR locus.

CRISPR-Cas immune systems must discriminate between self and non-self to avoid an autoimmune response. In "type I and II CRISPR-Cas systems", foreign DNA which contain the protospacer adjacent motif (PAM) sequences are targeted for degradation, whereas potential targets in CRISPR loci of the host do not contain PAMs and are thereby avoided by RNA-guided interference complexes.

As noted above, in certain embodiments the sensitizing components of the kits of the invention may comprise at least one cas gene. In more specific embodiments, such cas gene/s may be at least one cas gene of at least one of type I, type II and type III CRISPR systems.

In some particular embodiments, such at least one cas gene may be at least one cas gene of type I-E CRISPR system. The "type-IE CRISPR" system refers to native to K-type *Escherichia coli*. It has been shown to inhibit phage infection, cure plasmids, prevent conjugal element transfer and kill cells. This CRISPR machinery can be used to degrade specific intracellular DNA in an inducible and targeted manner, leaving the remainder DNA intact.

In yet some other embodiments, the at least one type I-E cas gene comprised within the temperate phage of the invention may be at least one of cse1, cse2, cas7, cas5 cas6e and cas3 genes. In certain embodiments, in addition to at least one of cse1, cse2, cas7, cas5 cas6e and cas3 genes, the sensitizing component of the invention may further comprise at least one of cas1 and cas2 genes.

In some specific embodiments the cas genes of the sensitizing component of the invention includes cse1, gene. In more specific embodiments, such cse1 gene encodes the Cse1 protein of *Escherichia coli* str. K-12 substr. MG1655, as denoted by protein_id AAC75802.1. In more specific embodiments, the cse1 gene may comprise the nucleic acid sequence as denoted by SEQ ID NO. 60. In more specific embodiments, the cse1 gene encodes the Cse1 protein that comprises the amino acid sequence as denoted by SEQ ID NO. 67. In yet some further embodiments, the sensitizing component of the invention includes the cse2 gene. In more specific embodiments, such Cse2 protein may be the *Escherichia coli* str. K-12 substr. MG1655, as denoted by protein_id AAC75801.1. In further embodiments, the Cse2 protein used by the invention may be encoded by the nucleic acid sequence as denoted by SEQ ID NO. 61. In more particular embodiments, the cse2 protein may comprise the amino acid sequence as denoted by SEQ ID NO. 68. Still further, in certain embodiments, the sensitizing component of the invention may comprise cas7. In more specific embodiments, said cas7 protein may be the *Escherichia coli* str. K-12 substr. MG1655 Cas7 protein of id AAC75800.1. In some embodiments, the Cas7 protein is encoded by the nucleic acid sequence as denoted by SEQ ID NO. 62. Still further embodiments, relate to the Cas7 protein comprising the amino acid sequence as denoted by SEQ ID NO. 69.

Still further, the sensitizing component of the invention may comprise the cas5. More specifically, the *Escherichia coli* str. K-12 substr. MG1655 Cas5 protein_of idAAC75799.2. In some embodiments, the Cas5 protein is encoded by the nucleic acid sequence as denoted by SEQ ID NO. 63. In further embodiments, the Cas5 protein comprises the amino acid sequence as denoted by SEQ ID NO. 70.

In yet some further embodiments, the sensitizing component of the invention may comprise cas6e. In more specific embodiments, the Cas6e protein may be the *Escherichia coli* str. K-12 substr. MG1655 Cas6e protein of_id AAC75798.1. In certain embodiments, the Cas6e protein used by the invention may be encoded by a nucleic acid sequence as denoted by SEQ ID NO. 64. In further embodiments, the Cas6e protein may comprise the amino acid sequence as denoted by SEQ ID NO. 71. In some further embodiments, the temperate phage of the invention may further comprise the cas3 gene. In more specific embodiments, the cas3 gene encodes the *Escherichia coli* str. K-12 substr. MG1655 Cas3 protein of id AAC75803.1. In further embodiments, the Cas3 protein is encoded by the nucleic acid sequence as denoted by SEQ ID NO. 65. In further embodiments, the Cas3 protein may comprise the amino acid sequence as denoted by SEQ ID NO. 72.

It should be noted that the kits of the invention and particularly, the sensitizing components thereof in accordance with the present invention applies to a plurality of CRISPR-cas proteins orthologs or homologues having a sequence homology or identity to the cas proteins used as described herein before, of at least 50%, at least 60% and specifically 65%, 70%, 75%, 80%, 85%, 90%, 91%, 92%, 93%, 94%, 95%, 96%, 97%, 98%, 99%, or higher.

There are a number of well known approaches for identification and isolation of candidate orthologs or functional homologues from different species, most of which use sequence similarity on a nucleotide or protein levels. Isolated candidates are then subjected to sequencing and sequence comparisons using customary software programs such as Basic Local Alignment Search Tool (BLAST) at NCBI (The National Center for Biotechnology Information), LASERGENE bioinformatics computing suite, which is produced by DNASTAR (Madison, Wis.), or other methods (e.g. Wu et al. (eds.) "Information Superhighway and Computer Databases of Nucleic Acids and Proteins" in Methods in Gene Biotechnology (CRC Press, Inc. 1997) and Bishop (ed.) "Guide to Human Genome Computing" 2nd Edition (Academic Press, Inc. 1998).

As noted above, in certain embodiments the CRISPR cascade genes used by the kits, systems and methods of the invention may be of the *E. coli* type I-E CRISPR system. Nevertheless, as also indicated above, it should be appreciated that any other CRISPR systems may be applicable for the purpose of the invention.

Thus, in yet some further and alternative embodiments, the at least one cas gene used in the kits and systems of the invention may be at least one cas gene of type II CRISPR system (either typeII-A or typeII-B). In more particular embodiments, at least one cas gene of type II CRISPR system used by the kits of the invention may be the cas9 gene. It should be appreciated that such system may further comprise at least one of cas1, cas2, csn2 and cas4 genes.

Double-stranded DNA (dsDNA) cleavage by Cas9 is a hallmark of "type II CRISPR-Cas" immune systems. The CRISPR-associated protein Cas9 is an RNA-guided DNA endonuclease that uses RNA:DNA complementarity to identify target sites for sequence-specific doublestranded DNA (dsDNA) cleavage. The targeted DNA sequences are specified by the CRISPR array, which is a series of B30-40 bp spacers separated by short palindromic repeats. The array is transcribed as a pre-crRNA and is processed into shorter crRNAs that associate with the Cas protein complex to target complementary DNA sequences known as proto-spacers. These proto-spacer targets must also have an additional neighbouring sequence known as a proto-spacer adjacent motif (PAM) that is required for target recognition. After binding, a Cas protein complex serves as a DNA endonuclease to cut both strands at the target and subsequent DNA degradation occurs via exonuclease activity.

In some specific embodiments, the Cas9 of *Streptococcus pyogenes* M1 GAS, specifically, the Cas9 of protein id: AAK33936.1 may be applicable in the kit of the invention. In some embodiments, the Cas9 protein may be encoded by the nucleic acid sequence as denoted by SEQ ID NO. 66. In further specific embodiments, the Cas9 protein may comprise the amino acid sequence as denoted by SEQ ID NO. 73. As noted above, it should be recognized that with few adaptations, the use of the strategy may be further broadened. For example, the system may be designed to specifically eliminate phage lysogenizations and transductions by targeting specific phages, thus reducing a significant source of virulence-genes transfer. Another alteration of this strategy may deal with resistance genes encoded by chromosomal elements (as also referred to herein, endogeneous gene) rather than those transferred on mobile elements. In such cases, targeting the DNA would counter select against the transferred CRISPR-Cas as it will kill the host. However, elimination of the resistance element can still be achieved using CRISPR-Cas system that target RNA, for example, the type III-B system. While targeting the RNA will eliminate the resistance conferred by the encoded gene, it will not kill the pathogen, and would thus avoid counter selection against the delivering temperate phage. The flexibility and ease of genetically engineering spacers combined with the availability of various types of CRISPR-Cas systems may thus allow many useful variations of the strategy. In this respect, the fact that the inventors used the CRISPR-Cas subtype I-E, rather than the more frequently used subtype-IIA, demonstrates that desired outcomes may be obtained with different subtypes. Thus, in some embodiments, for targeting epichromosomal or extrachromosomal pathogenic genes, the CRISPR-Cas type I, TYPE II and type III-A systems may be used, however, where the target pathogenic gene is an endogeneous, or chromosomal gene, the type III-B system may be applicable for the components, kits and methods of the invention.

Still further, in certain specific and non-limiting embodiments, the genetically modified lysogenic phage lambda of the sensitizing component of the invention may be a phage designated IYMMPh3. In yet more specific embodiments, such genetically modified phage may comprise the nucleic acid sequence as denoted by SEQ ID No. 59.

The invention provides efficient kits, systems and methods targeting and destroying pathogenic genes of bacterial pathogens. More specifically, such bacteria or bacterial populations may be antibiotic resistant bacteria. Of particular interest are any bacteria involved in nosocomial infections. The term "Nosocomial Infections" refers to Hospital-acquired infections, namely, an infection whose development is favored by a hospital environment, such as surfaces and/or medical personnel, and is acquired by a patient during hospitalization. Nosocomial infections are infections that are potentially caused by organisms resistant to antibiotics. Nosocomial infections have an impact on morbidity and mortality, and pose a significant economic burden. In view of the rising levels of antibiotic resistance and the increasing severity of illness of hospital in-patients, this problem needs an urgent solution.

In the United States, the Centers for Disease Control and Prevention estimated roughly 1.7 million hospital-associated infections, from all types of microorganisms, however, Gram-negative infections are estimated to account for two-thirds of the annual patients' deaths. A Gram-negative bacterium *Clostridium difficile* is now recognized as the chief cause of nosocomial diarrhea in the US and Europe. Other common nosocomial organisms include methicillin-resistant *Staphylococcus aureus*, coagulase-negative Staphylococci, vancomycin-resistant Enteroccocci, resistant Enterobacteriaceae, *Pseudomonas aeruginosa, Acinetobacter* and *Stenotrophomonas maltophilia*.

The nosocomial-infection pathogens could be subdivided into Gram-positive bacteria (*Staphylococcus aureus*, Coagulase-negative staphylococci), Gram-positive cocci (*Enterococcus faecalis* and *Enterococcus faecium*), Gram-negative rod-shaped organisms (*Klebsiella pneumonia, Klebsiella oxytoca, Escherichia coli, Proteus aeruginosa, Serratia* spp.), Gram-negative bacilli (*Enterobacter aerogenes, Enterobacter cloacae*), aerobic Gram-negative coccobacilli (*Acinetobacter baumanii, Stenotrophomonas maltophilia*) and Gram-negative aerobic *bacillus* (*Stenotrophomonas maltophilia*, previously known as *Pseudomonas maltophilia*). Among many others *Pseudomonas aeruginosa* is an extremely important nosocomial Gram-negative aerobic rod pathogen.

Some embodiments of the invention relates to the kit or a system of the invention for use in targeting and eliminating pathogenic genes in bacteria of any strain of at least one of *E. coli, Pseudomonas aeruginosa, Staphylococcus aureus, Streptococcus pyogenes, Clostidium difficile, Enterococcus faecium, Klebsiella pneumonia, Acinetobacter baumanni* and *Enterobacter* species (specifically, ESKAPE bacteria).

In more specific embodiments the bacterium may be any one of *Pseudomonas aeruginosa, Streptococcus pyogenes, Clostidium difficile* and *Staphylococcus aureus*.

In further embodiments, the bacteria as referred to herein by the invention may include *Yersinia enterocolitica, Yersinia pseudotuberculosis, Salmonella typhi, Pseudomonas aeruginosa, Vibrio cholerae, Shigella sonnei, Bordetella Pertussis, Plasmodium falciparum, Chlamydia trachomatis, Bacillus anthracis, Helicobacter pylori* and *Listeria monocytogens*.

In other specific embodiments, the kit or a system of the invention are particularly suitable for use in any *E. coli* strain, specifically, any one of O157:H7, enteroaggregative (EAEC), enterohemorrhagic (EHEC), enteroinvasive (EIEC), enteropathogenic (EPEC), enterotoxigenic (ETEC) and diffuse adherent (DAEC) *E. coli*.

It should be appreciated that any unit or component or element of the kits or systems of the invention may be comprised or presented in any composition, preparation or device.

Still further, it should be understood that any composition or preparation used by the invention may comprise at least one of the kits of the invention, or at least one of its elements, components or units. In more specific embodiments, the kits, or any elements or components thereof, for example, at least one selective component and at least one sensitizing component/s may be presented at any suitable ration. For example, between about 0.0001-10,000:0.0001-10,000. More specifically, 0.0001:10000 and 10000:0.0001. In certain embodiments a cocktail of kits that are directed against different pathogenic genes, and/or different pathogenic bacteria may be used. In some embodiments, the disclosure includes CRISPR systems on the genetically modified phage of the invention which target virulent bacterial genes in bacteria within a bacterial population. The bacterial population can comprise one type of bacteria, but with virulent and non-virulent members, or the bacterial population can comprise a plurality of bacterial species, with only certain species having virulent and non-virulent members in the population. In some embodiments, a mixed bacterial population comprises at least two different strains or species of bacteria. In other embodiments, the mixed bacterial population may comprise from between two distinct types of bacteria, to up to a thousand distinct types of bacteria, or more. The kits and systems of the invention may specifically target only bacteria comprising pathogenic genes and lead to specific and targeted elimination of said pathogenic gene from any homogenous or heterogeneous bacterial population.

The proof of principle presented here is a step toward decreasing the threat of emerging drug-resistant pathogens, against which limited weapons have been developed. It demonstrates that with simple genetic engineering, bacteria can be sensitized to approved and useful antibiotics. The system may be a simple treatment for hospital surfaces and useful in hand sanitizers and possibly as a probiotic food additive to reverse the resistance of pathogens residing on hospital surfaces and in the normal flora of the medical personnel. In contrast to antibiotics and disinfectants that select for resistant pathogens, the proposed treatment enriches and selects for sensitive pathogens. Moreover, as shown by the Examples, the system enriches for pathogens that cannot transfer or receive resistance determinants horizontally, and may thus reduce the spread of antibiotic resistance. The enriched, sensitive population could prevent newly introduced resistant pathogens from becoming established by overtaking their ecological niche.

Since the CRISPR-Cas system can be programmed to eliminate any gene of interest, the system could be used to restrict transfer of any antibiotic-resistance gene. In fact, the short sequence of spacer required to eliminate an antibiotic-resistant gene enables the construction of dozens of such spacers in a single array, thus re-enabling the use of a vast number of antibiotics against which resistance has developed. It can also be programmed to simultaneously protect against several lytic phages that will be used for selection, thus reducing the occurrence of unsensitized mutants that escaped these lytic phages. Moreover, the system may be used to target lysogenic phages or any plasmid or DNA element carrying virulence genes, and by using a CRISPR-Cas system that targets RNA, it can even target virulence genes encoded by the pathogen itself.

The activity of the CRISPR-Cas system against plasmid DNA as well as against lytic phages is well established. Nevertheless, its utility in clinical settings as a tool to render pathogens sensitive to antibiotics and to reduce horizontal gene transfer of resistance determinants is novel. The proof of principle provided herein can be applied to different pathogen-phage systems as temperate phages can be found for most of the pathogens, and a compatible CRISPR-Cas system should work in many pathogens. Broad use of the proposed system, in contrast to antibiotics and phage therapy, will potentially change the nature of nosocomial infections by making the bacteria more susceptible rather than more resistant to antibiotics.

The present inventors contemplate use of the above described temperate bacteriophages to infect bacterial populations on surfaces, for example solid or liquid surface/s, or solid support, any substance, or any article, rendering antibiotic insensitive bacteria residing thereon to become sensitive to antibiotic.

Cocktails of different temperate bacteriophages that serve as the sensitizing components of the invention may be applied to surfaces, for example solid or liquid surfaces or solid support, any substance ar any article, each temperate bacteriophage having different host specificity, each carrying a CRISPR array which specifically targets antibiotic resistance genes by encoding homologous sequences to these genes in the spacers of the CRISPR array. To select and enrich for the bacteria carrying the arrays, the arrays may also carry spacers against lytic phages, thus protecting them from these agents. These lytic phages may be sprayed in the environment to exert selection pressure for the pathogens to take the sensitizing CRISPR array. It will be appreciated that the temperate bacteriophages are not bactericidal to their hosts since the bacteriophages are not modified to express agents that are toxic to bacteria.

The enriched, antibiotic-sensitive populations might then interfere with the establishment of newly introduced resistant pathogens by overtaking their ecological niche. The present approach differs from conventional phage therapy in the sense that it does not use phages to kill the pathogens directly. Consequently, there is no selection against the used phage, but rather selection for pathogens harboring the phage because it contains resistance to a lytic phage. Moreover, the approach avoids the use of phages inside the patient's body, thus overcoming toxicity issues and other drawbacks of phage therapy, such as phage neutralization by the spleen and the immune system. Extended use of this treatment will result in replacing also the natural bacterial flora of the hospital personnel (skin, respiratory and GI tracts), to carry less resistant pathogens. In yet some further embodiments, the kit of the invention may be applied on any mucosal surface, and thereby may sensitize bacterial population therein to antibiotics.

It should thus be appreciated that in certain embodiments, the temperate bacteriophage used as the sensitizing component of the kit or the system of the invention may be formulated as a spray, a stick, a paint, a gel, a cream, wash, a wipe, a foam, a soap, an oil, a solution, a lotion, an ointment, a hand sanitizer or a paste.

In yet other embodiments, the lytic bacteriophage used as the selective component of the kit or a system of the invention may be formulated as a spray, a stick, paint, a gel, a cream, a wash, a liquid, a wipe, foam, soap, oil, a solution, a lotion, an ointment or a paste.

It should be noted that in certain embodiments, the temperate bacteriophages of the sensitizing component of the kit of the invention and the lytic bacteriophages that serve as the selective component of the kit of the invention may be applied concurrently, or one following the other. Alternatively, the temperate and lytic bacteriophages may be applied on consecutive days. It should be further noted that each of these components may be comprised within any composition, formulation or vehicle that may optionally comprise at least one of pharmaceutically acceptable carrier/s, excipient/s, auxiliaries, and/or diluent/s. It should be further appreciated that in accordance with routine procedures as compositions adapted for external or internal application. Where necessary, the composition may also include a solubilizing agent or any compound facilitating application thereof.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Still further, the kits and systems of the invention and any components thereof may be applied as a single daily dose or multiple daily doses, preferably, every 1 to 7 days. It is specifically contemplated that such application may be carried out once, twice, thrice, four times, five times or six times daily, or may be performed once daily, once every 2 days, once every 3 days, once every 4 days, once every 5 days, once every 6 days, once every week, two weeks, three weeks, four weeks or even a month. The application of the kits of the invention or of any component thereof may last up to a day, two days, three days, four days, five days, six days, a week, two weeks, three weeks, four weeks, a month, two months three months or even more. Specifically, application may last from one day to one month. Most specifically, application may last from one day to 7 days. In yet some other embodiments, application of the kits and systems of the invention or any component thereof may be a routine procedure, specifically, daily procedure of treating surfaces, articles or any substance, for example, in a hospital environment.

Single or multiple applications of the kits and systems of the invention and any components thereof are applied depending on the amount and frequency as required. In any event, the kits and systems of the invention and any components thereof should provide a sufficient quantity to effectively prevent horizontal transfer of a pathogenic bacterial gene and most importantly, to prevent any pathologic disorder in a mammalian subject, caused by bacteria comprising said pathogenic gene. Preferably, the effective amount may be applied once but may be applied periodically until a result is achieved.

Hospital surfaces contain complex mixtures of bacterial populations: some of them are resistant pathogens belonging to different species. Spraying surfaces may be an effective method to target these pathogens. In certain embodiments, the spray should contain both the temperate CRISPRCas-encoding phages and the lytic phages. Delivery may also be carried out in the form of liquid added to soaps or other hand sanitizers in hospitals. These delivery methods avoid the use of phages inside the patient's tissues, thus overcoming toxicity issues and other drawbacks of phage therapy.

As noted above, this strategy may be applied for treating hospital surfaces and hand sanitizers soaps or other liquids for targeting the skin flora of medical personnel. In contrast to antibiotics and disinfectants that select for resistant pathogens, the proposed treatment enriches and selects for sensitive pathogens. Specifically, this strategy may be further broadened to Medical Departments where immune compromised patients are hospitalized in whom antibiotic resistance is a life threatening condition. In yet some further embodiments, this strategy may be also applied to elderly people, for example, subjects infected with C. difJicile, that due to antibiotic resistance may cause complications. In contrast to antibiotics and disinfectants that select for resistant pathogens, the proposed treatment enriches and selects for sensitive pathogens. Moreover, the system enriches for pathogens that cannot receive or transfer resistance determinants horizontally and may thus further reduce the spread of antibiotic resistance. The enriched sensitive population could prevent newly introduced resistant pathogens from becoming established by overtaking their ecological niche.

It should be further noted that contacting the bacterial cells with a specific CRISPR-Cas construct that targets resistance-conferring plasmids, can discriminate between antibiotic resistant and -sensitive pathogens within the same strain in complex bacterial populations.

A second aspect of the invention relates to a method of interference with a horizontal transfer of a pathogenic gene between bacteria. More specifically, the method involves the step of contacting a solid surface containing bacteria harboring such pathogenic gene, with at least one of (i) at least one selective component as described by the invention; (ii) at least one sensitizing component of the invention; and (iii) any kit comprising at least one of (i) and (ii), thereby inactivating the pathogenic gene and interfering with horizontal transfer thereof. In some embodiments, the kits or systems of the invention may be any of those described herein before.

Thus, the present invention provides a method for preventing, reducing, attenuating, inhibiting and eliminating horizontal transfer of pathogenic genes in bacterial populations. "Horizontal gene transfer" (HGT), as used herein refers to the transfer of genes between organisms in a manner other than traditional reproduction. Also termed lateral gene transfer (LGT), it contrasts with vertical transfer, the transmission of genes from the parental generation to offspring via sexual or asexual reproduction. As noted above, horizontal gene transfer is the primary reason for bacterial antibiotic resistance and transmission of virulence. This horizontal gene transfer often involves temperate bacteriophages and plasmids. Genes that are responsible for antibiotic resistance in one species of bacteria can be transferred to another species of bacteria through various mechanisms (e.g., via F-pilus). In more specific embodiments, horizontal transfer interfered, inhibited, eliminated or reduced by the kits and methods of the invention may be HGT affected by conjugative pili that allow for the transfer of DNA between bacteria, in the process of bacterial conjugation. More specifically, a pilus is typically 6 to 7 nm in diameter. During conjugation, a pilus emerging from the donor bacterium ensnares the recipient bacterium, draws it in close, and eventually triggers the formation of a mating bridge, which establishes direct contact and the formation of a controlled pore that allows transfer of DNA from the donor to the recipient. Occasionally, the DNA transferred consists of antibiotic resistance genes (often encoded on a plasmid). It should be further understood that the methods and kits of the invention may interfere with any pathway or mechanism that leads to transfer of pathogenic genes, specifically horizontal transfer, between bacteria. It should be further noted that the method of the invention may be applicable for interfering with HGT mediated either by transduction, by natural competence or by trasposons.

It should be understood that interfering with horizontal transfer in accordance with the invention may encompass any elimination, inhibition, reduction, moderation, decrease, attenuation, restraining or retardation of any transfer of pathogenic gene/s between bacteria (for example, horizontal transfer) by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

In more specific embodiments, such interference may be of at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100% of the horizontal transfer of a bacterial pathogenic gene as compared to the transfer occurred in the absence of the kits and methods of the invention.

The invention further provides a method of preventing a pathologic condition in a mammalian subject caused by a bacterial infection of bacteria containing a pathogenic gene. The method comprises contacting at least one solid or liquid surface, substance, article or support in the vicinity of the subject with at least one of (i) at least one selective component as described by the invention; (ii) at least one sensitizing component of the invention; and (iii) any kit comprising at least one of (i) and (ii), thereby targeting and inactivating the pathogenic gene that may be comprised in bacteria that exist in the environment of such subject. In such a way, the method of the invention leads to inactivation of these pathogenic genes in the bacteria, thereby preventing pathologic condition that may be caused by bacteria expressing at least one intact pathogenic gene. In some embodiments, any of the kits described by the invention may be used for any of the methods of the invention.

In some specific embodiments, the methods of the invention involve the steps of contacting a surface, specifically a solid or liquid surface, article, or any substance (specifically, in the vicinity of the subject) with the temperate bacteriophage, that is the sensitizing component of the invention, and subsequently contacting the solid surface with the lytic bacteriophage, that is the selective component of the kit or a system of the invention.

As used herein the term "contacting" refers to the positioning of the temperate bacteriophages (and optionally, the lytic bacteriophage) of the present invention such that they are in direct or indirect contact with the bacterial cells. Thus, the present invention contemplates both applying the temperate bacteriophages (and optionally the lytic bacteriophages) of the present invention to a desirable surface and/or directly to the bacterial cells.

Contacting surfaces with the kits of the invention, and specifically with the temperate bacteriophages (sensitizing component) and the lytic bacteriophages (selective component) can be effected using any method known in the art including spraying, spreading, wetting, immersing, dipping, painting, ultrasonic welding, welding, bonding or adhering.

The present invention envisages contacting a wide variety of surfaces with the bacteriophages of the present invention including fabrics, fibers, foams, films, concretes, masonries, glass, metals, plastics, polymers, and like.

According to a particular embodiment, the bacteriophages are contacted with surfaces present in a hospital, hospice, old age home, or other such care facility.

Other surfaces related to health include the inner and outer aspects of those articles involved in water purification, water storage and water delivery, and those articles involved in food processing. Thus the present invention envisions coating a solid surface in a food or beverage factory.

Surfaces related to health can also include the inner and outer aspects of those household articles involved in providing for nutrition, sanitation or disease prevention. Thus, the bacteriophages of the present invention may also be used for disinfecting toilet bowls, catheters, NG tubes, inhalators and the like. More specifically, colonization of bacteria on the interior surfaces of the catheter or other part of the device can produce serious complications, including the need to remove and/or replace the implanted device and to vigorously treat secondary infective conditions.

The medical devices which are amenable to coating, rinsing, flushing or storing with the kits of the invention generally have surfaces composed of thermoplastic or polymeric materials such as polyethylene, Dacron, nylon, polyesters, polytetrafluoroethylene, polyurethane, latex, silicone elastomers and the like. Devices with metallic surfaces are also amenable to coatings rinsing or storing with the kits of the invention, or any solution or material comprising the same. Particular devices especially suited for application of the kit of the invention include intravascular, peritoneal, pleural and urological catheters, heart valves, cardiac pacemakers, vascular shunts, and orthopedic, intraocular, or penile prosthesis.

Still further, small bore tubing that delivers ordinary running water, purified or not, to fixtures such as dental units, internal endoscopy tubing, catheter tubing, sterile filling ports, and tubing used for sterile manufacturing, food processing and the like, develop bacterial growth and bacterial resistance on their interior surfaces, as is well known. It should be appreciated that the kits of the invention may be applicable also for preventing and reducing bacterial resistance in small bore tubing as discussed herein.

In other embodiments, the kit of the invention may be applied in the vicinity of the treated subject. In some specific embodiments, the kit may be applied on any surface, device or object in the vicinity of the treated subject. The expression "vicinity of the treated subject" relates to the perimeter surrounding said subject onto which the kit according to the invention may be applied in order to prevent horizontal transfer of antibiotic resistance gene/s. Therefore, it is understood that the "vicinity of said subject" encompasses all objects present within a range of up to at least about 1 centimeter (cm), 2 cm, 3 cm, 4 cm, 5 cm, 6 cm, 7 cm, 8 m, 9 m, 10 cm, 20 cm, 30 cm, 40 cm, 50 cm, 60 cm, 70 cm, 80 cm, 90 cm, 1 meter (m), 2 m, 3 m, 4 m, 5 m, 6 m, 7 m, 8 m, 9m, 10m, 11 m, 12 m, 13 m, 14 m, 15 m, 16 m, 17, m 18 m, 19 m, 20 m, 30 m, 40 m or even 50 m of said subject. The term "vicinity of said subject" also relates to objects to which the kit of the invention is applied to prior to their placement in said range of the treated subject.

According to one embodiment, the kits or any components or any bacteriophages of the invention may be applied every 12 hours, daily, 6 times a week, 5 times a week, four times a week, three times a week, twice a week or even once a week to the solid surface.

In some embodiments, the kits of the invention may be used and applied on any surface that is used in food industry or is in contact with any food or food or food product. For example, foods or food products include any suitable meat or meat product derived from, but not limited to, pork, beef, veal, mutton, lamb, sheep, goat, bison, elk, deer, antelope, horse, dog, poultry (e. g., such as chicken, turkey, duck, goose, guinea fowl, ostrich, quail, dove, pigeon, emu, pea hen), or the meat of any other mammalian or bird (avian) species. A "beef product" contains the meat of an adult mammal of the subfamily Bovinae, including cattle, buffalo, bison, and kudus. A "pork product" contains the meat of a pig. A "poultry product" contains the meat of a bird, such as a chicken, duck, goose, turkey, ostrich, emu, dove, pigeon, quail, pheasant, peafowl, or guinea fowl. It should be noted that "Meat" includes whole or ground muscle or organ (e. g. liver).

Slaughtering of animals is challenged by severe hygienic problems which results in heavy bacterial loads on the produced meat through cross contamination. Thus, in some embodiments, the kits of the invention may be applied on any surface or article used in slaughterhouse or grocery stores preparing and storing meat or any meat products, specifically, containers, stainless steel boxes, beef tenderizers, grinders, knives, mixers, sausage stuffers, plastic boxes, floors and drains. In the slaughterhouse, such surfaces include sausage stuffers, platforms, floors and drains. In yet some further specific embodiments, the kits of the invention may be applied on any biological or non-biological surface used in food industry, specifically, any surface involved in the preparation, delivery and storage of meat products. More specifically, any surface in slaughterhouses, including the carcasses of hogs, beef, and other livestock may also be treated with the kit of the invention to reduce bacterial load and increase sensitivity to antibiotics. More specifically, the entire carcass of the animal may be dipped in or sprayed with a solution or liquid containing the kit of the invention.

In yet some further embodiments, the kits of the invention may be applied on any containers and food-handling implements for holding a foodstuff, which includes containing, packaging, covering, storing, displaying, processing, cutting, chopping, impaling, kneading, manipulating or otherwise handling the foodstuff, such that a surface of the food container or implement comes in contact with the food.

As noted above, the kits of the invention may be applicable for any surface used for storage or delivery of any food, specifically, meat. Packaging may be by any conventional meat packaging means, including containing the meat product with a tray, a transparent film, such as shrink-wrap or Saran, or with a paper, including unwaxed or waxed paper, or wrapping, bagging, boxing, canning or jarring by any means suitable for a meat product.

More specifically, the containers and implements are in any suitable disposable (i. e., single-use) or non-disposable (i. e., multi-use) configuration capable of holding a foodstuff. These configurations include, but are not limited to, shear wraps, sheets, papers, waxed papers, bags, cartons, trays, plates, bowls, covered and uncovered storage vessels, serving dishes, cups, cans, jars, bottles, or any other suitable container configuration for a particular foodstuff. Additional configurations especially useful for food handling purposes include, but are not limited to, gloves or mitts; utensils such as forks, spoons, knives, slicers, processors, juicers, grinders, chippers, hooks, presses, screws, openers, cutters, peelers, tongs, ladles, scoops, cups, chutes or spatulas; and cutting boards, kneading boards, mixing bowls, drying or cooling racks, or shelves.

In yet some further embodiments, the kits of the invention may be used on any surface or container used in sea food. Specifically, seafood includes any marine or freshwater aquatic organisms, such as various fishes (e. g., tuna, salmon, halibut, cod, shark, swordfish, bass, herring, sardines, trout, carp, whitefish, and perch), mollusks (clams, scallops, oysters, mussels, snails, octopus, and squid), or crustaceans (e. g., crabs, shrimps, lobsters, and crayfish).

Eggs are also subject to contamination, particularly *Salmonella* contamination and contamination of chicken eggs can occur in a number of ways. Prior to being laid, chicken eggs may become horizontally infected, constituting movement of bacteria into the developing egg, while the egg is still in the oviduct of the hen.

Bacterial contamination can also occur through vertical infection during the laying process. Hens are a common carrier of a number of bacteria and many of which, like *Salmonella*, exist in the alimentary canals. Eggs can be contaminated by these bacteria as they are deposited through the cloaca, a structure which serves as the end of the reproductive, urinary, and intestinal tract. Generally, the bacteria existing on and in the chicken (both pathogenic and normal flora) are deposited with the egg, and upon making contact, they are able to permeate the shell before the outer layer (the cuticle) hardens. After deposition, eggs may also come into contact with environmental bacteria. These bacteria may permeate the shell, especially if contamination occurs shortly after lay, or may accumulate on the shell, resulting in eventual penetration of the shell. Bacteria that accumulate on the shell may penetrate the shell during processing. More specifically, when eggs experience temperature changes, as often occurs during washing and sterilization of commercial eggs, the contents of the egg contract, creating a negative pressure gradient, which effectively pulls bacteria through the shell and outer membrane. Thus, in some embodiments, the kits of the invention may be sprinkled on the egg. Alternatively, the egg may be rolled in a powder containing the kit of the invention or immersed in a solution containing the same.

Still further, in some embodiments, the kit of the invention may be applied on any housing systems, cages and any equipment used for and in contact with laying hens.

In yet some further embodiments, the kits of the invention may be used as food-additive in pets food to reduce transmission of antibiotic-resistant pathogens to humans, and to treat them efficiently with antibiotics when required, the product herein described may also be used as, in or as an additive to foods intended for consumption by any essentially domesticated or tamed animal or bird, such as rabbits, guinea pigs, tropical fish and birds. The term "pet food" as used herein generally refers to any food intended for consumption by pets. Specifically, "pet food additive" as used herein generally refers to any product which is intended to be added to (e. g. incorporated into and/or applied to) a pet food, for example during the process or immediately prior to consumption of the food.

In should be appreciated that in some embodiments, the methods of the invention may use any of the kits and systems as defined by the invention, herein above. More specifically, in some embodiments, the selective component of the kits used by the methods of the invention may be any DNA sequence comprising at least one protospacer recognized by at least one spacer of the sensitizing component, and a sequence encoding at least one toxic agent or any bacterial killer. In yet some other embodiment, the selective component may comprise at least one lytic bacteriophage. In some specific embodiments such lytic bacteriophage may be at least one genetically modified bacteriophages comprising at least one proto-spacer having an identity of at least 70% to at least one nucleic acid sequence comprised within said bacterial pathogenic gene. In further embodiments, the sensitizing component of the kits used by the methods of the invention may comprise at least one recombinant vector comprising a nucleic acid sequence encoding at least one cas protein. Such vector may further comprise a nucleic acid sequence of at least one of said CRISPR array.

Still further, such vector may be at least one genetically modified bacteriophage comprising at least one CRISPR spacer that targets at least one nucleic acid sequence comprised within said lytic bacteriophage and at least one CRISPR spacer that targets a nucleic acid sequence comprised within said at least one pathogenic gene, thereby targeting and inactivating both, the lytic phage and said pathogenic gene.

In certain embodiments, the target bacterial pathogenic gene may be at least one bacterial endogenous gene or alternatively, an epichromosomal gene. In certain embodiments, the pathogenic gene may be an antibiotic resistance gene. Alternatively, the pathogenic gene may be a gene encoding at least one of a virulence factor and at least one toxin. In certain embodiments, the antibiotic resistance gene targeted by the kits of used by the methods of the invention may encode a resistance factor selected from the group consisting of CTX-M-15, New Delhi metallo-3-lactamase (NDM)-1, 2, 5, 6, an extended-spectrum beta-lactamase resistance factor (ESBL factor), beta lactamase, and tetracycline A (tetA). In more specific embodiments, the at least one CRISPR spacer of the sensitizing component of the kits used by the methods of the invention may comprise a nucleic acid sequence that targets at least one of: at least one proto-spacer of CTX-M-15, at least one proto-spacer of NDM-1, 2, 5, 6, at least one proto-spacer of ESBL factor, at least one proto-spacer of beta lactamase, at least one proto-spacer of tetA and at least one at least one proto-spacer of a lytic bacteriophage.

More specifically, at least one of the proto-spacer of CTX-M-15, may comprise a nucleic acid sequence as denoted by any one of SEQ ID NO. 49, 50 and 51 and at least one of said proto-spacer of NDM-1, may comprise a nucleic acid sequence as denoted by any one of SEQ ID NO. 46, 47 and 48.

In yet some further embodiments, the genetically modified lytic bacteriophage used as the selective component of the kits used by the methods of the invention may comprise at least one of: (a) at least one proto-spacer of CTX-M-15, comprising a nucleic acid sequence as denoted by any one of SEQ ID NO. 49, 50 and 51; and (b) at least one proto-spacer of NDM-1 comprising a nucleic acid sequence as denoted by any one of SEQ ID NO. 46, 47 and 48.

In certain particular and alternative embodiments, the sensitizing component of the kits used by the methods of the invention may comprise at least one CRISPR spacer that targets a nucleic acid sequence comprised within an essential gene of the lytic bacteriophage. More specifically, such lytic bacteriophage may be at least one of T7like-virus and T4like-virus. In some specific embodiments, such T7like-virus may be at least one Enterobacteria phage T7.

In yet some other embodiments, the sensitizing component of the kits used by the methods of the present invention may comprise a bacteriophages, specifically, a lambda temperate bacteriophage. Still further, the at least one cas gene of the sensitizing component of the kits used by the methods of the invention may be at least one cas gene of at least one of type I, type II and type III CRISPR systems.

In some specific embodiments, the sensitizing component of the kits used by the methods of the invention may comprise at least one cas gene of type I-E CRISPR system. In more specific embodiments, such type I-E cas gene may be at least one of cse1, cse2, cas7, cas5e cas6 and cas3 genes. In some alternative embodiments, the at least one cas gene of the sensitizing component of the kits used by the methods of the invention may be at least one cas gene of type II CRISPR system. In more specific embodiments, at least one cas gene of type II CRISPR system may be cas9 gene. It should be further noted that the methods and kits of the invention may target at least one bacterium of any strain of at least one of *E. coli, Pseudomonas aeruginosa, Staphylococcus aureus, Streptococcus pyogenes, Clostidium difficile, Enterococcus faecium, Klebsiella pneumonia, Acinetobacter baumanni* and *Enterobacter* species. In more specific embodiments, such bacteria may be at least one *E. coli* strain selected from the group consisting of O157:H7, enteroaggregative (EAEC), enterohemorrhagic (EHEC), enteroinvasive (EIEC), enteropathogenic (EPEC), enterotoxigenic (ETEC) and diffuse adherent (DAEC) *E. coli*.

In further embodiments, the at least one of the temperate bacteriophage and the lytic bacteriophage of the kits used by the methods of the invention may be formulated as a spray, a stick, a paint, a gel, a cream, wash, a wipe, a foam, a soap, a liquid, an oil, a solution, a lotion, an ointment or a paste.

Another aspect of the invention relates to a genetically modified, temperate bacteriophage. More specifically, the temperate bacteriophage may comprise at least one CRISPR array. In more specific embodiments, at least one spacer of the CRISPR is complementary to a nucleic acid sequence comprised within at least one pathogenic gene of a bacterium (that is a portion of said gene), so as to target and inactivate the at least one pathogenic gene in the bacterium. It should be further noted that at least one spacer of said CRISPR array is sufficiently complementary to a nucleic acid sequence comprised within a lytic bacteriophage so as to target and inactivate the lytic phage. In such a way, a bacterium infected by the temperate phage of the invention is insensitive and resistant to the lytic phage.

Still further aspect of the invention relates to any of the genetically modified lytic phages described by the invention.

As used herein, the term 'polynucleotide' or a 'nucleic acid sequence' refers to a polymer of nucleic acids, such as deoxyribonucleic acid (DNA) or ribonucleic acid (RNA). As used herein, 'nucleic acid' (also or nucleic acid molecule or nucleotide) refers to any DNA or RNA polynucleotides, oligonucleotides, fragments generated by the polymerase chain reaction (PCR) and fragments generated by any of ligation, scission, endonuclease action, and exonuclease action, either single- or double-stranded. Nucleic acid molecules can be composed of monomers that are naturally-occurring nucleotides (such as DNA and RNA), or analogs of naturally-occurring nucleotides (e.g., alpha-enantiomeric forms of naturally-occurring nucleotides), or modified nucleotides or any combination thereof. Herein this term also encompasses a cDNA, i.e. complementary or copy DNA produced from an RNA template by the action of reverse transcriptase (RNA-dependent DNA polymerase).

In this connection an 'isolated polynucleotide' is a nucleic acid molecule that is separated from the genome of an organism. For example, a DNA molecule that encodes the cas gens used by the kit of the invention or any derivatives or homologs thereof, as well as the sequences comprised within the CRISPR spacers and repeats of the kit of the invention, that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

The invention further relates to recombinant DNA constructs comprising the polynucleotides of the invention, specifically, those encoding the cas-CRISPR system of the invention, or any variants, homologues or derivatives thereof. The constructs of the invention may further comprise additional elements such as promoters, regulatory and control elements, translation, expression and other signals, operably linked to the nucleic acid sequence of the invention. As used herein, the term "recombinant DNA" or "recombinant gene" refers to a nucleic acid comprising an open reading frame encoding one of the proteins of the invention.

It should be appreciated that in some embodiments, the selective and the sensitizing components of the kits of the invention may be applied on any biological surface or tissue. In yet some further specific embodiments, the kits of the invention may be applied on any mucosal surface. More specifically, mucosal surfaces or the mucosae (singular mucosa), as used herein refer to mucosal epithelia that secrets mucus and line the gastrointestinal, respiratory, genital and urogenital tracts, and are also present in the exocrine glands associated with these organs: the pancreas, the conjunctivae and lachrymal glands of the eye, the salivary glands, and the mammary glands of lactating breast. Because of their physiological functions of gas exchange (lungs), food absorption (gut), sensory activity (eyes, nose, mouth, and throat), and reproduction (uterus, vagina, and breast), the mucosal surfaces are by necessity dynamic, thin, permeable barriers to the interior of the body. These properties make the mucosal tissues particularly vulnerable to subversion and breach by pathogens. Thus, applying the kits of the invention on mucosal surfaces may lead to reduction in bacterial load (due to the selective component), sensitize remaining pathogens (due to the sensitizing component), and thereby may boost antibiotic treatment of bacterial infections and associated conditions. It should be noted that reduction of bacterial load as used herein refers to by any one of about 1% to 100%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9% or more, specifically, 100% of bacterial load.

In yet some further specific embodiments, applying the kit of the invention on mucosal surfaces, for example, lung tissue (e.g., by using any inhalator), may be specifically applicable for patients suffering from chronic respiratory infections. For example, *Pseudomonas aeruginosa* (PA) is commonly isolated from the respiratory tracts of individuals with cystic fibrosis and is associated with an accelerated decline in lung function in these patients, and therefore, increasing the sensitivity of these bacteria to antibiotic treatment using the kit of the invention may improve and ameliorate CF patients condition and associated symptoms. More specifically, Cystic fibrosis (also known as CF) as used herein, refers to the characteristic scarring (fibrosis) and cyst formation within the pancreas. Difficulty breathing is the most serious symptom and results from frequent lung infections that are treated, though not cured, by antibiotics and other medications. A multitude of other symptoms, including sinus infections, Door growth, diarrhea, and infertility result from the effects of CF on other parts of the body. CF is caused by a mutation in the oene for the protein cystic fibrosis transmemnbrane conductance regulator (CFTR), and is considered as an autosomal recessive disease. As noted above, applying the kit of the invention on lung tissue of CF patients, may improve patient's condition.

Still further, the kit of the invention may be also applicable for any chronic lung colonization and infection that may also occur in bronchiectasis, a disease of the bronchial tree, and in chronic obstructive pulmonary disease, a disease characterized by narrowing of the airways and abnormalities in air flow. Still further, it may be applicable also for pneumonia in hospitalized patients, especially in mechanically ventilated patients.

In yet some further embodiments, application of the kit of the invention on urogenital or genital tract may be also applicable for urinary tract infections. It should be appreciated that the kit of the invention may be also applicable on any surface that is in contact with the mucosal tissue, for example, peds, tempones and the like.

Still further, as a biological surface, the kits of the invention may be applied or sprayed on a skin, specificaly, wounded skin, for example in case of burns. Therefore, spraying or any topical administration or dressing of the affected skin areas of an ointment, cream, suspensions, paste, lotions, powders, solutions, oils, gel or powder containing the kit/s of the invention, or sprayable aerosol or vapors containing the kits disclosed by the invention or any components thereof, are also encompassed by the invention. Conventional pharmaceutical carriers, aqueous, powder or oily bases, thickeners and the like may be necessary or desirable. The term "topically applied" or "topically administered" means that the ointment, cream, emollient, balm, lotion, solution, salve, unguent, or any other pharmaceutical form is applied to some or all of that portion of the skin of the patient skin that is, or has been, affected by, or shows, or has shown, one or more symptoms of bacterial infectious disease, or any other symptoms involving the skin. It should be appreciated that the kits of the invention may be applied on any matrix, fabric or bandage used for treating skin disorders, thereby sensitizing bacterial population to antibiotic treatment.

As noted above, it should be appreciated that the kits of the invention or any component thereof may be applied on any surface, device, container or apparatus that may be in contact with mucosal tissue. In yet some specific example, eye infections caused by bacteria on contact lenses (CLs), CL storage cases and care solutions may be a risk factor for CL-associated corneal infection and may explain the persistence of organisms in CL storage cases. Different types of lens wear modalities require the use of a contact lens storage case and care solutions for overnight storage and disinfection. However, the contact lens storage cases as well as storage solutions can become contaminated by bacteria. Factors other than hygiene behaviors, including microbial resistance, may be associated with persistent microbial contamination of contact lens storage cases and care solutions. During storage the lenses are susceptible to colonization by a variety of bacterial strains and other microorganisms, and this problem exists even when the lenses are stored in a disinfecting solution containing hydrogen peroxide, chiorhexidine, biguanides or quaternary ammonium compounds. While the most serious infection associated with contact lens use may be microbial keratitis, contamination of the lens care system could lead to production of toxins that can affect the eye. By providing efficient sensitizing kit/s, the invention provides compositions and methods for storing contact lens, and thus also encompasses methods for inhibiting, reducing or eliminating corneal infections. The methods described above may comprise the steps of providing a lens storage container coated with the kit/s of the invention or any component thereof and alternatively or additionally, providing care solutions (storage solution) comprising the kits of the invention, and inserting the contact lens into the container coated with the kits of the invention and/or or rinsing the contact lens with a solution comprising an effective amount of the kits of the invention.

It should be further appreciated that the invention thus provides contact lenses storage case/s coated with, applied or containing the kit/s of the invention. In yet some further embodiments, the invention provides contact lenses storage and care solutions containing the kits of the invention.

Still further, the invention further provides therapeutic methods comprising the step of administering a therapeutically effective amount of the kit of the invention, optionally in combination with at least one antibiotic compound, specifically, any of the antibiotics disclosed herein before), to a subject suffering from an infectious disease. It should be further noted that the application of the kit of the invention or any component thereof, may form a complementary treatment regimen for subjects suffering from an infectious disease or condition.

The term "treatment" in accordance with disorders associated with infectious conditions may refer to one or more of the following: elimination, reducing or decreasing the intensity or frequency of disorders associated with said infectious condition. The treatment may be undertaken when disorders associated with said infection, incidence is beginning or may be a continuous administration, for example by administration every 1 to 14 days, to prevent or decrease occurrence of infectious condition in an individual prone to said condition.

The term "prophylaxis" refers to prevention or reduction the risk of occurrence of the biological or medical event, specifically, the occurrence or re occurrence of disorders associated with infectious disease, that is sought to be prevented in a tissue, a system, animal or human by a researcher, veterinarian, medical doctor or other clinician, and the term "prophylactically effective amount" is intended to mean that amount of a pharmaceutical composition that will achieve this goal. Thus, in particular embodiments, the methods of the invention are particularly effective in the prophylaxis, i.e., prevention of conditions associated with infectious disease. Thus, subjects administered with said compositions are less likely to experience symptoms associated with said infectious condition that are also less likely to re-occur in a subject who has already experienced them in the past.

The term "amelioration" as referred to herein, relates to a decrease in the symptoms, and improvement in a subject's condition brought about by the compositions and methods according to the invention, wherein said improvement may be manifested in the forms of inhibition of pathologic processes associated with bacterial infections, a significant reduction in their magnitude, or an improvement in a diseased subject physiological state.

The term "inhibit" and all variations of this term is intended to encompass the restriction or prohibition of the progress and exacerbation of pathologic symptoms or a pathologic process progress, said pathologic process symptoms or process are associated with.

The term "eliminate" relates to the substantial eradication or removal of the pathologic symptoms and possibly pathologic etiology, optionally, according to the methods of the invention described below.

The terms "delay", "delaying the onset", "retard" and all variations thereof are intended to encompass the slowing of the progress and/or exacerbation of a pathologic disorder or an infectious disease and their symptoms slowing their progress, further exacerbation or development, so as to appear later than in the absence of the treatment according to the invention.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, "disease", "disorder", "condition" and the like, as they relate to a subject's health, are used interchangeably and have meanings ascribed to each and all of such terms.

The present invention relates to the treatment of subjects, or patients, in need thereof. By "patient" or "subject in need" it is meant any organism who may be infected by the above-mentioned pathogens, and to whom the preventive and prophylactic kit/s, system/s and methods herein described is desired, including humans, domestic and non-domestic mammals such as canine and feline subjects, bovine, simian, equine and murine subjects, rodents, domestic birds, aquaculture, fish and exotic aquarium fish. It should be appreciated that the treated subject may be also any reptile or zoo animal. More specifically, the kit/s and method/s of the invention are intended for preventing pathologic condition in mammals. By "mammalian subject" is meant any mammal for which the proposed therapy is desired, including human, equine, canine, and feline subjects, most specifically humans. It should be noted that specifically in cases of non-human subjects, the method of the invention may be performed using administration via injection, drinking water, feed, spraying, oral gavage and directly into the digestive tract of subjects in need thereof.

Still further, it should be noted that the invention further provides methods for sensitizing bacterial population or increasing the sensitivity of said population to at least one antibiotic compound, by applying the kits of the invention and any components thereof on said bacterial population.

In yet some further aspects, the invention provides methods for preventing or reducing resistance of bacteria or bacterial population/s to at least one antibiotic compound using the kits of the invention and any component thereof.

The invention further provides a method for treating outbreak of pathogenic bacteria by applying the kits of the invention or any components thereof on surfaces comprising said bacteria.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

All scientific and technical terms used herein have meanings commonly used in the art unless otherwise specified. The definitions provided herein are to facilitate understanding of certain terms used frequently herein and are not meant to limit the scope of the present disclosure.

As used herein the term "about" refers to +10% The terms "comprises", "comprising", "includes", "including", "having" and their conjugates mean "including but not limited to". The term "consisting essentially of" means that the composition, method or structure may include additional ingredients, steps and/or parts, but only if the additional ingredients, steps and/or parts do not materially alter the basic and novel characteristics of the claimed systems, kit, composition, method or structure.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to +10%.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It should be noted that various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Experimental Procedures

Reagents, Strains, and Plasmids

Luria-Bertani (LB) medium (10 g/L tryptone, 5 g/L yeast extract, and 5 g/L NaCl) and agar were from Acumedia. 2YT medium contained 1.6% (w/v) Bacto-tryptone (Acumedia), 1% (w/v) Bacto-yeast extract (Acumedia), and 0.5% (w/v) NaCl (Acumedia) in distilled water. Antibiotics, lysozyme, L-arabinose, and maltose were from Calbiochem. Sodium chloride and magnesium sulphate were from Merck. Restriction enzymes, ligation enzymes, and Phusion® High-Fidelity DNA Polymerase were from New England Biolabs. The bacterial strains, plasmids, and phages used in this study are listed in Table 1.

TABLE 1

Bacterial strains, plasmids and phages

| | Description | Source of reference |
|---|---|---|
| Bacterial strains | | |
| NEB5α | F$^-$ φ80lacZΔM15Δ(lacZYA-argF) U169 deoR recA1 endA1 hsdR17 ($r_k^-$, $m_k^+$) gal$^-$ phoA supE44 λ$^-$ thi$^-$ 1 gyrA96 relA1 | New England Biolabs |
| DY378 | W3110 λcI857 Δ(cro-bioA) | (25) |
| BW25113ΔyeeX | F$^-$, Δ(araD-araB)567, ΔyeeX::kan, ΔlacZ4787(::rrnB-3), λ$^-$, rph-1, Δ(rhaD-rhaB)568, hsdR514 | (30) |
| RE1001 | K12-araB::T7RNAP-tetA | (26) |
| RK6471 | K12-araB::T7RNAP-tetA, T7cas3::kan, T7 cse1::cm | The present invention |
| IYB5101 | BW25113 araB::T7-RNAp-tetA, tet$^r$ | (26) |
| IYB5666 | IYB5101 Δ(cas3-cas2):: cm | The present invention |
| IYB5670 | BW25113 araB::T7-RNAp-tetA, tet$^r$. harbors λcas prophage. | The present invention |
| IYB5671 | BW25113 araB::T7-RNAp-tetA, tet$^r$. harbors λcas-CRISPR prophage. | The present invention |
| BL21-AI | F$^-$ ompT hsdSB(rB-, mB-) gal dcm araB::T7RNAP-tetA, tet$^r$ | Invitrogen (25) |
| IYB5297 | F$^-$ ompT hsdSB(rB-, mB-) gal dcm araB::T7RNAP-tetA, tet$^r$. harbors λcI857-kan prophage. | The present invention |
| IYB5614 | F$^-$ ompT hsdSB(rB-, mB-) gal dcm araB::T7RNAP-tetA, tet$^r$. harbors λcas prophage. | The present invention |
| IYB5656 | F$^-$ ompT hsdSB(rB-, mB-) gal dcm araB::T7RNAP-tetA, tet$^r$. harbors λcas-CRISPR prophage. | The present invention |
| Phages | | |
| λcI857-kan | cI857 Kan$^R$- | (31) |
| λcas-cm | cI857 Kan$^R$, cm$^R$. Contains cas3 under T7 promoter and casABCDE under T7 promoter | The present invention |
| λcas | cI857 Kan$^R$. Contains cas3 under T7 promoter and casABCDE under T7 promoter | The present invention |
| λcas-CRISPR | cI857 Kan$^R$, cm$^R$. Contains cas3 under T7 promoter, casABCDE under T7 promoter and engineered CRISPR array under T7 promoter. | The present invention |
| T7$_{FRT\ trxA}$ | T7 with trxA flanked by FRT sites | (27) |

TABLE 1-continued

Bacterial strains, plasmids and phages

| | Description | Source of reference |
|---|---|---|
| Plasmids | | |
| pCas 1 + 2 | pCDF-1b (Novagen) cloned with cas1,2 under T7 promoter, $str^r$ | (23) |
| pIYEC1 | pUC57 cloned with anti NDM-1, CTX-M-15 and T7 phage spacers under T7 promoter, $Amp^R$ | The present invention |
| pIYEC2 | pUC57 cloned with anti NDM-1, CTX-M-15 and T7 phage spacers under T7 promoter, $Cam^R$, $Amp^R$ | The present invention |
| pNDM | pCDF-1b (Novagen) based containing New Delhi Metallo-beta-lactamase-1 (NDM-1). | The present invention |
| pCTX | pCDF-1b (Novagen) based containing CTX-M-15 beta-lactamase. | The present invention |
| pVEC | pCDF-1b (Novagen) based plasmid. | The present invention |
| pNDM | Pbil2c BASED CONTAINING New Delhi Metallo-bata-lactamase-1 $Gentamicin^r$, $Carbapenem^r$ | The present invention |
| pTRX1 | pGEM t-vector (promega) cloned with gp8 proto-spacer (ref severinov). | The present invention |
| PTRX2 | pGEM T-vector (promega) cloned with NDM-1 proto-spacer. | The present invention |
| PTRX3 | pGEM T-vector (promega) cloned with CTX-M-15 proto-spacer. | The present invention |
| pTRX4 | pGEM T-vector (promega) cloned with NDM-1 and CTX-M-15 proto-spacer. | The present invention |
| pTRX5 | pGEM T-vector (promega) cloned with NDM-1 and CTX-M-15 proto-spacer. | The present invention |
| pKD3 | pSC101 encoding chloramphenicol resistance marker flanked by FRT sites. | (22) |

Plasmid Construction

Plasmids were constructed using standard molecular biology techniques. DNA segments were amplified by PCR. Standard digestion of the PCR products and vector by restriction enzymes was carried out according to the manufacturer's instructions. pIYEC1 plasmid, synthesized by GenScript, encodes a CRISPR array transcribed by a T7 promoter encoding three spacers targeting the ndm-1 gene ($N_1$, $N_2$, $N_3$, the spacers are denoted by SEQ ID NO. 37, 38, 39 and their corresponding proto-spacers as denoted by SEQ ID NO. 46, 47, 48), three spacers targeting the ctx-M-15 gene ($C_1$, $C_2$, $C_3$, the spacers are denoted by SEQ ID NO. 40, 41, 42. Said spacers target proto-spacers comprising the nucleic acid sequence of any one of SEQ ID NO. 49, 50, 51)), and three spacers targeting the T4 phage genome (T1, T2, T3 the spacers are denoted by SEQ ID NO. 43, 44, 45. Said spacers target proto-spacers comprising the nucleic acid sequence of any one of SEQ ID NO. 52, 53, 54). pIYEC2 is similar to pIYEC1 except that it also encodes a chloramphenicol resistance marker. To construct pIYEC2, the chloramphenicol resistance marker from pKD3 (22) was amplified using oligonucleotides IY344F and IY344R. The amplified DNA and pIYEC1, both digested by HindIII, were ligated to yield pIYEC2. pNDM and pCTX plasmids were constructed by ligating PCR fragments encoding ndm-1 or ctx-M-15 to another PCR fragment containing an origin of replication and a $str^r$ marker derived from plasmid pCas 1+2 (23) using oligonucleotides IY246F and IY246R for pNDM and IY346F and IY346R for pCTX. Plasmid pVEC was constructed by ligating an irrelevant DNA fragment to the origin of replication and the $str^r$ marker derived from plasmid pCas1+2. Plasmids pTRX1, pTRX2, pTRX3, pTRX4, and pTRX5 were constructed to insert protospacers into the T7 genome (Table 1). The plasmids encode the trxA gene, a positive selection marker for T7 grown on hosts lacking trxA, flanked by desired protospacers and followed by 50 bp upstream and downstream of a DNA sequence corresponding to the end of T7 gene 1.3 and the beginning of T7 gene 1.4, respectively. The plasmids were constructed by PCR amplification of T7 phage encoding a trxA gene flanked by Flippase recognition target sites using the primers indicated in Tables 2 and 3. The resulting PCR product was used as a template for PCR using primers IY260F and IY260R (SEQ ID NO. 24 and 25 Table 2). The final PCR fragment was ligated into pGEM-T vector (Promega). Constructed plasmids were validated as encoding the desired fragments by DNA sequencing.

TABLE 2

Oligonucleotide primers

| Oligo-nucleotides | 5'→3' | SEQ ID. NO: |
|---|---|---|
| IY344F | ACCGAAGCTTTGAATATCCTCCTTAGTTCC | 1 |
| IY344R | CGCCAAGCTTACGGGGCAACCTCATGTCAAGTGTAGGCTGGAGCTGCTTC | 2 |
| IY246F | ATGGAATTGCCCAATATTAT | 3 |
| IY246R | TCAGCGCAGCTTGTCGGCCA | 4 |
| IY247F | GAACTAAATCAGGCACTTGAGCATCAAGATTGGTG | 5 |
| IY247R | CACCAATCTTGATGCTCAAGTGCCTGATTTAGTTC | 6 |
| IY346F | ATGGTTAAAAAATCACTGCGCCAGT | 7 |
| IY346R | TTACAAACCGTCGGTGACGA | 8 |
| IY142Fb | CACACGGTCACACTGCTTCC | 9 |
| MG110R | CGATGCCCTTGAGAGCCTTC | 10 |
| MG17F | ATAAGTCGGACACCATGGCA | 11 |
| IY80F | AATAGCCCGCTGATATCATCGATAATACTAAAAAAACAGGGAGGCTATTAGTGTAGGCTGGAGCTGCTTC | 12 |
| IY80R | ACCTTAATGTAACATTTCCTTATTATTAAAGATCAGCTAATTCTTTGTTTTGAATATCCTCCTTAGTTCC | 13 |

TABLE 2-continued

Oligonucleotide primers

| Oligo-nucleotides | 5'→3' | SEQ ID. NO: |
|---|---|---|
| IY333F | ATGCGTAATGTGTGTATTGCCGTTGCTG TCTTTGCCGCACTTGCGGTGACCCGGAA TGAAATTAATACGACTC | 14 |
| IY333R | AACCTGTCGCACTCCAGAGAAGCACAAA GCCTCGCAATCCAGTGCAAAGCTCACAG TGGAGCCAAAGATA | 15 |
| IY347F | GGCCAGCTAAATCGATGGGATGTGGCTT GCTATCTTTGGCTCCACTGTGAGGGATG TGCTGCAAGGCGAT | 16 |
| IY347R | AACCTGTCGCACTCCAGAGAAGCACAAA GCCTCGCAATCCAGTGCAAAGCACGGGG CAACCTCATGTCAA | 17 |
| IY309F | ACCCTCAAGAGAAAATGTAAAAGCTGTC TTTCGCTGCTGAGGGTGACGATCCCGCG ATCCGTCAGCCTGCAGTTC | 18 |
| IY309R | CCGAAGGTGAGCCAGTGTGAAAGCTGTC TTTCGCTGCTGAGGGTGACGATCCCGCT GTAGGCTGGAGCTGCTTCG | 19 |
| IY340Fa | ACCCTCAAGAGAAAATGTAAAAGCTGAG CACCGCATTAGCCGCTGCATTGATGCTG ATCCGTCAGCCTGCAGTTC | 20 |
| IY340Fb | ACCCTCAAGAGAAAATGTAAAAGCTGAT TGCTCACGTTGGCGGCCCGGCTAGCGTG ATCCGTCAGCCTGCAGTTC | 21 |
| IY340Ra | CCGAAGGTGAGCCAGTGTGAGTACGTCC GCCGTTTGCGCATACAGCGGCACACTTT GTAGGCTGGAGCTGCTTCG | 22 |
| IY340Rb | CCGAAGGTGAGCCAGTGTGAACCGCCAG CGCGACCGGCAGGTTGATCTCCTGCTTT GTAGGCTGGAGCTGCTTCG | 23 |
| IY260F | TGGCTCTTTGCGGCACCCATCGTTCGTA ATGTTCCGTGGCACCGAGGACAACCCTC AAGAGAAATGTAA | 24 |
| IY260R | CCAACCTTCTTAAACATAAAGTGTCTCC TTATAAACGCAGAAAGGCCCACCCGAAG GTGAGCCAGTGTGA | 25 |
| RK41F | GGAATTACTTCGCTTCGCC | 26 |
| RK41R | CCTCCTTATCTCCCTATAGTGAGTCGTA TTAATTTCATTCCGGGGATCCGTCGACC | 27 |
| RK42F | AAACGCGTTTCTTTGGCTTAAAAAGGGA ATGTGGGTTACACGAAGGGTAATGTAGG CTGGAGCTGCTTCG | 28 |
| RK42R | GGATTTTCCCCAGTAATGGCATATATAT TTAAAAGGTTCCATTAATAGCCCCTCCT TATCTCCCTATAGT | 29 |
| RK43F | GCAGCATTACACGTCTTGAG | 30 |
| RK43R | CTCCTTATCTCCCTATAGTGAGTCGTAT TAATTTCTGAATATCCTCCTTAGTTCC | 31 |
| RK44F | TTCGGGAATGATTGTTATCAATGACGAT AATAAGACCAATAACGGTTTATGTGTAG GCTGGAGCTGCTTC | 32 |
| RK44R | CGCGGGCGTACAGGGATCCAGTTATCAA TAAGCAAATTCATTTGTTCTCCCTCCTT ATCTCCCTATAGTG | 33 |
| RK29R | GACTCTCGAGGCCACTGATCTCTACTGC AG | 34 |
| RK33R | GACTCTCGAGGCAACAGCAGCAACATCA AG | 35 |

Homologous Recombination-Based Genetic Engineering

Homologous recombination using short-homology flanking ends was carried out as previously described (24). To insert the six cas genes required for CRISPR interference under T7 control, the inventors first cloned the T7 promoters upstream of the cas3 and cse1 genes in *Escherichia coli* K-12. An overnight culture of *E. coli* RE1001 (Table 1) harboring the pSIM6 plasmid was diluted 1:100 in 50 mL fresh LB supplemented with 100 µg/mL ampicillin at 32° C. and aerated until the $OD_{600}$ reached 0.4-0.6. The culture was then heat-induced for expression of the red recombination enzymes at 42° C. for 15 min in a shaking water bath followed by incubation in ice water for 10 min. The culture was then centrifuged at 4600×g for 10 min at 4° C. The supernatant was removed and the pellet was washed three times in ice-cold double-distilled water ($ddH_2O$). The pellet was resuspended in 200 µL of ice-cold ddH2O and kept on ice. The cultures were then electroporated with ~500 ng of PCR products encoding a T7 promoter fused to either kanamycin or chloramphenicol resistance markers flanked by 50 bp of sequences flanking the original promoters of cas3 (fragment T7cas3::kan) and cse1 (fragment T7cse1::cm) genes. T7cas3::kan fragment was constructed by PCR amplification of the kanamycin resistance gene encoding FRT sites from BW25113ΔyeeX (Table 1) by using primers RK41F and a primer encoding the T7 promoter in its 5' end, RK41R (Table 1). The PCR fragment was then amplified with RK42F and RK42R (Table 1), encoding 50-bp homology to the immediate 5' region of cas3. The T7cse1::cm fragment was constructed by PCR amplification of the chloramphenicol fragment encoding FRT sites from the pKD3 plasmid (Table 1) by using primers RK43F and a primer encoding the T7 promoter in its 5' end, RK43R (Table 1). The PCR fragment was then amplified with RK44F and RK44R (Table 1), encoding 50-bp homology of the immediate 5' region of cse1. Electroporation of these fragments was carried out using a 50-µL aliquot of electrocompetent bacteria in a 0.2-cm cuvette at 25 F, 2.5 kV, and 200Ω. After electroporation 1 mL of 2YT medium was added to the cuvette, followed by aeration at 32° C. for 3 h. The cultures were then inoculated on LB agar plates supplemented with 25 µg/mL kanamycin and 17.5 rtg/mL chloramphenicol and incubated overnight at 32° C. Recombinant colonies were streaked on 25 µg/mL kanamycin and 17.5 µg/mL chloramphenicol plates and incubated at 42° C. to eliminate the temperature-sensitive pSIM6 plasmid. A single colony was validated as encoding the desired substitutions by DNA sequencing using RK33R and RK29R. The entire manipulated cassette encoding cas3 and cse1 under the T7 promoters was transduced to the RE1001 strain and selected using both antibiotic markers to yield the RK6471 strain. The cas genes were deleted as described previously (25). Briefly, *E. coli* DY378 was electroporated with about 500 ng of PCR product generated by amplifying plasmid pKD3 using primers IY80F and IY80R (Tables 1 and 2). This amplified DNA encoded a chloramphenicol resistance marker flanked on one end by 50 bp of sequences of the cas3 promoter and on another end by 50 bp of the CRISPR leader sequence. Desired recombinants were selected on LB agar plates supplemented with 17 µg/ml chloramphenicol. The deletion was then transferred to IYB5101 using P1 transduction as described (26), yielding IYB5666.

To construct a λ phage encoding the cas genes under T7 promoters, an overnight culture of IYB5297/pSIM6 was diluted 50-fold in 25 mL of LB medium with appropriate antibiotics and grown at 32° C. to an $OD_{600}$ of 0.5. The culture was then heat-induced for expression of recombination enzymes from both the λ prophage and the plasmid at 42° C. for exactly 4 min in a shaking water bath. The induced samples were immediately cooled on ice slurry and then pelleted at 4600×g at 4° C. for 10 min. The pellet was washed twice in ice-cold ddH$_2$O, resuspended in 200 µL of ice-cold ddH$_2$O, and kept on ice until electroporation with ~1600 ng of a gel-purified PCR product obtained by amplifying the genomic DNA of RK6471 using primers IY333F and IY333R. A 25-µL aliquot of electrocompetent cells was used for each electroporation in a 0.2-cm cuvette at 25 µF, 2.5 kV, and 200Ω. After electroporation, the bacteria were grown in 1 mL LB for 1 h in a 32° C. shaking water bath and inoculated on selection plates containing 17 µg/mL chloramphenicol. The chloramphenicol resistance marker was removed using the Flippase recombination enzyme encoded by plasmid pCP20 (24) and chloramphenicol-sensitive colonies were used for phage induction at 42° C. The resulting phage, $2_{cas}$, encoding the six cas genes transcribed from T7 promoters but lacking a CRISPR array, was used to lysogenize BL21-AI, yielding IYB5614. The engineered CRISPR array was inserted into IYB5614/pSIM6 as described above by using a PCR fragment obtained from amplifying pIYEC2 by primers IY347F and IY347R. The resulting strain, IYB5656, harbors $\lambda_{cas\text{-}CRISPR}$, which encodes the six cas genes transcribed from T7 promoters and the CRISPR array encoding spacers against ndm-1, ctx-M-15, and the T4 phage genome.

TABLE 3

Oligonucleotides and templates used for construction of bacteria, phages and plasmids

| Constructed phage/plasmid | Oligonucleotides for PCR | DNA template |
|---|---|---|
| IYB5300 | IY80F, IY80R | pKD3 |
| RK6471 | RK41F, RK41R, RK42F, RK42R, RK43F, RK43R, RK44F, RK44R | pKD3 and Genomic DNA of BW25113ΔyeeX |
| λcas-cm | IY333F, IY333R | Genomic DNA of RK6471 |
| λcas-CRISPR | IY347F, IY347R | pIYEC2 |
| T7-gp8 | IY309F, IY309R | $T7_{FRTtrxA}$ (24) |
| T7-$N_1N_2$ | IY340Fa, IY340Rb | $T7_{FRTtrxA}$ |
| T7-$C_2C_1$ | IY340Fb, IY340Ra | $T7_{FRTtrxA}$ |
| T7-$N_1C_1$ | IY340Fa, IY340Ra | $T7_{FRTtrxA}$ |
| T7-$C_2N_2$ | IY340Fb, IY340Rb | $T7_{FRTtrxA}$ |
| pTRX1 | IY309F, IY309R | $T7_{FRTtrxA}$ |
| pTRX2 | IY340Fa, IY340Rb | $T7_{FRTtrxA}$ |
| pTRX3 | IY340Fb, IY340Ra | $T7_{FRTtrxA}$ |
| pTRX4 | IY340Fa, IY340Ra | $T7_{FRTtrxA}$ |
| pTRX5 | IY340Fb, IY340Rb | $T7_{FRTtrxA}$ |

Homologous Recombination of Bacteriophage T7

T7 phages encoding desired protospacers were constructed as described (29) by using plasmids pTRX1, pTRX2, pTRX3, pTRX4, and pTRX5.

Transformation Efficiency Assays

Overnight cultures of E. coli IYB5670 and IYB5671 were diluted 1:50 and aerated at 32° C. in 10 mL of LB medium supplemented with 25 µg/mL kanamycin and 10 µg/mL chloramphenicol. When the culture reached an $OD_{600}$ of 0.2, 0.2% L-arabinose was added, and the cultures were incubated at 32° C. until an $OD_{600}$ of 0.5-0.6 was reached. Bacteria were then centrifuged at 4600×g at 4° C., the supernatant was disposed, and the bacteria were resuspended in 1 mL of ice-cold ddH$_2$O and transferred to a 1.5-mL tube. The cells were spun down for 1 min at 13000×g at 4° C. After an additional washing step, the cells were suspended in 250 µL of ice-cold ddH$_2$O. Bacterial cells (50 µL) were then mixed in an ice-cold 0.2-mm electroporation cuvette (Bio-Rad) with 12 ng of pVEC, pNDM, or pCTX plasmids. The mixture was pulsed in a Bio-Rad micropulser at 200 Ω, 25 µF, and 1.8 kV. Immediately after the pulse, 0.1 mL of 2YT broth containing 0.2% L-arabinose was added, and the cells were aerated for 1 h at 32° C. Various dilutions of the reaction were plated on LB-agar plates supplemented with 50 µg/mL streptomycin and 0.2% L-arabinose. Plates were incubated overnight at 32° C. Colonies emerging on the selection plates were counted, and the CFU number per mL was calculated accordingly.

Assays of Lytic Phage Growth Efficiency

Overnight cultures of E. coli IYB5670 and IYB5671 were diluted 1:50 and aerated at 32° C. in 10 mL of LB medium supplemented with 25 µg/mL kanamycin. When the culture reached an $OD_{600}$ of 0.2, 0.2% L-arabinose was added and the cultures were incubated at 32° C. until an $OD_{600}$ of 0.5-0.6 was reached. The bacteria were harvested by centrifugation and concentrated to an $OD_{600}$ of ~3. One mL from the concentrated cultures IYB5670 and IYB5671 was mixed with 10 mL of soft agar supplemented with 0.2% L-arabinose and spread onto LB agar plates supplemented with 25 jg of kanamycin and 0.2% L-arabinose. After the agar solidified, the plates were incubated at 32° C. for 40 min. Fifteen microlitres of phage dilutions was plated onto the soft agar, allowed to dry, and then incubated at 32° C. for 15 h. Plaque-forming units were counted on several dilutions, and their number per mL was calculated accordingly.

Lysogenization

Overnight culture of IYB5666 harboring pNDM, pCTX or control plasmid (pVEC) were diluted 1:50 in LB medium supplemented with 50 µg/mL of streptomycin, 10 mM MgSO$_4$, and 0.2% (w/v) maltose. Culture was grown to an $OD_{600}$ of 0.5 and then centrifuged at 13000 g for 1 min. The supernatant was discarded and the pellet was resuspended in LB medium supplemented with 10 mM MgSO$_4$, and 0.2% (w/v) maltose. 10 µL of the treated culture was mixed with 10 µL of phage $\lambda_{cas}$ or $\lambda_{cas\text{-}CRISPR}$ at a multiplicity of infection of ~10 in a 1.5-mL tube and incubated at room temperature for 30 min. 60 µL of LB medium supplemented with 0.2% L-arabinose was then added, and the cultures were aerated at 32° C. for an additional 2.5 h. Cultures were then diluted 1:10 and 84 µL was spread onto LB plates containing 5 µg/mL of tetracycline and 0.2% L-arabinose and 3 mL of soft agar containing 5.5×10$^5$ T7-$C_1N_1$ phage. The plates were incubated 36 h at 32° C. To determine plasmid loss, 20-48 of the surviving colonies were resuspended in 0.1 mL of LB, and using a plate replicator the suspension was plated on LB agar plates supplemented with 5 g/mL tetracycline and 0.2% L-arabinose either with or without 50 µg/mL streptomycin. Colonies sensitive to streptomycin were determined as those grown on medium lacking streptomycin but not on medium having streptomycin.

Example 1

CRISPR-Cas System Delivery by a λ Phage

Figure 1:
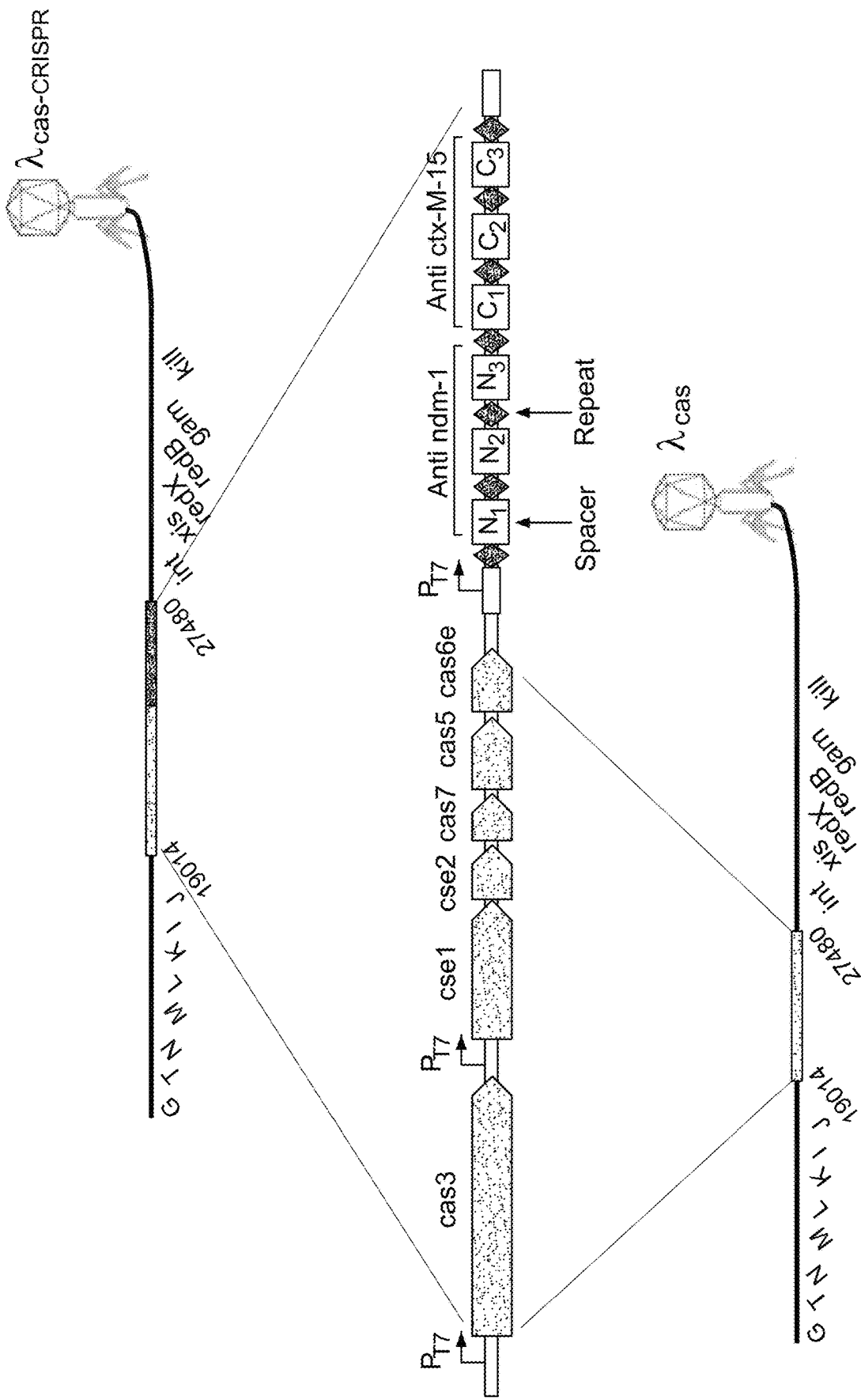
FIG. 1. Schematics of the lysogenizing phages

CRISPR/Cas systems have evolved in bacteria to limit the transfer of nucleic acids, such as phages, plasmids, or other parasitic elements. These systems consist of an array of short repeats of about 30 bp flanked by similarly sized sequences, called spacers (FIG. 1). The spacers serve as molecular "labels" of undesired nucleic acids. An invading DNA molecule will be eliminated from the cell if the system encodes a spacer that is identical in sequence to any part of this DNA molecule (26, 27). The elimination is carried out by specific proteins which "sense" the alignment, and target and destroy the invading molecule. Recently, a CRISPR/Cas system consisting of a single gene adjacent to a CRISPR array was reported to be active in *Escherichia coli* (27). The system was shown to target a plasmid which had a sequence identical to a spacer in the CRISPR array.

The system of the invention comprises two components or elements, the first component is a sensitizing element that is a temperate phage designed to induce CRISPR-mediated inactivation of pathogenic genes, for example, genes conferring resistance to antibiotics. As such, inactivation of antibiotics resistant genes renders the bacteria sensitive to such antibiotic agents. The second component of the system of the invention is a lytic phage that is used for selection. Some embodiments of the invention encompass genetically modified lytic phage comprising proto-spacers identical to proto-spacers in pathogenic genes that are recognized by the spacers of the CRISPR-array in the temperate phage of the sensitizing component of the invention.

To sensitize bacteria carrying antibiotic resistance genes, a transferable CRISPR-Cas system that targets the ndm-1 and ctx-M-15 genes (as shown in FIG. 1) was first constructed. These genes encode extended spectrum β lactamases that confer resistance to carbapenems, β lactam antibiotics which are often the last line of effective antibiotics against resistant pathogens (28). Polymerase chain reaction (PCR) was used to amplify the CRISPR cascade genes (cse1, cse2, cas7, cas5, and cas6e) and cas3 of the *E. coli* type I-E CRISPR system. The PCR product was introduced by homologous recombination into a λ prophage. These genes encode proteins that are sufficient to eliminate DNA molecules encoding targeted protospacers (29). A CRISPR array, encoding spacers that target conserved sequences of the resistance genes ndm-1 and ctx-M-15 was also introduced into the same lysogen, immediately downstream of the cas genes, as illustrated by FIG. 1. The prophage was then induced, and its progeny were used to lysogenize naïve *E. coli* bacteria. The engineered CRISPR-Cas system, designed to target and destroy plasmids encoding genes ndm-1 and ctx-M-15, was thus made transferable to bacteria by lysogenization.

Lysogenized bacteria could outcompete bacteria harboring resistance plasmids, indicating that the genetic fitness cost of the transferred prophage is smaller than that of the tested plasmids (FIG. 2).

Example 2

Lysogenized Bacteria Block Transformation

Naïve *E. coli* lysogenized with the λ phage encoding the CRISPR-Cas system ($\lambda_{cas\text{-}CRISPR}$) or with a similar phage lacking the CRISPR array ($\lambda_{cas}$) as a negative control were made competent and transformed with a control plasmid or plasmids encoding ndm-1 or ctx-M-15, all conferring streptomycin resistance. Transformation efficiency was determined by counting colonies that acquired streptomycin resistance. Lysogens of the $\lambda_{cas\text{-}CRISPR}$ were transformed equally well with the control plasmid compared to lysogens of the $\lambda_{cas}$. In contrast, as shown in FIG. 3, these lysogens were transformed less efficiently with the targeted plasmids by approximately three orders of magnitude. These results clearly indicate that the lysogenized CRISPR-Cas system can be transferred into bacteria and moreover, this system specifically prevents horizontal gene transfer of antibiotic-resistance elements by plasmid transformations. To demonstrate that lysogenization can also cure established resistance plasmids, the inventors lysogenized resistant bacteria and determined plasmid loss. Plasmids were cured specifically from bacteria lysogenized with λcas-CRISPR but not with λcas (FIG. 4). Together, these results indicate that the CRISPR-Cas system can be transferred by temperate phages into bacteria to specifically prevent horizontal gene transfer of antibiotic resistance elements.

Example 3

Protection from Lytic Bacteriophages

A desired feature of the sensitizing CRISPR-Cas system is the ability to concomitantly confer advantage to the pathogens harboring it. For example, resistance to lytic phages would enable selection and enrichment of sensitized pathogens exposed to them. Therefore, the inventors next genetically engineered lytic T7 phages encoding protospacers identical to the ndm-1 and ctx-M-15 spacers targeted by the transferred CRISPR-Cas system. These engineered phages would thus be targeted concomitantly with the resistance genes. These similar protospacers were intentionally cloned to ensure that the lysogens could not lose the sensitizing element without also losing phage resistance. In addition, targeting a synthetic protospacer of the phage rather than a naturally occurring sequence does not provide the lysogens with protection against the wild-type phage, and thus does not interfere with the natural ecological balance. Naïve *E. coli* were lysogenized with $\lambda_{cas\text{-}CRISPR}$ or $\lambda_{cas}$, and the bacteria were then infected with the engineered T7 phages. As clearly shown in FIG. 5, bacteria lysogenized with $\lambda_{cas\text{-}CRISPR}$ did not resist growth of a control T7-gp8 phage compared to bacteria lysogenized with the control $\lambda_{cas}$ phage. In contrast, these lysogens resisted growth of the T7 phages encoding either two protospacers of ndm-1 (T7-$N_1$-$N_2$, SEQ ID NO. 55) or two protospacers of ctx-M-15 (T7-$C_2$C1, SEQ ID NO. 56) or one of each (T7-$N_1$C1, SEQ ID NO.57 or T7-$C_2$N2, SEQ ID NO.58) by at least four orders of magnitude (FIG. 5). These results indicate that the lysogenized CRISPR-Cas system can be transferred to bacteria and protect them from a modified T7 bacteriophage, thus linking pathogen sensitization to antibiotics with resistance to lytic phage. Moreover, the system confers resistance only to phages encoding artificial matching protospacers, demonstrating that the system does not interfere with natural ecological interactions.

Example 4

Lytic Phage Selection of Sensitized Bacteria

The transferred CRISPR-Cas system prevented plasmid transformation and concomitantly protected the lysogenized bacteria from lytic phages. This indicates that lysogenization can be used to sensitize antibiotic-resistant bacteria, and that the population of sensitized bacteria may be enriched by lytic phages. To simulate treatments that could be applied on hospital surfaces or skin flora, bacteria harboring control, ctx-M-15, or ndm1 encoding plasmids were next propagated.

Lysogenizing phages encoding the CRISPR-Cas system ($\lambda_{cas\text{-}CRISPR}$) or control ($\lambda_{cas}$) phages were then added to the cultures. The cultures were then overlaid on agar plates containing the T7-$N_1C_1$ lytic phage, against which the lysogenized bacteria have CRISPR-Cas-mediated protection. Surviving colonies were counted after overnight incubation (FIG. 6A). In all cultures, more than 20-fold more colonies treated with the targeting $\lambda_{cas\text{-}CRISPR}$ phage were resistant to the engineered T7-$N_1C_1$ phage compared with those treated with the control $\lambda_{cas}$ phage (FIG. 6B). Phage-resistant colonies treated with either $\lambda_{cas\text{-}CRISPR}$ or $\lambda_{cas}$ were inoculated on plates having or lacking streptomycin to test for loss of the antibiotic resistance conferring plasmid. As expected, cultures harboring the nontargeted plasmid (pVEC) remained streptomycin resistant in both types of lysogenizations. However, all of the bacteria lysogenized with $\lambda_{cas\text{-}CRISPR}$ and harboring targeted plasmids (pNDM or pCTX) concomitantly became sensitive to streptomycin, whereas all of the bacteria treated with $\lambda_{cas}$ maintained this resistance (FIG. 6C). Finally, to demonstrate that multiple resistances in the same bacterium can also be eliminated, the inventors repeated the above described procedure using bacteria harboring two different antibiotic resistance plasmids (pNDM*+pCTX). As expected, in this case also, bacterial cultures treated with the $\lambda_{cas\text{-}CRISPR}$ resisted the lytic phages, as they carry antiphage spacers (FIG. 6B). Bacteria surviving the lytic phage infection and treated with $\lambda_{cas\text{-}CRISPR}$ were cured from both resistance plasmids, whereas survivors treated with $\lambda_{cas}$ maintained the resistance plasmids (FIG. 6C). Altogether, these experiments provide a proof of principle that an engineered temperate phage delivering the CRISPR-Cas system can be used along with an engineered lytic phage to facilitate the simultaneous loss of multiple resistance determinants, reduce their horizontal transfer, and enrich for bacterial populations that exhibit both features. Altogether, these experiments demonstrate the feasibility of using an engineered temperate phage delivering the CRISPR-Cas system, along with an engineered lytic phage to facilitate the loss of multiple resistance determinants, reduce their horizontal transfer, and enrich for bacterial populations that exhibit both features.

Example 5

In Vivo Testing

The present inventors next test the technology's ability to reduce infection of mice by drug-resistant pathogens. Mouse cages are used to simulate hospital rooms, and mice are used to simulate patients. ESBL-resistant pathogens are spread throughout all of the cages. The engineered phages' efficiency for enrichment of drug-sensitive pathogen populations in cages is assessed by spraying the sensitizing phages followed by the lytic phages for several days. Mice are then placed into these or untreated cages. Mice developing bacterial disease are treated with antibiotics. It is expected that the mice in the phage-treated cages will be cured by the antibiotics whereas mice in the control cages will succumb to the bacterial disease.

It should be noted that the CRISPR system can also target virulence factors such as shiga and cholera toxins, which are horizontally transferred by phages, thereby reducing the severity of pathogen infections. In addition, CRISPR/Cas systems targeting RNA molecules can be used to target genomic resistance determinants and virulence factors. RNA targeting systems can be used without counter selection since the bacterial genome remains intact whereas only the specific virulence genes are silenced. These possibilities are examined by the inventors.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A kit comprising:
 at least one selective component comprising at least one genetic element comprising a nucleic acid sequence comprising at least one proto-spacer, wherein said genetic element is a lytic bacteriophage or a vector that encode a toxic element or protein that kill bacterial cells or disrupt and/or inhibit bacterial growth; and
 (ii) at least one sensitizing component comprising at least one cas gene and at least one clustered, regularly interspaced short palindromic repeat (CRISPR) array, wherein at least one spacer of said CRISPR targets a proto-spacer comprised within at least one pathogenic gene of a bacterium so as to specifically inactivate said pathogenic gene in said bacterium, and wherein at least one spacer of said CRISPR targets a proto-spacer comprised within said lytic bacteriophage or within said vector that encode a toxic element or protein that kill bacterial cells or disrupt and/or inhibit bacterial growth, so as to specifically inactivate said selective component of (i).

2. The kit according to claim 1, wherein said selective component comprises said at least one lytic bacteriophage.

3. The kit according to claim 2, wherein said lytic bacteriophage is at least one genetically modified bacteriophage comprising at least one proto-spacer having an identity of at least 70% to at least one nucleic acid sequence comprised within said bacterial pathogenic gene.

4. The kit according to claim 1, wherein said sensitizing component comprises at least one recombinant vector comprising a nucleic acid sequence encoding at least one cas protein, said vector further comprise a nucleic acid sequence of at least one of said CRISPR array.

5. The kit according to claim 4, wherein said vector is at least one genetically modified bacteriophage comprising at least one CRISPR spacer that targets at least one nucleic acid sequence comprised within said lytic bacteriophage and at least one CRISPR spacer that targets a nucleic acid sequence comprised within said at least one pathogenic gene, thereby targeting and inactivating both, said lytic phage and said pathogenic gene.

6. The kit according to claim 1, wherein:
 (a) said at least one bacterial pathogenic gene is at least one bacterial endogenous gene; or
 (b) wherein said at least one bacterial pathogenic gene is at least one epichromosomal gene.

7. The kit according to claim 6, wherein at least one of said pathogenic gene is an antibiotic resistance gene.

8. The kit according to claim 6, wherein said at least one of said pathogenic gene is a gene encoding at least one of a virulence factor and at least one toxin.

9. The kit according to claim 7, wherein said at least one antibiotic resistance gene encodes a resistance factor selected from the group consisting of CTX-M-15, New Delhi metallo-β-lactamase (NDM)-1, 2, 5, 6, an extended-spectrum beta-lactamase resistance factor (ESBL factor), beta lactamase, and tetracycline A (tetA).

10. The kit according to claim 9, wherein said at least one CRISPR spacer comprises a nucleic acid sequence that targets at least one of: at least one proto-spacer of CTX-M-15, at least one proto-spacer of NDM-1, 2, 5, 6, at least one proto-spacer of ESBL factor, at least one proto-spacer of beta lactamase, at least one proto-spacer of tetA and at least one at least one proto-spacer of said lytic bacteriophage.

11. The kit according to claim 10, wherein at least one of said proto-spacer of CTX-M-15, comprises a nucleic acid sequence as denoted by any one of SEQ ID NO. 49, 50 and 51 and at least one of said proto-spacer of NDM-1, comprises a nucleic acid sequence as denoted by any one of SEQ ID NO. 46, 47 and 48.

12. The kit according to claim 3, wherein said genetically modified lytic bacteriophage comprises at least one of: (a) at least one proto-spacer of CTX-M-15, comprising a nucleic acid sequence as denoted by any one of SEQ ID NO. 49, 50 and 51; and (b) at least one proto-spacer of NDM-1 comprising a nucleic acid sequence as denoted by any one of SEQ ID NO. 46, 47 and 48.

13. The kit according to claim 5, wherein said at least one CRISPR spacer targets a nucleic acid sequence comprised within an essential gene of said lytic bacteriophage.

14. The kit according to claim 13, wherein said lytic bacteriophage is at least one of T7like-virus and T4like-virus.

15. The kit according to claim 14, wherein said T7like-virus is at least one Enterobacteria phage T7.

16. The kit according to claim 5, wherein said bacteriophage is a lambda temperate bacteriophage.

17. The kit according to claim 1, wherein said at least one cas gene is at least one cas gene of at least one of type I, type II and type III CRISPR systems.

18. The kit according to claim 17, wherein said at least one cas gene is at least one cas gene of type I-E CRISPR system.

19. The kit according to claim 18, wherein said at least one type I-E cas gene is at least one of cse1, cse2, cas7, cas5e cas6 and cas3 genes.

20. The kit according to claim 17, wherein said at least one cas gene is at least one cas gene of type II CRISPR system.

21. The kit according to claim 20, wherein said at least one cas gene of type II CRISPR system is cas9 gene.

22. The kit according to claim 1, wherein said bacterium is at least one bacterium of any strain of at least one of *E. coli, Pseudomonas aeruginosa, Staphylococcus aureus, Streptococcus pyogenes, Clostidium difficile, Enterococcus faecium, Klebsiella pneumonia, Acinetobacter* baumanni and *Enterobacter* species.

23. The kit according to claim 22, wherein said bacteria are at least one *E. coli* strain selected from the group consisting of O157:H7, enteroaggregative (EAEC), enterohemorrhagic (EHEC), enteroinvasive (EIEC), enteropathogenic (EPEC), enterotoxigenic (ETEC) and diffuse adherent (DAEC) *E. coli*.

24. The kit according to claim 5, wherein at least one of the temperate bacteriophage and the lytic bacteriophage is formulated as a spray, a stick, a paint, a gel, a cream, wash, a wipe, a foam, a soap, a liquid, an oil, a solution, a lotion, an ointment or a paste.

25. A method of interfering with a horizontal transfer of a genetic element comprising at least one pathogenic gene between bacteria, the method comprises the steps of: contacting at least one of a surface, a substance and an article containing bacteria harboring said pathogenic gene with:
- at least one selective component comprising at least one genetic element comprising a nucleic acid sequence comprising at least one proto-spacer, wherein said genetic element is a lytic bacteriophage or a vector that encode a toxic element or protein that kill bacterial cells or disrupt and/or inhibit bacterial growth; and
- (ii) at least one sensitizing component comprising at least one cas gene and at least one CRISPR array, wherein at least one spacer of said CRISPR targets a proto-spacer comprised within at least one pathogenic gene of a bacterium so as to specifically inactivate said pathogenic gene in said bacterium and wherein at least one spacer of said CRISPR targets a proto-spacer comprised within said lytic bacteriophage or within said vector that encode a toxic element or protein that kill bacterial cells or disrupt and/or inhibit bacterial growth, so as to specifically inactivate said selective component, of (i); or
- (iii) at least one kit comprising (i) and (ii), thereby inactivating said pathogenic gene and interfering with horizontal transfer thereof.

26. A method of treating a pathologic condition in a mammalian subject caused by a bacterial infection of bacteria containing a pathogenic gene, the method comprising contacting at least one of surface, a substance and an article, in the vicinity of said subject with:
- (i) at least one selective component comprising at least one genetic element comprising a nucleic acid sequence comprising at least one proto-spacer, wherein said genetic element is a lytic bacteriophage or a vector that encode a toxic element or protein that kill bacterial cells or disrupt and/or inhibit bacterial growth; and
- (ii) at least one sensitizing component comprising at least one ecu gene and at least one clustered, regularly interspaced short palindromic repeat (CRISPR) array, wherein at least one spacer of said CRISPR targets a proto-spacer comprised within at least one pathogenic gene of a bacterium so as to specifically inactivate said pathogenic gene in said bacterium and wherein at least one spacer of said CRISPR targets a proto-spacer comprised within said lytic bacteriophage or within said vector that encode a toxic element or protein that kill bacterial cells or disrupt and/or inhibit bacterial growth, so as to specifically inactivate said selective component of (i); or
- (iii) at least one kit comprising (i) and (ii);

thereby targeting and inactivating said pathogenic gene and treating said pathologic condition.

27. The method according to claim 26, comprising contacting said at least one of surface, substance and article with said sensitizing component being a temperate bacteriophage and subsequently contacting said solid surface with said selective component being said lytic bacteriophage.

* * * * *

SEQUENCE LISTING

```
<160> NUMBER OF SEQ ID NOS: 77

<210> SEQ ID NO 1
<211> LENGTH: 30
<212> TYPE: DNA
<213> ORGANISM: Artificial Sequence
<220> FEATURE:
<223> OTHER INFORMATION: Oligonucleotide primer IY344F

<400> SEQUENCE: 1
accgaagctt tgaatatcct ccttagttcc                                      30

<210> SEQ ID NO 2
<211> LENGTH: 50
<212> TYPE: DNA
<213> ORGANISM: Artificial Sequence
<220> FEATURE:
<223> OTHER INFORMATION: Oligonucleotide primer IY344R

<400> SEQUENCE: 2
```
cgccaagctt acggggcaac ctcatgtcaa gtgtaggctg gagctgcttc                50

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer IY246F

<400> SEQUENCE: 3
atggaattgc ccaatattat                                                 20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide primer IY246R

<400> SEQUENCE: 4
tcagcgcagc ttgtcggcca                                                 20

<210> SEQ ID NO 5
<211> LENGTH: 35
<212> TYPE: DNA
<213> ORGANISM: Artificial Sequence
<220> FEATURE:
<223> OTHER INFORMATION: Oligonucleotide primer IY247F

<400> SEQUENCE: 5
gaactaaatc aggcacttga gcatcaagat tggtg                                35

<210> SEQ ID NO 6
<211> LENGTH: 35
<212> TYPE: DNA
<213> ORGANISM: Artificial Sequence
<220> FEATURE:
<223> OTHER INFORMATION: Oligonucleotide primer IY247R

<400> SEQUENCE: 6
caccaatctt gatgctcaag tgcctgattt agttc                                35

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide primer IY346F

<400> SEQUENCE: 7
atggttaaaa aatcactgcg ccagt                                           25

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer IY346R

<400> SEQUENCE: 8
ttacaaaccg tcggtgacga                                                 20

<210> SEQ ID NO 9
<211> LENGTH: 20
<212> TYPE: DNA

```
<213> ORGANISM: Artificial Sequence
<220> FEATURE:
<223> OTHER INFORMATION: Oligonucleotide primer IY142Fb

<400> SEQUENCE: 9
cacacggtca cactgcttcc                                                  20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer MG110R

<400> SEQUENCE: 10
cgatgccctt gagagccttc                                                  20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer MG17F

<400> SEQUENCE: 11
ataagtcgga caccatggca                                                  20

<210> SEQ ID NO 12
<211> LENGTH: 70
<212> TYPE: DNA
<213> ORGANISM: Artificial Sequence
<220> FEATURE:
<223> OTHER INFORMATION: Oligonucleotide primer IY80F

<400> SEQUENCE: 12
aatagcccgc tgatatcatc gataatacta aaaaaacagg gaggctatta gtgtaggctg      60
gagctgcttc                                                             70

<210> SEQ ID NO 13
<211> LENGTH: 70
<212> TYPE: DNA
<213> ORGANISM: Artificial Sequence
<220> FEATURE:
<223> OTHER INFORMATION: Oligonucleotide primer IY80R

<400> SEQUENCE: 13
accttaatgt aacatttcct tattattaaa gatcagctaa ttctttgttt tgaatatcct      60
ccttagttcc                                                             70

<210> SEQ ID NO 14
<211> LENGTH: 73
<212> TYPE: DNA
<213> ORGANISM: Artificial Sequence
<220> FEATURE:
<223> OTHER INFORMATION: Oligonucleotide primer IY333F

<400> SEQUENCE: 14
atgcgtaatg tgtgtattgc cgttgctgtc tttgccgcac ttgcggtgac ccggaatgaa      60
attaatacga ctc                                                         73

<210> SEQ ID NO 15
<211> LENGTH: 70
<212> TYPE: DNA
<213> ORGANISM: Artificial Sequence
```

```
<220> FEATURE:
<223> OTHER INFORMATION: Oligonucleotide primer IY333R

<400> SEQUENCE: 15
aacctgtcgc actccagaga agcacaaagc ctcgcaatcc agtgcaaagc tcacagtgga    60
gccaaagata                                                           70

<210> SEQ ID NO 16
<211> LENGTH: 70
<212> TYPE: DNA
<213> ORGANISM: Artificial Sequence
<220> FEATURE:
<223> OTHER INFORMATION: Oligonucleotide primer IY347F

<400> SEQUENCE: 16
ggccagctaa atcgatggga tgtggcttgc tatctttggc tccactgtga gggatgtgct    60
gcaaggcgat                                                           70

<210> SEQ ID NO 17
<211> LENGTH: 70
<212> TYPE: DNA
<213> ORGANISM: Artificial Sequence
<220> FEATURE:
<223> OTHER INFORMATION: Oligonucleotide primer IY347R

<400> SEQUENCE: 17
aacctgtcgc actccagaga agcacaaagc ctcgcaatcc agtgcaaagc acggggcaac    60
ctcatgtcaa                                                           70

<210> SEQ ID NO 18
<211> LENGTH: 75
<212> TYPE: DNA
<213> ORGANISM: Artificial Sequence
<220> FEATURE:
<223> OTHER INFORMATION: Oligonucleotide primer IY309F

<400> SEQUENCE: 18
accctcaaga gaaaatgtaa aagctgtctt tcgctgctga gggtgacgat cccgcgatcc    60
gtcagcctgc agttc                                                     75

<210> SEQ ID NO 19
<211> LENGTH: 75
<212> TYPE: DNA
<213> ORGANISM: Artificial Sequence
<220> FEATURE:
<223> OTHER INFORMATION: Oligonucleotide primer IY309R

<400> SEQUENCE: 19
ccgaaggtga gccagtgtga aagctgtctt tcgctgctga gggtgacgat cccgctgtag    60
gctggagctg cttcg                                                     75

<210> SEQ ID NO 20
<211> LENGTH: 75
<212> TYPE: DNA
<213> ORGANISM: Artificial Sequence
<220> FEATURE:
<223> OTHER INFORMATION: Oligonucleotide primer IY340Fa

<400> SEQUENCE: 20
accctcaaga gaaaatgtaa aagctgagca ccgcattagc cgctgcattg atgctgatcc    60
gtcagcctgc agttc                                                     75
```

<210> SEQ ID NO 21
<211> LENGTH: 75
<212> TYPE: DNA
<213> ORGANISM: Artificial Sequence
<220> FEATURE:
<223> OTHER INFORMATION: Oligonucleotide primer IY340Fb

<400> SEQUENCE: 21
accctcaaga gaaaatgtaa aagctgattg ctcacgttgg cggcccggct agcgtgatcc    60
gtcagcctgc agttc                                                    75

<210> SEQ ID NO 22
<211> LENGTH: 75
<212> TYPE: DNA
<213> ORGANISM: Artificial Sequence
<220> FEATURE:
<223> OTHER INFORMATION: Oligonucleotide primer IY340Ra

<400> SEQUENCE: 22
ccgaaggtga gccagtgtga gtacgtccgc cgtttgcgca tacagcggca cactttgtag    60
gctggagctg cttcg                                                    75

<210> SEQ ID NO 23
<211> LENGTH: 75
<212> TYPE: DNA
<213> ORGANISM: Artificial Sequence
<220> FEATURE:
<223> OTHER INFORMATION: Oligonucleotide primer IY340Rb

<400> SEQUENCE: 23
ccgaaggtga gccagtgtga accgccagcg cgaccggcag gttgatctcc tgctttgtag    60
gctggagctg cttcg                                                    75

<210> SEQ ID NO 24
<211> LENGTH: 70
<212> TYPE: DNA
<213> ORGANISM: Artificial Sequence
<220> FEATURE:
<223> OTHER INFORMATION: Oligonucleotide primer IY260F

<400> SEQUENCE: 24
tggctctttg cggcacccat cgttcgtaat gttccgtggc accgaggaca accctcaaga    60
gaaaatgtaa                                                          70

<210> SEQ ID NO 25
<211> LENGTH: 70
<212> TYPE: DNA
<213> ORGANISM: Artificial Sequence
<220> FEATURE:
<223> OTHER INFORMATION: Oligonucleotide primer IY260R

<400> SEQUENCE: 25
ccaaccttct taaacataaa gtgtctcctt ataaacgcag aaaggcccac ccgaaggtga    60
gccagtgtga                                                          70

<210> SEQ ID NO 26
<211> LENGTH: 19
<212> TYPE: DNA
<213> ORGANISM: Artificial Sequence
<220> FEATURE:
<223> OTHER INFORMATION: Oligonucleotide primer RK41F

<400> SEQUENCE: 26

```
ggaattactt cgcttcgcc                                                  19
```

<210> SEQ ID NO 27
<211> LENGTH: 56
<212> TYPE: DNA
<213> ORGANISM: Artificial Sequence
<220> FEATURE:
<223> OTHER INFORMATION: Oligonucleotide primer RK41R

<400> SEQUENCE: 27

```
cctccttatc tccctatagt gagtcgtatt aatttcattc cggggatccg tcgacc        56
```

<210> SEQ ID NO 28
<211> LENGTH: 70
<212> TYPE: DNA
<213> ORGANISM: Artificial Sequence
<220> FEATURE:
<223> OTHER INFORMATION: Oligonucleotide primer RK42F

<400> SEQUENCE: 28

```
aaacgcgttt ctttggctta aaaagggaat gtgggttaca cgaagggtaa tgtaggctgg    60
agctgcttcg                                                           70
```

<210> SEQ ID NO 29
<211> LENGTH: 70
<212> TYPE: DNA
<213> ORGANISM: Artificial Sequence
<220> FEATURE:
<223> OTHER INFORMATION: Oligonucleotide primer RK42R

<400> SEQUENCE: 29

```
ggattttccc cagtaatggc atatatattt aaaaggttcc attaatagcc cctccttatc    60
tccctatagt                                                           70
```

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide primer RK43F

<400> SEQUENCE: 30

```
gcagcattac acgtcttgag                                                20
```

<210> SEQ ID NO 31
<211> LENGTH: 55
<212> TYPE: DNA
<213> ORGANISM: Artificial Sequence
<220> FEATURE:
<223> OTHER INFORMATION: Oligonucleotide primer RK43R

<400> SEQUENCE: 31

```
ctccttatct ccctatagtg agtcgtatta atttctgaat atcctcctta gttcc         55
```

<210> SEQ ID NO 32
<211> LENGTH: 70
<212> TYPE: DNA
<213> ORGANISM: Artificial Sequence
<220> FEATURE:
<223> OTHER INFORMATION: Oligonucleotide primer RK44F

<400> SEQUENCE: 32

```
ttcgggaatg attgttatca atgacgataa taagaccaat aacggtttat gtgtaggctg    60
```

-continued gagctgcttc                                                            70

<210> SEQ ID NO 33
<211> LENGTH: 70
<212> TYPE: DNA
<213> ORGANISM: Artificial Sequence
<220> FEATURE:
<223> OTHER INFORMATION: Oligonucleotide primer RK44R

<400> SEQUENCE: 33
cgcgggcgta cagggatcca gttatcaata agcaaattca tttgttctcc ctccttatct     60
ccctatagtg                                                            70

<210> SEQ ID NO 34
<211> LENGTH: 30
<212> TYPE: DNA
<213> ORGANISM: Artificial Sequence
<220> FEATURE:
<223> OTHER INFORMATION: Oligonucleotide primer RK29R

<400> SEQUENCE: 34
gactctcgag gccactgatc tctactgcag                                      30

<210> SEQ ID NO 35
<211> LENGTH: 30
<212> TYPE: DNA
<213> ORGANISM: Artificial Sequence
<220> FEATURE:
<223> OTHER INFORMATION: Oligonucleotide primer RK33R

<400> SEQUENCE: 35
gactctcgag gcaacagcag caacatcaag                                      30

<210> SEQ ID NO 36
<211> LENGTH: 48502
<212> TYPE: DNA
<213> ORGANISM: Bacteriophage lambda

<400> SEQUENCE: 36
gggcggcgac ctcgcgggtt ttcgctattt atgaaaattt tccggtttaa ggcgtttccg     60
ttcttcttcg tcataactta atgtttttat ttaaaatacc ctctgaaaag aaaggaaacg    120
acaggtgctg aaagcgaggc ttttttggcct ctgtcgtttc cttttctctgt ttttgtccgt    180 ggaatgaaca atggaagtca caaaaagca gctggctgac attttcggtg cgagtatccg    240
taccattcag aactggcagg aacagggaat gcccgttctg cgaggcggtg caagggtaa    300 tgaggtgctt tatgactctg ccgccgtcat aaaatggtat gccgaaaggg atgctgaaat    360
tgagaacgaa aagctgcgcc gggaggttga agaactgcgg caggccagcg aggcagatct    420
ccagccagga actattgagt acgaacgcca tcgacttacg cgtgcgcagg ccgacgcaca    480
ggaactgaag aatgccagag actccgctga agtggtggaa accgcattct gtactttcgt    540
gctgtcgcgg atcgcaggtg aaattgccag tattctcgac gggctccccc tgtcggtgca    600
gcggcgtttt ccggaactgg aaaaccgaca tgttgatttc ctgaaacggg atatcatcaa    660
agccatgaac aaagcagccg cgctggatga actgataccg gggttgctga gtgaatatat    720
cgaacagtca ggttaacagg ctgcggcatt ttgtccgcgc cgggcttcgc tcactgttca    780
ggccggagcc acagaccgcc gttgaatggg cggatgctaa ttactatctc ccgaaagaat    840
ccgcatacca ggaagggcgc tgggaaacac tgccctttca gcgggccatc atgaatgcga    900
tgggcagcga ctacatccgt gaggtgaatg tggtgaagtc tgcccgtgtc ggttattcca    960

```
aaatgctgct gggtgtttat gcctacttta tagagcataa gcagcgcaac acccttatct    1020
ggttgccgac ggatggtgat gccgagaact ttatgaaaac ccacgttgag ccgactattc    1080
gtgatattcc gtcgctgctg gcgctggccc cgtggtatgg caaaaagcac cgggataaca    1140
cgctcaccat gaagcgtttc actaatgggc gtggcttctg gtgcctgggc ggtaaagcgg    1200
caaaaaacta ccgtgaaaag tcggtggatg tggcgggtta tgatgaactt gctgcttttg    1260
atgatgatat tgaacaggaa ggctctccga cgttcctggg tgacaagcgt attgaaggct    1320
cggtctggcc aaagtccatc cgtggctcca cgccaaaagt gagaggcacc tgtcagattg    1380
agcgtgcagc cagtgaatcc ccgcatttta tgcgttttca tgttgcctgc ccgcattgcg    1440
gggaggagca gtatcttaaa tttggcgaca agagacgcc gtttggcctc aaatggacgc    1500
cggatgaccc ctccagcgtg ttttatctct gcgagcataa tgcctgcgtc atccgccagc    1560
aggagctgga ctttactgat gcccgttata tctgcgaaaa gaccgggatc tggacccgtg    1620
atggcattct ctggttttcg tcatccggtg aagagattga ccacctgac agtgtgacct    1680 ttcacatctg gacagcgtac agcccgttca ccacctgggt gcagattgtc aaagactgga    1740
tgaaaacgaa aggggatacg ggaaaacgta aaccttcgt aaacaccacg ctcggtgaga    1800
cgtgggaggc gaaaattggc gaacgtccgg atgctgaagt gatggcagag cggaaagagc    1860
attattcagc gcccgttcct gaccgtgtgg cttacctgac cgccggtatc gactcccagc    1920
tggaccgcta cgaaatgcgc gtatggggat ggggccggg tgaggaaagc tggctgattg    1980
accggcagat tattatgggc cgccacgacg atgaacagac gctgctgcgt gtggatgagg    2040
ccatcaataa aacctatacc cgccggaatg gtgcagaaat gtcgatatcc cgtatctgct    2100
gggatactgg cgggattgac ccgaccattg tgtatgaacg ctcgaaaaaa catgggctgt    2160
tccgggtgat ccccattaaa ggggcatccg tctacgaaaa gccggtggcc agcatgccac    2220
gtaagcgaaa caaaacggg gtttaccta ccgaaatcgg tacggatacc gcgaaagagc    2280
agatttataa ccgcttcaca ctgacgccgg aaggggatga accgcttccc ggtgccgttc    2340
acttcccgaa taacccggat attttttgatc tgaccgaagc gcagcagctg actgctgaag    2400
agcaggtcga aaatgggtg gatggcagga aaaaaatact gtgggacagc aaaaagcgac    2460
gcaatgaggc actcgactgc ttcgtttatg cgctggcggc gctgcgcatc agtatttccc    2520
gctggcagct ggatctcagt gcgctgctgg cgagcctgca ggaagaggat ggtgcagcaa    2580
ccaacaagaa acactggca gattacgccc gtgccttatc cggagaggat gaatgacgcg    2640
acaggaagaa cttgccgctg cccgtgcggc actgcatgac ctgatgacag gtaaacgggt    2700
ggcaacagta cagaaagacg gacgaagggt ggagtttacg gccacttccg tgtctgacct    2760
gaaaaaatat attgcagagc tggaagtgca gaccggcatg acacagcgac gcaggggacc    2820
tgcaggattt tatgtatgaa aacgcccacc attcccaccc ttctggggcc ggacggcatg    2880
acatcgctgc gcgaatatgc cggttatcac ggcggtggca gcggatttgg agggcagttg    2940
cggtcgtgga acccaccgag tgaaagtgtg gatgcagccc tgttgcccaa ctttacccgt    3000
ggcaatgccc gcgcagacga tctggtacgc aataacggct atgccgccaa cgccatccag    3060
ctgcatcagg atcatatcgt cgggtctttt ttccggctca gtcatcgccc aagctggcgc    3120
tatctgggca tcggggagga agaagcccgt gccttttccc gcgaggttga agcggcatgg    3180
aaagagtttg ccgaggatga ctgctgctgc attgacgttg agcgaaaacg cacgtttacc    3240
atgatgattc gggaaggtgt ggccatgcac gcctttaacg gtgaactgtt cgttcaggcc    3300
```

```
acctgggata ccagttcgtc gcggcttttc cggacacagt tccggatggt cagcccgaag   3360
cgcatcagca acccgaacaa taccggcgac agccggaact gccgtgccgg tgtgcagatt   3420
aatgacagcg gtgcggcgct gggatattac gtcagcgagg acgggtatcc tggctggatg   3480
ccgcagaaat ggacatggat accccgtgag ttacccggcg gcgcgcctc gttcattcac     3540
gttttttgaac ccgtggagga cgggcagact cgcggtgcaa atgtgttta cagcgtgatg    3600
gagcagatga agatgctcga cacgctgcag aacacgcagc tgcagagcgc cattgtgaag   3660
gcgatgtatg ccgccaccat tgagagtgag ctggatacgc agtcagcgat ggatttatt    3720
ctgggcgcga acagtcagga gcagcgggaa aggctgaccg gctggattgg tgaaattgcc   3780
gcgtattacg ccgcagcgcc ggtccggctg ggaggcgcaa aagtaccgca cctgatgccg   3840
ggtgactcac tgaacctgca gacggctcag gataccggata acggctactc cgtgtttgag  3900
cagtcactgc tgcggtatat cgctgccggg ctgggtgtct cgtatgagca gctttcccgg   3960
aattacgccc agatgagcta ctccacggca cgggccagtg cgaacgagtc gtgggcgtac   4020
tttatggggc ggcgaaaatt cgtcgcatcc cgtcaggcga ccagatgtt tctgtgctgg    4080
ctggaagagg ccatcgttcg ccgcgtggtg acgttacctt caaaagcgcg cttcagtttt   4140
caggaagccc gcagtgcctg ggggaactgc gactggatag gctccggtcg tatggccatc   4200
gatggtctga agaagttca ggaagcggtg atgctgatag aagccggact gagtacctac    4260
gagaaagagt gcgcaaaacg cggtgacgac tatcaggaaa tttttgccca gcaggtccgt   4320
gaaacgatgg agcgccgtgc agccggtctt aaaccgcccg cctgggcggc tgcagcattt   4380
gaatccgggc tgcgacaatc aacagaggag gagaagagtg acagcagagc tgcgtaatct   4440
cccgcatatt gccagcatgg cctttaatga gccgctgatg cttgaacccg cctatgcgcg   4500
ggttttcttt tgtgcgcttg caggccagct tgggatcagc agcctgacgg atgcggtgtc   4560
cggcgacagc ctgactgccc aggaggcact cgcgacgctg gcattatccg gtgatgatga   4620
cggaccacga caggcccgca gttatcaggt catgaacggc atcgccgtgc tgccggtgtc   4680
cggcacgctg gtcagccgga cgcgggcgct gcagccgtac tcggggatga ccggttacaa   4740
cggcattatc gcccgtctgc aacaggctgc cagcgatccg atggtggacg gcattctgct   4800
cgatatggac acgcccggcg ggatggtggc ggggcatt gactgcgctg acatcatcgc     4860
ccgtgtgcgt gacataaaac cggtatggc gcttgccaac gacatgaact gcagtgcagg    4920
tcagttgctt gccagtgccg cctcccggcg tctggtcacg cagaccgccc ggacaggctc   4980
catcggcgtc atgatggctc acagtaatta cggtgctgcg ctggagaaac agggtgtgga   5040
aatcacgctg atttacagcg gcagccataa ggtggatggc aacccctaca gccatcttcc   5100
ggatgacgtc cgggagacac tgcagtcccg gatggacgca acccgccaga tgtttgcgca  5160
gaaggtgtcg gcatataccg gcctgtccgt gcaggttgtg ctggataccg aggctgcagt   5220
gtacagcggt caggaggcca ttgatgccgg actggctgat gaacttgtta acagcaccga   5280
tgcgatcacc gtcatgcgtg atgcactgga tgcacgtaaa tcccgtctct caggagggcg   5340
aatgaccaaa gagactcaat caacaactgt ttcagccact gcttcgcagg ctgacgttac   5400
tgacgtggtg ccagcgacgg agggcgagaa cgccagcgcg cgcagccgg acgtgaacgc    5460
gcagatcacc gcagcggttg cggcagaaaa cagccgcatt atggggatcc tcaactgtga   5520
ggaggctcac ggacgcgaag aacaggcacg cgtgctggca gaaaccccg gtatgaccgt    5580
gaaaacggcc cgccgcattc tggccgcagc accacagagt gcacaggcgc gcagtgacac   5640
tgcgctggat cgtctgatgc aggggcacc ggcaccgctg gctgcaggta accggcatc    5700
```

```
tgatgccgtt aacgatttgc tgaacacacc agtgtaaggg atgtttatga cgagcaaaga    5760
aacctttacc cattaccagc cgcagggcaa cagtgacccg gctcataccg caaccgcgcc    5820
cggcggattg agtgcgaaag cgcctgcaat gaccccgctg atgctggaca cctccagccg    5880
taagctggtt gcgtgggatg gcaccaccga cggtgctgcc gttggcattc ttgcggttgc    5940
tgctgaccag accagcacca cgctgacgtt ctacaagtcc ggcacgttcc gttatgagga    6000
tgtgctctgg ccgaggctg ccagcgacga gacgaaaaaa cggaccgcgt ttgccggaac    6060
ggcaatcagc atcgtttaac tttacccttc atcactaaag gccgcctgtg cggcttttt    6120 tacgggattt ttttatgtcg atgtacacaa ccgcccaact gctggcggca aatgagcaga    6180
aatttaagtt tgatccgctg tttctgcgtc tcttttccg tgagagctat cccttcacca    6240
cggagaaagt ctatctctca caaattccgg gactggtaaa catggcgctg tacgtttcgc    6300
cgattgtttc cggtgaggtt atccgttccc gtggcggctc cacctctgaa tttacgccgg    6360
gatatgtcaa gccgaagcat gaagtgaatc cgcagatgac cctgcgtcgc ctgccggatg    6420
aagatccgca gaatctggcg gacccggctt accgccgccg tcgcatcatc atgcagaaca    6480
tgcgtgacga gagctggcc attgctcagg tcgaagagat gcaggcagtt tctgccgtgc    6540
ttaagggcaa atacaccatg accggtgaag ccttcgatcc ggttgaggtg gatatgggcc    6600
gcagtgagga gaataacatc acgcagtccg gcggcacgga gtggagcaag cgtgacaagt    6660
ccacgtatga cccgaccgac gatatcgaag cctacgcgct gaacgccagc ggtgtggtga    6720
atatcatcgt gttcgatccg aaaggctggg cgctgttccg ttccttcaaa gccgtcaagg    6780
agaagctgga tacccgtcgt ggctctaatt ccgagctgga gacagcggtg aaagacctgg    6840
gcaaagcggt gtcctataag gggatgtatg gcgatgtggc catcgtcgtg tattccggac    6900
agtacgtgga aaacggcgtc aaaaagaact tcctgccgga caacacgatg gtgctgggga    6960
acactcaggc acgcggtctg cgcacctatg gctgcattca ggatgcggac gcacagcgcg    7020
aaggcattaa cgcctctgcc cgttacccga aaaactgggt gaccaccggc gatccggcgc    7080
gtgagttcac catgattcag tcagcaccgc tgatgctgct ggctgaccct gatgagttcg    7140
tgtccgtaca actggcgtaa tcatggccct tcggggccat tgtttctctg tggaggagtc    7200
catgacgaaa gatgaactga ttgcccgtct ccgctcgctg ggtgaacaac tgaaccgtga    7260
tgtcagcctg acgggacga agaagaact ggcgctccgt gtggcagagc tgaaagagga    7320
gcttgatgac acgatgaaa ctgccggtca ggacacccct ctcagccggg aaaatgtgct    7380
gaccggacat gaaaatgagg tgggatcagc gcagccggat accgtgattc tggatacgtc    7440
tgaactggtc acggtcgtgg cactggtgaa gctgcatact gatgcacttc acgccacgcg    7500
ggatgaacct gtggcatttg tgctgccggg aacggcgttt cgtgtctctg ccggtgtggc    7560
agccgaaatg acagagcgcg gcctggccag aatgcaataa cgggaggcgc tgtggctgat    7620
ttcgataacc tgttcgatgc tgccattgcc cgcgccgatg aaacgatacg cgggtacatg    7680
ggaacgtcag ccaccattac atccggtgag cagtcaggtg cggtgatacg tggtgttttt    7740
gatgaccctg aaaatatcag ctatgccgga cagggcgtgc gcgttgaagg ctccagcccg    7800
tccctgtttg tccggactga tgaggtgcgg cagctgcggc gtggagacac gctgaccatc    7860
ggtgaggaaa atttctgggt agatcgggtt cgccggatg atggcggaag ttgtcatctc    7920
tggcttggac ggggcgtacc gcctgccgtt aaccgtcgcc gctgaaaggg ggatgtatgg    7980
ccataaaagg tcttgagcag gccgttgaaa acctcagccg tatcagcaaa acggcggtgc    8040
```

```
ctggtgccgc cgcaatggcc attaaccgcg ttgcttcatc cgcgatatcg cagtcggcgt    8100
cacaggttgc ccgtgagaca aaggtacgcc ggaaactggt aaaggaaagg gccaggctga    8160
aaagggccac ggtcaaaaat ccgcaggcca gaatcaaagt taaccggggg gatttgcccg    8220
taatcaagct gggtaatgcg cgggttgtcc tttcgcgccg caggcgtcgt aaaaaggggc    8280
agcgttcatc cctgaaaggt ggcggcagcg tgcttgtggt gggtaaccgt cgtattccgg    8340
gcgcgtttat tcagcaactg aaaaatggcc ggtggcatgt catgcagcgt gtggctggga    8400
aaaaccgtta ccccattgat gtggtgaaaa tcccgatggc ggtgccgctg accacggcgt    8460
ttaaacaaaa tattgagcgg atacggcgtg aacgtcttcc gaaagagctg ggctatgcgc    8520
tgcagcatca actgaggatg gtaataaagc gatgaaacat actgaactcc gtgcagccgt    8580
actggatgca ctggagaagc atgacaccgg ggcgacgttt tttgatggtc gccccgctgt    8640
ttttgatgag gcggattttc cggcagttgc cgtttatctc accggcgctg aatacacggg    8700
cgaagagctg gacagcgata cctggcaggc ggagctgcat atcgaagttt tcctgcctgc    8760
tcaggtgccg gattcagagc tggatgcgtg gatggagtcc cggatttatc cggtgatgag    8820
cgatatcccg gcactgtcag atttgatcac cagtatggtg ccagcggct atgactaccg    8880 gcgcgacgat gatgcgggct gtggagttc agccgatctg acttatgtca ttacctatga    8940
aatgtgagga cgctatgcct gtaccaaatc ctacaatgcc ggtgaaaggt gccgggacca    9000
ccctgtgggt ttataagggg agcggtgacc cttacgcgaa tccgctttca gacgttgact    9060
ggtcgcgtct ggcaaaagtt aaagacctga cgcccggcga actgaccgct gagtcctatg    9120
acgacagcta tctcgatgat gaagatgcag actggactgc gaccgggcag gggcagaaat    9180
ctgccggaga taccagcttc acgctggcgt ggatgcccgg agagcagggg cagcaggcgc    9240
tgctggcgtg gtttaatgaa ggcgataccc gtgcctataa aatccgcttc ccgaacggca    9300
cggtcgatgt gttccgtggc tgggtcagca gtatcggtaa ggcggtgacg gcgaaggaag    9360
tgatcacccg cacggtgaaa gtcaccaatg tgggacgtcc gtcgatggca gaagatcgca    9420
gcacggtaac agcggcaacc ggcatgaccg tgacgcctgc cagcacctcg gtggtgaaag    9480
ggcagagcac cacgctgacc gtggccttcc agccggaggg cgtaaccgac aagagcttc    9540 gtgcggtgtc tgcggataaa acaaaagcca ccgtgtcggt cagtggtatg accatcaccg    9600 tgaacgcgt tgctgcaggc aaggtcaaca ttccggttgt atccggtaat ggtgagtttg    9660
ctgcggttgc agaaattacc gtcaccgcca gttaatccgg agagtcagcg atgttcctga    9720
aaaccgaatc atttgaacat aacggtgtga ccgtcacgct ttctgaactg tcagccctgc    9780
agcgcattga gcatctcgcc ctgatgaaac ggcaggcaga acaggcggag tcagacagca    9840
accggaagtt tactgtggaa gacgccatca gaaccggcgc gtttctggtg gcgatgtccc    9900
tgtggcataa ccatccgcag aagacgcaga tgccgtccat gaatgaagcc gttaaacaga    9960
ttgagcagga agtgcttacc acctggccca cggaggcaat ttctcatgct gaaaacgtgg    10020
tgtaccggct gtctggtatg tatgagtttg tggtgaataa tgcccctgaa cagacagagg    10080
acgccgggcc cgcagagcct gtttctgcgg gaaagtgttc gacggtgagc tgagttttgc    10140
cctgaaactg gcgcgtgaga tggggcgacc cgactggcgt gccatgcttg ccgggatgtc    10200
atccacggag tatgccgact ggcaccgctt ttacagtacc cattattttc atgatgttct    10260
gctggatatg cactttttccg ggctgacgta caccgtgctc agcctgtttt tcagcgatcc    10320
ggatatgcat ccgctggatt tcagtctgct gaaccggcgc gaggctgacg aagagcctga    10380
agatgatgtg ctgatgcaga aagcggcagg gcttgccgga ggtgtccgct ttggcccgga    10440
```

```
cgggaatgaa gttatcccg cttccccgga tgtggcggac atgacggagg atgacgtaat    10500
gctgatgaca gtatcagaag ggatcgcagg aggagtccgg tatggctgaa ccggtaggcg    10560
atctggtcgt tgatttgagt ctggatgcgg ccagatttga cgagcagatg ccagagtca    10620 ggcgtcattt ttctggtacg gaaagtgatg cgaaaaaaac agcggcagtc gttgaacagt    10680
cgctgagccg acaggcgctg gctgcacaga aagcggggat ttccgtcggg cagtataaag    10740
ccgccatgcg tatgctgcct gcacagttca ccgacgtggc cacgcagctt gcaggcgggc    10800
aaagtccgtg gctgatcctg ctgcaacagg ggggcaggt gaaggactcc ttcggcggga    10860
tgatccccat gttcaggggg cttgccggtg cgatcaccct gccgatggtg ggggccacct    10920
cgctggcggt ggcgaccggt gcgctggcgt atgcctggta tcagggcaac tcaaccctgt    10980
ccgatttcaa caaaacgctg gtcctttccg gcaatcaggc gggactgacg gcagatcgta    11040
tgctggtcct gtccagagcc gggcaggcgg caggctgac gtttaaccag accagcgagt    11100
cactcagcgc actggttaag gcgggggtaa gcggtgaggc tcagattgcg tccatcagcc    11160
agagtgtggc gcgtttctcc tctgcatccg gcgtggaggt ggacaaggtc gctgaagcct    11220
tcgggaagct gaccacagac ccgacgtcgg ggctgacggc gatggctcgc cagttccata    11280
acgtgtcggc ggagcagatt gcgtatgttg ctcagttgca gcgttccggc gatgaagccg    11340
gggcattgca ggcggcgaac gaggccgcaa cgaaagggtt tgatgaccag acccgccgcc    11400
tgaaagagaa catgggcacg ctggagacct gggcagacag gactgcgcgg gcattcaaat    11460
ccatgtggga tgcggtgctg gatattggtc gtcctgatac cgcgcaggag atgctgatta    11520
aggcagaggc tgcgtataag aaagcagacg acatctggaa tctgcgcaag gatgattatt    11580
ttgttaacga tgaagcgcgg gcgcgttact gggatgatcg tgaaaaggcc cgtcttgcgc    11640
ttgaagccgc ccgaaagaag gctgagcagc agactcaaca ggacaaaaat gcgcagcagc    11700
agagcgatac cgaagcgtca cggctgaaat ataccgaaga ggcgcagaag gcttacgaac    11760
ggctgcagac gccgctggag aaatataccg cccgtcagga agaactgaac aaggcactga    11820
aagacgggaa aatcctgcag gcggattaca acacgctgat ggcggcggcg aaaaaggatt    11880
atgaagcgac gctgaaaaag ccgaaacagt ccagcgtgaa ggtgtctgcg ggcgatcgtc    11940
aggaagacag tgctcatgct gccctgctga cgcttcaggc agaactccgg acgctggaga    12000
agcatgccga agcaaatgag aaaatcagcc agcagcgccg ggatttgtgg aaggcggaga    12060
gtcagttcgc ggtactggag gaggcggcgc aacgtcgcca gctgtctgca caggagaaat    12120
ccctgctggc gcataaagat gagacgctgg agtacaaacg ccagctggct gcacttggcg    12180
acaaggttac gtatcaggag cgcctgaacg cgctggcgca gcaggcggat aaattcgcac    12240
agcagcaacg ggcaaaacgg gccgccattg atgcgaaaag ccggggctg actgaccggc    12300 aggcagaacg ggaagccacg gaacagcgcc tgaaggaaca gtatggcgat aatccgctgg    12360
cgctgaataa cgtcatgtca gagcagaaaa agacctgggc ggctgaagac cagcttcgcg    12420
ggaactggat ggcaggcctg aagtccggct ggagtgagtg ggaagagagc gccacggaca    12480
gtatgtcgca ggtaaaaagt gcagccacgc agaccttga tggtattgca cagaatatgg    12540
cggcgatgct gaccggcagt gagcagaact ggcgcagctt cacccgttcc gtgctgtcca    12600
tgatgacaga aattctgctt aagcaggcaa tggtgggat tgtcgggagt atcggcagcg    12660
ccattggcgg ggctgttggt ggcggcgcat ccgcgtcagg cggtacagcc attcaggccg    12720
ctgcggcgaa attccatttt gcaaccggag gatttacggg aaccggcggc aaatatgagc    12780
```

-continued

```
cagcggggat tgttcaccgt ggtgagtttg tcttcacgaa ggaggcaacc agccggattg    12840
gcgtggggaa tctttaccgg ctgatgcgcg gctatgccac cggcggttat gtcggtacac    12900
cgggcagcat ggcagacagc cggtcgcagg cgtccgggac gtttgagcag aataaccatg    12960
tggtgattaa caacgacggc acgaacgggc agataggtcc ggctgctctg aaggcggtgt    13020
atgacatggc ccgcaagggt gcccgtgatg aaattcagac acagatgcgt gatggtggcc    13080
tgttctccgg aggtggacga tgaagacctt ccgctggaaa gtgaaacccg gtatggatgt    13140
ggcttcggtc ccttctgtaa gaaaggtgcg ctttggtgat ggctattctc agcgagcgcc    13200
tgccgggctg aatgccaacc tgaaaacgta cagcgtgacg cttctgtcc cccgtgagga    13260 ggccacggta ctggagtcgt ttctggaaga gcacggggc tggaaatcct ttctgtggac    13320
gccgccttat gagtggcggc agataaaggt gacctgcgca aaatggtcgt cgcgggtcag    13380
tatgctgcgt gttgagttca gcgcagagtt tgaacaggtg gtgaactgat gcaggatatc    13440
cggcaggaaa cactgaatga atgcacccgt gcggagcagt cggccagcgt ggtgctctgg    13500
gaaatcgacc tgacagaggt cggtggagaa cgttattttt tctgtaatga gcagaacgaa    13560
aaaggtgagc cggtcacctg gcaggggcga cagtatcagc cgtatcccat tcaggggagc    13620
ggttttgaac tgaatggcaa aggcaccagt acgcgcccca cgctgacggt ttctaacctg    13680
tacggtatgg tcaccgggat ggcggaagat atgcagagtc tggtcggcgg aacggtggtc    13740
cggcgtaagg tttacgcccg ttttctggat gcggtgaact cgtcaacgg aaacagttac    13800 gccgatccgg agcaggaggt gatcagccgc tggcgcattg agcagtgcag cgaactgagc    13860
gcggtgagtg cctcctttgt actgtccacg ccgacggaaa cggatggcgc tgttttccg    13920 ggacgtatca tgctggccaa cacctgcacc tggacctatc gcggtgacga gtgcggttat    13980
agcggtccgg ctgtcgcgga tgaatatgac cagccaacgt ccgatatcac gaaggataaa    14040
tgcagcaaat gcctgagcgg ttgtaagttc cgcaataacg tcggcaactt tggcggcttc    14100 cttttccatta acaaactttc gcagtaaatc ccatgacaca gacagaatca gcgattctgg    14160
cgcacgcccg gcgatgtgcg ccagcggagt cgtgcggctt cgtggtaagc acgccggagg    14220
gggaaagata tttcccctgc gtgaatatct ccggtgagcc ggaggctatt tccgtatgtc    14280
gccggaagac tggctgcagg cagaaatgca gggtgagatt gtggcgctgg tccacagcca    14340
ccccggtggg ctgccctggc tgagtgaggc cgaccggcgg ctgcaggtgc agagtgattt    14400
gccgtggtgg ctggtctgcc gggggacgat tcataagttc cgctgtgtgc cgcatctcac    14460
cgggcggcgc tttgagcacg gtgtgacgga ctgttacaca ctgttccggg atgcttatca    14520
tctggcgggg attgagatgc cggactttca tcgtgaggat gactggtggc gtaacggcca    14580
gaatctctat ctggataatc tggaggcgac ggggctgtat caggtgccgt tgtcagcggc    14640
acagccgggc gatgtgctgc tgtgctgttt tggttcatca gtgccgaatc acgccgcaat    14700
ttactgcggc gacggcgagc tgctgcacca tattcctgaa caactgagca acgagagag    14760 gtacaccgac aaatggcagc gacgcacaca ctccctctgg cgtcaccggg catggcgcgc    14820
atctgccttt acggggattt acaacgattt ggtcgccgca tcgaccttcg tgtgaaaacg    14880
ggggctgaag ccatccgggc actggccaca cagctcccgg cgtttcgtca gaaactgagc    14940
gacggctggt atcaggtacg gattgccggg cgggacgtca gcacgtccgg gttaacggcg    15000
cagttacatg agactctgcc tgatggcgct gtaattcata ttgttcccag agtcgccggg    15060
gccaagtcag gtgcgtatt ccagattgtc ctggggggctg ccgccattgc cggatcattc    15120
tttaccgccg gagccaccct tgcagcatgg ggggcagcca ttggggccgg tggtatgacc    15180
```

-continued

```
ggcatcctgt tttctctcgg tgccagtatg gtgctcggtg gtgtggcgca gatgctggca   15240
ccgaaagcca gaactccccg tatacagaca acgataacg gtaagcagaa cacctatttc    15300
tcctcactgg ataacatggt tgcccagggc aatgttctgc ctgttctgta cggggaaatg   15360
cgcgtggggt cacgcgtggt ttctcaggag atcagcacgg cagacgaagg ggacggtggt   15420
caggttgtgg tgattggtcg ctgatgcaaa atgttttatg tgaaaccgcc tgcgggcggt   15480
tttgtcattt atggagcgtg aggaatgggt aaaggaagca gtaaggggca taccccgcgc   15540
gaagcgaagg acaacctgaa gtccacgcag ttgctgagtg tgatcgatgc catcagcgaa   15600
gggccgattg aaggtccggt ggatggctta aaaagcgtgc tgctgaacag tacgccggtg   15660
ctggacactg aggggaatac caacatatcc ggtgtcacgg tggtgttccg ggctggtgag   15720
caggagcaga ctccgccgga gggatttgaa tcctccggct ccgagacggt gctgggtacg   15780
gaagtgaaat atgacacgcc gatcacccgc accattacgt ctgcaaacat cgaccgtctg   15840
cgctttacct tcggtgtaca ggcactggtg gaaaccacct caaagggtga caggaatccg   15900
tcggaagtcc gcctgctggt tcagatacaa cgtaacggtg gctgggtgac ggaaaaagac   15960
atcaccatta agggcaaaac cacctcgcag tatctggcct cggtggtgat gggtaacctg   16020
ccgccgcgcc cgtttaatat ccggatgcgc aggatgacgc cggacagcac cacagaccag   16080
ctgcagaaca aaacgctctg gtcgtcatac actgaaatca tcgatgtgaa acagtgctac   16140
ccgaacacgg cactggtcgg cgtgcaggtg gactcggagc agttcggcag ccagcaggtg   16200
agccgtaatt atcatctgcg cgggcgtatt ctgcaggtgc cgtcgaacta taacccgcag   16260
acgcggcaat acagcggtat ctgggacgga acgtttaaac cggcatacag caacaacatg   16320
gcctggtgtc tgtgggatat gctgacccat ccgcgctacg gcatggggaa acgtcttggt   16380
gcggcggatg tggataaatg ggcgctgtat gtcatcggcc agtactgcga ccagtcagtg   16440
ccggacggct ttggcggcac ggagccgcgc atcacctgta atgcgtacct gaccacacag   16500
cgtaaggcgt gggatgtgct cagcgatttc tgctcggcga tgcgctgtat gccggtatgg   16560
aacgggcaga cgctgacgtt cgtgcaggac cgaccgtcgg ataagacgtg gacctataac   16620
cgcagtaatg tggtgatgcc ggatgatggc gcgccgttcc gctacagctt cagcgccctg   16680
aaggaccgcc ataatgccgt tgaggtgaac tggattgacc cgaacaacgg ctgggagacg   16740
gcgacagagc ttgttgaaga tacgcaggcc attgcccgtt acggtcgtaa tgttacgaag   16800
atggatgcct ttggctgtac cagccggggg caggcacacc gcgccgggct gtggctgatt   16860
aaaacagaac tgctggaaac gcagaccgtg gatttcagcg tcggcgcaga agggcttcgc   16920
catgtaccgg gcgatgttat tgaaatctgc gatgatgact atgccggtat cagcaccggt   16980
ggtcgtgtgc tggcggtgaa cagccagacc cggacgctga cgctcgaccg tgaaatcacg   17040
ctgccatcct ccggtaccgc gctgataagc ctggttgacg gaagtggcaa tccggtcagc   17100
gtggaggttc agtccgtcac cgacggcgtg aaggtaaaag tgagccgtgt tcctgacggt   17160
gttgctgaat acagcgtatg ggagctgaag ctgccgacgc tgcgccagcg actgttccgc   17220
tgcgtgagta tccgtgagaa cgacgacggc acgtatgcca tcaccgccgt gcagcatgtg   17280
ccggaaaaag aggccatcgt ggataacggg gcgcactttg acggcgaaca gagtggcacg   17340
gtgaatggtg tcacgccgcc agcggtgcag cacctgaccg cagaagtcac tgcagacagc   17400
ggggaatatc aggtgctggc gcgatggac acaccgaagg tggtgaaggg cgtgagtttc   17460
ctgctccgtc tgaccgtaac agcggacgac ggcagtgagc ggctggtcag cacggcccgg   17520
```

```
acgacggaaa ccacataccg cttcacgcaa ctggcgctgg ggaactacag gctgacagtc    17580
cgggcggtaa atgcgtgggg gcagcagggc gatccggcgt cggtatcgtt ccggattgcc    17640
gcaccggcag caccgtcgag gattgagctg acgccgggct attttcagat aaccgccacg    17700
ccgcatcttg ccgtttatga cccgacggta cagtttgagt tctggttctc ggaaaagcag    17760
attgcggata tcagacaggt tgaaaccagc acgcgttatc ttggtacggc gctgtactgg    17820
atagccgcca gtatcaatat caaaccgggc catgattatt acttttatat ccgcagtgtg    17880
aacaccgttg gcaaatcggc attcgtggag gccgtcggtc gggcgagcga tgatgcggaa    17940
ggttacctgg attttttcaa aggcaagata accgaatccc atctcggcaa ggagctgctg    18000
gaaaaagtcg agctgacgga ggataacgcc agcagactgg aggagttttc gaaagagtgg    18060
aaggatgcca gtgataagtg gaatgccatg tgggctgtca aaattgagca gaccaaagac    18120
ggcaaacatt atgtcgcggg tattggcctc agcatggagg cacgcgagga aggcaaactg    18180
agccagtttc tggttgccgc caatcgtatc gcatttattg acccggcaaa cgggaatgaa    18240
acgccgatgt ttgtggcgca gggcaaccag atattcatga cgacgtgtt cctgaagcgc    18300 ctgacggccc ccaccattac cagcggcggc aatcctccgg cctttccct gacaccggac    18360 ggaaagctga ccgctaaaaa tgcggatatc agtggcagtg tgaatgcgaa ctccgggacg    18420
ctcagtaatg tgacgatagc tgaaaactgt acgataaacg gtacgctgag ggcgaaaaaa    18480
atcgtcgggg acattgtaaa ggcggcgagc gcggcttttc cgcgccagcg tgaaagcagt    18540
gtggactggc cgtcaggtac ccgtactgtc accgtgaccg atgaccatcc tttgatcgc    18600 cagatagtgg tgcttccgct gacgtttcgc ggaagtaagc gtactgtcag cggcaggaca    18660
acgtattcga tgtgttatct gaaagtactg atgaacggtg cggtgattta tgatggcgcg    18720
gcgaacgagg cggtacaggt gttctcccgt attgttgaca tgccagcggg tcggggaaac    18780
gtgatcctga cgttcacgct tacgtccaca cggcattcgg cagatattcc gccgtatacg    18840
tttgccagcg atgtgcaggt tatggtgatt aagaaacagg cgctgggcat cagcgtggtc    18900
tgagtgtgtt acagaggttc gtccgggaac gggcgtttta ttataaaaca gtgagaggtg    18960
aacgatgcgt aatgtgtgta ttgccgttgc tgtctttgcc gcacttgcgg tgacagtcac    19020
tccggcccgt gcggaaggtg gacatggtac gtttacggtg ggctattttc aagtgaaacc    19080
gggtacattg ccgtcgttgt cgggcgggga taccggtgtg agtcatctga aagggattaa    19140
cgtgaagtac cgttatgagc tgacggacag tgtgggggtg atggcttccc tggggttcgc    19200
cgcgtcgaaa aagagcagca cagtgatgac cggggaggat acgtttcact atgagagcct    19260
gcgtggacgt tatgtgagcg tgatggccgg accggttta caaatcagta agcaggtcag    19320
tgcgtacgcc atggccggag tggctcacag tcggtggtcc ggcagtacaa tggattaccg    19380
taagacggaa atcactcccg ggtatatgaa agagacgacc actgccaggg acgaaagtgc    19440
aatgcggcat acctcagtgg cgtggagtgc aggtatacag attaatccgg cagcgtccgt    19500
cgttgttgat attgcttatg aaggctccgg cagtggcgac tggcgtactg acggattcat    19560
cgttggggtc ggttataaat tctgattagc caggtaacac agtgttatga cagcccgccg    19620
gaaccggtgg gcttttttgt ggggtgaata tggcagtaaa gatttcagga gtcctgaaag    19680
acggcacagg aaaaccggta cagaactgca ccattcagct gaaagccaga cgtaacagca    19740
ccacggtggt ggtgaacacg gtgggctcag agaatccgga tgaagccggg cgttacagca    19800
tggatgtgga gtacggtcag tacagtgtca tcctgcaggt tgacgtttt ccaccatcgc    19860 acgccgggac catcaccgtg tatgaagatt cacaaccggg gacgctgaat gatttctct    19920
```

```
gtgccatgac ggaggatgat gcccggccgg aggtgctgcg tcgtcttgaa ctgatggtgg   19980
aagaggtggc gcgtaacgcg tccgtggtgg cacagagtac ggcagacgcg aagaaatcag   20040
ccggcgatgc cagtgcatca gctgctcagg tcgcggccct tgtgactgat gcaactgact   20100
cagcacgcgc cgccagcacg tccgccggac aggctgcatc gtcagctcag gaagcgtcct   20160
ccggcgcaga agcggcatca gcaaaggcca ctgaagcgga aaaagtgccg gcagccgcag   20220
agtcctcaaa aaacgcggcg gccaccagtg ccggtgcggc gaaaacgtca gaaacgaatg   20280
ctgcagcgtc acaacaatca gccgccacgt ctgcctccac cgcggccacg aaagcgtcag   20340
aggccgccac ttcagcacga gatgcggtgg cctcaaaaga ggcagcaaaa tcatcagaaa   20400
cgaacgcatc atcaagtgcc ggtcgtgcag cttcctcggc aacggcggca gaaaattctg   20460 ccagggcgg aaaaacgtcc gagacgaatg ccaggtcatc tgaaacagca gcggaacgga   20520
gcgcctctgc cgcggcagac gcaaaaacag cggcggcggg gagtgcgtca acggcatcca   20580
cgaaggcgac agaggctgcg ggaagtgcgg tatcagcatc gcagagcaaa agtgcggcag   20640
aagcggcggc aatacgtgca aaaaattcgg caaaacgtgc agaagatata gcttcagctg   20700
tcgcgcttga ggatgcggac acaacgagaa aggggatagt gcagctcagc agtgcaacca   20760
acagcacgtc tgaaacgctt gctgcaacgc caaaggcggt taaggtggta atggatgaaa   20820
cgaacagaaa agcccactgg acagtccggc actgaccgga acgccaacag caccaaccgc   20880
gctcagggga caaacaata cccagattgc gaacaccgct tttgtactgg ccgcgattgc   20940
agatgttatc gacgcgtcac ctgacgcact gaatacgctg aatgaactgg ccgcagcgct   21000
cgggaatgat ccagattttg ctaccaccat gactaacgcg cttgcgggta acaaccgaa   21060 gaatgcgaca ctgacggcgc tggcagggct ttccacggcg aaaaataaat taccgtattt   21120
tgcggaaaat gatgccgcca gcctgactga actgactcag gttggcaggg atattctggc   21180
aaaaaattcc gttgcagatg ttcttgaata ccttggggcc ggtgagaatt cggccttttcc   21240 ggcaggtgcg ccgatcccgt ggccatcaga tatcgttccg tctggctacg tcctgatgca   21300
ggggcaggcg tttgacaaat cagcctaccc aaaacttgct gtcgcgtatc catcgggtgt   21360
gcttcctgat atgcgaggct ggacaatcaa ggggaaaccc gccagcggtc gtgctgtatt   21420
gtctcaggaa caggatggaa ttaagtcgca cacccacagt gccagtgcat ccggtacgga   21480
tttggggacg aaaaccacat cgtcgtttga ttacgggacg aaaacaacag gcagtttcga   21540
ttacggcacc aaatcgacga ataacacggg ggctcatgct cacagtctga gcggttcaac   21600
aggggccgcg ggtgctcatg cccacacaag tggtttaagg atgaacagtt ctggctggag   21660
tcagtatgga acagcaacca ttacaggaag tttatccaca gttaaaggaa ccagcacaca   21720
gggtattgct tatttatcga aaacggacag tcagggcagc cacagtcact cattgtccgg   21780
tacagccgtg agtgccggtg cacatgcgca tacagttggt attggtgcgc accagcatcc   21840
ggttgttatc ggtgctcatg cccattcttt cagtattggt tcacacggac acaccatcac   21900
cgttaacgct gcgggtaacg cggaaaacac cgtcaaaaac attgcattta actatattgt   21960
gaggcttgca taatggcatt cagaatgagt gaacaaccac ggaccataaa aatttataat   22020
ctgctggccg gaactaatga atttattggt gaaggtgacg catatattcc gcctcatacc   22080
ggtctgcctg caaacagtac cgatattgca ccgccagata ttccggctgg ctttgtggct   22140
gttttcaaca gtgatgaggc atcgtggcat ctcgttgaag accatcgggg taaaaccgtc   22200
tatgacgtgg cttccggcga cgcgttattt atttctgaac tcggtccgtt accggaaaat   22260
```

| | |
|---|---|
| tttacctggt tatcgccggg aggggaatat cagaagtgga acggcacagc ctgggtgaag | 22320 |
| gatacggaag cagaaaaact gttccggatc cgggaggcgg aagaaacaaa aaaaagcctg | 22380 |
| atgcaggtag ccagtgagca tattgcgccg cttcaggatg ctgcagatct ggaaattgca | 22440 |
| acgaaggaag aaacctcgtt gctggaagcc tggaagaagt atcgggtgtt gctgaaccgt | 22500 |
| gttgatacat caactgcacc tgatattgag tggcctgctg tccctgttat ggagtaatcg | 22560 |
| ttttgtgata tgccgcagaa acgttgtatg aaataacgtt ctgcggttag ttagtatatt | 22620 |
| gtaaagctga gtattggttt atttggcgat tattatcttc aggagaataa tggaagttct | 22680 |
| atgactcaat tgttcatagt gtttacatca ccgccaattg cttttaagac tgaacgcatg | 22740 |
| aaatatggtt tttcgtcatg ttttgagtct gctgttgata tttctaaagt cggttttttt | 22800 |
| tcttcgtttt ctctaactat tttccatgaa atacattttt gattattatt tgaatcaatt | 22860 |
| ccaattacct gaagtctttc atctataatt ggcattgtat gtattggttt attggagtag | 22920 |
| atgcttgctt ttctgagcca tagctctgat atccaaatga agccataggc atttgttatt | 22980 |
| ttggctctgt cagctgcata acgccaaaaa atatatttat ctgcttgatc ttcaaatgtt | 23040 |
| gtattgatta aatcaattgg atggaattgt ttatcataaa aaattaatgt ttgaatgtga | 23100 |
| taaccgtcct ttaaaaaagt cgtttctgca agcttggctg tatagtcaac taactcttct | 23160 |
| gtcgaagtga tattttttagg cttatctacc agttttagac gctctttaat atcttcagga | 23220 |
| attattttat tgtcatattg tatcatgcta aatgacaatt tgcttatgga gtaatctttt | 23280 |
| aattttaaat aagttattct cctggcttca tcaaataaag agtcgaatga tgttggcgaa | 23340 |
| atcacatcgt cacccattgg attgtttatt tgtatgccaa gagagttaca gcagttatac | 23400 |
| attctgccat agattatagc taaggcatgt aataattcgt aatcttttag cgtattagcg | 23460 |
| acccatcgtc tttctgattt aataatagat gattcagtta aatatgaagg taatttcttt | 23520 |
| tgtgcaagtc tgactaactt ttttatacca atgtttaaca tactttcatt tgtaataaac | 23580 |
| tcaatgtcat tttcttcaat gtaagatgaa ataagagtag cctttgcctc gctatacatt | 23640 |
| tctaaatcgc cttgtttttc tatcgtattg cgagaatttt tagcccaagc cattaatgga | 23700 |
| tcattttttcc attttttcaat aacattattg ttataccaaa tgtcatatcc tataatctgg | 23760 |
| tttttgtttt tttgaataat aaatgttact gttcttgcgg tttggaggaa ttgattcaaa | 23820 |
| ttcaagcgaa ataattcagg gtcaaaaatat gtatcaatgc agcatttgag caagtgcgat | 23880 |
| aaatctttaa gtcttctttc ccatggtttt ttagtcataa aactctccat tttgataggt | 23940 |
| tgcatgctag atgctgatat attttagagg tgataaaatt aactgcttaa ctgtcaatgt | 24000 |
| aatacaagtt gtttgatctt tgcaatgatt cttatcagaa accatatagt aaattagtta | 24060 |
| cacaggaaat ttttaatatt attattatca ttcattatgt attaaaatta gagttgtggc | 24120 |
| ttggctctgc taacacgttg ctcataggag atatggtaga gccgcagaca cgtcgtatgc | 24180 |
| aggaacgtgc tgcggctggc tggtgaactt ccgatagtgc gggtgttgaa tgatttccag | 24240 |
| ttgctaccga ttttacatat ttttttgcatg agagaatttg taccacctcc caccgaccat | 24300 |
| ctatgactgt acgccactgt ccctaggact gctatgtgcc ggagcggaca ttacaaacgt | 24360 |
| ccttctcggt gcatgccact gttgccaatg acctgcctag gaattggtta gcaagttact | 24420 |
| accggatttt gtaaaaacag ccctcctcat ataaaaagta ttcgttcact tccgataagc | 24480 |
| gtcgtaattt tctatctttc atcatattct agatccctct gaaaaaatct tccgagtttg | 24540 |
| ctaggcactg atacataact ctttttccaat aatttggggaa gtcattcaaa tctataatag | 24600 |
| gtttcagatt tgcttcaata aattctgact gtagctgctg aaacgttgcg gttgaactat | 24660 |

```
atttccttat aacttttacg aaagagtttc tttgagtaat cacttcactc aagtgcttcc    24720
ctgcctccaa acgatacctg ttagcaatat ttaatagctt gaaatgatga agagctctgt    24780
gtttgtcttc ctgcctccag ttcgccgggc attcaacata aaaactgata gcacccggag    24840
ttccggaaac gaaatttgca tatacccatt gctcacgaaa aaaatgtcc ttgtcgatat     24900 agggatgaat cgcttggtgt acctcatcta ctgcgaaaac ttgacctttc tctcccatat    24960
tgcagtcgcg gcacgatgga actaaattaa taggcatcac cgaaaattca ggataatgtg    25020
caataggaag aaaatgatct atatttttg tctgtcctat atcaccacaa aatggacatt     25080
tttcacctga tgaaacaagc atgtcatcgt aatatgttct agcgggtttg tttttatctc    25140
ggagattatt ttcataaagc ttttctaatt taacctttgt caggttacca actactaagg    25200
ttgtaggctc aagagggtgt gtcctgtcgt aggtaaataa ctgacctgtc gagcttaata    25260
ttctatattg ttgttctttc tgcaaaaaag tggggaagtg agtaatgaaa ttatttctaa    25320
catttatctg catcatacct tccgagcatt tattaagcat ttcgctataa gttctcgctg    25380
gaagaggtag tttttcatt gtacttacc ttcatctctg ttcattatca tcgcttttaa      25440
aacggttcga ccttctaatc ctatctgacc attataattt tttagaatgg tttcataaga    25500
aagctctgaa tcaacggact gcgataataa gtggtggtat ccagaatttg tcacttcaag    25560
taaaaacacc tcacgagtta aaacacctaa gttctcaccg aatgtctcaa tatccggacg    25620
gataatattt attgcttctc ttgaccgtag gactttccac atgcaggatt ttggaacctc    25680
ttgcagtact actggggaat gagttgcaat tattgctaca ccattgcgtg catcgagtaa    25740
gtcgcttaat gttcgtaaaa aagcagagag caaaggtgga tgcagatgaa cctctggttc    25800
atcgaataaa actaatgact tttcgccaac gacatctact aatcttgtga tagtaaataa    25860
aacaattgca tgtccagagc tcattcgaag cagatatttc tggatattgt cataaaacaa    25920
tttagtgaat ttatcatcgt ccacttgaat ctgtggttca ttacgtctta actcttcata    25980
tttagaaatg aggctgatga gttccatatt tgaaaagttt tcatcactac ttagttttt    26040 gatagcttca agccagagtt gtcttttct atctactctc atacaaccaa taaatgctga    26100
aatgaattct aagcggagat cgcctagtga ttttaaacta ttgctggcag cattcttgag    26160
tccaatataa aagtattgtg tacctttgc tgggtcaggt tgttctttag gaggagtaaa     26220
aggatcaaat gcactaaacg aaactgaaac aagcgatcga aatatccct ttgggattct     26280 tgactcgata agtctattat tttcagagaa aaaatattca ttgttttctg ggttggtgat    26340
tgcaccaatc attccattca aaattgttgt tttaccacac ccattccgcc cgataaaagc    26400
atgaatgttc gtgctgggca tagaattaac cgtcacctca aaaggtatag ttaaatcact    26460
gaatccggga gcactttttc tattaaatga aaagtggaaa tctgacaatt ctggcaaacc    26520
atttaacaca cgtgcgaact gtccatgaat ttctgaaaga gttacccctc taagtaatga    26580
ggtgttaagg acgctttcat tttcaatgtc ggctaatcga tttggccata ctactaaatc    26640
ctgaatagct ttaagaaggt tatgtttaaa accatcgctt aatttgctga gattaacata    26700
gtagtcaatg ctttcaccta aggaaaaaaa catttcaggg agttgactga attttttatc    26760
tattaatgaa taagtgctta cttcttcttt ttgacctaca aaaccaattt taacatttcc    26820
gatatcgcat ttttcaccat gctcatcaaa gacagtaaga taaaacattg taacaaagga    26880
atagtcattc caaccatctg ctcgtaggaa tgccttattt ttttctactg caggaatata    26940
cccgcctctt tcaataacac taaactccaa catatagtaa cccttaatt tattaaaata     27000
```

```
accgcaattt atttggcggc aacacaggat ctctctttta agttactctc tattacatac   27060
gttttccatc taaaaattag tagtattgaa cttaacgggg catcgtattg tagttttcca   27120
tatttagctt tctgcttcct tttggataac ccactgttat tcatgttgca tggtgcactg   27180
tttataccaa cgatatagtc tattaatgca tatatagtat cgccgaacga ttagctcttc   27240
aggcttctga agaagcgttt caagtactaa taagccgata gatagccacg gacttcgtag   27300 ccattttttca taagtgttaa cttccgctcc tcgctcataa cagacattca ctacagttat   27360
ggcggaaagg tatgcatgct gggtgtgggg aagtcgtgaa agaaaagaag tcagctgcgt   27420
cgtttgacat cactgctatc ttcttactgg ttatgcaggt cgtagtgggt ggcacacaaa   27480
gctttgcact ggattgcgag gctttgtgct tctctggagt gcgacaggtt tgatgacaaa   27540
aaattagcgc aagaagacaa aaatcacctt gcgctaatgc tctgttacag gtcactaata   27600
ccatctaagt agttgattca tagtgactgc atatgttgtg ttttacagta ttatgtagtc   27660
tgttttttat gcaaaatcta atttaatata ttgatattta tcattttta cgtttctcgt   27720 tcagcttttt tatactaagt tggcattata aaaaagcatt gcttatcaat ttgttgcaac   27780
gaacaggtca ctatcagtca aaataaaatc attatttgat ttcaattttg tcccactccc   27840
tgcctctgtc atcacgatac tgtgatgcca tggtgtccga cttatgcccg agaagatgtt   27900
gagcaaactt atcgcttatc tgcttctcat agagtcttgc agacaaactg cgcaactcgt   27960
gaaaggtagg cggatcccct tcgaaggaaa gacctgatgc ttttcgtgcg cgcataaaat   28020
accttgatac tgtgccggat gaaagcggtt cgcgacgagt agatgcaatt atggtttctc   28080
cgccaagaat ctctttgcat ttatcaagtg tttccttcat tgatattccg agagcatcaa   28140
tatgcaatgc tgttgggatg gcaattttta cgcctgtttt gctttgctcg acataaagat   28200
atccatctac gatatcagac cacttcattt cgcataaatc accaactcgt tgcccggtaa   28260
caacagccag ttccattgca agtctgagcc aacatggtga tgattctgct gcttgataaa   28320
ttttcaggta ttcgtcagcc gtaagtcttg atctccttac ctctgatttt gctgcgcgag   28380
tggcagcgac atggtttgtt gttatatggc cttcagctat tgcctctcgg aatgcatcgc   28440
tcagtgttga tctgattaac ttggctgacg ccgccttgcc ctcgtctatg tatccattga   28500
gcattgccgc aatttctttt gtggtgatgt cttcaagtgg agcatcaggc agacccctcc   28560
ttattgcttt aattttgctc atgtaattta tgagtgtctt ctgcttgatt cctctgctgg   28620
ccaggatttt ttcgtagcga tcaagccatg aatgtaacgt aacggaatta tcactgttga   28680
ttctcgctgt cagaggcttg tgtttgtgtc ctgaaaataa ctcaatgttg gcctgtatag   28740
cttcagtgat tgcgattcgc ctgtctctgc ctaatccaaa ctctttaccc gtccttgggt   28800
ccctgtagca gtaatatcca ttgttcttta tataaaggtt aggggtaaa tcccggcgct   28860 catgacttcg ccttcttccc atttctgatc ctcttcaaaa ggccacctgt tactggtcga   28920
tttaagtcaa cctttaccgc tgattcgtgg aacagatact ctcttccatc cttaaccgga   28980
ggtgggaata tcctgcattc ccgaacccat cgacgaactg tttcaaggct tcttggacgt   29040
cgctggcgtg cgttccactc ctgaagtgtc aagtacatcg caaagtctcc gcaattacac   29100
gcaagaaaaa accgccatca ggcggcttgg tgttctttca gttcttcaat tcgaatattg   29160
gttacgtctg catgtgctat ctgcgcccat atcatccagt ggtcgtagca gtcgttgatg   29220
ttctccgctt cgataactct gttgaatggc tctccattcc attctcctgt gactcggaag   29280
tgcatttatc atctccataa aacaaaaccc gccgtagcga gttcagataa aataaatccc   29340
cgcgagtgcg aggattgtta tgtaatattg ggtttaatca tctatatgtt ttgtacagag   29400
```

```
agggcaagta tcgtttccac cgtactcgtg ataataattt tgcacggtat cagtcatttc   29460
tcgcacattg cagaatgggg atttgtcttc attagactta taaaccttca tggaatattt   29520
gtatgccgac tctatatcta taccttcatc tacataaaca ccttcgtgat gtctgcatgg   29580
agacaagaca ccggatctgc acaacattga taacgcccaa tcttttttgct cagactctaa  29640 ctcattgata ctcatttata aactccttgc aatgtatgtc gtttcagcta acggtatca    29700 gcaatgttta tgtaaagaaa cagtaagata atactcaacc cgatgtttga gtacggtcat   29760
catctgacac tacagactct ggcatcgctg tgaagacgac gcgaaattca gcattttcac   29820
aagcgttatc ttttacaaaa ccgatctcac tctcctttga tgcgaatgcc agcgtcagac   29880
atcatatgca gatactcacc tgcatcctga acccattgac ctccaacccc gtaatagcga   29940
tgcgtaatga tgtcgatagt tactaacggg tcttgttcga ttaactgccg cagaaactct   30000
tccaggtcac cagtgcagtg cttgataaca ggagtcttcc caggatggcg aacaacaaga   30060
aactggtttc cgtcttcacg gacttcgttg cttttccagtt tagcaatacg cttactccca   30120
tccgagataa caccttcgta atactcacgc tgctcgttga gttttgattt tgctgtttca   30180
agctcaacac gcagtttccc tactgttagc gcaatatcct cgttctcctg gtcgcggcgt   30240
ttgatgtatt gctggtttct ttcccgttca tccagcagtt ccagcacaat cgatggtgtt   30300
accaattcat ggaaaaggtc tgcgtcaaat ccccagtcgt catgcattgc ctgctctgcc   30360
gcttcacgca gtgcctgaga gttaatttcg ctcacttcga acctctctgt ttactgataa   30420
gttccagatc ctcctggcaa cttgcacaag tccgacaacc ctgaacgacc aggcgtcttc   30480
gttcatctat cggatcgcca cactcacaac aatgagtggc agatatagcc tggtggttca   30540
ggcggcgcat ttttattgct gtgttgcgct gtaattcttc tatttctgat gctgaatcaa   30600
tgatgtctgc catctttcat taatccctga actgttggtt aatacgcttg agggtgaatg   30660
cgaataataa aaaaggagcc tgtagctccc tgatgatttt gcttttcatg ttcatcgttc   30720
cttaaagacg ccgtttaaca tgccgattgc caggcttaaa tgagtcggtg tgaatcccat   30780
cagcgttacc gtttcgcggt gcttcttcag tacgctacgg caaatgtcat cgacgttttt   30840
atccggaaac tgctgtctgg ctttttttga tttcagaatt agcctgacgg gcaatgctgc   30900
gaagggcgtt ttcctgctga ggtgtcattg aacaagtccc atgtcggcaa gcataagcac   30960
acagaatatg aagcccgctg ccagaaaaat gcattccgtg gttgtcatac ctggtttctc   31020
tcatctgctt ctgctttcgc caccatcatt tccagctttt gtgaaaggga tgcggctaac   31080
gtatgaaatt cttcgtctgt ttctactggt attggcacaa acctgattcc aatttgagca   31140
aggctatgtg ccatctcgat actcgttctt aactcaacag aagatgcttt gtgcatacag   31200
cccctcgttt attatttatc tcctcagcca gccgctgtgc tttcagtgga tttcggataa   31260
cagaaaggcc gggaaatacc cagcctcgct ttgtaacgga gtagacgaaa gtgattgcgc   31320
ctacccggat attatcgtga ggatgcgtca tcgccattgc tccccaaata caaaaccaat   31380
ttcagccagt gcctcgtcca tttttttcgat gaactccggc acgatctcgt caaaactcgc   31440
catgtacttt tcatcccgct caatcacgac ataatgcagg ccttcacgct tcatacgcgg   31500
gtcatagttg gcaaagtacc aggcattttt tcgcgtcacc cacatgctgt actgcacctg   31560
ggccatgtaa gctgacttta tggcctcgaa accaccgagc cggaacttca tgaaatcccg   31620
ggaggtaaac gggcatttca gttcaaggcc gttgccgtca ctgcataaac catcgggaga   31680
gcaggcggta cgcatacttt cgtcgcgata gatgatcggg gattcagtaa cattcacgcc   31740
```

```
ggaagtgaat tcaaacaggg ttctggcgtc gttctcgtac tgttttcccc aggccagtgc    31800
tttagcgtta acttccggag ccacaccggt gcaaacctca gcaagcaggg tgtggaagta    31860
ggacattttc atgtcaggcc acttctttcc ggagcggggt tttgctatca cgttgtgaac    31920
ttctgaagcg gtgatgacgc cgagccgtaa tttgtgccac gcatcatccc cctgttcgac    31980
agctctcaca tcgatcccgg tacgctgcag gataatgtcc ggtgtcatgc tgccaccttc    32040
tgctctgcgg ctttctgttt caggaatcca agagctttta ctgcttcggc ctgtgtcagt    32100
tctgacgatg cacgaatgtc gcggcgaaat atctgggaac agagcggcaa taagtcgtca    32160
tcccatgttt tatccagggc gatcagcaga gtgttaatct cctgcatggt ttcatcgtta    32220
accggagtga tgtcgcgttc cggctgacgt tctgcagtgt atgcagtatt ttcgacaatg    32280
cgctcggctt catccttgtc atagatacca gcaaatccga aggccagacg ggcacactga    32340
atcatggctt tatgacgtaa catccgtttg ggatgcgact gccacggccc cgtgatttct    32400
ctgccttcgc gagttttgaa tggttcgcgg cggcattcat ccatccattc ggtaacgcag    32460
atcggatgat tacggtcctt gcggtaaatc cggcatgtac aggattcatt gtcctgctca    32520
aagtccatgc catcaaactg ctggttttca ttgatgatgc gggaccagcc atcaacgccc    32580
accaccggaa cgatgccatt ctgcttatca ggaaaggcgt aaatttcttt cgtccacgga    32640
ttaaggccgt actggttggc aacgatcagt aatgcgatga actgcgcatc gctggcatca    32700
cctttaaatg ccgtctggcg aagagtggtg atcagttcct gtgggtcgac agaatccatg    32760
ccgacacgtt cagccagctt cccagccagc gttgcgagtg cagtactcat tcgtttttata    32820 cctctgaatc aatatcaacc tggtggtgag caatggtttc aaccatgtac cggatgtgtt    32880
ctgccatgcg ctcctgaaac tcaacatcgt catcaaacgc acgggtaatg gattttttgc    32940
tggccccgtg gcgttgcaaa tgatcgatgc atagcgattc aaacaggtgc tggggcaggc    33000 cttttttccat gtcgtctgcc agttctgcct cttctcttc acgggcgagc tgctggtagt    33060
gacgcgccca gctctgagcc tcaagacgat cctgaatgta ataagcgttc atggctgaac    33120
tcctgaaata gctgtgaaaa tatcgcccgc gaaatgccgg gctgattagg aaaacaggaa    33180 aggggggttag tgaatgcttt tgcttgatct cagtttcagt attaatatcc attttttata    33240
agcgtcgacg gcttcacgaa acatcttttc atcgccaata aaagtggcga tagtgaattt    33300
agtctggata gccataagtg tttgatccat tctttgggac tcctggctga ttaagtatgt    33360
cgataaggcg tttccatccg tcacgtaatt tacgggtgat tcgttcaagt aaagattcgg    33420
aagggcagcc agcaacaggc caccctgcaa tggcatattg catggtgtgc tccttattta    33480
tacataacga aaaacgcctc gagtgaagcg ttattggtat gcggtaaaac cgcactcagg    33540
cggccttgat agtcatatca tctgaatcaa atattcctga tgtatcgata tcggtaattc    33600
ttattccttc gctaccatcc attggaggcc atccttcctg accatttcca tcattccagt    33660
cgaactcaca cacaacacca tatgcattta agtcgcttga aattgctata agcagagcat    33720
gttgcgccag catgattaat acagcattta atacagagcc gtgtttattg agtcggtatt    33780
cagagtctga ccagaaatta ttaatctggt gaagtttttc ctctgtcatt acgtcatggt    33840
cgatttcaat ttctattgat gctttccagt cgtaatcaat gatgtatttt ttgatgtttg    33900
acatctgttc atatcctcac agataaaaaa tcgccctcac actggagggc aaagaagatt    33960
tccaataatc agaacaagtc ggctcctgtt tagttacgag cgacattgct ccgtgtattc    34020
actcgttgga atgaatacac agtgcagtgt ttattctgtt atttatgcca aaaataaagg    34080
ccactatcag gcagctttgt tgttctgttt accaagttct ctggcaatca ttgccgtcgt    34140
```

```
tcgtattgcc catttatcga catatttccc atcttccatt acaggaaaca tttcttcagg    34200
cttaaccatg cattccgatt gcagcttgca tccattgcat cgcttgaatt gtccacacca    34260
ttgattttta tcaatagtcg tagtcatacg gatagtcctg gtattgttcc atcacatcct    34320
gaggatgctc ttcgaactct tcaaattctt cttccatata tcaccttaaa tagtggattg    34380
cggtagtaaa gattgtgcct gtcttttaac cacatcaggc tcggtggttc tcgtgtaccc    34440
ctacagcgag aaatcggata aactattaca acccctacag tttgatgagt atagaaatgg    34500
atccactcgt tattctcgga cgagtgttca gtaatgaacc tctggagaga accatgtata    34560
tgatcgttat ctgggttgga cttctgcttt taagcccaga taactggcct gaatatgtta    34620
atgagagaat cggtattcct catgtgtggc atgttttcgt ctttgctctt gcattttcgc    34680
tagcaattaa tgtgcatcga ttatcagcta ttgccagcgc cagatataag cgatttaagc    34740
taagaaaacg cattaagatg caaaacgata aagtgcgatc agtaattcaa aaccttacag    34800
aagagcaatc tatggttttg tgcgcagccc ttaatgaagg caggaagtat gtggttacat    34860
caaaacaatt cccatacatt agtgagttga ttgagcttgg tgtgttgaac aaaactttt    34920 cccgatggaa tggaaagcat atattattcc ctattgagga tatttactgg actgaattag    34980
ttgccagcta tgatccatat aatattgaga taaagccaag gccaatatct aagtaactag    35040
ataagaggaa tcgatttcc cttaattttc tggcgtccac tgcatgttat gccgcgttcg    35100
ccaggcttgc tgtaccatgt gcgctgattc ttgcgctcaa tacgttgcag gttgctttca    35160
atctgtttgt ggtattcagc cagcactgta aggtctatcg gatttagtgc gctttctact    35220
cgtgatttcg gtttgcgatt cagcgagaga ataggqcggt taactggttt tgcgcttacc    35280
ccaaccaaca ggggatttgc tgcttttccat tgagcctgtt tctctgcgcg acgttcgcgg    35340
cggcgtgttt gtgcatccat ctggattctc ctgtcagtta gctttggtgg tgtgtggcag    35400
ttgtagtcct gaacgaaaac cccccgcgat tggcacattg gcagctaatc cggaatcgca    35460
cttacggcca atgcttcgtt tcgtatcaca cacccccaaag ccttctgctt tgaatgctgc    35520
ccttcttcag ggcttaattt ttaagagcgt caccttcatg gtggtcagtg cgtcctgctg    35580
atgtgctcag tatcaccgcc agtggtattt atgtcaacac cgccagagat aatttatcac    35640
cgcagatggt tatctgtatg ttttttatat gaatttattt tttgcagggg ggcattgttt    35700
ggtaggtgag agatctgaat tgctatgttt agtgagttgt atctatttat ttttcaataa    35760
atacaattgg ttatgtgttt tgggggcgat cgtgaggcaa agaaaacccg gcgctgaggc    35820
cgggttattc ttgttctctg gtcaaattat atagttggaa acaaggatg catatatgaa    35880 tgaacgatgc agaggcaatg ccgatggcga tagtgggtat catgtagccg cttatgctgg    35940
aaagaagcaa taacccgcag aaaaacaaag ctccaagctc aacaaaacta agggcataga    36000
caataactac cgatgtcata tacccatact ctctaatctt ggccagtcgg cgcgttctgc    36060
ttccgattag aaacgtcaag gcagcaatca ggattgcaat catggttcct gcatatgatg    36120
acaatgtcgc cccaagacca tctctatgag ctgaaaaaga aacaccagga atgtagtggc    36180
ggaaaaggag atagcaaatg cttacgataa cgtaaggaat tattactatg taaacaccag    36240
gcatgattct gttccgcata attactcctg ataattaatc cttaactttg cccacctgcc    36300 tttaaaaca ttccagtata tcactttca ttcttgcgta gcaatatgcc atctcttcag    36360
ctatctcagc attggtgacc ttgttcagag gcgctgagag atggccttt tctgatagat    36420 aatgttctgt taaatatct ccggcctcat cttttgcccg caggctaatg tctgaaaatt    36480
```

```
gaggtgacgg gttaaaaata atatccttgg caaccttttt tatatccctt ttaaattttg   36540
gcttaatgac tatatccaat gagtcaaaaa gctcccctto aatatctgtt gcccctaaga   36600
cctttaatat atcgccaaat acaggtagct tggcttctac cttcaccgtt gttcggccga   36660
tgaaatgcat atgcataaca tcgtctttgg tggttcccct catcagtggc tctatctgaa   36720
cgcgctctcc actgcttaat gacattcctt tcccgattaa aaaatctgtc agatcggatg   36780
tggtcggccc gaaaacagtt ctggcaaaac caatggtgtc gccttcaaca aacaaaaaag   36840
atgggaatcc caatgattcg tcatctgcga ggctgttctt aatatcttca actgaagctt   36900
tagagcgatt tatcttctga accagactct tgtcatttgt tttggtaaag agaaaagttt   36960
ttccatcgat tttatgaata tacaaataat tggagccaac ctgcaggtga tgattatcag   37020
ccagcagaga attaaggaaa acagacaggt ttattgagcg cttatctttc cctttatttt   37080
tgctgcggta agtcgcataa aaaccattct tcataattca atccatttac tatgttatgt   37140
tctgagggga gtgaaaattc ccctaattcg atgaagattc ttgctcaatt gttatcagct   37200
atgcgccgac cagaacacct tgccgatcag ccaaacgtct cttcaggcca ctgactagcg   37260
ataactttcc ccacaacgga acaactctca ttgcatggga tcattgggta ctgtgggttt   37320
agtggttgta aaaacacctg accgctatcc ctgatcagtt tcttgaaggt aaactcatca   37380
cccccaagtc tggctatgca gaaatcacct ggctcaacag cctgctcagg gtcaacgaga   37440
attaacattc cgtcaggaaa gcttggcttg agcctgttg tgcggtcat ggaattacct   37500 tcaacctcaa gccagaatgc agaatcactg gcttttttgg ttgtgcttac ccatctctcc   37560
gcatcacctt tggtaaaggt tctaagctca ggtgagaaca tccctgcctg aacatgagaa   37620
aaaacagggt actcatactc acttctaagt gacggctgca tactaaccgc ttcatacatc   37680
tcgtagattt ctctggcgat tgaagggcta aattcttcaa cgctaacttt gagaattttt   37740
gcaagcaatg cggcgttata agcatttaat gcattgatgc cattaaataa agcaccaacg   37800
cctgactgcc ccatccccat cttgtctgcg acagattcct gggataagcc aagttcattt   37860 ttctttttt cataaattgc tttaaggcga cgtgcgtcct caagctgctc ttgtgttaat   37920
ggtttctttt ttgtgctcat acgttaaatc tatcaccgca agggataaat atctaacacc   37980
gtgcgtgttg actattttac ctctggcggt gataatggtt gcatgtacta aggaggttgt   38040
atggaacaac gcataaccct gaaagattat gcaatgcgct ttgggcaaac caagacagct   38100
aaagatctcg gcgtatatca aagcgcgatc aacaaggcca ttcatgcagg ccgaaagatt   38160
tttttaacta taaacgctga tggaagcgtt tatgcggaag aggtaaagcc cttcccgagt   38220
aacaaaaaaa caacagcata ataaccccg ctcttacaca ttccagccct gaaaagggc    38280 atcaaattaa accacaccta tggtgtatgc atttatttgc atacattcaa tcaattgtta   38340
tctaaggaaa tacttacata tggttcgtgc aaacaaacgc aacgaggctc tacgaatcga   38400
gagtgcgttg cttaacaaaa tcgcaatgct tggaactgag aagacagcgg aagctgtggg   38460
cgttgataag tcgcagatca gcaggtggaa gagggactgg attccaaagt tctcaatgct   38520
gcttgctgtt cttgaatggg gggtcgttga cgacgacatg gctcgattgg cgcgacaagt   38580
tgctgcgatt ctcaccaata aaaacgccc ggcggcaacc gagcgttctg aacaaatcca    38640
gatggagttc tgaggtcatt actggatcta tcaacaggag tcattatgac aaatacagca   38700
aaaatactca acttcggcag aggtaacttt gccggacagg agcgtaatgt ggcagatctc   38760
gatgatggtt acgccagact atcaaatatg ctgcttgagg cttattcggg cgcagatctg   38820
accaagcgac agtttaaagt gctgcttgcc attctgcgta aaacctatgg gtggaataaa   38880
```

```
ccaatggaca gaatcaccga ttctcaactt agcgagatta caaagttacc tgtcaaacgg    38940
tgcaatgaag ccaagttaga actcgtcaga atgaatatta tcaagcagca aggcggcatg    39000
tttggaccaa ataaaaacat ctcagaatgg tgcatccctc aaaacgaggg aaaatcccct    39060
aaaacgaggg ataaaacatc cctcaaattg ggggattgct atccctcaaa acaggggac    39120 acaaaagaca ctattacaaa agaaaaaaga aaagattatt cgtcagagaa ttctggcgaa    39180
tcctctgacc agccagaaaa cgacctttct gtggtgaaac cggatgctgc aattcagagc    39240
ggcagcaagt gggggacagc agaagacctg accgccgcag agtggatgtt tgacatggtg    39300
aagactatcg caccatcagc cagaaaaccg aattttgctg ggtgggctaa cgatatccgc    39360
ctgatgcgtg aacgtgacgg acgtaaccac cgcgacatgt gtgtgctgtt ccgctgggca    39420
tgccaggaca acttctggtc cggtaacgtg ctgagcccgg ccaaactccg cgataagtgg    39480
acccaactcg aaatcaaccg taacaagcaa caggcaggcg tgacagccag caaaccaaaa    39540
ctcgacctga caaacacaga ctggatttac ggggtggatc tatgaaaaac atcgccgcac    39600
agatggttaa ctttgaccgt gagcagatgc gtcggatcgc caacaacatg ccggaacagt    39660
acgacgaaaa gccgcaggta cagcaggtag cgcagatcat caacggtgtg ttcagccagt    39720
tactggcaac tttcccggcg agcctggcta accgtgacca gaacgaagtg aacgaaatcc    39780
gtcgccagtg ggttctggct tttcgggaaa acggatcgac cacgatggaa caggttaacg    39840
caggaatgcg cgtagcccgt cggcagaatc gaccatttct gccatcaccc gggcagtttg    39900
ttgcatggtg ccgggaagaa gcatccgtta ccgccggact gccaaacgtc agcgagctgg    39960
ttgatatggt ttacgagtat tgccggaagc gaggcctgta tccggatgcg gagtcttatc    40020
cgtggaaatc aaacgcgcac tactggctgg ttaccaacct gtatcagaac atgcgggcca    40080
atgcgcttac tgatgcggaa ttcgccgta aggccgcaga tgagcttgtc catatgactg    40140
cgagaattaa ccgtggtgag gcgatccctg aaccagtaaa acaacttcct gtcatgggcg    40200
gtagacctct aaatcgtgca caggctctgg cgaagatcgc agaaatcaaa gctaagttcg    40260
gactgaaagg agcaagtgta tgacgggcaa agaggcaatt attcattacc tgggacgca    40320 taatagcttc tgtgcgccgg acgttgccgc gctaacaggc gcaacagtaa ccagcataaa    40380
tcaggccgcg gctaaaatgg cacgggcagg tcttctggtt atcgaaggta aggtctggcg    40440
aacggtgtat taccggtttg ctaccaggga agaacgggaa ggaaagatga gcacgaacct    40500 ggttttaag gagtgtcgcc agagtgccgc gatgaaacgg gtattggcgg tatatggagt    40560
taaaagatga ccatctacat tactgagcta ataacaggcc tgctggtaat cgcaggcctt    40620
tttatttggg ggagagggaa gtcatgaaaa aactaacctt tgaaattcga tctccagcac    40680
atcagcaaaa cgctattcac gcagtacagc aaatccttcc agacccaacc aaaccaatcg    40740
tagtaaccat tcaggaacgc aaccgcagct tagaccaaaa caggaagcta tgggcctgct    40800
taggtgacgt ctctcgtcag gttgaatggc atggtcgctg gctggatgca gaaagctgga    40860
agtgtgtgtt taccgcagca ttaaagcagc aggatgttgt tcctaacctt gccgggaatg    40920
gctttgtggt aataggccag tcaaccagca ggatgcgtgt aggcgaattt gcggagctat    40980
tagagcttat acaggcattc ggtacagagc gtggcgttaa gtggtcagac gaagcgagac    41040
tggctctgga gtggaaagcg agatgggag acagggctgc atgataaatg tcgttagttt    41100
ctccggtggc aggacgtcag catatttgct ctggctaatg gagcaaaagc gacgggcagg    41160
taaagacgtg cattacgttt tcatggatac aggttgtgaa catccaatga catatcggtt    41220
```

```
tgtcagggaa gttgtgaagt tctgggatat accgctcacc gtattgcagg ttgatatcaa    41280
cccggagctt ggacagccaa atggttatac ggtatgggaa ccaaaggata ttcagacgcg    41340
aatgcctgtt ctgaagccat ttatcgatat ggtaaagaaa tatggcactc catacgtcgg    41400
cggcgcgttc tgcactgaca gattaaaact cgttccnttc accaaatact gtgatgacca    41460
```
(Note: reading as faithfully as possible)
```
tttcgggcga gggaattaca ccacgtggat tggcatcaga gctgatgaac cgaagcggct    41520
aaagccaaag cctggaatca gatatcttgc tgaactgtca gactttgaga aggaagatat    41580
cctcgcatgg tggaagcaac aaccattcga tttgcaaata ccggaacatc tcggtaactg    41640
catattctgc attaaaaaat caacgcaaaa aatcggactt gcctgcaaag atgaggaggg    41700
attgcagcgt gttttnaatg aggtcatcac gggatcccat gtgcgtgacg acatcggga    41760 aacgccaaag gagattatgt accgaggaag aatgtcgctg acggtatcg cgaaaatgta    41820 ttcagaaaat gattatcaag ccctgtatca ggacatggta cgagctaaaa gattcgatac    41880
cggctcttgt tctgagtcat gcgaaatatt tggagggcag cttgatttcg acttcgggag    41940
ggaagctgca tgatgcgatg ttatcggtgc ggtgaatgca agaagataa ccgcttccga    42000 ccaaatcaac cttactggaa tcgatggtgt ctccggtgtg aaagaacacc aacaggggtg    42060
ttaccactac cgcaggaaaa ggaggacgtg tggcgagaca cgacgaagt atcaccgaca    42120 taatctgcga aaactgcaaa taccttccaa cgaaacgcac cagaaataaa cccaagccaa    42180
tcccaaaaga atctgacgta aaaaccttca actacacggc tcacctgtgg gatatccggt    42240
ggctaagacg tcgtgcgagg aaaacaaggt gattgaccaa aatcgaagtt acgaacaaga    42300
aagcgtcgag cgagctttaa cgtgcgctaa ctgcggtcag aagctgcatg tgctggaagt    42360
tcacgtgtgt gagcactgct gcgcagaact gatgagcgat ccgaatagct cgatgcacga    42420
ggaagaagat gatggctaaa ccagcgcgaa gacgatgtaa aaacgatgaa tgccgggaat    42480
ggtttcaccc tgcattcgct aatcagtggt ggtgctctcc agagtgtgga accaagatag    42540
cactcgaacg acgaagtaaa gaacgcgaaa aagcggaaaa agcagcagag aagaaacgac    42600
gacgagagga gcagaaacag aaagataaac ttaagattcg aaaactcgcc ttaaagcccc    42660
gcagttactg gattaaacaa gcccaacaag ccgtaaacgc cttcatcaga gaaagagacc    42720
gcgacttacc atgtatctcg tgcggaacgc tcacgtctgc tcagtgggat gccggacatt    42780
accggacaac tgctgcggca cctcaactcc gatttaatga acgcaatatt cacaagcaat    42840
gcgtggtgtg caaccagcac aaaagcggaa atctcgttcc gtatcgcgtc gaactgatta    42900
gccgcatcgg gcaggaagca gtagacgaaa tcgaatcaaa ccataaccgc catcgctgga    42960
ctatcgaaga gtgcaaggcg atcaaggcag agtaccaaca gaaactcaaa gacctgcgaa    43020
atagcagaag tgaggccgca tgacgttctc agtaaaaacc attccagaca tgctcgttga    43080
agcatacgga aatcagacag aagtagcacg cagactgaaa tgtagtcgcg gtacggtcag    43140
aaaatacgtt gatgataaag acgggaaaat gcacgccatc gtcaacgacg ttctcatggt    43200
tcatcgcgga tggagtgaaa gagatgcgct attacgaaaa aattgatggc agcaaatacc    43260
gaaatatttg ggtagttggc gatctgcacg gatgctacac gaacctgatg aacaaactgg    43320
atacgattgg attcgacaac aaaaaagacc tgcttatctc ggtgggcgat ttggttgatc    43380
gtggtgcaga gaacgttgaa tgcctggaat taatcacatt cccctggttc agagctgtac    43440
gtggaaacca tgagcaaatg atgattgatg cttatcaga gcgtggaaac gttaatcact    43500
ggctgcttaa tggcggtggc tggttctttta atctcgatta cgacaaagaa attctggcta    43560
aagctcttgc ccataaagca gatgaacttc cgttaatcat cgaactggtg agcaaagata    43620
```

```
aaaaatatgt tatctgccac gccgattatc cctttgacga atacgagttt ggaaagccag    43680
ttgatcatca gcaggtaatc tggaaccgcg aacgaatcag caactcacaa aacgggatcg    43740
tgaaagaaat caaaggcgcg gacacgttca tctttggtca tacgccagca gtgaaaccac    43800
tcaagtttgc caaccaaatg tatatcgata ccggcgcagt gttctgcgga aacctaacat    43860
tgattcaggt acagggagaa ggcgcatgag actcgaaagc gtagctaaat ttcattcgcc    43920
aaaaagcccg atgatgagcg actcaccacg gccacggct tctgactctc tttccggtac     43980
tgatgtgatg gctgctatgg ggatggcgca atcacaagcc ggattcggta tggctgcatt    44040
ctgcggtaag cacgaactca gccagaacga caaacaaaag gctatcaact atctgatgca    44100
atttgcacac aaggtatcgg ggaaataccg tggtgtggca aagcttgaag gaaatactaa    44160
ggcaaaggta ctgcaagtgc tcgcaacatt cgcttatgcg gattattgcc gtagtgccgc    44220
gacgccgggg gcaagatgca gagattgcca tggtacaggc cgtgcggttg atattgccaa    44280
aacagagctg tgggggagag ttgtcgagaa agagtgcgga agatgcaaag gcgtcggcta    44340
ttcaaggatg ccagcaagcg cagcatatcg cgctgtgacg atgctaatcc caaaccttac    44400
ccaacccacc tggtcacgca ctgttaagcc gctgtatgac gctctggtgg tgcaatgcca    44460
caaagaagag tcaatcgcag acaacatttt gaatgcggtc acacgttagc agcatgattg    44520
ccacggatgg caacatatta acggcatgat attgacttat tgaataaaat tgggtaaatt    44580
tgactcaacg atgggttaat tcgctcgttg tggtagtgag atgaaaagag gcggcgctta    44640
ctaccgattc cgcctagttg gtcacttcga cgtatcgtct ggaactccaa ccatcgcagg    44700
cagagaggtc tgcaaaatgc aatcccgaaa cagttcgcag gtaatagtta gagcctgcat    44760
aacggtttcg ggattttta tatctgcaca acaggtaaga gcattgagtc gataatcgtg      44820
aagagtcggc gagcctggtt agccagtgct ctttccgttg tgctgaatta agcgaatacc    44880
ggaagcagaa ccggatcacc aaatgcgtac aggcgtcatc gccgcccagc aacagcacaa    44940
cccaaactga gccgtagcca ctgtctgtcc tgaattcatt agtaatagtt acgctgcggc    45000
cttttacaca tgaccttcgt gaaagcgggg ggcaggaggt cgcgctaaca acctcctgcc    45060
gttttgcccg tgcatatcgg tcacgaacaa atctgattac taaacacagt agcctggatt    45120
tgttctatca gtaatcgacc ttattcctaa ttaaatagag caaatcccct tattgggggt    45180
aagacatgaa gatgccagaa aaacatgacc tgttggccgc cattctcgcg gcaaaggaac    45240
aaggcatcgg ggcaatcctt gcgtttgcaa tggcgtacct tcgcggcaga tataatggcg    45300
gtgcgtttac aaaaacagta atcgacgcaa cgatgtgcgc cattatcgcc tggttcattc    45360
gtgaccttct cgacttcgcc ggactaagta gcaatctcgc ttatataacg agcgtgttta    45420
tcggctacat cggtactgac tcgattggtt cgcttatcaa acgcttcgct gctaaaaaag    45480
ccggagtaga agatggtaga aatcaataat caacgtaagg cgttcctcga tatgctggcg    45540
tggtcggagg gaactgataa cggacgtcag aaaaccagaa atcatggtta tgacgtcatt    45600
gtaggcggag agctatttac tgattactcc gatcaccctc gcaaacttgt cacgctaaac    45660
ccaaaactca aatcaacagg cgccggacgc taccagcttc tttcccgttg gtgggatgcc    45720
taccgcaagc agcttggcct gaaagacttc tctccgaaaa gtcaggacgc tgtggcattg    45780
cagcagatta aggagcgtgg cgctttacct atgattgatc gtggtgatat ccgtcaggca    45840
atcgaccgtt gcagcaatat ctgggcttca ctgccgggcg ctggttatgg tcagttcgag    45900
cataaggctg acagcctgat tgcaaaattc aaagaagcgg gcggaacggt cagagagatt    45960
```

```
gatgtatgag cagagtcacc gcgattatct ccgctctggt tatctgcatc atcgtctgcc   46020
tgtcatgggc tgttaatcat taccgtgata acgccattac ctacaaagcc cagcgcgaca   46080
aaaatgccag agaactgaag ctggcgaacg cggcaattac tgacatgcag atgcgtcagc   46140
gtgatgttgc tgcgctcgat gcaaaataca cgaaggagtt agctgatgct aaagctgaaa   46200
atgatgctct gcgtgatgat gttgccgctg tcgtcgtcg gttgcacatc aaagcagtct   46260
gtcagtcagt gcgtgaagcc accaccgcct ccggcgtgga taatgcagcc tcccccgac   46320 tggcagacac cgctgaacgg gattatttca ccctcagaga gaggctgatc actatgcaaa   46380
aacaactgga aggaacccag aagtatatta atgagcagtg cagatagagt tgcccatatc   46440
gatgggcaac tcatgcaatt attgtgagca atacacacgc gcttccagcg gagtataaat   46500
gcctaaagta ataaaaccga gcaatccatt tacgaatgtt tgctgggttt ctgttttaac   46560
aacattttct gcgccgccac aaattttggc tgcatcgaca gttttcttct gcccaattcc   46620
agaaacgaag aaatgatggg tgatggtttc ctttggtgct actgctgccg gtttgttttg   46680
aacagtaaac gtctgttgag cacatcctgt aataagcagg gccagcgcag tagcgagtag   46740 cattttttc atggtgttat tcccgatgct ttttgaagtt cgcagaatcg tatgtgtaga   46800
aaattaaaca accctaaac aatgagttga aatttcatat tgttaatatt tattaatgta   46860
tgtcaggtgc gatgaatcgt cattgtattc ccggattaac tatgtccaca gccctgacgg   46920
ggaacttctc tgcgggagtg tccgggaata attaaaacga tgcacacagg gtttagcgcg   46980
tacacgtatt gcattatgcc aacgccccgg tgctgacacg gaagaaaccg gacgttatga   47040
tttagcgtgg aaagatttgt gtagtgttct gaatgctctc agtaaatagt aatgaattat   47100
caaaggtata gtaatatctt ttatgttcat ggatatttgt aacccatcgg aaaactcctg   47160
ctttagcaag atttttccctg tattgctgaa atgtgatttc tcttgatttc aacctatcat   47220
aggacgtttc tataagatgc gtgtttcttg agaatttaac atttacaacc tttttaagtc   47280
cttttattaa cacggtgtta tcgttttcta acacgatgtg aatattatct gtggctagat   47340
agtaaatata atgtgagacg ttgtgacgtt ttagttcaga ataaaacaat tcacagtcta   47400
aatcttttcg cacttgatcg aatatttctt taaaaatggc aacctgagcc attggtaaaa   47460
ccttccatgt gatacgaggg cgcgtagttt gcattatcgt ttttatcgtt tcaatctggt   47520
ctgacctcct tgtgttttgt tgatgattta tgtcaaatat taggaatgtt ttcacttaat   47580
agtattggtt gcgtaacaaa gtgcggtcct gctggcattc tggagggaaa tacaaccgac   47640
agatgtatgt aaggccaacg tgctcaaatc ttcatacaga aagatttgaa gtaatatttt   47700
aaccgctaga tgaagagcaa gcgcatggag cgacaaaatg aataaagaac aatctgctga   47760
tgatccctcc gtggatctga ttcgtgtaaa aaatatgctt aatagcacca tttctatgag   47820
ttaccctgat gttgtaattg catgtataga acataaggtg tctctggaag cattcagagc   47880
aattgaggca gcgttggtga agcacgataa taatatgaag gattattccc tggtggttga   47940
ctgatcacca taactgctaa tcattcaaac tatttagtct gtgacagagc caacacgcag   48000
tctgtcactg tcaggaaagt ggtaaaactg caactcaatt actgcaatgc cctcgtaatt   48060
aagtgaattt acaatatcgt cctgttcgga gggaagaacg cgggatgttc attcttcatc   48120
acttttaatt gatgtatatg ctctcttttc tgacgttagt ctccgacggc aggcttcaat   48180
gacccaggct gagaaattcc cggaccctt ttgctcaaga gcgatgttaa tttgttcaat   48240
catttggtta ggaaagcgga tgttgcgggt tgttgttctg cgggttctgt tcttcgttga   48300
catgaggttg ccccgtattc agtgtcgctg atttgtattg tctgaagttg tttttacgtt   48360
```
aagttgatgc agatcaatta atacgatacc tgcgtcataa ttgattattt gacgtggttt    48420
gatggcctcc acgcacgttg tgatatgtag atgataatca ttatcacttt acgggtcctt    48480
tccggtgatc cgacaggtta cg                                              48502

<210> SEQ ID NO 37
<211> LENGTH: 32
<212> TYPE: DNA
<213> ORGANISM: Artificial Sequence
<220> FEATURE:
<223> OTHER INFORMATION: Anti NDM spacer (N1)

<400> SEQUENCE: 37
ctgagcaccg cattagccgc tgcattgatg ct                                   32

<210> SEQ ID NO 38
<211> LENGTH: 32
<212> TYPE: DNA
<213> ORGANISM: Artificial Sequence
<220> FEATURE:
<223> OTHER INFORMATION: Anti NDM spacer (N2)

<400> SEQUENCE: 38
caggagatca acctgccggt cgcgctggcg gt                                   32

<210> SEQ ID NO 39
<211> LENGTH: 32
<212> TYPE: DNA
<213> ORGANISM: Artificial Sequence
<220> FEATURE:
<223> OTHER INFORMATION: Anti NDM spacer (N3)

<400> SEQUENCE: 39
cgatgtcggt gccgtcgatc ccaacggtga ta                                   32

<210> SEQ ID NO 40
<211> LENGTH: 32
<212> TYPE: DNA
<213> ORGANISM: Artificial Sequence
<220> FEATURE:
<223> OTHER INFORMATION: Anti CTX-M-15 spacer (C1)

<400> SEQUENCE: 40
tgtgccgctg tatgcgcaaa cggcggacgt ac                                   32

<210> SEQ ID NO 41
<211> LENGTH: 32
<212> TYPE: DNA
<213> ORGANISM: Artificial Sequence
<220> FEATURE:
<223> OTHER INFORMATION: Anti CTX-M-15 spacer (C2)

<400> SEQUENCE: 41
ctgattgctc acgttggcgg cccggctagc gt                                   32

<210> SEQ ID NO 42
<211> LENGTH: 32
<212> TYPE: DNA
<213> ORGANISM: Artificial Sequence
<220> FEATURE:
<223> OTHER INFORMATION: Anti CTX-M-15 spacer (C3)

<400> SEQUENCE: 42
caggcagtcc agcctgaatg ctcgctgcac cg                                   32

```
<210> SEQ ID NO 43
<211> LENGTH: 32
<212> TYPE: DNA
<213> ORGANISM: Artificial Sequence
<220> FEATURE:
<223> OTHER INFORMATION: Anti T4 Spacer (T1)

<400> SEQUENCE: 43
gatcgtatgc tatccattac accagcggga cg                                32

<210> SEQ ID NO 44
<211> LENGTH: 32
<212> TYPE: DNA
<213> ORGANISM: Artificial Sequence
<220> FEATURE:
<223> OTHER INFORMATION: Anti T4 Spacer (T2)

<400> SEQUENCE: 44
tctgcatcac gagtaccttt catagtacga at                                32

<210> SEQ ID NO 45
<211> LENGTH: 32
<212> TYPE: DNA
<213> ORGANISM: Artificial Sequence
<220> FEATURE:
<223> OTHER INFORMATION: Anti T4 Spacer (T3)

<400> SEQUENCE: 45
cggagggcaa gaaatagctt cacggtccat at                                32

<210> SEQ ID NO 46
<211> LENGTH: 35
<212> TYPE: DNA
<213> ORGANISM: Artificial Sequence
<220> FEATURE:
<223> OTHER INFORMATION: NDM proto- spacer (N1)

<400> SEQUENCE: 46
aagctgagca ccgcattagc cgctgcattg atgct                             35

<210> SEQ ID NO 47
<211> LENGTH: 35
<212> TYPE: DNA
<213> ORGANISM: Artificial Sequence
<220> FEATURE:
<223> OTHER INFORMATION: NDM proto- spacer (N2)

<400> SEQUENCE: 47
aagcaggaga tcaacctgcc ggtcgcgctg gcggt                             35

<210> SEQ ID NO 48
<211> LENGTH: 35
<212> TYPE: DNA
<213> ORGANISM: Artificial Sequence
<220> FEATURE:
<223> OTHER INFORMATION: NDM proto- spacer (N3)

<400> SEQUENCE: 48
aagcgatgtc ggtgccgtcg atcccaacgg tgata                             35

<210> SEQ ID NO 49
<211> LENGTH: 35
<212> TYPE: DNA
<213> ORGANISM: Artificial Sequence
<220> FEATURE:
<223> OTHER INFORMATION: CTX-M-15 Proto-spacer (C1)
```

-continued

<400> SEQUENCE: 49
aagtgtgccg ctgtatgcgc aaacggcgga cgtac                                    35

<210> SEQ ID NO 50
<211> LENGTH: 35
<212> TYPE: DNA
<213> ORGANISM: Artificial Sequence
<220> FEATURE:
<223> OTHER INFORMATION: CTX-M-15 Proto-spacer (C2)

<400> SEQUENCE: 50
aagctgattg ctcacgttgg cggcccggct agcgt                                    35

<210> SEQ ID NO 51
<211> LENGTH: 35
<212> TYPE: DNA
<213> ORGANISM: Artificial Sequence
<220> FEATURE:
<223> OTHER INFORMATION: CTX-M-15 Proto-spacer (C3)

<400> SEQUENCE: 51
aagcaggcag tccagcctga atgctcgctg caccg                                    35

<210> SEQ ID NO 52
<211> LENGTH: 35
<212> TYPE: DNA
<213> ORGANISM: Artificial Sequence
<220> FEATURE:
<223> OTHER INFORMATION: T4 Proto-spacer (T1)

<400> SEQUENCE: 52
aaggatcgta tgctatccat tacaccagcg ggacg                                    35

<210> SEQ ID NO 53
<211> LENGTH: 35
<212> TYPE: DNA
<213> ORGANISM: Artificial Sequence
<220> FEATURE:
<223> OTHER INFORMATION: T4 Proto-spacer (T2)

<400> SEQUENCE: 53
aagtctgcat cacgagtacc tttcatagta cgaat                                    35

<210> SEQ ID NO 54
<211> LENGTH: 35
<212> TYPE: DNA
<213> ORGANISM: Artificial Sequence
<220> FEATURE:
<223> OTHER INFORMATION: T4 Proto-spacer (T3)

<400> SEQUENCE: 54
aagcggaggg caagaaatag cttcacggtc catat                                    35

<210> SEQ ID NO 55
<211> LENGTH: 2022
<212> TYPE: DNA
<213> ORGANISM: Artificial Sequence
<220> FEATURE:
<223> OTHER INFORMATION: T7 phage with proto-spacers T7-N1N2

<400> SEQUENCE: 55
atgatgaaca ttaagactaa cccgtttaaa gccgtgtctt tcgtagagtc tgccattaag         60
aaggctctgg ataacgctgg gtatcttatc gctgaaatca gtacgatgg tgtacgcggg        120

| | |
|---|---|
| aacatctgcg tagacaatac tgctaacagt tactggctct ctcgtgtatc taaaacgatt | 180 |
| ccggcactgg agcacttaaa cgggtttgat gttcgctgga agcgtctact gaacgatgac | 240 |
| cgttgcttct acaaagatgg ctttatgctt gatggggaac tcatggtcaa gggcgtagac | 300 |
| tttaacacag gtccggcct actgcgtacc aaatggactg acacgaagaa ccaagagttc | 360 |
| catgaagagt tattcgttga accaatccgt aagaaagata agttcccctt taagctgcac | 420 |
| actggacacc ttcacataaa actgtacgct atcctcccgc tgcacatcgt ggagtctgga | 480 |
| gaagactgtg atgtcatgac gttgctcatg caggaacacg ttaagaacat gctgcctctg | 540 |
| ctacaggaat acttccctga aatcgaatgg caagcggctg aatcttacga ggtctacgat | 600 |
| atggtagaac tacagcaact gtacgagcag aagcgagcag aaggccatga gggtctcatt | 660 |
| gtgaaagacc cgatgtgtat ctataagcgc ggtaagaaat ctggctggtg aaaatgaaa | 720 |
| cctgagaacg aagctgacgg tatcattcag ggtctggtat ggggtacaaa aggtctggct | 780 |
| aatgaaggta aagtgattgg ttttgaggtg cttcttgaga gtggtcgttt agttaacgcc | 840 |
| acgaatatct ctcgcgcctt aatggatgag ttcactgaga cagtaaaaga ggccacccta | 900 |
| agtcaatggg gattctttag cccatacggt attggcgaca acgatgcttg tactattaac | 960 |
| ccttacgatg gctgggcgtg tcaaattagc tacatggagg aaacacctga tggctctttg | 1020 |
| cggcacccat cgttcgtaat gttccgtggc accgaggaca accctcaaga gaaaatgtaa | 1080 |
| aagctgagca ccgcattagc cgctgcattg atgctgatcc gtcagcctgc agttcgaagt | 1140 |
| tcctatactt tctagagaat aggaacttcg tgtggtagaa tatcagctta ctattgcttt | 1200 |
| acgaaagcgt atccggtgaa ataaagtcaa cctttagttg gttaatgtta caccaacaac | 1260 |
| gaaaccaaca cgccaggctt attcctgtgg agttatatat gagcgataaa attattcacc | 1320 |
| tgactgacga cagttttgac acggatgtac tcaaagcgga cggggcgatc ctcgtcgatt | 1380 |
| tctgggcaga gtggtgcggt ccgtgcaaaa tgatcgcccc gattctggat gaaatcgctg | 1440 |
| acgaatatca gggcaaactg accgttgcaa aactgaacat cgatcaaaac cctggcactg | 1500 |
| cgccgaaata tggcatccgt ggtatcccga ctctgctgct gttcaaaaac ggtgaagtgg | 1560 |
| cggcaaccaa agtgggcgca ctgtctaaag gtcagttgaa agagttcctc gacgctaacc | 1620 |
| tggcgtaaga agttcctata cttttctagag aataggaact tcgaagcagc tccagcctac | 1680 |
| aaaagcaggag atcaacctgc cggtcgcgct ggcggttcac actggctcac cttcgggtgg | 1740 |
| gcctttctgc gtttataagg agacacttta tgtttaagaa ggttggtaaa ttccttgcgg | 1800 |
| ctttggcagc tatcctgacg cttgcgtata ttcttgcggt ataccctcaa gtagcactag | 1860 |
| tagtagttgg cgcttgttac ttagcggcag tgtgtgcttg cgtgtggagt atagttaact | 1920 |
| ggtaatacga ctcactaaag gaggtacaca ccatgatgta cttaatgcca ttactcatcg | 1980 |
| tcattgtagg atgccttgcg ctccactgta gcgatgatga ta | 2022 |

<210> SEQ ID NO 56
<211> LENGTH: 2022
<212> TYPE: DNA
<213> ORGANISM: Artificial Sequence
<220> FEATURE:
<223> OTHER INFORMATION: T7 phage with proto-spacers T7-C2C1

<400> SEQUENCE: 56

| | |
|---|---|
| atgatgaaca ttaagactaa cccgtttaaa gccgtgtctt tcgtagagtc tgccattaag | 60 |
| aaggctctgg ataacgctgg gtatcttatc gctgaaatca gtacgatgg tgtacgcggg | 120 |
| aacatctgcg tagacaatac tgctaacagt tactggctct ctcgtgtatc taaaacgatt | 180 |

```
ccggcactgg agcacttaaa cgggtttgat gttcgctgga agcgtctact gaacgatgac      240
cgttgcttct acaaagatgg ctttatgctt gatggggaac tcatggtcaa gggcgtagac      300
tttaacacag gtccggcct actgcgtacc aaatggactg acacgaagaa ccaagagttc      360
catgaagagt tattcgttga accaatccgt aagaaagata aagttccctt taagctgcac      420
actggacacc ttcacataaa actgtacgct atcctcccgc tgcacatcgt ggagtctgga      480
gaagactgtg atgtcatgac gttgctcatg caggaacacg ttaagaacat gctgcctctg      540
ctacaggaat acttccctga aatcgaatgg caagcggctg aatcttacga ggtctacgat      600
atggtagaac tacagcaact gtacgagcag aagcgagcag aaggccatga gggtctcatt      660
gtgaaagacc cgatgtgtat ctataagcgc ggtaagaaat ctggctggtg aaaatgaaa      720 cctgagaacg aagctgacgg tatcattcag ggtctggtat ggggtacaaa aggtctggct      780
aatgaaggta aagtgattgg ttttgaggtg cttcttgaga gtggtcgttt agttaacgcc      840
acgaatatct ctcgcgcctt aatggatgag ttcactgaga cagtaaaaga ggccacccta      900
agtcaatggg gattctttag cccatacggt attggcgaca acgatgcttg tactattaac      960
ccttacgatg gctgggcgtg tcaaattagc tacatggagg aaacacctga tggctctttg     1020
cggcacccat cgttcgtaat gttccgtggc accgaggaca accctcaaga gaaaatgtaa    1080
aagctgattg ctcacgttgg cggcccggct agcgtgatcc gtcagcctgc agttcgaagt    1140
tcctatactt tctagagaat aggaacttcg tgtggtagaa tatcagctta ctattgcttt    1200
acgaaagcgt atccggtgaa ataaagtcaa cctttagttg gttaatgtta caccaacaac    1260
gaaaccaaca cgccaggctt attcctgtgg agttatatat gagcgataaa attattcacc    1320
tgactgacga cagttttgac acggatgtac tcaaagcgga cggggcgatc ctcgtcgatt    1380
tctgggcaga gtggtgcggt ccgtgcaaaa tgatcgcccc gattctggat gaaatcgctg    1440
acgaatatca gggcaaactg accgttgcaa aactgaacat cgatcaaaac cctggcactg    1500
cgccgaaata tggcatccgt ggtatcccga ctctgctgct gttcaaaaac ggtgaagtgg    1560
cggcaaccaa agtgggcgca ctgtctaaag gtcagttgaa agagttcctc gacgctaacc    1620
tggcgtaaga agttcctata ctttctagag aataggaact tcgaagcagc tccagcctac    1680
aaagtgtgcc gctgtatgcg caaacggcgg acgtactcac actggctcac cttcgggtgg    1740
gcctttctgc gtttataagg agacacttta tgtttaagaa ggttggtaaa ttccttgcgg    1800
ctttggcagc tatcctgacg cttgcgtata ttcttgcggt ataccctcaa gtagcactag    1860
tagtagttgg cgcttgttac ttagcggcag tgtgtgcttg cgtgtggagt atagttaact    1920
ggtaatacga ctcactaaag gaggtacaca ccatgatgta cttaatgcca ttactcatcg    1980
tcattgtagg atgccttgcg ctccactgta gcgatgatga ta                       2022
```

<210> SEQ ID NO 57  
<211> LENGTH: 2022  
<212> TYPE: DNA  
<213> ORGANISM: Artificial Sequence  
<220> FEATURE:  
<223> OTHER INFORMATION: T7 phage with proto-spacers T7N1C1

<400> SEQUENCE: 57

```
atgatgaaca ttaagactaa cccgtttaaa gccgtgtctt tcgtagagtc tgccattaag       60
aaggctctgg ataacgctgg gtatcttatc gctgaaatca agtacgatgg tgtacgcggg     120
aacatctgcg tagacaatac tgctaacagt tactggctct ctcgtgtatc taaaacgatt     180
```

```
ccggcactgg agcacttaaa cgggtttgat gttcgctgga agcgtctact gaacgatgac      240
cgttgcttct acaaagatgg ctttatgctt gatggggaac tcatggtcaa gggcgtagac      300
tttaacacag gtccggcct actgcgtacc aaatggactg acacgaagaa ccaagagttc       360
catgaagagt tattcgttga accaatccgt aagaaagata agttcccctt aagctgcac       420 actggacacc ttcacataaa actgtacgct atcctcccgc tgcacatcgt ggagtctgga      480
gaagactgtg atgtcatgac gttgctcatg caggaacacg ttaagaacat gctgcctctg      540
ctacaggaat acttccctga aatcgaatgg caagcggctg aatcttacga ggtctacgat      600
atggtagaac tacagcaact gtacgagcag aagcgagcag aaggccatga gggtctcatt       660
gtgaaagacc cgatgtgtat ctataagcgc ggtaagaaat ctggctggtg aaaatgaaa       720 cctgagaacg aagctgacgg tatcattcag ggtctggtat ggggtacaaa aggtctggct      780
aatgaaggta aagtgattgg ttttgaggtg cttcttgaga gtggtcgttt agttaacgcc      840
acgaatatct ctcgcgcctt aatggatgag ttcactgaga cagtaaaaga ggccacccta      900
agtcaatggg gattctttag cccatacggt attggcgaca acgatgcttg tactattaac     960
ccttacgatg gctgggcgtg tcaaattagc tacatggagg aaacacctga tggctctttg     1020
cggcacccat cgttcgtaat gttccgtggc accgaggaca ccctcaaga gaaaatgtaa      1080 aagctgagca ccgcattagc cgctgcattg atgctgatcc gtcagcctgc agttcgaagt     1140
tcctatactt tctagagaat aggaacttcg tgtggtagaa tatcagctta ctattgcttt     1200
acgaaagcgt atccggtgaa ataaagtcaa ccttttagttg gttaatgtta caccaacaac    1260
gaaaccaaca cgccaggctt attcctgtgg agttatatat gagcgataaa attattcacc     1320
tgactgacga cagttttgac acggatgtac tcaaagcgga cggggcgatc ctcgtcgatt     1380
tctgggcaga gtggtgcggt ccgtgcaaaa tgatcgcccc gattctggat gaaatcgctg    1440
acgaatatca gggcaaactg accgttgcaa aactgaacat cgatcaaaac cctggcactg    1500
cgccgaaata tggcatccgt ggtatcccga ctctgctgct gttcaaaaac ggtgaagtgg    1560
cggcaaccaa agtgggcgca ctgtctaaag gtcagttgaa agagttcctc gacgctaacc    1620
tggcgtaaga agttcctata cttctagag aataggaact tcgaagcagc tccagcctac     1680
aaagtgtgcc gctgtatgcg caaacggcgg acgtactcac actggctcac cttcgggtgg    1740
gcctttctgc gttataagg agacacttta tgtttaagaa ggttggtaaa ttccttgcgg     1800
ctttggcagc tatcctgacg cttgcgtata ttcttgcggt ataccctcaa gtagcactag    1860
tagtagttgg cgcttgttac ttagcggcag tgtgtgcttg cgtgtggagt atagttaact    1920
ggtaatacga ctcactaaag gaggtacaca ccatgatgta cttaatgcca ttactcatcg    1980
tcattgtagg atgccttgcg ctccactgta gcgatgatga ta                        2022
```

<210> SEQ ID NO 58
<211> LENGTH: 2022
<212> TYPE: DNA
<213> ORGANISM: Artificial Sequence
<220> FEATURE:
<223> OTHER INFORMATION: T7 phage with proto-spacers T7-C2N2

<400> SEQUENCE: 58

```
atgatgaaca ttaagactaa cccgtttaaa gccgtgtctt tcgtagagtc tgccattaag       60
aaggctctgg ataacgctgg gtatcttatc gctgaaatca agtacgatgg tgtacgcggg      120
aacatctgcg tagacaatac tgctaacagt tactggctct ctcgtgtatc taaaacgatt      180
ccggcactgg agcacttaaa cgggtttgat gttcgctgga agcgtctact gaacgatgac     240
```

```
cgttgcttct acaaagatgg ctttatgctt gatgggaac tcatggtcaa gggcgtagac      300
tttaacacag ggtccggcct actgcgtacc aaatggactg acacgaagaa ccaagagttc      360
catgaagagt tattcgttga accaatccgt aagaaagata agttcccctt taagctgcac      420
actggacacc ttcacataaa actgtacgct atcctcccgc tgcacatcgt ggagtctgga      480
gaagactgtg atgtcatgac gttgctcatg caggaacacg ttaagaacat gctgcctctg      540
ctacaggaat acttccctga aatcgaatgg caagcggctg aatcttacga ggtctacgat      600
atggtagaac tacagcaact gtacgagcag aagcgagcag aaggccatga gggtctcatt      660
gtgaaagacc cgatgtgtat ctataagcgc ggtaagaaat ctggctggtg aaaatgaaa      720 cctgagaacg aagctgacgg tatcattcag ggtctggtat ggggtacaaa aggtctggct      780
aatgaaggta aagtgattgg ttttgaggtg cttcttgaga gtggtcgttt agttaacgcc      840
acgaatatct ctcgcgcctt aatggatgag ttcactgaga cagtaaaaga ggccacccta      900
agtcaatggg gattctttag cccatacggt attggcgaca acgatgcttg tactattaac      960
ccttacgatg gctgggcgtg tcaaattagc tacatggagg aaacacctga tggctctttg     1020
cggcacccat cgttcgtaat gttccgtggc accgaggaca ccctcaaga gaaaatgtaa     1080 aagctgattg ctcacgttgg cggcccggct agcgtgatcc gtcagcctgc agttcgaagt     1140
tcctatactt tctagagaat aggaacttcg tgtggtagaa tatcagctta ctattgcttt     1200
acgaaagcgt atccggtgaa ataaagtcaa cctttagttg gttaatgtta caccaacaac     1260
gaaaccaaca cgccaggctt attcctgtgg agttatatat gagcgataaa attattcacc     1320
tgactgacga cagttttgac acggatgtac tcaaagcgga cggggcgatc ctcgtcgatt     1380
tctgggcaga gtggtgcggt ccgtgcaaaa tgatcgcccc gattctggat gaaatcgctg     1440
acgaatatca gggcaaactg accgttgcaa aactgaacat cgatcaaaac cctggcactg     1500
cgccgaaata tggcatccgt ggtatcccga ctctgctgct gttcaaaaac ggtgaagtgg     1560
cggcaaccaa agtgggcgca ctgtctaaag gtcagttgaa agagttcctc gacgctaacc     1620
tggcgtaaga agttcctata ctttctagag aataggaact tcgaagcagc tccagcctac     1680 aaaagcaggag atcaacctgc cggtcgcgct ggcggttcac actggctcac cttcgggtgg     1740
gcctttctgc gtttataagg agacacttta tgtttaagaa ggttggtaaa ttccttgcgg     1800
ctttggcagc tatcctgacg cttgcgtata ttcttgcggt ataccctcaa gtagcactag     1860
tagtagttgg cgcttgttac ttagcggcag tgtgtgcttg cgtgtggagt atagttaact     1920
ggtaatacga ctcactaaag gaggtacaca ccatgatgta cttaatgcca ttactcatcg     1980
tcattgtagg atgccttgcg ctccactgta gcgatgatga ta                        2022
```

<210> SEQ ID NO 59
<211> LENGTH: 48528
<212> TYPE: DNA
<213> ORGANISM: Artificial Sequence
<220> FEATURE:
<223> OTHER INFORMATION: Recombinant lambda phage with the cas proteins and CRISPR array IYMMPh3

<400> SEQUENCE: 59

```
gggcggcgac ctcgcgggtt ttcgctattt atgaaaattt tccggtttaa ggcgtttccg       60
ttcttcttcg tcataactta atgttttttat ttaaaatacc ctctgaaaag aaaggaaacg     120
acaggtgctg aaagcgaggc tttttggcct ctgtcgtttc ctttctctgt ttttgtccgt     180
ggaatgaaca atggaagtca acaaaaagca gctggctgac attttcggtg cgagtatccg     240
```

```
taccattcag aactggcagg aacagggaat gcccgttctg cgaggcggtg gcaagggtaa      300
tgaggtgctt tatgactctg ccgccgtcat aaaatggtat gccgaagggg atgctgaaat      360
tgagaacgaa aagctgcgcc gggaggttga agaactgcgg caggccagcg aggcagatct      420
ccagccagga actattgagt acgaacgcca tcgacttacg cgtgcgcagg ccgacgcaca      480
ggaactgaag aatgccagag actccgctga agtggtggaa accgcattct gtactttcgt      540
gctgtcgcgg atcgcaggtg aaattgccag tattctcgac gggctccccc tgtcggtgca      600
gcggcgtttt ccggaactgg aaaaccgaca tgttgatttc ctgaaacggg atatcatcaa      660
agccatgaac aaagcagccg cgctggatga actgataccg gggttgctga gtgaatatat      720
cgaacagtca ggttaacagg ctgcggcatt ttgtccgcgc cgggcttcgc tcactgttca      780
ggccggagcc acagaccgcc gttgaatggg cggatgctaa ttactatctc ccgaaagaat      840
ccgcatacca ggaagggcgc tgggaaacac tgcccttttca gcggccatc atgaatgcga      900 tgggcagcga ctacatccgt gaggtgaatg tggtgaagtc tgcccgtgtc ggttattcca      960
aaatgctgct gggtgtttat gcctacttta tagagcataa gcagcgcaac acccttatct     1020
ggttgccgac ggatggtgat gccgagaact ttatgaaaac ccacgttgag ccgactattc     1080
gtgatattcc gtcgctgctg cgctggccc cgtggtatgg caaaaagcac cgggataaca     1140
cgctcaccat gaagcgtttc actaatgggc gtggcttctg gtgcctgggc ggtaaagcgg     1200
caaaaaacta ccgtgaaaag tcggtggatg tggcgggtta tgatgaactt gctgcttttg     1260
atgatgatat tgaacaggaa ggctctccga cgttcctggg tgacaagcgt attgaaggct     1320
cggtctggcc aaagtccatc cgtggctcca cgccaaaagt gagaggcacc tgtcagattg     1380
agcgtgcagc cagtgaatcc ccgcatttta tgcgttttca tgttgcctgc ccgcattgcg     1440
gggaggagca gtatcttaaa tttggcgaca aagagacgcc gtttggcctc aaatggacgc     1500
cggatgaccc ctccagcgtg ttttatctct gcgagcataa tgcctgcgtc atccgccagc     1560
aggagctgga ctttactgat gcccgttata tctgcgaaaa gaccgggatc tggacccgtg     1620
atggcattct ctggttttcg tcatccggtg aagagattga gccacctgac agtgtgacct     1680
ttcacatctg gacagcgtac agcccgttca ccacctgggt gcagattgtc aaagactgga     1740
tgaaaacgaa aggggatacg ggaaaacgta aaaccttcgt aaacaccacg ctcggtgaga     1800
cgtgggaggc gaaaattggc gaacgtccgg atgctgaagt gatggcagag cggaaagagc     1860
attattcagc gcccgttcct gaccgtgtgg cttacctgac cgccggtatc gactcccagc     1920
tggaccgcta cgaaatgcgc gtatgggat ggggccggg tgaggaaagc tggctgattg     1980
accggcagat tattatgggc cgccacgacg atgaacagac gctgctgcgt gtggatgagg     2040
ccatcaataa aacctatacc cgccggaatg gtgcagaaat gtcgatatcc cgtatctgct     2100
gggatactgg cgggattgac ccgaccattg tgtatgaacg ctcgaaaaaa catgggctgt     2160
tccgggtgat ccccattaaa ggggcatccg tctacgaaaa gccggtggcc agcatgccac     2220
gtaagcgaaa caaaaacggg gtttaccttta ccgaaatcgg tacggatacc gcgaaagagc     2280
agatttataa ccgcttcaca ctgacgccgg aaggggatga accgcttccc ggtgccgttc     2340
acttcccgaa taacccggat attttttgatc tgaccgaagc gcagcagctg actgctgaag     2400
agcaggtcga aaaatggggtg gatggcagga aaaaaatact gtgggacagc aaaaagcgac     2460 gcaatgagge actcgactgc ttcgtttatg cgctggcggc gctgcgcatc agtatttccc     2520
gctggcagct ggatctcagt gcgctgctgg cgagcctgca ggaagaggat ggtgcagcaa     2580
```

```
ccaacaagaa aacactggca gattacgccc gtgccttatc cggagaggat gaatgacgcg    2640
acaggaagaa cttgccgctg cccgtgcggc actgcatgac ctgatgacag gtaaacgggt    2700
ggcaacagta cagaaagacg gacgaagggt ggagtttacg ccacttccg tgtctgacct     2760
gaaaaaatat attgcagagc tggaagtgca gaccggcatg acacagcgac gcaggggacc    2820
tgcaggattt tatgtatgaa aacgcccacc attcccaccc ttctggggcc ggacggcatg    2880
acatcgctgc gcgaatatgc cggttatcac ggcggtggca gcggatttgg agggcagttg    2940
cggtcgtgga acccaccgag tgaaagtgtg gatgcagccc tgttgcccaa ctttacccgt    3000
ggcaatgccc gcgcagacga tctggtacgc aataacggct atgccgccaa cgccatccag    3060
ctgcatcagg atcatatcgt cgggtctttt ttccggctca gtcatcgccc aagctggcgc    3120
tatctgggca tcggggagga agaagcccgt gccttttccc gcgaggttga agcggcatgg    3180
aaagagtttg ccgaggatga ctgctgctgc attgacgttg agcgaaaacg cacgtttacc    3240
atgatgattc gggaaggtgt ggccatgcac gcctttaacg gtgaactgtt cgttcaggcc    3300
acctgggata ccagttcgtc gcggcttttc cggacacagt tccggatggt cagcccgaag    3360
cgcatcagca acccgaacaa taccggcgac agccggaact gccgtgccgg tgtgcagatt    3420
aatgacagcg gtgcggcgct gggatattac gtcagcgagg acgggtatcc tggctggatg    3480
ccgcagaaat ggacatggat accccgtgag ttacccggcg gcgcgcctc gttcattcac     3540
gtttttgaac ccgtggagga cgggcagact cgcggtgcaa atgtgtttta cagcgtgatg    3600
gagcagatga agatgctcga cacgctgcag aacacgcagc tgcagagcgc cattgtgaag    3660
gcgatgtatg ccgccaccat tgagagtgag ctggatacgc agtcagcgat ggattttatt    3720
ctgggcgcga cagtcagga gcagcgggaa aggctgaccg gctggattgg tgaaattgcc      3780
gcgtattacg ccgcagcgcc ggtccggctg ggaggcgcaa aagtaccgca cctgatgccg    3840
ggtgactcac tgaacctgca gacggctcag gatacggata acggctactc cgtgtttgag    3900
cagtcactgc tgcggtatat cgctgccggg ctgggtgtct cgtatgagca gctttcccgg    3960
aattacgccc agatgagcta ctccacggca cgggccagtg cgaacgagtc gtgggcgtac    4020
tttatggggc ggcgaaaatt cgtcgcatcc cgtcaggcga gccagatgtt tctgtgctgg    4080
ctggaagagg ccatcgttcg ccgcgtggtg acgttaccct caaaagcgcg cttcagtttt    4140
caggaagccc gcagtgcctg ggggaactgc gactggatag gctccggtcg tatggccatc    4200
gatggtctga agaagttca ggaagcggtg atgctgatag aagccggact gagtacctac     4260
gagaaagagt gcgcaaaacg cggtgacgac tatcaggaaa ttttttgccca gcaggtccgt    4320
gaaacgatgg agcgccgtgc agccggtctt aaaccgcccg cctgggcggc tgcagcattt    4380
gaatccgggc tgcgacaatc aacagaggag gagaagagtg acagcagagc tgcgtaatct    4440
cccgcatatt gccagcatgg cctttaatga gccgctgatg cttgaacccg cctatgcgcg    4500
ggttttcttt tgtgcgcttg caggccagct tgggatcagc agcctgacgg atgcggtgtc    4560
cggcgacagc ctgactgccc aggaggcact cgcgacgctg gcattatccg gtgatgatga    4620
cggaccacga caggcccgca gttatcaggt catgaacggc atcgccgtgc tgccggtgtc    4680
cggcacgctg gtcagccgga cgcgggcgct gcagccgtac tcggggatga ccggttacaa    4740
cggcattatc gcccgtctgc aacaggctgc cagcgatccg atggtggacg gcattctgct    4800
cgatatggac acgcccggcg ggatggtggc ggggcatttt gactgcgctg acatcatcgc    4860
ccgtgtgcgt gacataaaac cggtatggc gcttgccaac gacatgaact gcagtgcagg     4920
tcagttgctt gccagtgccg cctcccggcg tctggtcacg cagaccgccc ggacaggctc    4980
```

```
catcggcgtc atgatggctc acagtaatta cggtgctgcg ctggagaaac agggtgtgga    5040
aatcacgctg atttacagcg gcagccataa ggtggatggc aacccctaca gccatcttcc    5100
ggatgacgtc cgggagacac tgcagtcccg gatggacgca acccgccaga tgtttgcgca    5160
gaaggtgtcg gcatataccg gcctgtccgt gcaggttgtg ctggataccg aggctgcagt    5220
gtacagcggt caggaggcca ttgatgccgg actggctgat gaacttgtta acagcaccga    5280
tgcgatcacc gtcatgcgtg atgcactgga tgcacgtaaa tcccgtctct caggagggcg    5340
aatgaccaaa gagactcaat caacaactgt ttcagccact gcttcgcagg ctgacgttac    5400
tgacgtggtg ccagcgacgg agggcgagaa cgccagcgcg gcgcagccgg acgtgaacgc    5460
gcagatcacc gcagcggttg cggcagaaaa cagccgcatt atggggatcc tcaactgtga    5520
ggaggctcac ggacgcgaag aacaggcacg cgtgctggca gaaacccccg gtatgaccgt    5580
gaaaacggcc cgccgcattc tggccgcagc accacagagt gcacaggcgc gcagtgacac    5640
tgcgctggat cgtctgatgc aggggcaccc ggcaccgctg gctgcaggta acccggcatc    5700
tgatgccgtt aacgatttgc tgaacacacc agtgtaaggg atgtttatga cgagcaaaga    5760
aacctttacc cattaccagc cgcagggcaa cagtgacccg gctcataccg caaccgcgcc    5820
cggcggattg agtgcgaaag cgcctgcaat gaccccgctg atgctggaca cctccagccg    5880
taagctggtt gcgtgggatg gcaccaccga cggtgctgcc gttggcattc ttgcggttgc    5940
tgctgaccag accagcacca cgctgacgtt ctacaagtcc ggcacgttcc gttatgagga    6000
tgtgctctgg ccggaggctg ccagcgacga gacgaaaaaa cggaccgcgt ttgccggaac    6060
ggcaatcagc atcgtttaac tttacccttc atcactaaag gccgcctgtg cggcttttttt    6120
tacgggattt ttttatgtcg atgtacacaa ccgcccaact gctggcggca aatgagcaga    6180
aatttaagtt tgatccgctg tttctgcgtc tcttttttccg tgagagctat cccttcacca    6240
cggagaaagt ctatctctca caaattccgg gactggtaaa catggcgctg tacgtttcgc    6300
cgattgtttc cggtgaggtt atccgttccc gtggcggctc cacctctgaa tttacgccgg    6360
gatatgtcaa gccgaagcat gaagtgaatc cgcagatgac cctgcgtcgc ctgccggatg    6420
aagatccgca gaatctggcg gacccggctt accgccgccg tcgcatcatc atgcagaaca    6480
tgcgtgacga agagctggcc attgctcagg tcgaagagat gcaggcagtt tctgccgtgc    6540
ttaagggcaa atacaccatg accggtgaag ccttcgatcc ggttgaggtg gatatggggcc    6600
gcagtgagga gaataacatc acgcagtccg gcggcacgga gtggagcaag cgtgacaagt    6660
ccacgtatga cccgaccgac gatatcgaag cctacgcgct gaacgccagc ggtgtggtga    6720
atatcatcgt gttcgatccg aaaggctggg cgctgttccg ttccttcaaa gccgtcaagg    6780
agaagctgga tacccgtcgt ggctctaatt ccgagctgga gacagcggtg aaagacctgg    6840
gcaaagcggt gtcctataag gggatgtatg gcgatgtggc catcgtcgtg tattccggac    6900
agtacgtgga aaacggcgtc aaaaagaact cctgccgga caacacgatg gtgctgggga    6960
acactcaggc acgcggtctg cgcacctatg gctgcattca ggatgcggac gcacagcgcg    7020
aaggcattaa cgcctctgcc cgttacccga aaaactgggt gaccaccggc gatccggcgc    7080
gtgagttcac catgattcag tcagcaccgc tgatgctgct ggctgaccct gatgagttcg    7140
tgtccgtaca actggcgtaa tcatggccct tcggggccat tgtttctctg tggaggagtc    7200
catgacgaaa gatgaactga ttgcccgtct ccgctcgctg ggtgaacaac tgaaccgtga    7260
tgtcagcctg acggggacga aagaagaact ggcgctccgt gtggcagagc tgaaagagga    7320
```

```
gcttgatgac acggatgaaa ctgccggtca ggacacccct ctcagccggg aaaatgtgct    7380
gaccggacat gaaaatgagg tgggatcagc gcagccggat accgtgattc tggatacgtc    7440
tgaactggtc acggtcgtgg cactggtgaa gctgcatact gatgcacttc acgccacgcg    7500
ggatgaacct gtggcatttg tgctgccggg aacggcgttt cgtgtctctg ccggtgtggc    7560
agccgaaatg acagagcgcg gcctggccag aatgcaataa cgggaggcgc tgtggctgat    7620
ttcgataacc tgttcgatgc tgccattgcc cgcgccgatg aaacgatacg cgggtacatg    7680
ggaacgtcag ccaccattac atccggtgag cagtcaggtg cggtgatacg tggtgttttt    7740
gatgaccctg aaaatatcag ctatgccgga cagggcgtgc gcgttgaagg ctccagcccg    7800
tccctgtttg tccggactga tgaggtgcgg cagctgcggc gtggagacac gctgaccatc    7860
ggtgaggaaa atttctgggt agatcgggtt tcgccggatg atggcggaag ttgtcatctc    7920
tggcttggac ggggcgtacc gcctgccgtt aaccgtcgcc gctgaaaggg ggatgtatgg    7980
ccataaaagg tcttgagcag gccgttgaaa acctcagccg tatcagcaaa acggcggtgc    8040
ctggtgccgc cgcaatggcc attaaccgcg ttgcttcatc cgcgatatcg cagtcggcgt    8100
cacaggttgc ccgtgagaca aaggtacgcc ggaaactggt aaaggaaagg gccaggctga    8160
aaagggccac ggtcaaaaat ccgcaggcca gaatcaaagt taaccggggg gatttgcccg    8220
taatcaagct gggtaatgcg cgggttgtcc tttcgcgccg caggcgtcgt aaaaaggggc    8280
agcgttcatc cctgaaaggt ggcggcagcg tgcttgtggt gggtaaccgt cgtattcccg    8340
gcgcgtttat tcagcaactg aaaaatggcc ggtggcatgt catgcagcgt gtggctggga    8400
aaaaccgtta ccccattgat gtggtgaaaa tcccgatggc ggtgccgctg accacggcgt    8460
ttaaacaaaa tattgagcgg atacggcgtg aacgtcttcc gaaagagctg gctatgcgc    8520 tgcagcatca actgaggatg gtaataaagc gatgaaacat actgaactcc gtgcagccgt    8580
actggatgca ctggagaagc atgacaccgg ggcgacgttt tttgatggtc gccccgctgt    8640
ttttgatgag gcggattttc cggcagttgc cgtttatctc accggcgctg aatacacggg    8700
cgaagagctg gacagcgata cctggcaggc ggagctgcat atcgaagttt tcctgcctgc    8760
tcaggtgccg gattcagagc tggatgcgtg gatggagtcc cggatttatc cggtgatgag    8820
cgatatcccg gcactgtcag atttgatcac cagtatggtg gccagcggct atgactaccg    8880
gcgcgacgat gatgcgggct tgtggagttc agccgatctg acttatgtca ttacctatga    8940
aatgtgagga cgctatgcct gtaccaaatc ctacaatgcc ggtgaaaggt gccgggacca    9000
ccctgtgggg ttataagggg agcggtgacc cttacgcgaa tccgcttcca gacgttgact    9060
ggtcgcgtct ggcaaaagtt aaagacctga cgcccggcga actgaccgct gagtcctatg    9120
acgacagcta tctcgatgat gaagatgcag actggactgc gaccgggcag ggcagaaat    9180 ctgccggaga taccagcttc acgctggcgt ggatgcccgg agagcagggg cagcaggcgc    9240
tgctggcgtg gtttaatgaa ggcgataccc gtgcctataa aatccgcttc ccgaacggca    9300
cggtcgatgt gttccgtggc tgggtcagca gtatcggtaa ggcggtgacg cgaaggaag    9360 tgatcacccg cacggtgaaa gtcaccaatg tgggacgtcc gtcgatggca gaagatcgca    9420
gcacggtaac agcggcaacc ggcatgaccg tgacgcctgc cagcacctcg gtggtgaaag    9480
ggcagagcac cacgctgacc gtggccttcc agccggaggg cgtaaccgac aagagctttc    9540
gtgcggtgtc tgcggataaa acaaaagcca ccgtgtcggt cagtggtatg accatcaccg    9600 tgaacgcgt tgctgcaggc aaggtcaaca ttccggttgt atccggtaat ggtgagtttg    9660
ctgcggttgc agaaattacc gtcaccgcca gttaatccgg agagtcagcg atgttcctga    9720
```

```
aaaccgaatc atttgaacat aacggtgtga ccgtcacgct ttctgaactg tcagccctgc    9780
agcgcattga gcatctcgcc ctgatgaaac ggcaggcaga acaggcggag tcagacagca    9840
accggaagtt tactgtggaa gacgccatca gaaccggcgc gtttctggtg gcgatgtccc    9900
tgtggcataa ccatccgcag aagacgcaga tgccgtccat gaatgaagcc gttaaacaga    9960
ttgagcagga agtgcttacc acctggccca cggaggcaat ttctcatgct gaaaacgtgg   10020
tgtaccggct gtctggtatg tatgagtttg tggtgaataa tgcccctgaa cagacagagg   10080
acgccgggcc cgcagagcct gtttctgcgg gaaagtgttc gacggtgagc tgagttttgc   10140
cctgaaactg gcgcgtgaga tggggcgacc cgactggcgt gccatgcttg ccgggatgtc   10200
atccacggag tatgccgact ggcaccgctt ttacagtacc cattattttc atgatgttct   10260
gctggatatg cacttttccg ggctgacgta caccgtgctc agcctgtttt tcagcgatcc   10320
ggatatgcat ccgctggatt tcagtctgct gaaccggcgc gaggctgacg aagagcctga   10380
agatgatgtg ctgatgcaga aagcggcagg gcttgccgga ggtgtccgct ttggcccgga   10440
cgggaatgaa gttatccccg cttccccgga tgtggcggac atgacggagg atgacgtaat   10500
gctgatgaca gtatcagaag ggatcgcagg aggagtccgg tatggctgaa ccggtaggcg   10560
atctggtcgt tgatttgagt ctggatgcgg ccagatttga cgagcagatg gccagagtca   10620
ggcgtcattt ttctggtacg gaaagtgatg cgaaaaaaac agcggcagtc gttgaacagt   10680
cgctgagccg acaggcgctg gctgcacaga aagcgggat ttccgtcggg cagtataaag   10740
ccgccatgcg tatgctgcct gcacagttca ccgacgtggc cacgcagctt gcaggcgggc   10800
aaagtccgtg gctgatcctg ctgcaacagg gggggcaggt gaaggactcc ttcggcggga   10860
tgatccccat gttcaggggg cttgccggtg cgatcaccct gccgatggtg ggggccacct   10920
cgctggcggt ggcgaccggt gcgctggcgt atgcctggta tcagggcaac tcaaccctgt   10980
ccgatttcaa caaaacgctg gtcctttccg gcaatcaggc gggactgacg gcagatcgta   11040
tgctggtcct gtccagagcc gggcaggcgg cagggctgac gtttaaccag accagcgagt   11100
cactcagcgc actggttaag gcgggggtaa gcggtgaggc tcagattgcg tccatcagcc   11160
agagtgtggc gcgtttctcc tctgcatccg gcgtggaggt ggacaaggtc gctgaagcct   11220
tcgggaagct gaccacagac ccgacgtcgg ggctgacggc gatggctcgc cagttccata   11280
acgtgtcggc ggagcagatt gcgtatgttg ctcagttgca gcgttccggc gatgaagccg   11340
gggcattgca ggcggcgaac gaggccgcaa cgaaagggtt tgatgaccag acccgccgcc   11400
tgaaagagaa catgggcacg ctggagacct gggcagacag gactgcgcgg gcattcaaat   11460
ccatgtggga tgcggtgctg gatattggtc gtcctgatac cgcgcaggag atgctgatta   11520
aggcagaggc tgccgtataag aaagcagacg acatctggaa tctgcgcaag gatgattatt   11580
ttgttaacga tgaagcgcgg gcgcgttact gggatgatcg tgaaaaggcc cgtcttgcgc   11640
ttgaagccgc ccgaaagaag gctgagcagc agactcaaca ggacaaaaat gcgcagcagc   11700
agagcgatac cgaagcgtca cggctgaaat ataccgaaga ggcgcagaag gcttacgaac   11760
ggctgcagac gccgctggag aaatataccg cccgtcagga agaactgaac aaggcactga   11820
aagacgggaa aatcctgcag gcggattaca acacgctgat ggcggcggcg aaaaaggatt   11880
atgaagcgac gctgaaaaag ccgaaacagt ccagcgtgaa ggtgtctgcg ggcgatcgtc   11940
aggaagacag tgctcatgct gccctgctga cgcttcaggc agaactccgg acgctggaga   12000
agcatgccgg agcaaatgag aaaatcagcc agcagcgccg ggatttgtgg aaggcggaga   12060
```

| | |
|---|---|
| gtcagttcgc ggtactggag gaggcggcgc aacgtcgcca gctgtctgca caggagaaat | 12120 |
| ccctgctggc gcataaagat gagacgctgg agtacaaacg ccagctggct gcacttggcg | 12180 |
| acaaggttac gtatcaggag cgcctgaacg cgctggcgca gcaggcggat aaattcgcac | 12240 |
| agcagcaacg ggcaaaacgg gccgccattg atgcgaaaag ccggggggctg actgaccggc | 12300 |
| aggcagaacg ggaagccacg gaacagcgcc tgaaggaaca gtatggcgat aatccgctgg | 12360 |
| cgctgaataa cgtcatgtca gagcagaaaa agacctgggc ggctgaagac cagcttcgcg | 12420 |
| ggaactggat ggcaggcctg aagtccggct ggagtgagtg ggaagagagc gccacggaca | 12480 |
| gtatgtcgca ggtaaaaagt gcagccacgc agacctttga tggtattgca cagaatatgg | 12540 |
| cggcgatgct gaccggcagt gagcagaact ggcgcagctt cacccgttcc gtgctgtcca | 12600 |
| tgatgacaga aattctgctt aagcaggcaa tggtgggggat tgtcgggagt atcggcagcg | 12660 |
| ccattggcgg ggctgttggt ggcggcgcat ccgcgtcagg cggtacagcc attcaggccg | 12720 |
| ctgcggcgaa attccatttt gcaaccggag gatttacggg aaccggcggc aaatatgagc | 12780 |
| cagcggggat tgttcaccgt ggtgagtttg tcttcacgaa ggaggcaacc agccggattg | 12840 |
| gcgtggggaa tctttaccgg ctgatgcgcg gctatgccac cggcggttat gtcggtacac | 12900 |
| cgggcagcat ggcagacagc cggtcgcagg cgtccggac gttgagcag aataaccatg | 12960 |
| tggtgattaa caacgacggc acgaacgggc agataggtcc ggctgctctg aaggcggtgt | 13020 |
| atgacatggc ccgcaagggt gcccgtgatg aaattcagac acagatgcgt gatggtggcc | 13080 |
| tgttctccgg aggtggacga tgaagacctt ccgctggaaa gtgaaacccg gtatggatgt | 13140 |
| ggcttcggtc ccttctgtaa gaaaggtgcg ctttggtgat ggctattctc agcgagcgcc | 13200 |
| tgccgggctg aatgccaacc tgaaaacgta cagcgtgacg ctttctgtcc cccgtgagga | 13260 |
| ggccacggta ctggagtcgt ttctggaaga gcacggggggc tggaaatcct ttctgtggac | 13320 |
| gccgccttat gagtggcggc agataaaggt gacctgcgca aaatggtcgt cgcgggtcag | 13380 |
| tatgctgcgt gttgagttca gcgcagagtt tgaacaggtg gtgaactgat gcaggatatc | 13440 |
| cggcaggaaa cactgaatga atgcacccgt gcggagcagt cggccagcgt ggtgctctgg | 13500 |
| gaaatcgacc tgacagaggt cggtggagaa cgttattttt tctgtaatga gcagaacgaa | 13560 |
| aaaggtgagc cggtcacctg gcaggggcga cagtatcagc cgtatcccat tcaggggagc | 13620 |
| ggttttgaac tgaatggcaa aggcaccagt acgcgcccca cgctgacggt ttctaacctg | 13680 |
| tacggtatgg tcaccgggat ggcggaagat atgcagagtc tggtcggcgg aacggtggtc | 13740 |
| cggcgtaagg tttacgcccg ttttctggat gcggtgaact tcgtcaacgg aaacagttac | 13800 |
| gccgatccgg agcaggaggt gatcagccgc tggcgcattg agcagtgcag cgaactgagc | 13860 |
| gcggtgagtg cctcctttgt actgtccacg ccgacggaaa cggatggcgc tgttttccg | 13920 |
| ggacgtatca tgctggccaa cacctgcacc tggacctatc gcggtgacga gtgcggttat | 13980 |
| agcggtccgg ctgtcgcgga tgaatatgac cagccaacgt ccgatatcac gaaggataaa | 14040 |
| tgcagcaaat gcctgagcgg ttgtaagttc cgcaataacg tcggcaactt tggcggcttc | 14100 |
| ctttccatta acaaactttc gcagtaaatc ccatgacaca gacagaatca gcgattctgg | 14160 |
| cgcacgcccg gcgatgtgcg ccagcggagt cgtgcggctt cgtggtaagc acgcggagg | 14220 |
| gggaaagata tttcccctgc gtgaatatct ccggtgagcc ggaggctatt tccgtatgtc | 14280 |
| gccggaagac tggctgcagg cagaaatgca gggtgagatt gtggcgctgg tccacagcca | 14340 |
| ccccggtggt ctgccctggc tgagtgaggc cgaccggcgg ctgcaggtgc agagtgattt | 14400 |
| gccgtggtgg ctggtctgcc ggggggacgat tcataagttc cgctgtgtgc cgcatctcac | 14460 |

```
cgggcggcgc tttgagcacg gtgtgacgga ctgttacaca ctgttccggg atgcttatca    14520
tctggcgggg attgagatgc cggactttca tcgtgaggat gactggtggc gtaacggcca    14580
gaatctctat ctggataatc tggaggcgac ggggctgtat caggtgccgt tgtcagcggc    14640
acagccgggc gatgtgctgc tgtgctgttt tggttcatca gtgccgaatc acgccgcaat    14700
ttactgcggc gacggcgagc tgctgcacca tattcctgaa caactgagca acgagagag    14760 gtacaccgac aaatggcagc gacgcacaca ctccctctgg cgtcaccggg catgcgcgc    14820 atctgccttt acgggattt acaacgattt ggtcgccgca tcgaccttcg tgtgaaaacg    14880
ggggctgaag ccatccgggc actggccaca cagctcccgg cgtttcgtca gaaactgagc    14940
gacggctggt atcaggtacg gattgccggg cgggacgtca gcacgtccgg gttaacggcg    15000
cagttacatg agactctgcc tgatggcgct gtaattcata ttgttcccag agtcgccggg    15060
gccaagtcag gtggcgtatt ccagattgtc ctggggctg ccgccattgc cggatcattc    15120
tttaccgccg gagccaccct tgcagcatgg ggggcagcca ttggggccgg tggtatgacc    15180
ggcatcctgt tttctctcgg tgccagtatg gtgctcggtg gtgtggcgca gatgctggca    15240
ccgaaagcca gaactccccg tatacagaca acggataacg gtaagcagaa cacctatttc    15300
tcctcactgg ataacatggt tgcccagggc aatgttctgc ctgttctgta cggggaaatg    15360
cgcgtgcggg cacgcgtggt ttctcaggag atcagcacgg cagacgaagg ggacggtggt    15420
caggttgtgg tgattggtcg ctgatgcaaa atgttttatg tgaaaccgcc tgcgggcggt    15480
tttgtcattt atggagcgtg aggaatgggt aaaggaagca gtaaggggca taccccgcgc    15540
gaagcgaagg acaacctgaa gtccacgcag ttgctgagtg tgatcgatgc catcagcgaa    15600
gggccgattg aaggtccggt ggatggctta aaaagcgtgc tgctgaacag tacgccggtg    15660
ctggacactg aggggaatac caacatatcc ggtgtcacgg tggtgttccg ggctggtgag    15720
caggagcaga ctccgccgga gggatttgaa tcctccggct ccgagacggt gctgggtacg    15780
gaagtgaaat atgacacgcc gatcacccgc accattacgt ctgcaaacat cgaccgtctg    15840
cgctttacct tcggtgtaca ggcactggtg gaaaccacct caaagggtga caggaatccg    15900
tcggaagtcc gcctgctggt tcagatacaa cgtaacggtg gctgggtgac ggaaaaagac    15960
atcaccatta agggcaaaac cacctcgcag tatctggcct cggtggtgat gggtaacctg    16020
ccgccgcgcc cgtttaatat ccggatgcgc aggatgacgc cggacagcac cacagaccag    16080
ctgcagaaca aaacgctctg gtcgtcatac actgaaatca tcgatgtgaa acagtgctac    16140
ccgaacacgg cactggtcgg cgtgcaggtg gactcggagc agttcggcag ccagcaggtg    16200
agccgtaatt atcatctgcg cgggcgtatt ctgcaggtgc cgtcgaacta taacccgcag    16260
acgcggcaat acagcggtat ctgggacgga acgtttaaac cggcatacag caacaacatg    16320
gcctggtgtc tgtgggatat gctgacccat ccgcgctacg catggggaa acgtcttggt    16380 gcggcggatg tggataaatg ggcgctgtat gtcatcggcc agtactgcga ccagtcagtg    16440
ccggacggct ttggcggcac ggagccgcgc atcacctgta atgcgtacct gaccacacag    16500
cgtaaggcgt gggatgtgct cagcgatttc tgctcggcga tgcgctgtat gccggtatgg    16560
aacgggcaga cgctgacgtt cgtgcaggac cgaccgtcgg ataagacgtg gacctataac    16620
cgcagtaatg tggtgatgcc ggatgatggc gcgccgttcc gctacagctt cagcgccctg    16680
aaggaccgcc ataatgccgt tgaggtgaac tggattgacc cgaacaacgg ctgggagacg    16740
gcgacagagc ttgttgaaga tacgcaggcc attgcccgtt acggtcgtaa tgttacgaag    16800
```

```
atggatgcct ttggctgtac cagccggggg caggcacacc gcgccgggct gtggctgatt    16860
aaaacagaac tgctggaaac gcagaccgtg gatttcagcg tcggcgcaga agggcttcgc    16920
catgtaccgg gcgatgttat tgaaatctgc gatgatgact atgccggtat cagcaccggt    16980
ggtcgtgtgc tggcggtgaa cagccagacc cggacgctga cgctcgaccg tgaaatcacg    17040
ctgccatcct ccggtaccgc gctgataagc ctggttgacg gaagtggcaa tccggtcagc    17100
gtggaggttc agtccgtcac cgacggcgtg aaggtaaaag tgagccgtgt tcctgacggt    17160
gttgctgaat acagcgtatg ggagctgaag ctgccgacgc tgcgccagcg actgttccgc    17220
tgcgtgagta tccgtgagaa cgacgacggc acgtatgcca tcaccgccgt gcagcatgtg    17280
ccggaaaaag aggccatcgt ggataacggg gcgcactttg acggcgaaca gagtggcacg    17340
gtgaatggtg tcacgccgcc agcggtgcag cacctgaccg cagaagtcac tgcagacagc    17400
ggggaatatc aggtgctggc gcgatgggac acaccgaagg tggtgaaggg cgtgagtttc    17460
ctgctccgtc tgaccgtaac agcggacgac ggcagtgagc ggctggtcag cacggcccgg    17520
acgacggaaa ccacataccg cttcacgcaa ctggcgctgg ggaactacag gctgacagtc    17580
cgggcggtaa atgcgtgggg gcagcagggc gatccggcgt cggtatcgtt ccggattgcc    17640
gcaccggcag caccgtcgag gattgagctg acgccgggct attttcagat aaccgccacg    17700
ccgcatcttg ccgtttatga cccgacggta cagtttgagt tctggttctc ggaaaagcag    17760
attgcggata tcagacaggt tgaaaccagc acgcgttatc ttggtacggc gctgtactgg    17820
atagccgcca gtatcaatat caaaccgggc catgattatt acttttatat ccgcagtgtg    17880
aacaccgttg gcaaatcggc attcgtggag gccgtcggtc gggcgagcga tgatgcggaa    17940
ggttacctgg attttttcaa aggcaagata accgaatccc atctcggcaa ggagctgctg    18000
gaaaaagtcg agctgacgga ggataacgcc agcagactgg aggagttttc gaaagagtgg    18060
aaggatgcca gtgataagtg gaatgccatg tgggctgtca aaattgagca gaccaaagac    18120
ggcaaacatt atgtcgcggg tattggcctc agcatggagg acacggagga aggcaaactg    18180
agccagtttc tggttgccgc caatcgtatc gcatttattg acccggcaaa cgggaatgaa    18240
acgccgatgt ttgtggcgca gggcaaccag atattcatga cgacgtgtt cctgaagcgc    18300 ctgacggccc ccaccattac cagcggcggc aatcctccgg ccttttccct gacaccggac    18360
ggaaagctga ccgctaaaaa tgcggatatc agtggcagtg tgaatgcgaa ctccgggacg    18420
ctcagtaatg tgacgatagc tgaaaactgt acgataaacg gtacgctgag gcggaaaaa    18480 atcgtcgggg acattgtaaa ggcggcgagc gcggcttttc cgcgccagcg tgaaagcagt    18540
gtggactggc cgtcaggtac ccgtactgtc accgtgaccg atgaccatcc ttttgatcgc    18600
cagatagtgg tgcttccgct gacgtttcgc ggaagtaagc gtactgtcag cggcaggaca    18660
acgtattcga tgtgttatct gaaagtactg atgaacggtg cggtgattta tgatggcgcg    18720
gcgaacgagg cggtacaggt gttctcccgt attgttgaca tgccagcggg tcggggaaac    18780
gtgatcctga cgttcacgct tacgtccaca cggcattcgg cagatattcc gccgtatacg    18840
tttgccagcg atgtgcaggt tatggtgatt aagaaacagg cgctgggcat cagcgtggtc    18900
tgagtgtgtt acagaggttc gtccgggaac gggcgtttta ttataaaaca gtgagaggtg    18960
aacgatgcgt aatgtgtgta ttgccgttgc tgtctttgcc gcacttgcgg tgacccggaa    19020
tgaaattaat acgactcact ataggggagat aaggagggc tattaatgga acctttaaa    19080 tatatatgcc attactgggg aaaatcctca aaaagcttga cgaaaggaaa tgatattcat    19140
ctgttaattt atcattgcct tgatgttgct gctgttgcag attgctggtg ggatcaatca    19200
```

```
gtcgtactgc aaaatacttt ttgccgaaat gaaatgctat caaaacagag ggtgaaggcc   19260
tggctgttat ttttcattgc tcttcatgat attggaaagt ttgatatacg attccaatat   19320
aaatcagcag aaagttggct gaaattaaat cctgcaacgc catcacttaa tggtccatca   19380
acacaaatgt gccgtaaatt taatcatggt gcagccggtc tgtattggtt taaccaggat   19440
tcactttcag agcaatctct cggggatttt ttcagttttt ttgatgccgc tcctcatcct   19500
tatgagtcct ggtttccatg ggtagaggcc gttacaggac atcatggttt tatattacat   19560
tcccaggatc aagataagtc gcgttgggaa atgccagctt ctctggcatc ttatgctgcg   19620
caagataaac aggctcgtga ggagtggata tctgtactgg aagcattatt tttaacgcca   19680
gcggggttat ctataaacga tataccaccct gattgttcat cactgttagc aggttttgc    19740
tcgcttgctg actggttagg ctcctggact acaacgaata cctttctgtt taatgaggat   19800
gcgccttccg acataaatgc tctgagaacg tatttccagg accgacagca ggatgcgagc   19860
cgggtattgg agttgagtgg acttgtatca aataagcgat gttatgaagg tgttcatgca   19920
ctactggaca atggctatca acccagacaa ttacaggtgt tagttgatgc tcttccagta   19980
gctcccgggc tgacggtaat agaggcacct acaggctccg gtaaaacgga acagcgctg    20040
gcctatgctt ggaaacttat tgatcaacaa attgcggata gtgttatttt tgccctccca   20100
acacaagcta ccgcgaatgc tatgcttacg agaatggaag cgagcgcgag ccacttattt   20160
tcatccccaa atcttattct tgctcatggc aattcacggt ttaaccacct ctttcaatca   20220
ataaaatcac gcgcgattac tgaacagggg caagaagaag cgtgggttca gtgttgtcag   20280
tggttgtcac aaagcaataa gaaagtgttt cttgggcaaa tcggcgtttg cacgattgat   20340
caggtgttga tatcggtatt gccagttaaa caccgcttta tccgtggttt gggaattggt   20400
cgaagtgttt taattgttga tgaagttcat gcttacgaca cctatatgaa cggcttgctg   20460
gaggcagtgc tcaaggctca ggctgatgtg ggagggagtg ttattcttct ttccgcaacc   20520
ctaccaatga aacaaaaaca gaaacttctg gatacttatg gtctgcatac agatccagtg   20580
gaaaataact ccgcatatcc actcattaac tggcgaggtg tgaatggtgc gcaacgtttt   20640
gatctgctag ctcatccaga acaactcccg ccccgctttt cgattcagcc agaacctatt   20700
tgtttagctg acatgttacc tgaccttacg atgttagagc gaatgatcgc agcggcaaac   20760
gcgggtgcac aggtctgtct tatttgcaat ttggttgacg ttgcacaagt atgctaccaa   20820
cggctaaagg agctaaataa cacgcaagta gatatagatt tgtttcatgc gcgctttacg   20880
ctgaacgatc gtcgtgaaaa agagaatcga gttattagca atttcggcaa aaatgggaag   20940
cgaaatgttg gacggatact tgtcgcaacc caggtcgtgg aacaatcact cgacgttgat   21000
tttgattggt taattactca gcattgtcct gcagatttgc ttttccaacg attgggccgt   21060
ttacatcgcc atcatcgcaa atatcgtccc gctggttttg agattcctgt tgccaccatt   21120
ttgctgcctg atggcgaggg ttacggacga catgagcata tttatagcaa cgttagagtc   21180
atgtggcgga cgcagcaaca tattgaggag cttaatggag catccttatt tttccctgat   21240
gcttaccggc aatggctgga tagcatttac gatgatgcgg aaatggatga gccagaatgg   21300
gtcggcaatg gcatggataa atttgaaagc gccgagtgtg aaaaaaggtt caaggctcgc   21360
aaggtcctgc agtgggctga agaatatagc ttgcaggata acgatgaaac cattcttgcg   21420
gtaacgaggg atggggaaat gagcctgcca ttattgcctt atgtacaaac gtcttcaggt   21480
aaacaactgc tcgatggcca ggtctacgag gacctaagtc atgaacagca gtatgaggcg   21540
```

```
cttgcactta atcgcgtcaa tgtacccttc acctggaaac gtagtttttc tgaagtagta    21600
gatgaagatg ggttactttg gctggaaggg aaacagaatc tggatggatg ggtctggcag    21660
ggtaacagta ttgttattac ctatacaggg gatgaaggga tgaccagagt catccctgca    21720
aatcccaaat aacttcggga atgattgtta tcaatgacga taataagacc aataacggtt    21780
tatgtgtagg ctggagctgc ttcgaagttc ctatactttc tagagaatag gaacttcgga    21840
ataggaacta aggaggatat tcagaaatta atacgactca ctataggag ataaggaggg    21900 agaacaaatg aatttgctta ttgataactg gatccctgta cgcccgcgaa acgggggga    21960 agtccaaatc ataaatctgc aatcgctata ctgcagtaga gatcagtggc gattaagttt    22020
gccccgtgac gatatggaac tggccgcttt agcactgctg gtttgcattg ggcaaattat    22080
cgccccggca aaagatgacg ttgaatttcg acatcgcata atgaatccgc tcactgaaga    22140
tgagtttcaa caactcatcg cgccgtggat agatatgttc taccttaatc acgcagaaca    22200 tcccttatg cagaccaaag gtgtcaaagc aaatgatgtg actccaatgg aaaaactgtt    22260
ggctggggta agcggcgcga cgaattgtgc atttgtcaat caaccggggc agggtgaagc    22320
attatgtggt ggatgcactg cgattgcgtt attcaaccag gcgaatcagg caccaggttt    22380
tggtggtggt tttaaaagcg gtttacgtgg aggaacacct gtaacaacgt tcgtacgtgg    22440
gatcgatctt cgttcaacgg tgttactcaa tgtcctcaca ttacctcgtc ttcaaaaaca    22500
atttcctaat gaatcacata cggaaaacca acctacctgg attaaaccta tcaagtccaa    22560
tgagtctata cctgcttcgt caattgggtt tgtccgtggt ctattctggc aaccagcgca    22620
tattgaatta tgcgatccca ttgggattgg taaatgttct tgctgtggac aggaaagcaa    22680
tttgcgttat accggttttc ttaaggaaaa atttacctttt acagttaatg gctatggcc    22740 ccatccgcat tccccttgtc tggtaacagt caagaaaggg gaggttgagg aaaaatttct    22800
tgctttcacc acctccgcac catcatggac acaaatcagc cgagttgtgg tagataagat    22860
tattcaaaat gaaaatggaa atcgcgtggc ggcggttgtg aatcaattca gaaatattgc    22920
gccgcaaagt cctcttgaat tgattatggg gggatatcgt aataatcaag catctattct    22980
tgaacggcgt catgatgtgt tgatgtttaa tcaggggtgg caacaatacg gcaatgtgat    23040
aaacgaaata gtgactgttg gtttgggata taaaacagcc ttacgcaagg cgttatatac    23100
ctttgcagaa gggtttaaaa ataaagactt caaaggggcc ggagtctctg ttcatgagac    23160
tgcagaaagg catttctatc gacagagtga attattaatt cccgatgtac tggcgaatgt    23220
taatttttcc caggctgatg aggtaatagc tgatttacga gacaaacttc atcaattgtg    23280
tgaaatgcta tttaatcaat ctgtagctcc ctatgcacat catcctaaat taataagcac    23340
attagcgctt gcccgcgcca cgctatacaa acatttacgg gagttaaaac cgcaaggagg    23400
gccatcaaat ggctgatgaa attgatgcaa tggctttata tcgagcctgg caacaactgg    23460
ataatggatc atgtgcgcaa attagacgtg tttcagaacc tgatgaatta cgcgatatcc    23520 ctgcgttta taggctggtg caacctttg gttgggaaaa cccacgtcac cagcaggctc    23580
ttttgcgcat ggtgtttgc ctgagcgcag gaaagaatgt catccgacat caggacaaaa    23640
aatcggagca acaacaggt atctcgttgg gaagagcttt agccaatagt ggaagaatta    23700
acgagcgccg tatctttcaa ttaattcggg ctgacagaac agccgatatg gtccagttac    23760
gtcgattact tactcacgcc gaacccgtac ttgactggcc attaatggcc aggatgttga    23820
cctggtgggg aaagcgcgaa cgccagcaac ttctggaaga ttttgtattg accacaaaca    23880
aaaatgcgta aggaaaccttt tctatgtcta actttatcaa tattcatgtt ctgatctctc    23940
```

```
acagcccttc atgtctgaac cgcgacgata tgaacatgca gaaagacgct attttcggcg    24000
gcaaaagacg agtaagaatt tcaagtcaaa gccttaaacg tgcgatgcgt aaaagtggtt    24060
attacgcaca aaatattggt gaatccagtc tcagaaccat tcatcttgca caattacgtg    24120
atgttcttcg gcaaaaactt ggtgaacgtt ttgaccaaaa aatcatcgat aagacattag    24180
cgctgctctc cggtaaatca gttgatgaag ccgaaaagat ttctgccgat gcggttactc    24240
cctgggttgt gggagaaata gcctggttct gtgagcaggt tgcaaaagca gaggctgata    24300
atctggatga taaaaagctg ctcaaagttc ttaaggaaga tattgccgcc atacgtgtga    24360
atttacagca gggtgttgat attgcgctta gtggaagaat ggcaaccagc ggcatgatga    24420
ctgagttggg aaaagttgat ggtgcaatgt ccattgcgca tgcgatcact actcatcagg    24480
ttgattctga tattgactgg ttcaccgctg tagatgattt acaggaacaa ggttctgcac    24540
atctgggaac tcaggaattt tcatcgggtg ttttttatcg ttatgccaac attaacctcg    24600
ctcaacttca ggaaaattta ggtggtgcct ccagggagca ggctctggaa attgcaaccc    24660
atgttgttca tatgctggca acagaggtcc ctggagcaaa acagcgtact tatgccgctt    24720
ttaaccctgc ggatatggta atggttaatt tctccgatat gccactttct atggcaaatg    24780
cttttgaaaa agcggttaaa gcgaaagatg cttttttgca accgtctata caggcgttta    24840
atcaatattg ggatcgcgtt gccaatggat atggtctgaa cggagctgct gcgcaattca    24900
gcttatctga tgtagaccca attactgctc aagttaaaca aatgcctact ttagaacagt    24960
taaaatcctg ggttcgtaat aatggcgagg cgtgaacatg agatcttatt tgatcttgcg    25020
gcttgctggg ccaatgcaag cctgggggca gccgaccttt gaaggaacgc gacctaccgg    25080
aagatttccg acccgaagcg ggttattagg gctactcggg gcttgtcttg ggatccaacg    25140
tgatgatact tcttcattac aggcgttatc agagagtgtg caatttgcag tgcgctgcga    25200
tgaactcatt cttgacgatc gtcgtgtgtc tgtaacgggg ttgcgtgatt accatacagt    25260
ccttggagcg cgagaagatt accgtggttt gaaaagtcat gaaacgattc aaacatggcg    25320
cgaatattta tgtgatgcct cctttaccgt cgctctctgg ttaacacccc atgcaacgat    25380
ggttatctca gaacttgaaa aagcagtatt aaagcctcgg tatacacctt acctggggcg    25440
gagaagttgc ccactaacac acccgctttt tttggggaca tgtcaggcat cggatcctca    25500
gaaggcgcta ttaaattatg agcccgttgg cggcgatata tatagtgagg aatcagttac    25560
agggcatcat ttaaaattta cggcgcgcga cgaaccgatg atcaccttgc ctcgacaatt    25620
tgcttcccga gaatggtatg tgattaaagg aggtatggat gtatctcagt aaagtcatca    25680
ttgccagggc ctggagcagg gatctttacc aacttcacca gggattatgg catttatttc    25740
caaacagacc ggatgctgct cgtgattttc tttttcatgt tgagaagcga aacacaccag    25800
aaggctgtca tgttttattg cagtcagcgc aaatgcctgt ttcaactgcc gttgcgacag    25860
tcattaaaac taaacaggtt gaatttcaac ttcaggttgg tgttccactc tatttcggc    25920 ttcgggcaaa tccgatcaaa actattctcg acaatcaaaa gcgcctggac agtaaaggga    25980
atattaaacg ctgtcgggtt ccgttaataa aagaagcaga acaaatcgcg tggttgcaac    26040
gtaaattggg caatgcggcg cgcgttgaag atgtgcatcc catatcggaa cggccacagt    26100 attttctgg tgatggtaaa agtggaaaga tccaaacggt ttgctttgaa ggtgtgctca    26160
ccatcaacga cgcgccagcg ttaatagatc ttgtacagca aggtattggg ccagctaaat    26220
cgatgggatg tggcttgcta tctttggctc cactgtgagg gatgtgctgc aaggcgatta    26280
```

```
agttgggtaa cgccagggtt ttcccagtca cgacgttgta aaacgacggc cagtgaattc   26340
aattaatacg actcactata gggcccgggg gatccggaaa acaaagaatt agctgatctt   26400
taataataag gaaatgttac attaaggttg gtgggttgtt tttatgggaa aaaatgcttt   26460
aagaacaaat gtatactttt agagagttcc ccgcgccagc ggggataaac cgctgagcac   26520
cgcattagcc gctgcattga tgctgagttc cccgcgccag cggggataaa ccgcaggaga   26580
tcaacctgcc ggtcgcgctg gcggtgagtt ccccgcgcca gcgggataa accgcgatgt   26640 cggtgccgtc gatcccaacg gtgatagagt tccccgcgcc agcggggata aaccgtgtgc   26700
cgctgtatgc gcaaacggcg gacgtacgag ttccccgcgc cagcggggat aaaccgctga   26760
ttgctcacgt tggcggcccg gctagcgtga gttccccgcg ccagcgggga taaaccgcag   26820
gcagtccagc ctgaatgctc gctgcaccgg agttccccgc gccagcgggg ataaaccgga   26880
tcgtatgcta tccattacac cagcgggacg gagttccccg cgccagcggg gataaaccgt   26940
ctgcatcacg agtacctttc atagtacgaa tgagttcccc gcgccagcgg ggataaaccg   27000
cggagggcaa gaaatagctt cacgtccat atgagttccc cgcgccagcg gggataaacc   27060
ggtgatatcg catgcaagct ttgaatatcc tccttagttc ctattccgaa gttcctattc   27120
tctagaaagt ataggaactt cggcgcgcct acctgtgacg gaagatcact tcgcagaata   27180
aataaatcct ggtgtccctg ttgataccgg gaagccctgg gccaacttt ggcgaaaatg   27240 agacgttgat cggcacgtaa gaggttccaa ctttcaccat aatgaaataa gatcactacc   27300
gggcgtattt tttgagttgt cgagattttc aggagctaag gaagctaaaa tggagaaaaa   27360
aatcactgga tataccaccg ttgatatatc ccaatggcat cgtaaagaac attttgaggc   27420
atttcagtca gttgctcaat gtacctataa ccagaccgtt cagctggata ttacggcctt   27480
tttaaagacc gtaaagaaaa ataagcacaa gttttatccg gcctttattc acattcttgc   27540
ccgcctgatg aatgctcatc cggaattacg tatggcaatg aaagacggtg agctggtgat   27600
atgggatagt gttcacccct tgttacaccg ttttccatgag caaactgaaa cgttttcatc   27660
gctctggagt gaataccacg acgatttccg gcagtttcta cacatatatt cgcaagatgt   27720
ggcgtgttac ggtgaaaacc tggcctattt ccctaaaggg tttattgaga atatgttttt   27780
cgtctcagcc aatccctggg tgagtttcac cagttttgat ttaaacgtgg ccaatatgga   27840
caacttcttc gcccccgttt tcaccatggg caaatattat acgcaaggcg acaaggtgct   27900
gatgccgctg gcgattcagg ttcatcatgc cgtttgtgat ggcttccatg tcggcagatg   27960
cttaatgaat acaacagtac tgcgatgagt ggcagggcgg ggcgtaaggc gcgccattta   28020
aatgaagttc ctattccgaa gttcctattc tctagaaagt ataggaactt cgaagcagct   28080
ccagcctaca cttgacatga ggttgccccg tgctttgcac tggattgcga ggctttgtgc   28140
ttctctggag tgcgacaggt ttgatgacaa aaaattagcg caagaagaca aaaatcacct   28200
tgcgctaatg ctctgttaca ggtcactaat accatctaag tagttgattc atagtgactg   28260
catatgttgt gttttacagt attatgtagt ctgttttta tgcaaaatct aatttaatat   28320
attgatattt atatcatttt acgtttctcg ttcagctttt ttatactaag ttggcattat   28380
aaaaaagcat tgcttatcaa tttgttgcaa cgaacaggtc actatcagtc aaaataaaat   28440
cattatttga tttcaatttt gtcccactcc ctgcctctgt catcacgata ctgtgatgcc   28500
atggtgtccg acttatgccc gagaagatgt tgagcaaact tatcgcttat ctgcttctca   28560
tagagtcttg cagacaaact gcgcaactcg tgaaaggtag gcggatcccc ttcgaaggaa   28620
agacctgatg cttttcgtgc gcgcataaaa taccttgata ctgtgccgga tgaaagcggt   28680
```

```
tcgcgacgag tagatgcaat tatggtttct ccgccaagaa tctctttgca tttatcaagt   28740
gtttccttca ttgatattcc gagagcatca atatgcaatg ctgttgggat ggcaatttt    28800 acgcctgttt tgctttgctc gacataaaga tatccatcta cgatatcaga ccacttcatt   28860
tcgcataaat caccaactcg ttgcccggta acaacagcca gttccattgc aagtctgagc   28920
caacatggtg atgattctgc tgcttgataa attttcaggt attcgtcagc cgtaagtctt   28980
gatctcctta cctctgattt tgctgcgcga gtggcagcga catggtttgt tgttatatgg   29040
ccttcagcta ttgcctctcg gaatgcatcg ctcagtgttg atctgattaa cttggctgac   29100
gccgccttgc cctcgtctat gtatccattg agcattgccg caatttcttt tgtggtgatg   29160
tcttcaagtg gagcatcagg cagacccctc cttattgctt taattttgct catgtaattt   29220
atgagtgtct tctgcttgat tcctctgctg gccaggattt tttcgtagcg atcaagccat   29280
gaatgtaacg taacggaatt atcactgttg attctcgctg tcagaggctt gtgtttgtgt   29340
cctgaaaata actcaatgtt ggcctgtata gcttcagtga ttgcgattcg cctgtctctg   29400
cctaatccaa actctttacc cgtccttggg tccctgtagc agtaatatcc attgtttctt   29460
atataaaggt tagggggtaa atcccggcgc tcatgacttc gccttcttcc catttctgat   29520
cctcttcaaa aggccacctg ttactggtcg atttaagtca acctttaccg ctgattcgtg   29580
gaacagatac tctcttccat ccttaaccgg aggtgggaat atcctgcatt cccgaaccca   29640
tcgacgaact gtttcaaggc ttcttggacg tcgctggcgt gcgttccact cctgaagtgt   29700
caagtacatc gcaaagtctc cgcaattaca cgcaagaaaa aaccgccatc aggcggcttg   29760
gtgttctttc agttcttcaa ttcgaatatt ggttacgtct gcatgtgcta tctgcgccca   29820
tatcatccag tggtcgtagc agtcgttgat gttctccgct tcgataactc tgttgaatgg   29880
ctctccattc cattctcctg tgactcggaa gtgcatttat catctccata aaacaaaacc   29940
cgccgtagcg agttcagata aaataaatcc ccgcgagtgc gaggattgtt atgtaatatt   30000
gggtttaatc atctatatgt tttgtacaga gagggcaagt atcgtttcca ccgtactcgt   30060
gataataatt ttgcacggta tcagtcattt ctcgcacatt gcagaatggg gatttgtctt   30120
cattagactt ataaaccttc atggaatatt tgtatgccga ctctatatct ataccttcat   30180
ctacataaac accttcgtga tgtctgcatg gagacaagac accggatctg cacaacattg   30240
ataacgccca atctttttgc tcagactcta actcattgat actcatttat aaactccttg   30300
caatgtatgt cgtttcagct aaacggtatc agcaatgttt atgtaaagaa acagtaagat   30360
aatactcaac ccgatgtttg agtacggtca tcatctgaca ctacagactc tggcatcgct   30420
gtgaagacga cgcgaaattc agcattttca caagcgttat cttttacaaa accgatctca   30480
ctctcctttg atgcgaatgc cagcgtcaga catcatatgc agatactcac ctgcatcctg   30540
aacccattga cctccaaccc cgtaatagcg atgcgtaatg atgtcgatag ttactaacgg   30600
gtcttgttcg attaactgcc gcagaaactc ttccaggtca ccagtgcagt gcttgataac   30660
aggagtcttc ccaggatggc gaacaacaag aaactggttt ccgtcttcac ggacttcgtt   30720
gctttccagt ttagcaatac gcttactccc atccgagata acaccttcgt aatactcacg   30780
ctgctcgttg agttttgatt ttgctgtttc aagctcaaca cgcagtttcc ctactgttag   30840
cgcaatatcc tcgttctcct ggtcgcggcg tttgatgtat tgctggtttc tttcccgttc   30900
atccagcagt tccagcacaa tcgatggtgt taccaattca tggaaaaggt ctgcgtcaaa   30960
tccccagtcg tcatgcattg cctgctctgc cgcttcacgc agtgcctgag agttaatttc   31020
```

```
gctcacttcg aacctctctg tttactgata agttccagat cctcctggca acttgcacaa    31080
gtccgacaac cctgaacgac caggcgtctt cgttcatcta tcggatcgcc acactcacaa    31140
caatgagtgg cagatatagc ctggtggttc aggcggcgca tttttattgc tgtgttgcgc    31200
tgtaattctt ctatttctga tgctgaatca atgatgtctg ccatctttca ttaatccctg    31260
aactgttggt taatacgctt gagggtgaat gcgaataata aaaaggagc ctgtagctcc     31320
ctgatgattt tgcttttcat gttcatcgtt ccttaaagac gccgtttaac atgccgattg    31380
ccaggcttaa atgagtcggt gtgaatccca tcagcgttac cgtttcgcgg tgcttcttca    31440
gtacgctacg gcaaatgtca tcgacgtttt tatccggaaa ctgctgtctg gcttttttg     31500
atttcagaat tagcctgacg ggcaatgctg cgaagggcgt tttcctgctg aggtgtcatt    31560
gaacaagtcc catgtcggca agcataagca cacagaatat gaagcccgct gccagaaaaa    31620
tgcattccgt ggttgtcata cctggtttct ctcatctgct tctgctttcg ccaccatcat    31680
ttccagcttt tgtgaaaggg atgcggctaa cgtatgaaat tcttcgtctg tttctactgg    31740
tattggcaca aacctgattc caatttgagc aaggctatgt gccatctcga tactcgttct    31800
taactcaaca gaagatgctt tgtgcataca gcccctcgtt tattatttat ctcctcagcc    31860
agccgctgtg ctttcagtgg atttcggata acagaaaggc cgggaaatac ccagcctcgc    31920
tttgtaacgg agtagacgaa agtgattgcg cctacccgga tattatcgtg aggatgcgtc    31980
atcgccattg ctccccaaat acaaaaccaa tttcagccag tgcctcgtcc atttttcga    32040
tgaactccgg cacgatctcg tcaaaactcg ccatgtactt ttcatcccgc tcaatcacga    32100
cataatgcag gccttcacgc ttcatacgcg ggtcatagtt ggcaaagtac caggcatttt    32160
ttcgcgtcac ccacatgctg tactgcacct gggccatgta agctgacttt atggcctcga    32220
aaccaccgag ccggaacttc atgaaatccc gggaggtaaa cggcatttc agttcaaggc     32280
cgttgccgtc actgcataaa ccatcgggag agcaggcggt acgcatactt tcgtcgcgat    32340
agatgatcgg ggattcagta acattcacgc cggaagtgaa ttcaaacagg gttctggcgt    32400
cgttctcgta ctgttttccc caggccagtg ctttagcgtt aacttccgga gccacaccgg    32460
tgcaaacctc agcaagcagg gtgtggaagt aggacatttt catgtcaggc cacttctttc    32520
cggagcgggg ttttgctatc acgttgtgaa cttctgaagc ggtgatgacg ccgagccgta    32580
atttgtgcca cgcatcatcc ccctgttcga cagctctcac atcgatcccg gtacgctgca    32640
ggataatgtc cggtgtcatg ctgccacctt ctgctctgcg gctttctgtt tcaggaatcc    32700
aagagctttt actgcttcgg cctgtgtcag ttctgacgat gcacgaatgt cgcggcgaaa    32760
tatctgggaa cagagcggca ataagtcgtc atccatgtt ttatccaggg cgatcagcag     32820
agtgttaatc tcctgcatgg tttcatcgtt aaccggagtg atgtcgcgtt ccggctgacg    32880
ttctgcagtg tatgcagtat tttcgacaat gcgctcggct tcatccttgt catagatacc    32940
agcaaatccg aaggccagac gggcacactg aatcatggct ttatgacgta acatccgttt    33000
gggatgcgac tgccacggcc ccgtgatttc tctgccttcg cgagttttga atggttcgcg    33060
gcggcattca tccatccatt cggtaacgca gatcggatga ttacggtcct tgcggtaaat    33120
ccggcatgta caggattcat tgtcctgctc aaagtccatg ccatcaaact gctggttttc    33180
attgatgatg cggaccagc catcaacgcc caccaccgga acgatgccat tctgcttatc     33240
aggaaaggcg taaatttctt tcgtccacgg attaaggccg tactggttgg caacgatcag    33300
taatgcgatg aactgcgcat cgctggcatc acctttaaat gccgtctggc gaagagtggt    33360
gatcagttcc tgtgggtcga cagaatccat gccgacacgt tcagccagct tcccagccag    33420
```

```
cgttgcgagt gcagtactca ttcgttttat acctctgaat caatatcaac ctggtggtga   33480
gcaatggttt caaccatgta ccggatgtgt tctgccatgc gctcctgaaa ctcaacatcg   33540
tcatcaaacg cacgggtaat ggattttttg ctggccccgt ggcgttgcaa atgatcgatg   33600
catagcgatt caaacaggtg ctggggcagg cctttttcca tgtcgtctgc cagttctgcc   33660
tctttctctt cacgggcgag ctgctggtag tgacgcgccc agctctgagc ctcaagacga   33720
tcctgaatgt aataagcgtt catggctgaa ctcctgaaat agctgtgaaa atatcgcccg   33780
cgaaatgccg ggctgattag gaaaacagga aaggggtta gtgaatgctt ttgcttgatc   33840
tcagtttcag tattaatatc cattttttat aagcgtcgac ggcttcacga aacatctttt   33900
catcgccaat aaaagtggcg atagtgaatt tagtctggat agccataagt gtttgatcca   33960
ttctttggga ctcctggctg attaagtatg tcgataaggc gtttccatcc gtcacgtaat   34020
ttacgggtga ttcgttcaag taaagattcg aagggcagc cagcaacagg ccaccctgca   34080
atggcatatt gcatggtgtg ctccttattt atacataacg aaaaacgcct cgagtgaagc   34140
gttattggta tgcggtaaaa ccgcactcag gcggccttga tagtcatatc atctgaatca   34200
aatattcctg atgtatcgat atcggtaatt cttattcctt cgctaccatc cattggaggc   34260
catccttcct gaccatttcc atcattccag tcgaactcac acacaacacc atatgcattt   34320
aagtcgcttg aaattgctat aagcagagca tgttgcgcca gcatgattaa tacagcattt   34380
aatacagagc cgtgtttatt gagtcggtat tcagagtctg accagaaatt attaatctgg   34440
tgaagttttt cctctgtcat tacgtcatgg tcgatttcaa tttctattga tgctttccag   34500
tcgtaatcaa tgatgtattt tttgatgttt gacatctgtt catatcctca cagataaaaa   34560
atcgccctca cactggaggg caaagaagat ttccaataat cagaacaagt cggctcctgt   34620
ttagttacga gcgacattgc tccgtgtatt cactcgttgg aatgaataca cagtgcagtg   34680
tttattctgt tatttatgcc aaaaataaag gccactatca ggcagctttg ttgttctgtt   34740
taccaagttc tctggcaatc attgccgtcg ttcgtattgc ccatttatcg acatatttcc   34800
catcttccat tacaggaaac atttcttcag gcttaaccat gcattccgat tgcagcttgc   34860
atccattgca tcgcttgaat tgtccacacc attgattttt atcaatagtc gtagtcatac   34920
ggatagtcct ggtattgttc catcacatcc tgaggatgct cttcgaactc ttcaaattct   34980
tcttccatat atcaccttaa atagtggatt gcggtagtaa agattgtgcc tgtcttttaa   35040
ccacatcagg ctcggtggtt ctcgtgtacc cctacagcga gaaatcggat aaactattac   35100
aacccctaca gtttgatgag tatagaaatg gatccactcg ttattctcgg acgagtgttc   35160
agtaatgaac ctctggagag aaccatgtat atgatcgtta tctggttgg acttctgctt   35220 ttaagcccag ataactggcc tgaatatgtt aatgagagaa tcggtattcc tcatgtgtgg   35280
catgttttcg tctttgctct tgcattttcg ctagcaatta atgtgcatcg attatcagct   35340
attgccagcg ccagatataa gcgatttaag ctaagaaaac gcattaagat gcaaaacgat   35400
aaagtgcgat cagtaattca aaaccttaca gaagagcaat ctatggtttt gtgcgcagcc   35460
cttaatgaag gcaggaagta tgtggttaca tcaaaacaat tcccatacat tagtgagttg   35520
attgagcttg gtgtgttgaa caaaactttt tcccgatgga atggaaagca tatattattc   35580
cctattgagg atatttactg gactgaatta gttgccagct atgatccata taatattgag   35640
ataaagccaa ggccaatatc taagtaacta gataagagga atcgattttc ccttaatttt   35700
ctggcgtcca ctgcatgtta tgccgcgttc gccaggcttg ctgtaccatg tgcgctgatt   35760
```

```
cttgcgctca atacgttgca ggttgctttc aatctgtttg tggtattcag ccagcactgt   35820
aaggtctatc ggatttagtg cgcttctac tcgtgatttc ggtttgcgat tcagcgagag    35880
aatagggcgg ttaactggtt ttgcgcttac cccaaccaac aggggatttg ctgcttttcca  35940
ttgagcctgt ttctctgcgc gacgttcgcg cggcgtgtt tgtgcatcca tctggattct    36000
cctgtcagtt agctttggtg gtgtgtggca gttgtagtcc tgaacgaaaa cccccccgcga  36060
ttggcacatt ggcagctaat ccggaatcgc acttacggcc aatgcttcgt ttcgtatcac   36120
acaccccaaa gccttctgct ttgaatgctg cccttcttca gggcttaatt tttaagagcg   36180
tcaccttcat ggtggtcagt gcgtcctgct gatgtgctca gtatcaccgc cagtggtatt   36240
tatgtcaaca ccgccagaga taatttatca ccgcagatgg ttatctgtat gttttttata   36300
tgaatttatt ttttgcaggg gggcattgtt tggtaggtga gagatctgaa ttgctatgtt   36360
tagtgagttg tatctattta tttttcaata aatacaattg gttatgtgtt ttgggggcga   36420
tcgtgaggca aagaaaaccc ggcgctgagg ccgggttatt cttgttctct ggtcaaatta   36480
tatagttgga aaacaaggat gcatatatga atgaacgatg cagaggcaat gccgatggcg   36540
atagtgggta tcatgtagcc gcttatgctg gaaagaagca ataacccgca gaaaaacaaa   36600
gctccaagct caacaaaact aagggcatag acaataacta ccgatgtcat atacccatac   36660
tctctaatct tggccagtcg gcgcgttctg cttccgatta gaaacgtcaa ggcagcaatc   36720
aggattgcaa tcatggttcc tgcatatgat gacaatgtcg ccccaagacc atctctatga   36780
gctgaaaaag aaacaccagg aatgtagtgg cggaaaagga gatagcaaat gcttacgata   36840
acgtaaggaa ttattactat gtaaacacca ggcatgattc tgttccgcat aattactcct   36900
gataattaat ccttaacttt gcccacctgc cttttaaaac attccagtat atcactttc    36960
attcttgcgt agcaatatgc catctcttca gctatctcag cattggtgac cttgttcaga   37020
ggcgctgaga gatggccttt ttctgataga taatgttctg ttaaaatatc tccggcctca   37080
tcttttgccc gcaggctaat gtctgaaaat tgaggtgacg ggttaaaaat aatatccttg   37140
gcaacctttt ttatatccct tttaaatttt ggcttaatga ctatatccaa tgagtcaaaa   37200
agctcccctt caatatctgt tgcccctaag acctttaata tatcgccaaa tacaggtagc   37260
ttggcttcta ccttcaccgt tgttcggccg atgaaatgca tatgcataac atcgtctttg   37320
gtggttcccc tcatcagtgg ctctatctga acgcgctctc cactgcttaa tgacattcct   37380
ttcccgatta aaaaatctgt cagatcggat gtggtcggcc cgaaaacagt tctggcaaaa   37440
ccaatggtgt cgccttcaac aaacaaaaaa gatgggaatc ccaatgattc gtcatctgcg   37500
aggctgttct taatatcttc aactgaagct ttagagcgat ttatcttctg aaccagactc   37560
ttgtcatttg ttttggtaaa gagaaaagtt tttccatcga ttttatgaat atacaaataa   37620
ttggagccaa cctgcaggtg atgattatca gccagcagag aattaaggaa aacagacagg   37680
tttattgagc gcttatcttt cccttttattt ttgctgcgt aagtcgcata aaaaccattc    37740
ttcataattc aatccattta ctatgttatg ttctgagggg agtgaaaatt cccctaattc   37800
gatgaagatt cttgctcaat tgttatcagc tatgcgccga ccagaacacc ttgccgatca   37860
gccaaacgtc tcttcaggcc actgactagc gataactttc cccacaacgg aacaactctc   37920
attgcatggg atcattgggt actgtgggtt tagtggttgt aaaaacacct gaccgctatc   37980
cctgatcagt ttcttgaagg taaactcatc acccccaagt ctggctatgc agaaatcacc   38040
tggctcaaca gcctgctcag ggtcaacgag aattaacatt ccgtcaggaa agcttggctt   38100
ggagcctgtt ggtgcggtca tggaattacc ttcaacctca agccagaatg cagaatcact   38160
```

-continued

```
ggcttttttg gttgtgctta cccatctctc cgcatcacct ttggtaaagg ttctaagctc    38220
aggtgagaac atccctgcct gaacatgaga aaaaacaggg tactcatact cacttctaag    38280
tgacggctgc atactaaccg cttcatacat ctcgtagatt tctctggcga ttgaagggct    38340
aaattcttca acgctaactt tgagaatttt tgcaagcaat gcggcgttat aagcatttaa    38400
tgcattgatg ccattaaata aagcaccaac gcctgactgc cccatcccca tcttgtctgc    38460
gacagattcc tgggataagc caagttcatt tttctttttt tcataaattg ctttaaggcg    38520
acgtgcgtcc tcaagctgct cttgtgttaa tggtttcttt tttgtgctca tacgttaaat    38580
ctatcaccgc aagggataaa tatctaacac cgtgcgtgtt gactatttta cctctggcgg    38640
tgataatggt tgcatgtact aaggaggttg tatggaacaa cgcataaccc tgaaagatta    38700
tgcaatgcgc tttgggcaaa ccaagacagc taaagatctc ggcgtatatc aaagcgcgat    38760
caacaaggcc attcatgcag gccgaaagat tttttttaact ataaacgctg atggaagcgt    38820
ttatgcggaa gaggtaaagc ccttcccgag taacaaaaaa acaacagcat aaataacccc    38880
gctcttacac attccagccc tgaaaaaggg catcaaatta aaccacacct atggtgtatg    38940
catttatttg catacattca atcaattgtt atctaaggaa atacttacat atggttcgtg    39000
caaacaaacg caacgaggct ctacgaatcg agagtgcgtt gcttaacaaa atcgcaatgc    39060
ttggaactga aagacagcg gaagctgtgg gcgttgataa gtcgcagatc agcaggtgga    39120
agagggactg gattccaaag ttctcaatgc tgcttgctgt tcttgaatgg ggggtcgttg    39180
acgacgacat ggctcgattg gcgcgacaag ttgctgcgat tctcaccaat aaaaaacgcc    39240
cggcggcaac cgagcgttct gaacaaatcc agatggagtt ctgaggtcat tactggatct    39300
atcaacagga gtcattatga caaatacagc aaaaatactc aacttcggca gaggtaactt    39360
tgccggacag gagcgtaatg tggcagatct cgatgatggt tacgccagac tatcaaatat    39420
gctgcttgag gcttattcgg gcgcagatct gaccaagcga cagtttaaag tgctgcttgc    39480
cattctgcgt aaaacctatg ggtggaataa accaatggac agaatcaccg attctcaact    39540
tagcgagatt acaaagttac ctgtcaaacg gtgcaatgaa gccaagttag aactcgtcag    39600
aatgaatatt atcaagcagc aaggcggcat gtttggacca aataaaaaca tctcagaatg    39660
gtgcatccct caaaacgagg gaaaatcccc taaaacgagg gataaaacat ccctcaaatt    39720
gggggattgc tatccctcaa aacaggggga cacaaaagac actattacaa aagaaaaaag    39780
aaaagattat tcgtcagaga attctggcga atcctctgac cagccagaaa acgacctttc    39840
tgtggtgaaa ccggatgctg caattcagag cggcagcaag tggggacag cagaagacct    39900 gaccgccgca gagtggatgt ttgacatggt gaagactatc gcaccatcag ccagaaaacc    39960 gaatttgct gggtgggcta acgatatccg cctgatgcgt gaacgtgacg gacgtaacca    40020
ccgcgacatg tgtgtgctgt tccgctgggc atgccaggac aacttctggt ccggtaacgt    40080
gctgagcccg gccaaactcc gcgataagtg gacccaactc gaaatcaacc gtaacaagca    40140
acaggcaggc gtgacagcca gcaaaccaaa actcgacctg acaaacacag actggattta    40200
cggggtggat ctatgaaaaa catcgccgca cagatggtta actttgaccg tgagcagatg    40260
cgtcggatcg ccaacaacat gccggaacag tacgacgaaa agccgcaggt acagcaggta    40320
gcgcagatca tcaacggtgt gttcagccag ttactggcaa ctttcccggc gagcctggct    40380
aaccgtgacc agaacgaagt gaacgaaatc cgtcgccagt gggttctggc ttttcgggaa    40440
aacgggatca ccacgatgga acaggttaac gcaggaatgc gcgtagcccg tcggcagaat    40500
```

```
cgaccatttc tgccatcacc cgggcagttt gttgcatggt gccgggaaga agcatccgtt   40560
accgccggac tgccaaacgt cagcgagctg gttgatatgg tttacgagta ttgccggaag   40620
cgaggcctgt atccggatgc ggagtcttat ccgtggaaat caaacgcgca ctactggctg   40680
gttaccaacc tgtatcagaa catgcgggcc aatgcgctta ctgatgcgga attacgccgt   40740
aaggccgcag atgagcttgt ccatatgact gcgagaatta accgtggtga ggcgatccct   40800
gaaccagtaa acaacttcc tgtcatgggc ggtagacctc taaatcgtgc acaggctctg   40860
gcgaagatcg cagaaatcaa agctaagttc ggactgaaag gagcaagtgt atgacgggca   40920
aagaggcaat tattcattac ctggggacgc ataatagctt ctgtgcgccg gacgttgccg   40980
cgctaacagg cgcaacagta accagcataa atcaggccgc ggctaaaatg gcacgggcag   41040
gtcttctggt tatcgaaggt aaggtctggc gaacggtgta ttaccggttt gctaccaggg   41100
aagaacggga aggaaagatg agcacgaacc tggtttttaa ggagtgtcgc cagagtgccg   41160
cgatgaaacg ggtattggcg gtatatggag ttaaaagatg accatctaca ttactgagct   41220
aataacaggc ctgctggtaa tcgcaggcct ttttatttgg gggagaggga agtcatgaaa   41280
aaactaacct ttgaaattcg atctccagca catcagcaaa acgctattca cgcagtacag   41340
caaatccttc cagacccaac caaaccaatc gtagtaacca ttcaggaacg caaccgcagc   41400
ttagaccaaa acaggaagct atgggcctgc ttaggtgacg tctctcgtca ggttgaatgg   41460
catggtcgct ggctgatgc agaaagctgg aagtgtgtgt ttaccgcagc attaaagcag   41520
caggatgttg ttcctaacct tgccgggaat ggctttgtgg taataggcca gtcaaccagc   41580
aggatgcgtg taggcgaatt tgcggagcta ttagagctta tacaggcatt cggtacagag   41640
cgtggcgtta agtggtcaga cgaagcgaga ctggctctgg agtggaaagc gagatgggga   41700
gacagggctg catgataaat gtcgttagtt tctccggtgg caggacgtca gcatatttgc   41760
tctggctaat ggagcaaaag cgacgggcag gtaaagacgt gcattacgtt ttcatggata   41820
caggttgtga acatccaatg acatatcggt ttgtcaggga agttgtgaag ttctgggata   41880
taccgctcac cgtattgcag gttgatatca acccggagct tggacagcca aatggttata   41940
cggtatggga accaaaggat attcagacgc gaatgcctgt tctgaagcca tttatcgata   42000
tggtaaagaa atatggcact ccatacgtcg gcggcgcgtt ctgcactgac agattaaaac   42060
tcgttccctt caccaaatac tgtgatgacc atttcgggcg agggaattac accacgtgga   42120
ttggcatcag agctgatgaa ccgaagcggc taaagccaaa gcctggaatc agatatcttg   42180
ctgaactgtc agactttgag aaggaagata tcctcgcatg gtggaagcaa caaccattcg   42240
atttgcaaat accggaacat ctcggtaact gcatattctg cattaaaaaa tcaacgcaaa   42300
aaatcggact tgcctgcaaa gatgaggagg gattgcagcg tgtttttaat gaggtcatca   42360
cgggatccca tgtgcgtgac ggacatcggg aaacgccaaa ggagattatg taccgaggaa   42420
gaatgtcgct ggacggtatc gcgaaaatgt attcagaaaa tgattatcaa gccctgtatc   42480
aggacatggt acgagctaaa agattcgata ccggctcttg ttctgagtca tgcgaaatat   42540
ttggagggca gcttgatttc gacttcggga gggaagctgc atgatgcgat gttatcggtg   42600
cggtgaatgc aaagaagata accgcttccg accaaatcaa ccttactgga atcgatggtg   42660
tctccggtgt gaaagaacac caacagggt gttaccacta ccgcaggaaa aggaggacgt   42720
gtggcgagac agcgacgaag tatcaccgac ataatctgcg aaaactgcaa ataccttcca   42780
acgaaacgca ccagaaataa acccaagcca atcccaaaag aatctgacgt aaaaaccttc   42840
aactacacgg ctcacctgtg ggatatccgg tggctaagac gtcgtgcgag gaaaacaagg   42900
```

```
tgattgacca aaatcgaagt tacgaacaag aaagcgtcga gcgagcttta acgtgcgcta    42960
actgcggtca gaagctgcat gtgctggaag ttcacgtgtg tgagcactgc tgcgcagaac    43020
tgatgagcga tccgaatagc tcgatgcacg aggaagaaga tgatggctaa accagcgcga    43080
agacgatgta aaaacgatga atgccgggaa tggtttcacc ctgcattcgc taatcagtgg    43140
tggtgctctc cagagtgtgg aaccaagata gcactcgaac gacgaagtaa agaacgcgaa    43200
aaagcggaaa aagcagcaga gaagaaacga cgacgagagg agcagaaaca gaaagataaa    43260
cttaagattc gaaaactcgc cttaaagccc cgcagttact ggattaaaca gcccaacaa    43320 gccgtaaacg ccttcatcag agaaagagac cgcgacttac catgtatctc gtgcggaacg    43380
ctcacgtctg ctcagtggga tgccggacat taccggacaa ctgctgcggc acctcaactc    43440
cgatttaatg aacgcaatat tcacaagcaa tgcgtggtgt gcaaccagca caaaagcgga    43500
aatctcgttc cgtatcgcgt cgaactgatt agccgcatcg ggcaggaagc agtagacgaa    43560
atcgaatcaa accataaccg ccatcgctgg actatcgaag agtgcaaggc gatcaaggca    43620
gagtaccaac agaaactcaa agacctgcga aatagcagaa gtgaggccgc atgacgttct    43680
cagtaaaaac cattccagac atgctcgttg aagcatacgg aaatcagaca gaagtagcac    43740
gcagactgaa atgtagtcgc ggtacggtca gaaaatacgt tgatgataaa gacgggaaaa    43800
tgcacgccat cgtcaacgac gttctcatgg ttcatcgcgg atggagtgaa agagatgcgc    43860
tattacgaaa aaattgatgg cagcaaatac cgaaatattt gggtagttgg cgatctgcac    43920
ggatgctaca cgaacctgat gaacaaactg gatcgattg gattcgacaa caaaaaagac    43980
ctgcttatct cggtgggcga tttggttgat cgtggtgcag agaacgttga atgcctggaa    44040
ttaatcacat tccctggtt cagagctgta cgtggaaacc atgagcaaat gatgattgat    44100
ggcttatcag agcgtggaaa cgttaatcac tggctgctta atggcggtgg ctggttcttt    44160
aatctcgatt acgacaaaga aattctggct aaagctcttg cccataaagc agatgaactt    44220
ccgttaatca tcgaactggt gagcaaagat aaaaaatatg ttatctgcca cgccgattat    44280 cccttttgacg aatacgagtt tggaaagcca gttgatcatc agcaggtaat ctggaaccgc    44340
gaacgaatca gcaactcaca aaacgggatc gtgaagaaa tcaaaggcgc ggacacgttc    44400
atctttggtc atacgccagc agtgaaacca ctcaagtttg ccaaccaaat gtatatcgat    44460
accggcgcag tgttctgcgg aaacctaaca ttgattcagg tacagggaga aggcgcatga    44520
gactcgaaag cgtagctaaa tttcattcgc caaaaagccc gatgatgagc gactcaccac    44580
gggccacggc ttctgactct cttccggta ctgatgtgat ggctgctatg gggatggcgc    44640
aatcacaagc cggattcggt atggctgcat tctgcggtaa gcacgaactc agccagaacg    44700
acaaacaaaa ggctatcaac tatctgatgc aatttgcaca caaggtatcg gggaaatacc    44760
gtggtgtggc aaagcttgaa ggaaatacta aggcaaaggt actgcaagtg ctcgcaacat    44820
tcgcttatgc ggattattgc cgtagtgccg cgacgccggg ggcaagatgc agagattgcc    44880
atggtacagg ccgtgcggtt gatattgcca aaacagagct gtgggggaga gttgtcgaga    44940
aagagtgcgg aagatgcaaa ggcgtcggct attcaaggat gccagcaagc gcagcatatc    45000
gcgctgtgac gatgctaatc ccaaaccctta cccaacccac ctggtcacgc actgttaagc    45060
cgctgtatga cgctctggtg gtgcaatgcc acaaagaaga gtcaatcgca gacaacattt    45120
tgaatgcggt cacacgttag cagcatgatt gccacggatg gcaacatatt aacggcatga    45180
tattgactta ttgaataaaa ttgggtaaat ttgactcaac gatgggttaa ttcgctcgtt    45240
```

```
gtggtagtga gatgaaaaga ggcggcgctt actaccgatt ccgcctagtt ggtcacttcg    45300
acgtatcgtc tggaactcca accatcgcag gcagagaggt ctgcaaaatg caatcccgaa    45360
acagttcgca ggtaatagtt agagcctgca taacggtttc gggattttt atatctgcac     45420 aacaggtaag agcattgagt cgataatcgt gaagagtcgg cgagcctggt tagccagtgc    45480
tctttccgtt gtgctgaatt aagcgaatac cggaagcaga accggatcac caaatgcgta    45540
caggcgtcat cgccgcccag caacagcaca acccaaactg agccgtagcc actgtctgtc    45600
ctgaattcat tagtaatagt tacgctgcgg ccttttacac atgaccttcg tgaaagcggg    45660
tggcaggagg tcgcgctaac aacctcctgc cgttttgccc gtgcatatcg gtcacgaaca    45720
aatctgatta ctaaacacag tagcctggat ttgttctatc agtaatcgac cttattccta    45780
attaaataga gcaaatcccc ttattggggg taagacatga agatgccaga aaaacatgac    45840
ctgttggccg ccattctcgc ggcaaaggaa caaggcatcg gggcaatcct tgcgtttgca    45900
atggcgtacc ttcgcggcag atataatggc ggtgcgttta caaaaacagt aatcgacgca    45960
acgatgtgcg ccattatcgc ctggttcatt cgtgaccttc tcgacttcgc cggactaagt    46020
agcaatctcg cttatataac gagcgtgttt atcggctaca tcggtactga ctcgattggt    46080
tcgcttatca aacgcttcgc tgctaaaaaa gccggagtag aagatggtag aaatcaataa    46140
tcaacgtaag gcgttcctcg atatgctggc gtggtcggag ggaactgata acggacgtca    46200
gaaaaccaga aatcatggtt atgacgtcat tgtaggcgga gagctattta ctgattactc    46260
cgatcaccct cgcaaacttg tcacgctaaa cccaaaactc aaatcaacag gcgccggacg    46320
ctaccagctt ctttcccgtt ggtgggatgc ctaccgcaag cagcttggcc tgaaagactt    46380
ctctccgaaa agtcaggacg ctgtggcatt gcagcagatt aaggagcgtg gcgctttacc    46440
tatgattgat cgtggtgata ccgtcaggc aatcgaccgt tgcagcaata tctgggcttc    46500
actgccgggc gctggttatg gtcagttcga gcataaggct gacagcctga ttgcaaaatt    46560
caaagaagcg ggcggaacgg tcagagagat tgatgtatga gcagagtcac cgcgattatc    46620
tccgctctgg ttatctgcat catcgtctgc ctgtcatggg ctgttaatca ttaccgtgat    46680
aacgccatta cctacaaagc ccagcgcgac aaaaatgcca gagaactgaa gctggcgaac    46740
gcggcaatta ctgacatgca gatgcgtcag cgtgatgttg ctgcgctcga tgcaaaatac    46800
acgaaggagt tagctgatgc taaagctgaa aatgatgctc tgcgtgatga tgttgccgct    46860
ggtcgtcgtc ggttgcacat caaagcagtc tgtcagtcag tgcgtgaagc caccaccgcc    46920
tccggcgtgg ataatgcagc ctcccccga ctggcagaca ccgctgaacg ggattatttc     46980 acctcagag agaggctgat cactatgcaa aaacaactgg aaggaaccca gaagtatatt     47040
aatgagcagt gcagatagag ttgcccatcg acctgcaggg ggggggggc gctgaggtct     47100 gcctcgtgaa gaaggtgttg ctgactcata ccaggcctga atcgcccat catccagcca     47160 gaaagtgagg gagccacggt tgatgagagc tttgttgtag gtggaccagt tggtgatttt    47220
gaacttttgc tttgccacgg aacggtctgc gttgtcggga agatgcgtga tctgatcctt    47280
caactcagca aaagttcgat ttattcaaca aagccgccgt cccgtcaagt cagcgtaatg    47340
ctctgccagt gttacaacca attaaccaat tctgattaga aaaactcatc gagcatcaaa    47400
tgaaactgca atttattcat atcaggatta tcaataccat attttttgaaa aagccgtttc    47460 tgtaatgaag gagaaaactc accgaggcag ttccatagga tggcaagatc ctggtatcgg    47520
tctgcgattc cgactcgtcc aacatcaata caacctatta atttccctc gtcaaaaata    47580 aggttatcaa gtgagaaatc accatgagtg acgactgaat ccggtgagaa tggcaaaagc    47640
```

| | |
|---|---|
| ttatgcattt ctttccagac ttgttcaaca ggccagccat tacgctcgtc atcaaaatca | 47700 |
| ctcgcatcaa ccaaaccgtt attcattcgt gattgcgcct gagcgagacg aaatacgcga | 47760 |
| tcgctgttaa aaggacaatt acaaacagga atcgaatgca accggcgcag gaacactgcc | 47820 |
| agcgcatcaa caatattttc acctgaatca ggatattctt ctaatacctg gaatgctgtt | 47880 |
| ttcccgggga tcgcagtggt gagtaaccat gcatcatcag gagtacggat aaaatgcttg | 47940 |
| atggtcggaa gaggcataaa ttccgtcagc cagtttagtc tgaccatctc atctgtaaca | 48000 |
| tcattggcaa cgctacccttt gccatgtttc agaaacaact ctggcgcatc gggcttccca | 48060 |
| tacaatcgat agattgtcgc acctgattgc ccgacattat cgcgagccca tttataccca | 48120 |
| tataaatcag catccatgtt ggaatttaat cgcggcctcg agcaagacgt ttcccgttga | 48180 |
| atatggctca taacacccct tgtattactg tttatgtaag cagacagttt tattgttcat | 48240 |
| gatgatatat ttttatcttg tgcaatgtaa catcagagat tttgagacac aacgtggctt | 48300 |
| tccccccccc ccctgcaggt cgttgacatg aggttgcccc gtattcagtg tcgctgattt | 48360 |
| gtattgtctg aagttgtttt tacgttaagt tgatgcagat caattaatac gatacctgcg | 48420 |
| tcataattga ttatttgacg tggtttgatg gcctccacgc acgttgtgat atgtagatga | 48480 |
| taatcattat cactttacgg gtcctttccg gtgatccgac aggttacg | 48528 |

<210> SEQ ID NO 60
<211> LENGTH: 1509
<212> TYPE: DNA
<213> ORGANISM: Escherichia coli

<400> SEQUENCE: 60

| | |
|---|---|
| atgaatttgc ttattgataa ctggatccct gtacgcccgc gaaacggggg gaaagtccaa | 60 |
| atcataaatc tgcaatcgct atactgcagt agagatcagt ggcgattaag tttgccccgt | 120 |
| gacgatatgg aactggccgc tttagcactg ctggtttgca ttgggcaaat tatcgccccg | 180 |
| gcaaaagatg acgttgaatt tcgacatcgc ataatgaatc cgctcactga agatgagttt | 240 |
| caacaactca tcgcgccgtg gatagatatg ttctacccta atcacgcaga acatcccttt | 300 |
| atgcagacca aaggtgtcaa agcaaatgat gtgactccaa tggaaaaact gttggctggg | 360 |
| gtaagcggcg cgacgaattg tgcatttgtc aatcaaccgg ggcagggtga agcattatgt | 420 |
| ggtggatgca ctgcgattgc gttattcaac caggcgaatc aggcaccagg ttttggtggt | 480 |
| ggttttaaaa gcggtttacg tggaggaaca cctgtaacaa cgttcgtacg tgggatcgat | 540 |
| cttcgttcaa cggtgttact caatgtcctc acattacctc gtcttcaaaa acaatttcct | 600 |
| aatgaatcac atacggaaaa ccaacctacc tggattaaac ctatcaagtc caatgagtct | 660 |
| atacctgctt cgtcaattgg gtttgtccgt ggtctattct ggcaaccagc gcatattgaa | 720 |
| ttatgcgatc ccattgggat tggtaaatgt tcttgctgtg gacaggaaag caatttgcgt | 780 |
| tataccggtt tccttaagga aaaatttacc tttacagtta atgggctatg gccccatccg | 840 |
| cattcccctt gtctggtaac agtcaagaaa ggggaggttg aggaaaaatt tcttgctttc | 900 |
| accacctccg caccatcatg gacacaaatc agccgagttg tggtagataa gattattcaa | 960 |
| aatgaaaatg gaaatcgcgt ggcggcggtt gtgaatcaat tcagaaatat tgcgccgcaa | 1020 |
| agtcctcttg aattgattat gggggatat cgtaataatc aagcatctat tcttgaacgg | 1080 |
| cgtcatgatg tgttgatgtt taatcagggg tggcaacaat acggcaatgt gataaacgaa | 1140 |
| atagtgactg ttggtttggg atataaaaca gccttacgca aggcgttata tacctttgca | 1200 |

|  |  |
|---|---|
| gaagggttta aaaataaaga cttcaaaggg gccggagtct ctgttcatga gactgcagaa | 1260 |
| aggcatttct atcgacagag tgaattatta attcccgatg tactggcgaa tgttaatttt | 1320 |
| tcccaggctg atgaggtaat agctgattta cgagacaaac ttcatcaatt gtgtgaaatg | 1380 |
| ctatttaatc aatctgtagc tccctatgca catcatccta aattaataag cacattagcg | 1440 |
| cttgcccgcg ccacgctata caaacattta cgggagttaa aaccgcaagg agggccatca | 1500 |
| aatggctga | 1509 |

<210> SEQ ID NO 61
<211> LENGTH: 483
<212> TYPE: DNA
<213> ORGANISM: Escherichia coli

<400> SEQUENCE: 61

|  |  |
|---|---|
| atggctgatg aaattgatgc aatggcttta tatcgagcct ggcaacaact ggataatgga | 60 |
| tcatgtgcgc aaattagacg tgtttcagaa cctgatgaat tacgcgatat ccctgcgttt | 120 |
| tataggctgg tgcaacccttt tggttgggaa aacccacgtc accagcaggc tcttttgcgc | 180 |
| atggtgtttt gcctgagcgc aggaaagaat gtcatccgac atcaggacaa aaaatcggag | 240 |
| caaacaacag gtatctcgtt gggaagagct ttagccaata gtggaagaat taacgagcgc | 300 |
| cgtatctttc aattaattcg ggctgacaga acagccgata tggtccagtt acgtcgatta | 360 |
| cttactcacg ccgaacccgt acttgactgg ccattaatgg ccaggatgtt gacctggtgg | 420 |
| ggaaagcgcg aacgccagca acttctggaa gattttgtat tgaccacaaa caaaaatgcg | 480 |
| taa | 483 |

<210> SEQ ID NO 62
<211> LENGTH: 1092
<212> TYPE: DNA
<213> ORGANISM: Escherichia coli

<400> SEQUENCE: 62

|  |  |
|---|---|
| atgtctaact ttatcaatat tcatgttctg atctctcaca gcccttcatg tctgaaccgc | 60 |
| gacgatatga acatgcagaa agacgctatt ttcggcggca aaagacgagt aagaatttca | 120 |
| agtcaaagcc ttaaacgtgc gatgcgtaaa agtggttatt acgcacaaaa tattggtgaa | 180 |
| tccagtctca gaaccattca tcttgcacaa ttacgtgatg ttcttcggca aaacttggt | 240 |
| gaacgttttg accaaaaaat catcgataag acattagcgc tgctctccgg taaatcagtt | 300 |
| gatgaagccg aaaagatttc tgccgatgcg gttactccct gggttgtggg agaaatagcc | 360 |
| tggttctgtg agcaggttgc aaaagcagag gctgataatc tggatgataa aaagctgctc | 420 |
| aaagttctta aggaagatat tgccgccata cgtgtgaatt tacagcaggg tgttgatatt | 480 |
| gcgcttagtg aagaatggc aaccagcggc atgatgactg agttgggaaa agttgatggt | 540 |
| gcaatgtcca ttgcgcatgc gatcactact catcaggttg attctgatat tgactggttc | 600 |
| accgctgtag atgatttaca ggaacaaggt tctgcacatc tgggaactca ggaatttca | 660 |
| tcgggtgttt tttatcgtta tgccaacatt aacctcgctc aacttcagga aaatttaggt | 720 |
| ggtgcctcca gggagcaggc tctggaaatt gcaacccatg ttgttcatat gctggcaaca | 780 |
| gaggtccctg agcaaaaaca gcgtacttat gccgctttta accctgcgga tatggtaatg | 840 |
| gttaatttct ccgatatgcc actttctatg gcaaatgctt tgaaaaagc ggttaaagcg | 900 |
| aaagatggct ttttgcaacc gtctatacag gcgtttaatc aatattggga tcgcgttgcc | 960 |
| aatggatatg gtctgaacgg agctgctgcg caattcagct tatctgatgt agacccaatt | 1020 |

```
actgctcaag ttaaacaaat gcctacttta gaacagttaa aatcctgggt tcgtaataat    1080
ggcgaggcgt ga                                                        1092

<210> SEQ ID NO 63
<211> LENGTH: 675
<212> TYPE: DNA
<213> ORGANISM: Escherichia coli

<400> SEQUENCE: 63
atgagatctt atttgatctt gcggcttgct gggccaatgc aagcctgggg gcagccgacc      60
tttgaaggaa cgcgacctac cggaagattt ccgacccgaa gcgggttatt agggctactc     120
ggggcttgtc ttgggatcca acgtgatgat acttcttcat acaggcgtt atcagagagt      180 gtgcaatttg cagtgcgctg cgatgaactc attcttgacg atcgtcgtgt gtctgtaacg     240
gggttgcgtg attaccatac agtccttgga gcgcgagaag attaccgtgg tttgaaaagt     300
catgaaacga ttcaaacatg gcgcaatat ttatgtgatg cctcctttac cgtcgctctc     360
tggttaacac cccatgcaac gatggttatc tcagaacttg aaaaagcagt attaaagcct     420
cggtatacac cttacctggg gcggagaagt tgcccactaa cacacccgct ttttttgggg    480
acatgtcagg catcggatcc tcagaaggcg ctattaaatt atgagcccgt tggcggcgat     540
atatatagtg aggaatcagt tacagggcat catttaaaat ttacggcgcg cgacgaaccg     600
atgatcacct tgcctcgaca atttgcttcc cgagaatggt atgtgattaa aggaggtatg     660
gatgtatctc agtaa                                                     675

<210> SEQ ID NO 64
<211> LENGTH: 600
<212> TYPE: DNA
<213> ORGANISM: Escherichia coli

<400> SEQUENCE: 64
atgtatctca gtaaagtcat cattgccagg gcctggagca gggatcttta ccaacttcac      60
cagggattat ggcatttatt tccaaacaga ccggatgctg ctcgtgattt tcttttttcat    120 gttgagaagc gaaacacacc agaaggctgt catgttttat tgcagtcagc gcaaatgcct     180
gtttcaactg ccgttgcgac agtcattaaa actaaacagg ttgaatttca acttcaggtt     240
ggtgttccac tctattttcg gcttcgggca atccgatca aaactattct cgacaatcaa      300
aagcgcctgg acagtaaagg gaatattaaa cgctgtcggg ttccgttaat aaaagaagca     360
gaacaaatcg cgtggttgca acgtaaattg gcaatgcgg cgcgcgttga agatgtgcat     420
cccatatcgg aacggccaca gtatttttct ggtgatggta aaagtggaaa gatccaaacg     480
gtttgctttg aaggtgtgct caccatcaac gacgcgccag cgttaataga tcttgtacag     540
caaggtattg ggccagctaa atcgatggga tgtggcttgc tatctttggc tccactgtga     600

<210> SEQ ID NO 65
<211> LENGTH: 2667
<212> TYPE: DNA
<213> ORGANISM: Escherichia coli

<400> SEQUENCE: 65
atggaacctt ttaaatatat atgccattac tggggaaaat cctcaaaaag cttgacgaaa       60
ggaaatgata ttcatctgtt aatttatcat tgccttgatg ttgctgctgt tgcagattgc     120
tggtgggatc aatcagtcgt actgcaaaat acttttttgcc gaaatgaaat gctatcaaaa    180
```

| | |
|---|---|
| cagagggtga aggcctggct gttattttc attgctcttc atgatattgg aaagtttgat | 240 |
| atacgattcc aatataaatc agcagaaagt tggctgaaat taaatcctgc aacgccatca | 300 |
| cttaatggtc catcaacaca aatgtgccgt aaatttaatc atggtgcagc cggtctgtat | 360 |
| tggtttaacc aggattcact ttcagagcaa tctctcgggg attttttcag ttttttttgat | 420 |
| gccgctcctc atccttatga gtcctggttt ccatgggtag aggccgttac aggacatcat | 480 |
| ggttttatat tacattccca ggatcaagat aagtcgcgtt gggaaatgcc agcttctctg | 540 |
| gcatcttatg ctgcgcaaga taaacaggct cgtgaggagt ggatatctgt actggaagca | 600 |
| ttattttaa cgccagcggg gttatctata aacgatatac cacctgattg ttcatcactg | 660 |
| ttagcaggtt tttgctcgct tgctgactgg ttaggctcct ggactacaac gaatacctt | 720 |
| ctgtttaatg aggatgcgcc ttccgacata aatgctctga acgtatttt ccaggaccga | 780 |
| cagcaggatg cgagccgggt attggagttg agtggacttg tatcaaataa gcgatgttat | 840 |
| gaaggtgttc atgcactact ggacaatggc tatcaaccca gacaattaca ggtgttagtt | 900 |
| gatgctcttc cagtagctcc cgggctgacg gtaatagagg cacctacagg ctccggtaaa | 960 |
| acggaaacag cgctggccta tgcttggaaa cttattgatc aacaaattgc ggatagtgtt | 1020 |
| atttttgccc tccaacaca agctaccgcg aatgctatgc ttacgagaat ggaagcgagc | 1080 |
| gcgagccact tattttcatc cccaaatctt attcttgctc atggcaattc acggtttaac | 1140 |
| cacctctttc aatcaataaa atcacgcgcg attactgaac aggggcaaga agaagcgtgg | 1200 |
| gttcagtgtt gtcagtggtt gtcacaaagc aataagaaag tgtttcttgg gcaaatcggc | 1260 |
| gtttgcacga ttgatcaggt gttgatatcg gtattgccag ttaaacaccg ctttatccgt | 1320 |
| ggtttgggaa ttggtcgaag tgttttaatt gttgatgaag ttcatgctta cgacacctat | 1380 |
| atgaacggct gctgaggc agtgctcaag gctcaggctg atgtgggagg gagtgttatt | 1440 |
| cttctttccg caaccctacc aatgaaacaa aaacagaaac ttctggatac ttatggtctg | 1500 |
| catacagatc cagtggaaaa taactccgca tatccactca ttaactggcg aggtgtgaat | 1560 |
| ggtgcgcaac gttttgatct gctagctcat ccagaacaac tcccgccccg cttttcgatt | 1620 |
| cagccagaac ctatttgttt agctgacatg ttacctgacc ttacgatgtt agagcgaatg | 1680 |
| atcgcagcgg caaacgcggg tgcacaggtc tgtcttattt gcaatttggt tgacgttgca | 1740 |
| caagtatgct accaacggct aaaggagcta aataacacgc aagtagatat agatttgttt | 1800 |
| catgcgcgct ttacgctgaa cgatcgtcgt gaaaaagaga atcgagttat tagcaatttc | 1860 |
| ggcaaaaatg ggaagcgaaa tgttggacgg atacttgtcg caacccaggt cgtgaacaa | 1920 |
| tcactcgacg ttgattttga ttggttaatt actcagcatt gtcctgcaga tttgcttttc | 1980 |
| caacgattgg gccgtttaca tcgccatcat cgcaaatatc gtcccgctgg ttttgagatt | 2040 |
| cctgttgcca ccatttttgct gcctgatggc gagggttacg gacgacatga gcatatttat | 2100 |
| agcaacgtta gagtcatgtg gcggacgcag caacatattg aggagcttaa tggagcatcc | 2160 |
| ttatttttcc ctgatgctta ccggcaatgg ctggatagca tttacgatga tgcggaaatg | 2220 |
| gatgagccag aatgggtcgg caatggcatg ataaatttg aaagcgccga gtgtgaaaaa | 2280 |
| aggttcaagg ctcgcaaggt cctgcagtgg gctgaagaat atagcttgca ggataacgat | 2340 |
| gaaaccattc ttgcggtaac gagggatggg gaaatgagcc tgccattatt gccttatgta | 2400 |
| caaacgtctt caggtaaaca actgctcgat ggccaggtct acgaggacct aagtcatgaa | 2460 |
| cagcagtatg aggcgcttgc acttaatcgc gtcaatgtac ccttcacctg gaaacgtagt | 2520 |
| ttttctgaag tagtagatga agatgggtta ctttggctgg aagggaaaca gaatctggat | 2580 |

-continued

```
ggatgggtct ggcagggtaa cagtattgtt attacctata caggggatga agggatgacc    2640
agagtcatcc ctgcaaatcc caaataa                                        2667
```

<210> SEQ ID NO 66
<211> LENGTH: 4107
<212> TYPE: DNA
<213> ORGANISM: Streptococcus pyogenes

<400> SEQUENCE: 66

```
atggataaga aatactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaaatct tataggggct cttttatttg acagtggaga gacagcggaa     180
gcgactcgtc tcaaacggac agctcgtaga aggtatacac gtcggaagaa tcgtatttgt     240
tatctacagg agattttttc aaatgagatg gcgaaagtag atgatagttt ctttcatcga     300
cttgaagagt ctttttttggt ggaagaagac aagaagcatg aacgtcatcc tattttttgga    360 aatatagtag atgaagttgc ttatcatgag aaatatccaa ctatctatca tctgcgaaaa     420
aaattggtag attctactga taaagcggat ttgcgcttaa tctatttggc cttagcgcat     480
atgattaagt tcgtggtca ttttttgatt gagggagatt taaatcctga taatagtgat     540
gtggacaaac tatttatcca gttggtacaa acctacaatc aattatttga agaaaaccct     600
attaacgcaa gtggagtaga tgctaaagcg attcttctg cacgattgag taaatcaaga     660
cgattagaaa atctcattgc tcagctcccc ggtgagaaga aaaatggctt atttgggaat     720
ctcattgctt tgtcattggg tttgaccccct aattttaaat caaatttttga tttggcagaa    780 gatgctaaat tacagctttc aaaagatact tacgatgatg atttagataa tttattggcg     840
caaattggag atcaatatgc tgatttgttt ttggcagcta agaatttatc agatgctatt     900
ttactttcag atatcctaag agtaaatact gaaataacta aggctcccct atcagcttca     960
atgattaaac gctacgatga acatcatcaa gacttgactc ttttaaaagc tttagttcga    1020
caacaacttc cagaaaagta taaagaaatc ttttttgatc aatcaaaaaa cggatatgca    1080
ggttatattg atgggggagc tagccaagaa gaattttata aatttatcaa accaatttta    1140
gaaaaaatgg atggtactga ggaattattg gtgaaactaa atcgtgaaga tttgctgcgc    1200
aagcaacgga ccttttgacaa cggctctatt ccccatcaaa ttcacttggg tgagctgcat    1260
gctattttga agacaagaag actttttat ccatttttaa agacaatcg tgagaagatt    1320 gaaaaaatct tgacttttcg aattccttat tatgttggtc cattggcgcg tggcaatagt    1380
cgttttgcat ggatgactcg gaagtctgaa gaaacaatta ccccatggaa ttttgaagaa    1440
gttgtcgata aggtgcttc agctcaatca tttattgaac gcatgacaaa ctttgataaa    1500
aatcttccaa atgaaaaagt actaccaaaa catagtttgc tttatgagta ttttacggtt    1560
tataacgaat tgacaaaggt caaatatgtt actgaaggaa tgcgaaaacc agcatttctt    1620
tcaggtgaac agaagaaagc cattgttgat ttactcttca aaacaaatcg aaaagtaacc    1680
gttaagcaat aaaagaaga ttatttcaaa aaaatagaat gttttgatag tgttgaaatt    1740
tcaggagttg aagatagatt taatgcttca ttaggtacct accatgattt gctaaaaatt    1800
attaaagata agattttttt ggataatgaa gaaatgaag atatcttaga ggatattgtt    1860
ttaacattga cccttatttga agatagggag atgattgagg aaagacttaa acatatgct    1920 caccttttg atgataaggt gatgaaacag cttaaacgtc gccgttatac tggttgggga    1980
```

```
cgtttgtctc gaaaattgat taatggtatt agggataagc aatctggcaa acaatatta    2040 gatttttga  aatcagatgg ttttgccaat cgcaatttta tgcagctgat ccatgatgat   2100
agtttgacat ttaagaaga  cattcaaaaa gcacaagtgt ctggacaagg cgatagttta   2160
catgaacata ttgcaaattt agctggtagc cctgctatta aaaaggtat  tttacagact   2220 gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta agtgattac  cttaaaatct   2880 aaattagttt ctgacttccg aaaagatttc caattctata agtacgtga  gattaacaat   2940 taccatcatg cccatgatgc gtatctaaat gccgtcgttg gaactgcttt gattaagaaa   3000
tatccaaaac ttgaatcgga gtttgtctat ggtgattata agtttatga  tgttcgtaaa   3060 atgattgcta agtctgagca agaaataggc aaagcaaccg caaatatttt cttttactct   3120
aatatcatga acttcttcaa aacagaaatt acacttgcaa atggagagat cgcaaacgc    3180 cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aattatggaa agaagttcct ttgaaaaaaa tccgattgac   3540 ttttagaag  ctaaaggata taaggaagtt aaaaagagact taatcattaa actacctaaa   3600
tatagtcttt ttgagttaga aaacggtcgt aaacggatgc tggctagtgc cggagaatta   3660
caaaaaggaa atgagctggc tctgccaagc aaatatgtga ttttttata  tttagctagt   3720 cattatgaaa agttgaaggg tagtccagaa gataacgaac aaaaacaatt gtttgtggag   3780
cagcataagc attatttaga tgagattatt gagcaaatca gtgaatttc  taagcgtgtt   3840 attttagcag atgccaattt agataaagtt cttagtgcat ataacaaaca tagagacaaa   3900
ccaatacgtg aacaagcaga aaatattatt catttattta cgttgacgaa tcttggagct   3960
cccgctgctt ttaaatattt tgatacaaca attgatcgta acgatatac  gtctacaaaa   4020 gaagttttag atgccactct tatccatcaa tccatcactg gtctttatga aacacgcatt   4080
gatttgagtc agctaggagg tgactga                                       4107
```

<210> SEQ ID NO 67
<211> LENGTH: 502
<212> TYPE: PRT
<213> ORGANISM: Escherichia coli

<400> SEQUENCE: 67

-continued

```
Met Asn Leu Leu Ile Asp Asn Trp Ile Pro Val Arg Pro Arg Asn Gly
 1               5                  10                 15

Gly Lys Val Gln Ile Ile Asn Leu Gln Ser Leu Tyr Cys Ser Arg Asp
             20                  25                 30

Gln Trp Arg Leu Ser Leu Pro Arg Asp Asp Met Glu Leu Ala Ala Leu
         35                  40                 45

Ala Leu Leu Val Cys Ile Gly Gln Ile Ile Ala Pro Ala Lys Asp Asp
     50                  55                 60

Val Glu Phe Arg His Arg Ile Met Asn Pro Leu Thr Glu Asp Glu Phe
 65                  70                 75                 80

Gln Gln Leu Ile Ala Pro Trp Ile Asp Met Phe Tyr Leu Asn His Ala
                 85                  90                 95

Glu His Pro Phe Met Gln Thr Lys Gly Val Lys Ala Asn Asp Val Thr
                100                 105                110

Pro Met Glu Lys Leu Leu Ala Gly Val Ser Gly Ala Thr Asn Cys Ala
                115                 120                125

Phe Val Asn Gln Pro Gly Gln Gly Glu Ala Leu Cys Gly Gly Cys Thr
    130                 135                 140

Ala Ile Ala Leu Phe Asn Gln Ala Asn Gln Ala Pro Gly Phe Gly Gly
145                 150                 155                160

Gly Phe Lys Ser Gly Leu Arg Gly Gly Thr Pro Val Thr Thr Phe Val
                165                 170                 175

Arg Gly Ile Asp Leu Arg Ser Thr Val Leu Leu Asn Val Leu Thr Leu
                180                 185                 190

Pro Arg Leu Gln Lys Gln Phe Pro Asn Glu Ser His Thr Glu Asn Gln
        195                 200                 205

Pro Thr Trp Ile Lys Pro Ile Lys Ser Asn Glu Ser Ile Pro Ala Ser
    210                 215                 220

Ser Ile Gly Phe Val Arg Gly Leu Phe Trp Gln Pro Ala His Ile Glu
225                 230                 235                240

Leu Cys Asp Pro Ile Gly Ile Gly Lys Cys Ser Cys Cys Gly Gln Glu
                245                 250                 255

Ser Asn Leu Arg Tyr Thr Gly Phe Leu Lys Glu Lys Phe Thr Phe Thr
                260                 265                 270

Val Asn Gly Leu Trp Pro His Pro His Ser Pro Cys Leu Val Thr Val
                275                 280                 285

Lys Lys Gly Glu Val Glu Glu Lys Phe Leu Ala Phe Thr Thr Ser Ala
        290                 295                 300

Pro Ser Trp Thr Gln Ile Ser Arg Val Val Val Asp Lys Ile Ile Gln
305                 310                 315                 320

Asn Glu Asn Gly Asn Arg Val Ala Ala Val Asn Gln Phe Arg Asn
                325                 330                 335

Ile Ala Pro Gln Ser Pro Leu Glu Leu Ile Met Gly Gly Tyr Arg Asn
                340                 345                 350

Asn Gln Ala Ser Ile Leu Glu Arg Arg His Asp Val Leu Met Phe Asn
                355                 360                 365

Gln Gly Trp Gln Gln Tyr Gly Asn Val Ile Asn Glu Ile Val Thr Val
        370                 375                 380

Gly Leu Gly Tyr Lys Thr Ala Leu Arg Lys Ala Leu Tyr Thr Phe Ala
385                 390                 395                 400

Glu Gly Phe Lys Asn Lys Asp Phe Lys Gly Ala Gly Val Ser Val His
                405                 410                 415
```

```
Glu Thr Ala Glu Arg His Phe Tyr Arg Gln Ser Glu Leu Leu Ile Pro
                420                 425                 430

Asp Val Leu Ala Asn Val Asn Phe Ser Gln Ala Asp Glu Val Ile Ala
            435                 440                 445

Asp Leu Arg Asp Lys Leu His Gln Leu Cys Glu Met Leu Phe Asn Gln
        450                 455                 460

Ser Val Ala Pro Tyr Ala His Pro Lys Leu Ile Ser Thr Leu Ala
465                 470                 475                 480

Leu Ala Arg Ala Thr Leu Tyr Lys His Leu Arg Glu Leu Lys Pro Gln
                485                 490                 495

Gly Gly Pro Ser Asn Gly
            500

<210> SEQ ID NO 68
<211> LENGTH: 160
<212> TYPE: PRT
<213> ORGANISM: Escherichia coli

<400> SEQUENCE: 68

Met Ala Asp Glu Ile Asp Ala Met Ala Leu Tyr Arg Ala Trp Gln Gln
1               5                   10                  15

Leu Asp Asn Gly Ser Cys Ala Gln Ile Arg Arg Val Ser Glu Pro Asp
                20                  25                  30

Glu Leu Arg Asp Ile Pro Ala Phe Tyr Arg Leu Val Gln Pro Phe Gly
            35                  40                  45

Trp Glu Asn Pro Arg His Gln Gln Ala Leu Leu Arg Met Val Phe Cys
        50                  55                  60

Leu Ser Ala Gly Lys Asn Val Ile Arg His Gln Asp Lys Lys Ser Glu
65                  70                  75                  80

Gln Thr Thr Gly Ile Ser Leu Gly Arg Ala Leu Ala Asn Ser Gly Arg
                85                  90                  95

Ile Asn Glu Arg Arg Ile Phe Gln Leu Ile Arg Ala Asp Arg Thr Ala
            100                 105                 110

Asp Met Val Gln Leu Arg Arg Leu Leu Thr His Ala Glu Pro Val Leu
        115                 120                 125

Asp Trp Pro Leu Met Ala Arg Met Leu Thr Trp Trp Gly Lys Arg Glu
    130                 135                 140

Arg Gln Gln Leu Leu Glu Asp Phe Val Leu Thr Thr Asn Lys Asn Ala
145                 150                 155                 160

<210> SEQ ID NO 69
<211> LENGTH: 363
<212> TYPE: PRT
<213> ORGANISM: Escherichia coli

<400> SEQUENCE: 69

Met Ser Asn Phe Ile Asn Ile His Val Leu Ile Ser His Ser Pro Ser
1               5                   10                  15

Cys Leu Asn Arg Asp Asp Met Asn Met Gln Lys Asp Ala Ile Phe Gly
                20                  25                  30

Gly Lys Arg Arg Val Arg Ile Ser Ser Gln Ser Leu Lys Arg Ala Met
            35                  40                  45

Arg Lys Ser Gly Tyr Tyr Ala Gln Asn Ile Gly Glu Ser Ser Leu Arg
        50                  55                  60

Thr Ile His Leu Ala Gln Leu Arg Asp Val Leu Arg Gln Lys Leu Gly
65                  70                  75                  80
```

```
Glu Arg Phe Asp Gln Lys Ile Ile Asp Lys Thr Leu Ala Leu Leu Ser
                85                  90                  95

Gly Lys Ser Val Asp Glu Ala Glu Lys Ile Ser Ala Asp Ala Val Thr
            100                 105                 110

Pro Trp Val Gly Glu Ile Ala Trp Phe Cys Glu Gln Val Ala Lys
        115                 120                 125

Ala Glu Ala Asp Asn Leu Asp Asp Lys Lys Leu Leu Lys Val Leu Lys
130                 135                 140

Glu Asp Ile Ala Ala Ile Arg Val Asn Leu Gln Gln Gly Val Asp Ile
145                 150                 155                 160

Ala Leu Ser Gly Arg Met Ala Thr Ser Gly Met Met Thr Glu Leu Gly
                165                 170                 175

Lys Val Asp Gly Ala Met Ser Ile Ala His Ala Ile Thr Thr His Gln
            180                 185                 190

Val Asp Ser Asp Ile Asp Trp Phe Thr Ala Val Asp Asp Leu Gln Glu
        195                 200                 205

Gln Gly Ser Ala His Leu Gly Thr Gln Glu Phe Ser Ser Gly Val Phe
    210                 215                 220

Tyr Arg Tyr Ala Asn Ile Asn Leu Ala Gln Leu Gln Glu Asn Leu Gly
225                 230                 235                 240

Gly Ala Ser Arg Glu Gln Ala Leu Glu Ile Ala Thr His Val Val His
                245                 250                 255

Met Leu Ala Thr Glu Val Pro Gly Ala Lys Gln Arg Thr Tyr Ala Ala
            260                 265                 270

Phe Asn Pro Ala Asp Met Val Met Val Asn Phe Ser Asp Met Pro Leu
        275                 280                 285

Ser Met Ala Asn Ala Phe Glu Lys Ala Val Lys Ala Lys Asp Gly Phe
    290                 295                 300

Leu Gln Pro Ser Ile Gln Ala Phe Asn Gln Tyr Trp Asp Arg Val Ala
305                 310                 315                 320

Asn Gly Tyr Gly Leu Asn Gly Ala Ala Ala Gln Phe Ser Leu Ser Asp
                325                 330                 335

Val Asp Pro Ile Thr Ala Gln Val Lys Gln Met Pro Thr Leu Glu Gln
            340                 345                 350

Leu Lys Ser Trp Val Arg Asn Asn Gly Glu Ala
        355                 360

<210> SEQ ID NO 70
<211> LENGTH: 224
<212> TYPE: PRT
<213> ORGANISM: Escherichia coli

<400> SEQUENCE: 70

Met Arg Ser Tyr Leu Ile Leu Arg Leu Ala Gly Pro Met Gln Ala Trp
1               5                   10                  15

Gly Gln Pro Thr Phe Glu Gly Thr Arg Pro Thr Gly Arg Phe Pro Thr
            20                  25                  30

Arg Ser Gly Leu Leu Gly Leu Leu Gly Ala Cys Leu Gly Ile Gln Arg
        35                  40                  45

Asp Asp Thr Ser Ser Leu Gln Ala Leu Ser Glu Ser Val Gln Phe Ala
    50                  55                  60

Val Arg Cys Asp Glu Leu Ile Leu Asp Asp Arg Arg Val Ser Val Thr
65                  70                  75                  80

Gly Leu Arg Asp Tyr His Thr Val Leu Gly Ala Arg Glu Asp Tyr Arg
                85                  90                  95
```

-continued

```
Gly Leu Lys Ser His Glu Thr Ile Gln Thr Trp Arg Glu Tyr Leu Cys
                100                 105                 110

Asp Ala Ser Phe Thr Val Ala Leu Trp Leu Thr Pro His Ala Thr Met
            115                 120                 125

Val Ile Ser Glu Leu Glu Lys Ala Val Leu Lys Pro Arg Tyr Thr Pro
        130                 135                 140

Tyr Leu Gly Arg Arg Ser Cys Pro Leu Thr His Pro Leu Phe Leu Gly
145                 150                 155                 160

Thr Cys Gln Ala Ser Asp Pro Gln Lys Ala Leu Leu Asn Tyr Glu Pro
                165                 170                 175

Val Gly Gly Asp Ile Tyr Ser Glu Glu Ser Val Thr Gly His His Leu
            180                 185                 190

Lys Phe Thr Ala Arg Asp Glu Pro Met Ile Thr Leu Pro Arg Gln Phe
        195                 200                 205

Ala Ser Arg Glu Trp Tyr Val Ile Lys Gly Gly Met Asp Val Ser Gln
    210                 215                 220
```

<210> SEQ ID NO 71
<211> LENGTH: 199
<212> TYPE: PRT
<213> ORGANISM: Escherichia coli

<400> SEQUENCE: 71

```
Met Tyr Leu Ser Lys Val Ile Ile Ala Arg Ala Trp Ser Arg Asp Leu
1               5                   10                  15

Tyr Gln Leu His Gln Gly Leu Trp His Leu Phe Pro Asn Arg Pro Asp
            20                  25                  30

Ala Ala Arg Asp Phe Leu Phe His Val Glu Lys Arg Asn Thr Pro Glu
        35                  40                  45

Gly Cys His Val Leu Leu Gln Ser Ala Gln Met Pro Val Ser Thr Ala
    50                  55                  60

Val Ala Thr Val Ile Lys Thr Lys Gln Val Glu Phe Gln Leu Gln Val
65                  70                  75                  80

Gly Val Pro Leu Tyr Phe Arg Leu Arg Ala Asn Pro Ile Lys Thr Ile
                85                  90                  95

Leu Asp Asn Gln Lys Arg Leu Asp Ser Lys Gly Asn Ile Lys Arg Cys
            100                 105                 110

Arg Val Pro Leu Ile Lys Glu Ala Glu Gln Ile Ala Trp Leu Gln Arg
        115                 120                 125

Lys Leu Gly Asn Ala Ala Arg Val Glu Asp Val His Pro Ile Ser Glu
    130                 135                 140

Arg Pro Gln Tyr Phe Ser Gly Asp Gly Lys Ser Gly Lys Ile Gln Thr
145                 150                 155                 160

Val Cys Phe Glu Gly Val Leu Thr Ile Asn Asp Ala Pro Ala Leu Ile
                165                 170                 175

Asp Leu Val Gln Gln Gly Ile Gly Pro Ala Lys Ser Met Gly Cys Gly
            180                 185                 190

Leu Leu Ser Leu Ala Pro Leu
        195
```

<210> SEQ ID NO 72
<211> LENGTH: 888
<212> TYPE: PRT
<213> ORGANISM: Escherichia coli

<400> SEQUENCE: 72

```
Met Glu Pro Phe Lys Tyr Ile Cys His Tyr Trp Gly Lys Ser Ser Lys
1               5                   10                  15

Ser Leu Thr Lys Gly Asn Asp Ile His Leu Leu Ile Tyr His Cys Leu
            20                  25                  30

Asp Val Ala Ala Val Ala Asp Cys Trp Trp Asp Gln Ser Val Val Leu
        35                  40                  45

Gln Asn Thr Phe Cys Arg Asn Glu Met Leu Ser Lys Gln Arg Val Lys
    50                  55                  60

Ala Trp Leu Leu Phe Phe Ile Ala Leu His Asp Ile Gly Lys Phe Asp
65                  70                  75                  80

Ile Arg Phe Gln Tyr Lys Ser Ala Glu Ser Trp Leu Lys Leu Asn Pro
                85                  90                  95

Ala Thr Pro Ser Leu Asn Gly Pro Ser Thr Gln Met Cys Arg Lys Phe
            100                 105                 110

Asn His Gly Ala Ala Gly Leu Tyr Trp Phe Asn Gln Asp Ser Leu Ser
        115                 120                 125

Glu Gln Ser Leu Gly Asp Phe Phe Ser Phe Phe Asp Ala Ala Pro His
    130                 135                 140

Pro Tyr Glu Ser Trp Phe Pro Trp Val Glu Ala Val Thr Gly His His
145                 150                 155                 160

Gly Phe Ile Leu His Ser Gln Asp Gln Asp Lys Ser Arg Trp Glu Met
                165                 170                 175

Pro Ala Ser Leu Ala Ser Tyr Ala Ala Gln Asp Lys Gln Ala Arg Glu
            180                 185                 190

Glu Trp Ile Ser Val Leu Glu Ala Leu Phe Leu Thr Pro Ala Gly Leu
        195                 200                 205

Ser Ile Asn Asp Ile Pro Pro Asp Cys Ser Ser Leu Leu Ala Gly Phe
    210                 215                 220

Cys Ser Leu Ala Asp Trp Leu Gly Ser Trp Thr Thr Asn Thr Phe
225                 230                 235                 240

Leu Phe Asn Glu Asp Ala Pro Ser Asp Ile Asn Ala Leu Arg Thr Tyr
                245                 250                 255

Phe Gln Asp Arg Gln Asp Ala Ser Arg Val Leu Glu Leu Ser Gly
            260                 265                 270

Leu Val Ser Asn Lys Arg Cys Tyr Glu Gly Val His Ala Leu Leu Asp
        275                 280                 285

Asn Gly Tyr Gln Pro Arg Gln Leu Gln Val Leu Val Asp Ala Leu Pro
    290                 295                 300

Val Ala Pro Gly Leu Thr Val Ile Glu Ala Pro Thr Gly Ser Gly Lys
305                 310                 315                 320

Thr Glu Thr Ala Leu Ala Tyr Ala Trp Lys Leu Ile Asp Gln Gln Ile
                325                 330                 335

Ala Asp Ser Val Ile Phe Ala Leu Pro Thr Gln Ala Thr Ala Asn Ala
            340                 345                 350

Met Leu Thr Arg Met Glu Ala Ser Ala His Leu Phe Ser Ser Pro
        355                 360                 365

Asn Leu Ile Leu Ala His Gly Asn Ser Arg Phe Asn His Leu Phe Gln
    370                 375                 380

Ser Ile Lys Ser Arg Ala Ile Thr Glu Gln Gly Gln Glu Glu Ala Trp
385                 390                 395                 400

Val Gln Cys Cys Gln Trp Leu Ser Gln Ser Asn Lys Lys Val Phe Leu
                405                 410                 415
```

-continued

```
Gly Gln Ile Gly Val Cys Thr Ile Asp Gln Val Leu Ile Ser Val Leu
                420                 425                 430

Pro Val Lys His Arg Phe Ile Arg Gly Leu Gly Ile Gly Arg Ser Val
            435                 440                 445

Leu Ile Val Asp Glu Val His Ala Tyr Asp Thr Tyr Met Asn Gly Leu
        450                 455                 460

Leu Glu Ala Val Leu Lys Ala Gln Ala Asp Val Gly Gly Ser Val Ile
465                 470                 475                 480

Leu Leu Ser Ala Thr Leu Pro Met Lys Gln Lys Gln Lys Leu Leu Asp
                485                 490                 495

Thr Tyr Gly Leu His Thr Asp Pro Val Glu Asn Asn Ser Ala Tyr Pro
            500                 505                 510

Leu Ile Asn Trp Arg Gly Val Asn Gly Ala Gln Arg Phe Asp Leu Leu
        515                 520                 525

Ala His Pro Glu Gln Leu Pro Pro Arg Phe Ser Ile Gln Pro Glu Pro
        530                 535                 540

Ile Cys Leu Ala Asp Met Leu Pro Asp Leu Thr Met Leu Glu Arg Met
545                 550                 555                 560

Ile Ala Ala Ala Asn Ala Gly Ala Gln Val Cys Leu Ile Cys Asn Leu
                565                 570                 575

Val Asp Val Ala Gln Val Cys Tyr Gln Arg Leu Lys Glu Leu Asn Asn
            580                 585                 590

Thr Gln Val Asp Ile Asp Leu Phe His Ala Arg Phe Thr Leu Asn Asp
        595                 600                 605

Arg Arg Glu Lys Glu Asn Arg Val Ile Ser Asn Phe Gly Lys Asn Gly
610                 615                 620

Lys Arg Asn Val Gly Arg Ile Leu Val Ala Thr Gln Val Val Glu Gln
625                 630                 635                 640

Ser Leu Asp Val Asp Phe Asp Trp Leu Ile Thr Gln His Cys Pro Ala
                645                 650                 655

Asp Leu Leu Phe Gln Arg Leu Gly Arg Leu His Arg His His Arg Lys
            660                 665                 670

Tyr Arg Pro Ala Gly Phe Glu Ile Pro Val Ala Thr Ile Leu Leu Pro
        675                 680                 685

Asp Gly Glu Gly Tyr Gly Arg His Glu His Ile Tyr Ser Asn Val Arg
690                 695                 700

Val Met Trp Arg Thr Gln Gln His Ile Glu Glu Leu Asn Gly Ala Ser
705                 710                 715                 720

Leu Phe Phe Pro Asp Ala Tyr Arg Gln Trp Leu Asp Ser Ile Tyr Asp
                725                 730                 735

Asp Ala Glu Met Asp Glu Pro Glu Trp Val Gly Asn Gly Met Asp Lys
            740                 745                 750

Phe Glu Ser Ala Glu Cys Glu Lys Arg Phe Lys Ala Arg Lys Val Leu
        755                 760                 765

Gln Trp Ala Glu Glu Tyr Ser Leu Gln Asp Asn Asp Glu Thr Ile Leu
        770                 775                 780

Ala Val Thr Arg Asp Gly Glu Met Ser Leu Pro Leu Pro Tyr Val
785                 790                 795                 800

Gln Thr Ser Ser Gly Lys Gln Leu Leu Asp Gly Gln Val Tyr Glu Asp
                805                 810                 815

Leu Ser His Glu Gln Gln Tyr Glu Ala Leu Ala Leu Asn Arg Val Asn
            820                 825                 830

Val Pro Phe Thr Trp Lys Arg Ser Phe Ser Glu Val Val Asp Glu Asp
```

```
                835                 840                 845
Gly Leu Leu Trp Leu Glu Gly Lys Gln Asn Leu Asp Gly Trp Val Trp
850                 855                 860

Gln Gly Asn Ser Ile Val Ile Thr Tyr Thr Gly Asp Glu Gly Met Thr
865                 870                 875                 880

Arg Val Ile Pro Ala Asn Pro Lys
                885

<210> SEQ ID NO 73
<211> LENGTH: 1368
<212> TYPE: PRT
<213> ORGANISM: Streptococcus pyogenes

<400> SEQUENCE: 73

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320
```

```
Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
```

-continued

```
            740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
    770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
                850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
                930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
```

Ser Val Lys Glu Leu Leu Gly Ile Thr Ile Met Glu Arg Ser Ser
    1160                1165               1170

Phe Glu Lys Asn Pro Ile Asp Phe Leu Glu Ala Lys Gly Tyr Lys
    1175                1180               1185

Glu Val Lys Lys Asp Leu Ile Ile Lys Leu Pro Lys Tyr Ser Leu
    1190                1195               1200

Phe Glu Leu Glu Asn Gly Arg Lys Arg Met Leu Ala Ser Ala Gly
    1205                1210               1215

Glu Leu Gln Lys Gly Asn Glu Leu Ala Leu Pro Ser Lys Tyr Val
    1220                1225               1230

Asn Phe Leu Tyr Leu Ala Ser His Tyr Glu Lys Leu Lys Gly Ser
    1235                1240               1245

Pro Glu Asp Asn Glu Gln Lys Gln Leu Phe Val Glu Gln His Lys
    1250                1255               1260

His Tyr Leu Asp Glu Ile Ile Glu Gln Ile Ser Glu Phe Ser Lys
    1265                1270               1275

Arg Val Ile Leu Ala Asp Ala Asn Leu Asp Lys Val Leu Ser Ala
    1280                1285               1290

Tyr Asn Lys His Arg Asp Lys Pro Ile Arg Glu Gln Ala Glu Asn
    1295                1300               1305

Ile Ile His Leu Phe Thr Leu Thr Asn Leu Gly Ala Pro Ala Ala
    1310                1315               1320

Phe Lys Tyr Phe Asp Thr Thr Ile Asp Arg Lys Arg Tyr Thr Ser
    1325                1330               1335

Thr Lys Glu Val Leu Asp Ala Thr Leu Ile His Gln Ser Ile Thr
    1340                1345               1350

Gly Leu Tyr Glu Thr Arg Ile Asp Leu Ser Gln Leu Gly Gly Asp
    1355                1360               1365

<210> SEQ ID NO 74
<211> LENGTH: 270
<212> TYPE: PRT
<213> ORGANISM: Klebsiella pneumoniae

<400> SEQUENCE: 74

Met Glu Leu Pro Asn Ile Met His Pro Val Ala Lys Leu Ser Thr Ala
1               5                   10                  15

Leu Ala Ala Ala Leu Met Leu Ser Gly Cys Met Pro Gly Glu Ile Arg
                20                  25                  30

Pro Thr Ile Gly Gln Gln Met Glu Thr Gly Asp Gln Arg Phe Gly Asp
            35                  40                  45

Leu Val Phe Arg Gln Leu Ala Pro Asn Val Trp Gln His Thr Ser Tyr
    50                  55                  60

Leu Asp Met Pro Gly Phe Gly Ala Val Ala Ser Asn Gly Leu Ile Val
65                  70                  75                  80

Arg Asp Gly Gly Arg Val Leu Val Asp Thr Ala Trp Thr Asp Asp
                85                  90                  95

Gln Thr Ala Gln Ile Leu Asn Trp Ile Lys Gln Glu Ile Asn Leu Pro
            100                 105                 110

Val Ala Leu Ala Val Val Thr His Ala His Gln Asp Lys Met Gly Gly
                115                 120                 125

Met Asp Ala Leu His Ala Ala Gly Ile Ala Thr Tyr Ala Asn Ala Leu
            130                 135                 140

Ser Asn Gln Leu Ala Pro Gln Glu Gly Met Val Ala Ala Gln His Ser

```
                145                 150                 155                 160
Leu Thr Phe Ala Ala Asn Gly Trp Val Glu Pro Ala Thr Ala Pro Asn
                165                 170                 175
Phe Gly Pro Leu Lys Val Phe Tyr Pro Gly Pro Gly His Thr Ser Asp
                180                 185                 190
Asn Ile Thr Val Gly Ile Asp Gly Thr Asp Ile Ala Phe Gly Gly Cys
                195                 200                 205
Leu Ile Lys Asp Ser Lys Ala Lys Ser Leu Gly Asn Leu Gly Asp Ala
210                 215                 220
Asp Thr Glu His Tyr Ala Ala Ser Ala Arg Ala Phe Gly Ala Ala Phe
225                 230                 235                 240
Pro Lys Ala Ser Met Ile Val Met Ser His Ser Ala Pro Asp Ser Arg
                245                 250                 255
Ala Ala Ile Thr His Thr Ala Arg Met Ala Asp Lys Leu Arg
                260                 265                 270

<210> SEQ ID NO 75
<211> LENGTH: 813
<212> TYPE: DNA
<213> ORGANISM: Klebsiella pneumoniae

<400> SEQUENCE: 75
atggaattgc caatattat gcacccggtc gcgaagctga gcaccgcatt agccgctgca      60
ttgatgctga gcgggtgcat gcccggtgaa atccgcccga cgattggcca gcaaatggaa    120
actggcgacc aacggtttgg cgatctggtt ttccgccagc tcgcaccgaa tgtctggcag    180
cacacttcct atctcgacat gccgggtttc ggggcagtcg cttccaacgg tttgatcgtc    240
agggatggcg gccgcgtgct ggtggtcgat accgcctgga ccgatgacca gaccgcccag    300
atcctcaact ggatcaagca ggagatcaac ctgccggtcg cgctggcggt ggtgactcac    360
gcgcatcagg acaagatggg cggtatggac gcgctgcatg cggcggggat tgcgacttat    420
gccaatgcgt tgtcgaacca gcttgccccg caagagggga tggttgcggc gcaacacagc    480
ctgactttcg ccgccaatgg ctgggtcgaa ccagcaaccg cgcccaactt tggcccgctc    540
aaggtatttt accccggccc cggccacacc agtgacaata tcaccgttgg atcgacggc     600
accgacatcg cttttggtgg ctgcctgatc aaggacagca aggccaagtc gctcggcaat    660
ctcggtgatg ccgacactga gcactacgcc gcgtcagcgc gcgcgtttgg tgcggcgttc    720
cccaaggcca gcatgatcgt gatgagccat ccgccccccg atagccgcgc cgcaatcact    780
catacggccc gcatggccga caagctgcgc tga                                 813

<210> SEQ ID NO 76
<211> LENGTH: 291
<212> TYPE: PRT
<213> ORGANISM: Escherichia coli

<400> SEQUENCE: 76

Met Val Lys Lys Ser Leu Arg Gln Phe Thr Leu Met Ala Thr Ala Thr
1               5                   10                  15
Val Thr Leu Leu Leu Gly Ser Val Pro Leu Tyr Ala Gln Thr Ala Asp
                20                  25                  30
Val Gln Gln Lys Leu Ala Glu Leu Glu Arg Gln Ser Gly Gly Arg Leu
            35                  40                  45
Gly Val Ala Leu Ile Asn Thr Ala Asp Asn Ser Gln Ile Leu Tyr Arg
        50                  55                  60
```

```
Ala Asp Glu Arg Phe Ala Met Cys Ser Thr Ser Lys Val Met Ala Ala
 65                  70                  75                  80

Ala Ala Val Leu Lys Lys Ser Glu Ser Glu Pro Asn Leu Leu Asn Gln
                 85                  90                  95

Arg Val Glu Ile Lys Lys Ser Asp Leu Val Asn Tyr Asn Pro Ile Ala
            100                 105                 110

Glu Lys His Val Asn Gly Thr Met Ser Leu Ala Glu Leu Ser Ala Ala
        115                 120                 125

Ala Leu Gln Tyr Ser Asp Asn Val Ala Met Asn Lys Leu Ile Ala His
    130                 135                 140

Val Gly Gly Pro Ala Ser Val Thr Ala Phe Ala Arg Gln Leu Gly Asp
145                 150                 155                 160

Glu Thr Phe Arg Leu Asp Arg Thr Glu Pro Thr Leu Asn Thr Ala Ile
                165                 170                 175

Pro Gly Asp Pro Arg Asp Thr Thr Ser Pro Arg Ala Met Ala Gln Thr
            180                 185                 190

Leu Arg Asn Leu Thr Leu Gly Lys Ala Leu Gly Asp Ser Gln Arg Ala
        195                 200                 205

Gln Leu Val Thr Trp Met Lys Gly Asn Thr Thr Gly Ala Ala Ser Ile
    210                 215                 220

Gln Ala Gly Leu Pro Ala Ser Trp Val Val Gly Asp Lys Thr Gly Ser
225                 230                 235                 240

Gly Gly Tyr Gly Thr Thr Asn Asp Ile Ala Val Ile Trp Pro Lys Asp
                245                 250                 255

Arg Ala Pro Leu Ile Leu Val Thr Tyr Phe Thr Gln Pro Gln Pro Lys
            260                 265                 270

Ala Glu Ser Arg Arg Asp Val Leu Ala Ser Ala Ala Lys Ile Val Thr
        275                 280                 285

Asp Gly Leu
    290

<210> SEQ ID NO 77
<211> LENGTH: 876
<212> TYPE: DNA
<213> ORGANISM: Escherichia coli

<400> SEQUENCE: 77
atggttaaaa aatcactgcg ccagttcacg ctgatggcga cggcaaccgt cacgctgttg    60
ttaggaagtg tgccgctgta tgcgcaaacg gcggacgtac agcaaaaact tgccgaatta   120
gagcggcagt cggaggcag actgggtgtg cattgatta acacagcaga taattcgcaa   180
atactttatc gtgctgatga gcgctttgcg atgtgcagca ccagtaaagt gatggccgcg   240
gccgcggtgc tgaagaaaag tgaaagcgaa ccgaatctgt taaatcagcg agttgagatc   300
aaaaaatctg accttgttaa ctataatccg attgcgaaa agcacgtcaa tgggacgatg   360
tcactggctg agcttagcgc ggccgcgcta cagtacagcg ataacgtggc gatgaataag   420
ctgattgctc acgttggcgg cccggctagc gtcaccgcgt cgcccgaca gctgggagac   480 gaaacgttcc gtctcgaccg taccgagccg acgttaaaca ccgccattcc gggcgatccg   540
cgtgatacca cttcacctcg ggcaatggcg caaactctgc ggaatctgac gctgggtaaa   600
gcattgggcg acagccaacg ggcgcagctg gtgacatgga tgaaaggcaa taccaccggt   660
gcagcgagca ttcaggctgg actgcctgct tcctgggttg tggggataa aaccggcagc   720
```

```
ggtggctatg gcaccaccaa cgatatcgcg gtgatctggc caaaagatcg tgcgccgctg    780
attctggtca cttacttcac ccagcctcaa cctaaggcag aaagccgtcg cgatgtatta    840
gcgtcggcgg ctaaaatcgt caccgacggt ttgtaa                              876
```